US007790407B2

(12) United States Patent
Ma

(10) Patent No.: US 7,790,407 B2
(45) Date of Patent: Sep. 7, 2010

(54) TARGETING OF SALL4 FOR THE TREATMENT AND DIAGNOSIS OF PROLIFERATIVE DISORDERS ASSOCIATED WITH MYELODYSPLASTIC SYNDROME (MDS)

(75) Inventor: Yupo Ma, Las Vegas, NV (US)

(73) Assignee: Nevada Cancer Institute, Las Vegas, NV (US)

( * ) Notice: Subject to any disclaimer, the term of this patent is extended or adjusted under 35 U.S.C. 154(b) by 400 days.

(21) Appl. No.: 11/606,619

(22) Filed: Nov. 29, 2006

(65) Prior Publication Data
US 2007/0174923 A1 Jul. 26, 2007

Related U.S. Application Data

(60) Provisional application No. 60/741,015, filed on Nov. 29, 2005.

(51) Int. Cl.
*G01N 33/53* (2006.01)
(52) U.S. Cl. ..................................... 435/7.23; 435/7.21
(58) Field of Classification Search ........................ None
See application file for complete search history.

(56) References Cited

U.S. PATENT DOCUMENTS

| 2004/0265230 A1 | 12/2004 | Martinez et al. ........... 424/1.49 |
| 2005/0181381 A1 | 8/2005 | Wang et al. |
| 2007/0015271 A1 | 1/2007 | Rosen et al. |

OTHER PUBLICATIONS

Al-Baradie, et al., "Duane Radial Ray Syndrome (Okihiro Syndrome) Maps To 20q13 And Results From Mutations In SALL4, A New Member Of The SAL Family," *Am J Hum Genet*, 71:1195-1199 (2002).
Bonnet, et al., "Human Acute Myeloid Leukemia Is Organized As A Hierarchy That Originates From A Primitive Hematopoietic Cell," *Nat Med*, 3:730-737 (1997).
Friedman, A.D,, "Transcriptional Regulation Of Myelopoiesis," *Int J Hematol*, 75: 466-472 (2002).
Huntly, et al., "Leukaemia Stem Cells And The Evolution Of Cancer Stem Cell Research," *Nat Rev Cancer*, 5:311-321 (2005).
Kohlhase, et al., "Isolation, Characterization, And Organ-Specific Expression Of Two Novel Human Zinc Finger Genes Related To The Drosophila Gene Spalt," *Genomics*, 38:291-298 (1996).
Kohlhase, et al., "SALL3, A New Member Of The Human Spalt-Like Gene Family, Maps To 18q23," *Genomics*, 62:216-222 (1999).
Kohlhase, et al., "Mutations At The SALL4 Locus On Chromosome 20 Result In A Range Of Clinically Overlapping Phenotypes, Including Okihiro Syndrome, Holt-Oram Syndrome, Acro-Renal-Ocular Syndrome, And Patients Previously Reported To Represent Thalidomide Embryopathy," *J Med Genet*, 40:473-478 (2003).
Kühnlein, et al., "Spalt Encodes An Evolutionarily Conserved Zinc Finger Protein Of Novel Structure Which Provides Homeotic Gene Function In The Head And Tail Region Of The Drosophila Embryo," *Embo J*, 13:168-179 (1994).
Ma, et al., "Cloning And Characterization Of Two Promoters For The Human HSAL2 Gene And Their Transcriptional Repression By The Wilms Tumor Suppressor Gene Product," *J Biol Chem*, 276:48223-48230 (2001).
Ma, et al., "Hsal 1 Is Related To Kidney And Gonad Development And Is Expressed In Wilms Tumor," *Pediatr Nephrol*, 16:701-709 (2001).
Ma, et al., "SALL1 Expression In The Human Pituitary-Adrenal/Gonadal Axis," *J Endocrinol*, 173:437-448 (2002).
Ma, et al., "SALL4, A Novel Oncogene, Is Constitutively Expressed In Human Acute Myeloid Leukemia (AML) And Induces AML In Transgenic Mice," *Blood*, 108:2726-2735 (2006).
Marlin, et al, "Townes-Brocks Syndrome: Detection Of A SALL1 Mutation Hot Spot And Evidence For A Position Effect In One Patient," *Hum Mutat*, 14:377-386 (1999).
Reya, T., "Regulation Of Hematopoietic Stem Cell Self-Renewal," *Recent Prog Horm Res*, 58,:283-295 (2003).
Reya, et al., "A Role For WNT Signalling In Self-Renewal Of Haematopoietic Stem Cells," *Nature*, 423:409-414 (2003).
Reya, et al., "Wnt Signalling In Stem Cells and Cancer," *Nature*, 434:843-850 (2005).
Rosmarin, et al., "Transcriptional Regulation In Myelopoiesis: Hematopoietic Fate Choice, Myeloid Differentiation, And Leukemogenesis," *Exp Hematol*, 33: 131-143 (2005).
Sato, et al., "Sall1, A Causative Gene For Townes-Brocks Syndrome, Enhances The Canonical Wnt Signaling By Localizing To Heterochromatin," *Biochem Biophys Res Commun*, 319:103-113 (2004).
Simon, et al., "Constitutive Activation Of The Wnt/β-Catenin Signalling Pathway In Acute Myeloid Leukaemia," *Oncogene*, 24:2410-2420 (2005).
Staal, et al., "WNT Signalling And Haematopoiesis: A WNT-WNT Situation," *Nat Rev Immunol*, 5:21-30 (2005).
You, et al, "Inhibition Of WNT-2-Mediated Signaling Induces Programmed Cell Death In Non-Small-Cell Lung Cancer Cells," *Oncogene*, 23:6170-6174 (2004).

*Primary Examiner*—Sheela J Huff
(74) *Attorney, Agent, or Firm*—Cooley LLP

(57) ABSTRACT

The present invention discloses nucleic acids, proteins, and antibodies for SALL4 (including isoforms SALL4A, SALL4B, and SALL4C), a zinc finger transcriptional factor. Further, methods are disclosed which demonstrate that constitutive expression of SALL4 increases leukemogenic potential in cells of model animal systems. Moreover, constitutive expression of select isoforms (e.g., SALL4B) in transgenic mice demonstrate that these animals develop myelodysplastic syndrome (MDS)-like signs and symptoms, including subsequent acute myeloid leukemia (AML), which is transplantable. The disclosure also provides methods for identifying and purifying embryonic stem cells, adult stem cells, cancer stem cells, including leukemia stem cells, methods for identifying substances which bind to and/or modulate SALL4, methods for diagnosing MDS in a subject, and methods of treating a subject presenting MDS.

5 Claims, 25 Drawing Sheets

US 7,790,407 B2

TARGETING OF SALL4 FOR THE TREATMENT AND DIAGNOSIS OF PROLIFERATIVE DISORDERS ASSOCIATED WITH MYELODYSPLASTIC SYNDROME (MDS)

RELATED APPLICATIONS

This application claims benefit of priority under 35 U.S.C. §119(e) to U.S. Provisional Application No. 60/741,015, filed on Nov. 29, 2005 which is incorporated herein by reference in its entirety.

GOVERNMENT SUPPORT

This invention was made in part with government support under Grant Nos. K08CA097185, P20RR016464, and R01HL087948 awarded by the National Institutes of Health (NIH). The government has certain rights in this invention.

BACKGROUND OF THE INVENTION

1. Field of the Invention

The invention relates generally to factors associated with the Wnt/β-catenin signaling pathway and, more specifically, to interaction between transcription components of the pathway, including the SALL protein family and OCT4, which are involved in the regulation of embryonic and cancer stem cells, including methods for the diagnosis and treatment of proliferative disorders by targeting such interaction.

2. Background Information

ES cells derived from the inner cell mass (ICM) of the blastocyst are able to undergo self-renewing cell division and maintain their pluripotency over an indefinite period of time. ES cells can also differentiate into a variety of different cell types when cultured in vitro. The Wnt/β-catenin signaling pathway has been associated with the self-renewal of normal human stem cells (HSCs) and the granulocyte-macrophage progenitors (GMPs) of chronic myeloid leukemia (CML). Further, the transcriptional factor, OCT4, has been identified as a key regulator for the formation of ICM during preimplantation development. Moreover, OCT4 protein seems to plays a central role in maintaining the pluripotency of embryonic stem (ES) cells by regulating a wide range of genes.

The role of stem cells has been considered in the etiology of cancer. There has been increasing evidence that tumors might contain such cancer stems cells, i.e., rare cells that account for the growth of tumors. These rare cells with indefinite proliferative potential may account for the resistance observed for cancer cells in response to conventional therapeutic modalities. It is known that stem cells can be identified in adult tissues, where such cells arise from a specific tissue; e.g., hematopoietic cells. As the self renewal property of stem cells is tightly controlled in normal organogenesis, the de-regulation of self-renewal might result in carcinogenesis.

Myelodysplastic syndrome (MDS), for example, is a hematological disease marked by the accumulation of genomic abnormalities at the hematopoietic stem cell (HSC) level leading to pancytopenia, multilineage differentiation impairment, and bone marrow apoptosis.

Mortality in this disease results from pancytopenia or transformation to acute myeloid leukemia (AML). AML is a hematological cancer characterized by the accumulation of immature myeloid precursors in the bone marrow and peripheral blood.

From the analysis of genetic translocation in bone marrow samples from AML patients, it is clear that transcription factors critical for hematopoiesis play an important role in leukemogenesis. The pathogenesis of AML is considered to involve multistep genetic alternations. Because only HSCs are considered to have the ability to self-renew, they are the best candidates for the accumulation of multistep, preleukemic genetic changes and transforming them into so-called "leukemia stem cells" (LSCs).

Alternatively, downstream progenitors can acquire self-renewal capacity and give rise to leukemia. LSCs are not targeted specifically under current chemotherapy regimens yet such cells have been found to account for drug resistance and leukemia relapse.

The SALL gene family, SALL1, SALL2, SALL3, and SALL4, were originally cloned on the basis of their DNA sequence homology to *Drosophila* spalt (sal). In *Drosophila*, spalt is a homeotic gene essential for development of posterior head and anterior tail segments. It plays an important role in tracheal development, terminal differentiation of photoreceptors, and wing vein placement. In humans, the SALL gene family is associated with normal development, as well as tumorigenesis. SALL proteins belong to a group of $C_2H_2$ zinc finger transcription factors characterized by multiple finger domains distributed over the entire protein. During the tracheal development of *Drosophila*, spalt is an activated downstream target of Wingless, a Wnt ortholog. It has been demonstrated that SALL1 interacts with β-catenin by functioning as a coactivator, suggesting that the interaction between SALL and the Wnt/β-catenin pathway is bidirectional.

SUMMARY OF THE INVENTION

The present invention relates to SALL4, a human homolog to *Drosophila* spalt, which is a zinc finger transcriptional factor essential for development. SALL4 and its isoforms (SALL4A, SALL4B, and SALL4C) were cloned and sequenced. The present disclosure demonstrates that SALL4 failed to be turned off in human primary AML. Further, the leukemogenic potential of constitutive expression of SALL4 in a murine model is demonstrated. Moreover, SALL4B-transgenic mice which develop myelodysplastic syndrome (MDS)-like signs and symptoms and subsequent transplantable AML are described.

Increased apoptosis associated with dysmyelopoiesis is evident in transgenic mouse marrow and colony-formation (CFU) assays. Both isoforms are able to bind to β-catenin and synergistically enhance the Wnt/β-catenin signaling pathway. This demonstrates that the constitutive expression of SALL4 causes MDS/AML, and that such expression impinges on the Wnt/β-catenin pathway. In a related aspect, the murine model disclosed provides a platform to study human MDS/AML transformation, and the Wnt/β-catenin pathway's role in the pathogenesis of leukemia stem cells.

In one embodiment, an antibody or antibody fragment is disclosed which binds to a polypeptide that includes an amino acid sequence as set forth in SEQ ID NO: 13.

In another embodiment, a method of treating myelodysplastic syndrome (MDS) in a subject is disclosed, including administering a therapeutically effective amount of an antibody which binds to a polypeptide that includes an amino acid sequence as set forth in SEQ ID NO: 13 to the subject.

In another embodiment, a method of treating myelodysplastic syndrome (MDS) in a subject is provided, including administering to the subject a composition of a polynucleotide having a sequence as set forth in SEQ ID NO: 1, SEQ ID NO: 3, SEQ ID NO: 5, a complement of SEQ ID NO: 1, a complement of SEQ ID NO: 3, a complement of SEQ ID NO: 5, and fragments thereof including at least 15 consecutive nucleotides of a polynucleotide encoding the amino acid sequence as set forth in SEQ ID NO: 2, SEQ ID NO: 4, or SEQ ID NO:6.

In one embodiment, a method of treating myelodysplastic syndrome (MDS) in a subject is disclosed, including administering to the subject a polypeptide composition having a sequence as set forth in SEQ ID NO: 2, SEQ ID NO: 4 and/or SEQ ID NO: 6.

In a related aspect, the MDS is acute myeloid leukemia (AML).

In one embodiment, a method of diagnosing myelodysplastic syndrome (MDS) in a subject is disclosed, including, providing a biological sample from the subject, contacting the biological sample with a probe comprising a fragment of at least 15 consecutive nucleotides of a polynucleotide having a sequence set forth in SEQ ID NO: 1, SEQ ID NO: 3, SEQ ID NO: 5, a complement of SEQ ID NO: 1, a complement of SEQ ID NO: 3, or a complement of SEQ ID NO: 5 under hybridization conditions, and detecting the hybridization between the probe and the biological sample, where detecting of hybridization correlates with MDS.

In another embodiment, a method of diagnosing a myelodysplastic syndrome (MDS) in a subject is disclosed, including providing a biological sample from the subject, contacting the biological sample with an antibody which binds to a polypeptide comprising an amino acid sequence as set forth in SEQ ID NO: 2, SEQ ID NO: 4, or SEQ ID NO: 6, and detecting the binding of the antibody to the sample, where detecting binding correlates with MDS.

In one embodiment, a method for isolating leukemia stem cells is provided, including obtaining a sample of cells from a subject, sorting cells that express a polypeptide comprising an amino acid sequence as set forth in SEQ ID NO: 13 from cells that do not express the amino acid sequence, and selecting, by a myeloid surface marker, leukemia stem cells from the sample of cells that express the polypeptide comprising the amino acid sequence as set forth in SEQ ID NO: 13.

In another embodiment, a transgenic animal having a human SALL4 gene is provided, where the animal is modified to expresses a sequence of a human SALL4 gene comprising nucleotides encoding an amino acid as set forth in SEQ ID NO: 2, SEQ ID NO: 4, or SEQ ID NO: 6. In a related aspect, the animal constitutively expresses the inserted SALL4 gene.

In one embodiment, a method of preparing a transgenic animal comprising a human SALL4 gene is disclosed, where the animal is modified to constitutively express a sequence of a human SALL4 gene comprising nucleotides encoding an amino acid as set forth in SEQ ID NO: 2, SEQ ID NO: 4, or SEQ ID NO: 6, including introducing into embryonic cells a nucleic acid molecule a comprising a construct of human SALL4 gene comprising nucleotides encoding an amino acid as set forth in SEQ ID NO: 2, SEQ ID NO: 4, or SEQ ID NO: 6, generating a transgenic animal from the cells resulting from step the introduction of the construct, breeding the transgenic animal to obtain a transgenic animal homozygous for the human SALL4 gene, and detecting human SALL4 transcripts from tissue from the transgenic animal.

In one embodiment, a method of modulating the cellular expression of a polynucleotide encoding an amino acid sequence as set forth in SEQ ID NO: 2, SEQ ID NO: 4, or SEQ ID NO: 6 is disclosed, including introducing a double stranded RNA (dsRNA) which hybridizes to the polynucleotide, or an antisense RNA which hybridizes to the polynucleotide, or a fragment thereof, into a cell.

In one embodiment, a method of identifying a cell possessing pluripotent potential is disclosed including contacting a cell isolated from an inner cell mass (ICM), a neoplastic tissue, or a tumor with an agent that detects the expression of a SALL family member protein, and determining whether a SALL family member protein is expressed in the cell, where determining the expression of the SALL family member protein positively correlates with induction of self-renewal in the cell, whereby such expression is indicative of pluripotency.

In one aspect, the SALL family member includes SALL1, SALL3, and SALL4. In a related aspect, SALL4 is SALL4A or SALL4B.

In another aspect, the agent is an antibody directed against the SALL family member protein or a nucleic acid which is complementary to a mRNA encoding the SALL family member protein. In a related aspect, the SALL family member protein sequence includes SEQ ID NO: 2, SEQ ID NO:4, SEQ ID NO:6, SEQ ID NO:22, and SEQ ID NO:24. In another related aspect, the nucleic acid is complementary to a sense strand of a nucleic acid sequence including SEQ ID NO: 1, SEQ ID NO:3, SEQ ID NO:5; SEQ ID NO:21, and SEQ ID NO:23.

In one aspect, the cell is an embryonic stem (ES) cell, an embryonic carcinoma (EC) cell, an adult stem cell, or a cancer stem cell. In a related aspect, the tissues is plasma or a biopsy sample from a subject. In a further related aspect, the subject is a human.

In one embodiment, a method of identifying an agent which modulates the effect of a SALL family member protein on OCT4 expression is disclosed including co-transfecting a cell with a vector comprising a promoter-reporter construct, where the construct comprises an operatively linked OCT4 promoter and a nucleic acid encoding gene expression reporter protein, and a vector comprising a nucleic acid encoding a SALL family member protein, contacting the cell with an agent, and determining the activity of the promoter-reporter construct in the presence and absence of the agent, where determining the activity of the promoter-reporter construct correlates with the effect of the agent on SALL family member protein/OCT4 interaction.

In a related aspect, the promoter region comprises nucleic acid sequence as set forth in SEQ ID NO:26 and the expression reporter protein is luciferase.

In another embodiment, a method of diagnosing a neoplastic or proliferative disorder is disclosed including contacting a cell of a subject with an agent that detects the expression of a SALL family member protein and determining whether a SALL family member protein is expressed in the cell, where determining the expression of the SALL family member protein positively correlates with induction of self-renewal in the cell, whereby such expression is indicative of neoplasia or proliferation.

In one aspect, the agent is labeled and the determining step includes detection of the agent by exposing the subject to a device which images the location of the agent. In a related aspect, the images are generated by magnetic resonance, X-rays, or radionuclide emission.

In one embodiment, a method of treating a neoplastic or proliferative disorder, where cells of a subject exhibit deregulation of self-renewal, is disclosed including administering to the subject a pharmaceutical composition containing an agent which inhibits the expression of SALL4.

In another embodiment, a kit for identifying a cell possessing pluripotent potential is disclosed including an agent for detecting one or more SALL family member proteins, reagents and buffers to provide conditions sufficient for agent-cell interaction and labeling of the agent, instructions for labeling the detection reagent and for contacting the agent with the cell, and a container comprising the components.

A method of detecting cells associated with progression of a proliferative disease or neoplastic cell formation is disclosed including contacting the cells with an antibody directed against SALL4, applying cells bound to the antibody to a surface delimited cavity comprising at least two apertures for ingress and egress of fluids and cells, and allowing cells and fluids to pass through the cavity, where antibody bound cells in a fluid mixture are detected by optical detectors, and where voltage is applied to the fluid whereby the voltage assorts the bound cells in one or more collectors.

Exemplary methods and compositions according to this invention are described in greater detail below.

BRIEF DESCRIPTION OF THE DRAWINGS

FIGS. 1(a-c) illustrate properties of the three SALL4 isoforms (SALL4A, SEQ ID NO: 1[GenBank Acc. No.: AY172738]; SALL4B, SEQ ID NO: 3[GenBank Acc. No. AY170621]); and SALL4C, SEQ ID NO: 5 [GenBank Acc. No. AY170622]. Alternative splicing generates two variant forms of SALL4 mRNA.

FIGS. 2(a-b) demonstrate the expression of SALL4 in human primary AML and myeloid leukemia cell lines.

FIGS. 3(a-h) show that SALL4B transgenic mice have an MDS-like/AML phenotype.

FIGS. 4(a-d) demonstrate the interaction between SALL4 and the Wnt/β-catenin signaling pathway.

DETAILED DESCRIPTION OF THE INVENTION

Figure 1A:
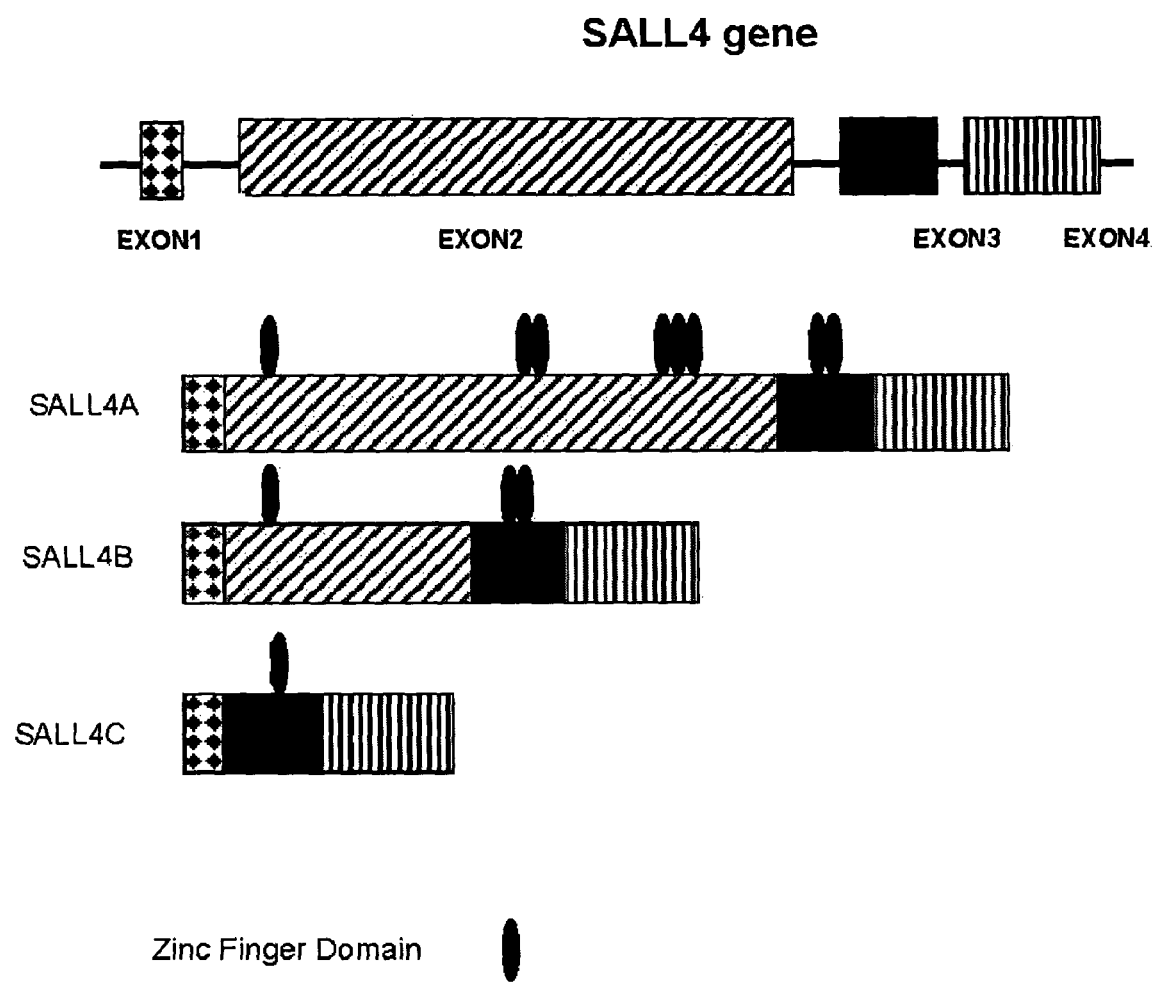
FIG. 1(a) SALL4A and SALL4B vary in protein length and in the presence of different numbers of characteristic sal-like zinc finger domains. SALL4A (encoding 1,067 amino acids) contains eight zinc finger domains, while SALL4B (encoding 623 amino acids) has three zinc finger domains. SALL4C contains 276 amino acids and lacks the region corresponding to amino acids 43 to 820 of the full length SALL4A. Both variants have exons 1, 3, and 4, and SALL4A contains all exons from 1 to 4. However, SALL4B uses an alternative splice acceptor that results in deletion of the large 3' portion of exon 2.

Before the present composition, methods, and culturing methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure. All publications mentioned herein are incorporated herein by reference in their entirety.

Homeobox and homeotic genes play important roles in normal development. Some homeobox genes, such as Hox and Pax, also function as oncogenes or as tumor suppressors in tumorigenesis or leukemogenesis. The important role of SALL4, a homeotic gene and a transcriptional factor, in human development was recognized because heterozygous SALL4 mutations lead to Duane Radial Ray syndrome. In a related aspect, SALL4's oncogenic role in leukemogenesis is described herein.

In one embodiment, the present disclosure identifies two SALL4 isoforms, SALL4A and SALL4B. In a related aspect, the disclosure provides an analysis of SALL4 nucleic acids and proteins as tools for diagnosing and treating patients having proliferation disorders such as hematologic malignancies and other tumors involving constitutive expression of SALL4 nucleic acid and protein. In a related aspect, SALL4 serves as a malignant stem cell marker for diagnosis and treatment of cancers.

For example, during normal hematopoiesis, SALL4 isoforms are expressed in the CD34+ HSC/HPC population and rapidly turned off (SALL4B) or down-regulated (SALL4A) in normal human bone marrow and peripheral blood. In contrast, SALL4 is constitutively expressed in all AML samples (N=81) that were examined, and failed to turn off in human primary AML and myeloid leukemia cell lines. In a related aspect, the leukemogenic potential of constitutive expression of SALL4 in vivo was directly tested via generation of SALL4B transgenic mice. Such transgenic mice exhibit dysregulated hematopoiesis, much like that of human MDS, and exhibited AML that was transplantable. The MDS-like features in these SALL4B transgenic mice do not require cooperating mutations and are observed as early as 2 months of age. The ineffective hematopoiesis observed in these mice is characterized, as it is in human MDS, by hypercellular bone marrow and paradoxical peripheral blood cytopenias (neutropenia and anemia) and dysplasia, which are probably secondary to the increased apoptosis noted in the bone marrow. While not being bound to theory, a reason for the late onset of leukemia development in these transgenic mice may be the accumulation of additional genetic damage during the $\geq 8$ months of replicative stress. Late onset of disease may also be a consequence of SALL4-induced genomic instability.

Further, specific, recurrent chromosomal translocations characterize many leukemias, which can result from a breakdown in the normal process of immunoglobulin or T-cell receptor gene rearrangement, causing inter-chromosomal translocations rather than normal intra-chromosomal rearrangement. The flow of genetic information from genes at chromosomal translocation breakpoints to proteins has several points which therapeutic reagents could intervene. Sequence specific binding elements that exploit zinc-finger binding protein domains can be used to create de novo sequence specific binding elements that could act as gene switches which can target chromosomal fusion junctions to turn off expression of aberrant gene fusion products.

In one embodiment, SALL4 can be used as a component of a fusion protein which targets chromosomal fusion junctions as a gene switch to modulate the expression of gene fusion products. Production of recombinant fusion protein is well known in the art (see, e.g., Sambrook et al., Molecular Cloning, A Laboratory Manual, 2nd Ed.; Cold Spring Harbor Laboratory Press, Cold Spring Harbor, N.Y. (1989).

In one embodiment, SALL4 proteins and/or nucleic acids are detected for diagnosing subpopulations of lymphomas and leukemias or other types of cancers. In another embodiment, the detection of the SALL4 proteins and nucleic acids can be used to identify a subject, including, but not limited to, a human subject, at risk for developing/acquiring a proliferative disease.

In a further embodiment, methods for identifying compounds which alter SALL4 protein and nucleic acid levels are disclosed. In a related aspect, SALL4 can serve as a therapeutic target, where blocking SALL4 function can inhibit tumor development and progression.

In another aspect, investigation of the potential mechanism of SALL4 involvement in leukemogenesis demonstrates that both SALL4A and SALL4B interacted with β-catenin, an essential component of the Wnt signaling pathway involving self-renewal of HSCs. In addition, both are able to activate the Wnt/β-catenin pathway in a reporter gene assay, consistent with SALL family function in *Drosophila* and humans. Furthermore, similar to the situation with β-catenin, SALL4 expression in CML varied at different phases of the disease: SALL4 expression being absent in the chronic phase, became detectable in the accelerated phase only in immature blasts, and is strongly positive in the blast phase.

Figure 4A:
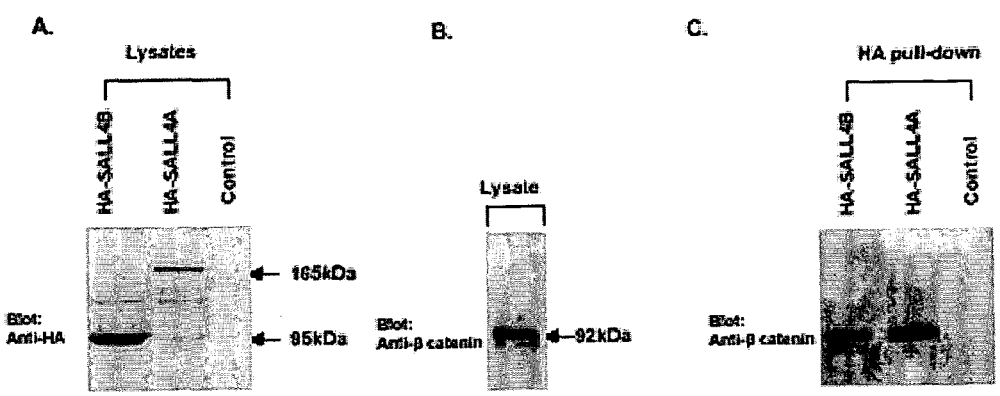
FIG. 4(a) shows that both SALL4A and SALL4B can interact with β-catenin. Nuclear extracts (lysates) prepared from Cos-7 cells were transiently transfected with HA-SALL4A or HA-SALL4B. (A) Anti-HA antibody recognized both SALL4A (165 kDa) and SALL4B (95 kDa). (B) β-Catenin was detected in the lysates. (C) Immunoprecipitation was performed with the use of an HA affinity resin and detected with an anti-α-catenin antibody. β-Catenin was readily detected in both HA-SALL4A and HA-SALL4B pull-downs.
Figure 4B:
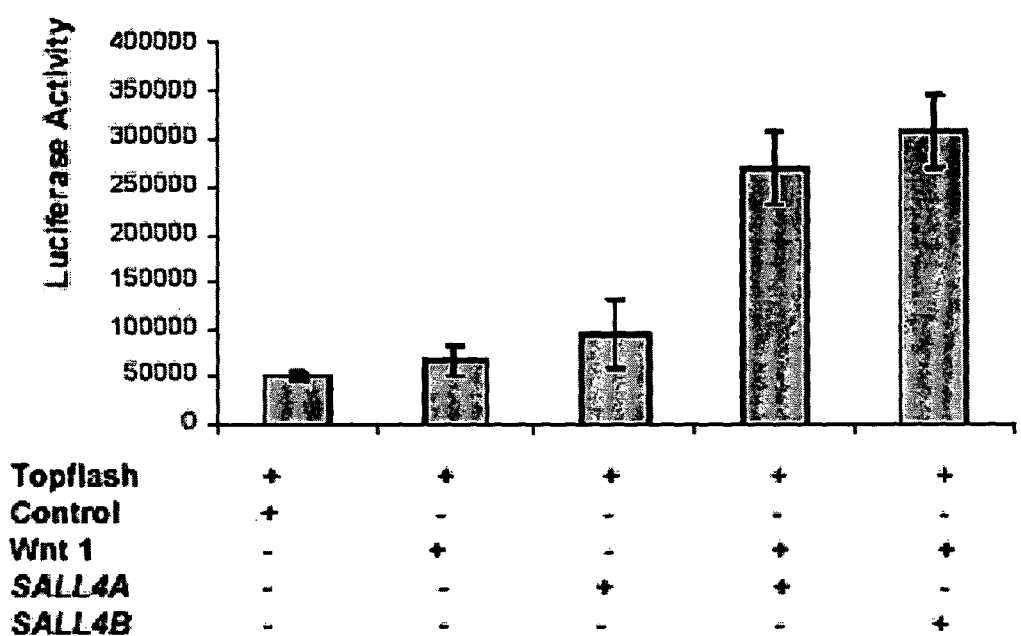
FIG. 4(b) shows the activation of the Wnt/β-catenin signaling pathway by both SALL4A and SALL4B. NIH3T3 cells were transfected with 1.0 μg of either SALL4A or SALL4B plasmid and TOPflash reporter plasmid (Upstate USA, Chicago, Ill.). After 24-h stimulation with Wnt1 or the mock, luciferase activity was measured.
Figure 4C:
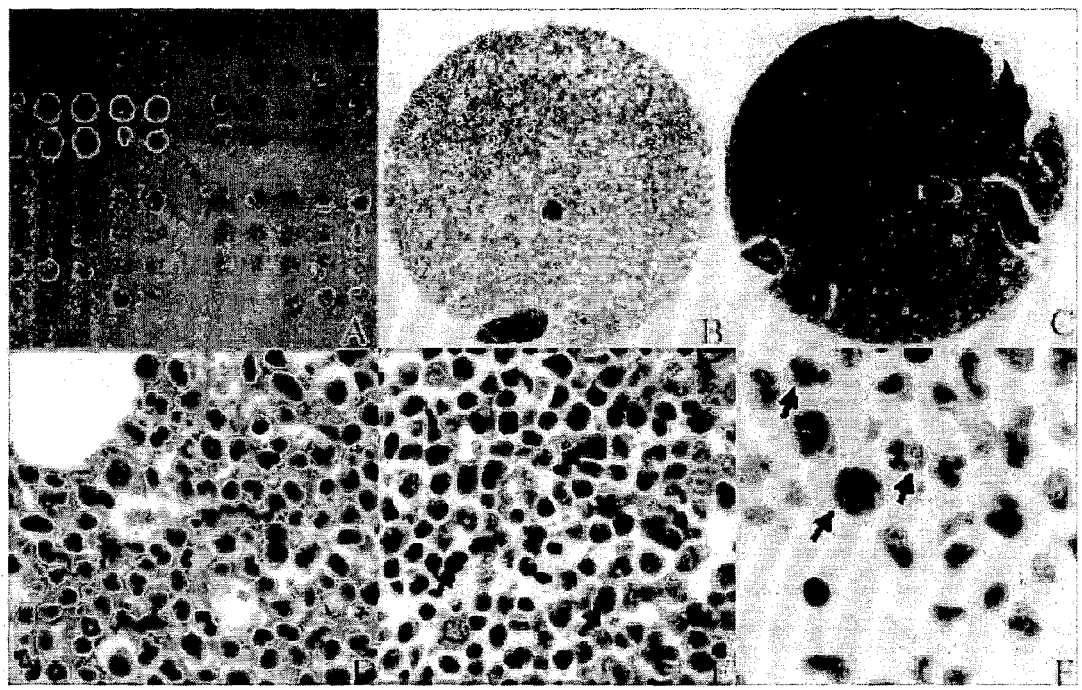
FIG. 4(c) demonstrates the presence of SALL4 protein expression at the blast phase (N=12) but not the chronic phase (N=11) of CML as demonstrated by immunohistochemical staining. (A) shows a low-power view of tissue arrays of the CML collection at different phases. SALL4 expression was absent in chronic-phase CML (B), with all cells' nuclei remaining blue (B, ×4; D, ×400). SALL4 expression, however, was present in blast-crisis-phase CML as indicated by the brown nuclear staining of SALL4 (C, ×4; E, ×400). In CML accelerated phase (N=6), in which the blast count is increased but still <15%, only immature blasts were observed to stain positively for SALL4 expression (F; red arrows); mature neutrophils did not stain (F, black arrows, ×600).
Figure 4D:
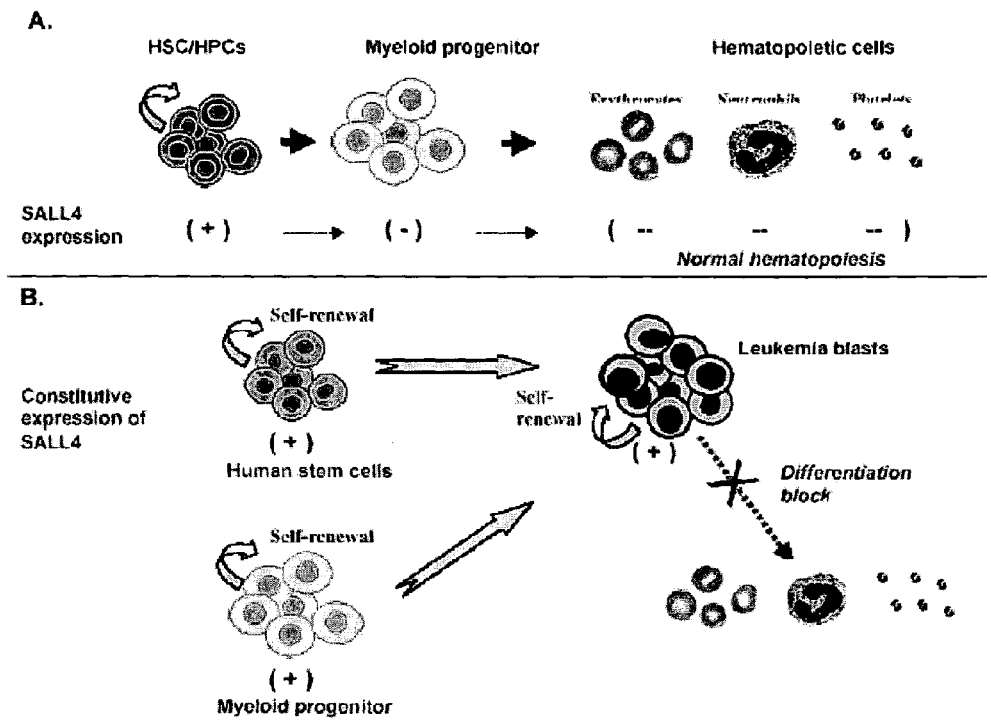
FIG. 4(d) illustrates a working hypothesis. SALL4 is expressed in human stem cells/progenitors but is absent in mature hematopoietic cells during normal hematopoiesis. Constitutive expression of SALL4 isoforms (failure to turn off SALL4) results in blocked differentiation and constitutive renewal with aberrant expansion of the stem cell pool that lead to leukemic transformation (+, presence of SALL4 expression; −, absence of SALL4 expression).

On the basis of these studies, a working hypothesis is disclosed (e.g., see FIG. 4d). While not being bound to theory, constitutive expression of SALL4 in AML may enable leukemic blasts to gain stem cell properties, such as self-renewal and/or dedifferentiation, and thus become LSCs. This hypothetical model would parallel what is seen in the case of β-catenin. For example, in normal myelopoiesis, β-catenin is only activated in HSCs bearing a self-renewal property. In the blast phase of CML, β-catenin gains function by becoming activated in the GMPs, resulting in leukemic transformation.

In another aspect, the oncogene SALL4 plays an important role in normal hematopoiesis and leukemogenesis. SALL4B transgenic mice exhibit MDS-like phenotype with subsequently AML transformation that is transplantable. Few animal models are currently available for the study of human MDS. The SALL4B transgenic mice that were generated by the methods described herein provide a suitable animal model for understanding and treating human MDS and its subsequent transformation to AML. The interaction between SALL4 and the Wnt/β-catenin signaling pathway not only provides a plausible mechanism for SALL4 involvement in leukemogenesis but also advances the understanding of the activation of the Wnt/β-catenin signaling pathway in CML blastic transformation.

As disclosed herein, the identification of SALL4 isoforms and their constitutive expression in all human AML were examined. The direct impact of SALL4 expression in AML was tested in vivo. The disclosure demonstrates that constitutive expression of SALL4 in mice is sufficient to induce MDS-like symptoms and transformation to AML that is transplantable. The disclosure also demonstrates that SALL4 is able to bind β-catenin and activate the Wnt/β-catenin signaling pathway. SALL4 and β-catenin share similar expression patterns at different phases of CML.

In one embodiment, an isolated polynucleotide comprising a sequence encoding an amino acid sequence as set forth in SEQ ID NO: 2 (GenBank Acc. No. AAO44950), SEQ ID NO: 4 (GenBank Acc. No. AAO16566), or SEQ ID NO: 6 (GenBank Acc. No. AAO16567) is provided. In a related aspect, such sequences comprise a nucleic acid sequence as set forth in SEQ ID NO: 1 (GenBank Acc. No. AY172738), SEQ ID NO: 3 (GenBank Acc. No. AY170621), SEQ ID NO: 5 (GenBank Acc. No. AY170622), or complements thereof. In another related aspect, a vector comprising such polynucleotides are also disclosed, including, but not limited to, expression vectors which are operably linked to a regulatory sequence which directs the expression of the polynucleotide in a host cell.

In another embodiment, an isolated polypeptide comprising an amino acid sequence as set forth in SEQ ID NO: 2, SEQ ID NO: 4, or SEQ ID NO: 6 is disclosed. In one aspect, a method of treating a myelodysplastic syndrome (MDS) in an individual including administering such a polypeptide is provided. In another aspect, antibodies or binding fragments thereof which bind to such a polypeptide are also disclosed.

Antibodies that are used in the methods disclosed include antibodies that specifically bind polypeptides comprising SALL4, or their isoforms as set forth in SEQ ID NO: 2, SEQ ID NO: 4, or SEQ ID NO: 6. In one aspect, a fragment of SEQ ID NO: 2, SEQ ID NO: 4, or SEQ ID NO: 6 is used to generate such antibodies. In a related aspect, such a fragment consists essentially of SEQ ID NO: 13.

In one embodiment, a method of identifying a cell possessing pluripotent potential is disclosed including contacting a cell isolated from an inner cell mass (ICM), a neoplastic tissue, or a tumor with an agent that detects the expression of a SALL family member protein, and determining whether a SALL family member protein is expressed in the cell, where determining the expression of the SALL family member protein positively correlates with induction of self-renewal in the cell, whereby such expression is indicative of pluripotency.

In one aspect, the SALL family member includes SALL1, SALL3, and SALL4. In a related aspect, SALL4 is SALL4A or SALL4B.

In another aspect, the agent is an antibody directed against the SALL family member protein or a nucleic acid which is complementary to a mRNA encoding the SALL family member protein. In a related aspect, the SALL family member protein sequence includes SEQ ID NO: 2, SEQ ID NO:4, SEQ ID NO:6, SEQ ID NO:22, and SEQ ID NO:24. In another related aspect, the nucleic acid is complementary to a sense strand of a nucleic acid sequence including SEQ ID NO:1, SEQ ID NO:3, SEQ ID NO:5; SEQ ID NO:21, and SEQ ID NO:23.

In one aspect, the cell is an embryonic stem (ES) cell, an embryonic carcinoma (EC) cell, an adult stem cell, or a cancer stem cell. In a related aspect, the tissues is plasma or a biopsy sample from a subject. In a further related aspect, the subject is a human.

As used herein, "pluripotent potential" means the ability of a cell to renew itself by mitosis.

As used herein "positively correlates" means affirmatively associated with the phenomenon observed. For example, induction of SALL4A or SALL4B is associated with increased cell renewal ability.

As used herein, "neoplasm," including grammatical variations thereof, means new and abnormal growth of tissue, which may be benign or cancerous.

As used herein "consisting essentially of" includes a specific molecular entity (e.g., but not limited to, a specific sequence identifier) and other molecular entities that do not materially affect the properties associated with the specific molecular entity. For example, a fusion protein comprising SEQ ID NO: 13 and an adjuvant, for generating an immunogenic response against SEQ ID NO: 2, SEQ ID NO: 4, and/or SEQ ID NO: 6, would consist essentially of SEQ ID NO: 13.

Antibodies are well-known in the art and discussed, for example, in U.S. Pat. No. 6,391,589. Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA, and IgY), class (e.g., IgG1, IgG2, IgG3, IgG4, IgA1, and IgA2) or subclass of immunoglobulin molecule.

Antibodies of the invention include antibody fragments that include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. In one aspect, the antibodies are human, murine (e.g., mouse and rat), donkey, sheep, rabbit, goat, guinea pig, camel, horse, or chicken. Further, such antibodies may be humanized versions of animal antibodies (see, e.g., U.S. Pat. No. 6,949,245). The antibodies of the invention may be monospecific, bispecific, trispecific or of greater multi specificity.

The antibodies of the invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. Further, antibodies and antibody-like binding proteins may be made by phage display (see, e.g., Smith and Petrenko, Chem Rev (1997) 97(2):391-410).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example; in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In one embodiment, a method for isolating leukemia stem cells using such antibodies is provided, including obtaining a sample of cells from a subject, sorting cells that express an amino acid sequence as set forth in SEQ ID NO: 13 from cells that do not express the amino acid sequence, and selecting, by a myeloid surface marker, leukemia stem cells from the sample of cells that express the amino acid sequence as set forth in SEQ ID NO: 13. In a related aspect, the step of sorting includes sorting by fluorescent activated cell sorting and/or magnetic bead sorting.

In another related aspect, the marker is CD34, c-kit, Gr-1, Mac-1, MPO, and/or nonspecific esterase. In a further related aspect, wherein the leukemia stem cells are negative for B-cell (B220 and CD19), T-cell (CD4, CD8, CD3, and CD5), megakaryocytic (CD41), and erythroid (Ter119) markers.

In one embodiment, a kit for identifying a cell possessing pluripotent potential is disclosed including an agent for detecting one or more SALL family member protein markers, reagents and buffers to provide conditions sufficient for agent-cell interaction and labeling of the agent, instructions for labeling the detection reagent and for contacting the agent with the cell, and a container comprising the components.

One identifies stem cells according to the method of the disclosure by first sorting, from a population of cells, cells that are positive for expression a marker comprising SEQ ID NO: 13 from cells that are not. One then selects from the positive marker cells the stem cell of interest; this is performed by sorting cells by their expression of a known cell marker. Any marker that is known to be associated with the stem cells of interest may be used.

Any population of cells where stem cells are suspected of being found may be sorted according to the methods disclosed. In one aspect, cells are obtained from the bone marrow of a non-fetal animal, including, but not limited to, human cells. Fetal cells may also be used.

Cell sorting may be by any method known in the art to sort cells, including sorting by fluorescent activated cell sorting (FACS) (see, e.g., Baumgarth and Roederer, J Immunol Methods (2000) 243:77-97) and Magnetic bead cell sorting (MACS). The conventional MACS procedure is described by Miltenyi et al., "High Gradient Magnetic Cell Separation with MACS," Cytometry 11:231-238 (1990). To sort cells by MACS, one labels cells with magnetic beads and passes the cells through a paramagnetic separation column. The separation column is placed in a strong permanent magnet, thereby creating a magnetic field within the column. Cells that are magnetically labeled are trapped in the column; cells that are not pass through. One then elutes the trapped cells from the column. In one embodiment, an antibody directed against SALL4 is used in cell sorting to isolate embryonic stem cells, adult stem cells and/or cancer stem cells. In another embodiment, an antibody directed against SALL4 is used in flow cytometry analysis to detect cells expressing SALL4, where such cells are associated with proliferative disease progression or neoplastic cell formation. In a related aspect, SALL4 is SALL4A or SALL4B.

In one embodiment, a method for detecting the presence or absence of the polynucleotide comprising a nucleic acid sequence encoding SEQ ID NO: 2, SEQ ID NO: 4, or SEQ ID NO: 6 in a biological sample is disclosed including, but not limited to, contacting the biological sample under hybridizing conditions with a probe comprising a fragment of at least 15 consecutive nucleotides of a polynucleotide having a sequence set forth in SEQ ID NO: 1, SEQ ID NO: 3, or SEQ ID NO: 5, or a complement of SEQ ID NO: 1, SEQ ID NO: 3 or SEQ ID NO: 5, and detecting hybridization between the probe and the sample, where hybridization is indicative of the presence of the polynucleotide.

In another embodiment, a method for detecting a polypeptide comprising an amino acid sequence as set forth in SEQ ID NO: 2, SEQ ID NO: 4, or SEQ ID NO: 6 present in a biological sample is disclosed including, but not limited to, providing an antibody that binds to the polypeptide, contacting the biological sample with the antibody, and determining the binding between the antibody to the biological sample, where binding is indicative of the presence of the polypeptide.

In one embodiment, a method of treating myelodysplastic syndrome (MDS) in a subject is described, including administering to the subject a polynucleotide having a nucleic acid sequence as set forth in SEQ ID NO: 1, SEQ ID NO: 3, SEQ ID NO: 5, a complement of SEQ ID NO: 1, a complement of SEQ ID NO: 3, a complement of SEQ ID NO: 5, or fragments thereof comprising at least 15 consecutive nucleotides of a polynucleotide encoding the amino acid sequence as set forth in SEQ ID NO: 2, SEQ ID NO: 4, or SEQ ID NO: 6. In a related aspect, the method includes administering a polynucleotide as set forth in SEQ ID NO: 1, SEQ ID NO: 3, or SEQ ID NO: 5. In one aspect, the MDS is acute myeloid leukemia (AML).

In one embodiment, a method of identifying an agent which modulates the effect of a SALL family member protein on OCT4 expression is disclosed including co-transfecting a cell with a vector comprising a promoter-reporter construct, wherein the construct comprises an operatively linked OCT4 promoter and a nucleic acid encoding gene expression reporter protein, and a vector comprising a nucleic acid encoding a SALL family member protein, contacting the cell with an agent, and determining the activity of the promoter-reporter construct in the presence and absence of the agent, where determining the activity of the promoter-reporter construct correlates with the effect of the agent on SALL family member protein/OCT4 interaction.

In a related aspect, the promoter region comprises nucleic acid sequence including but not limited to, SEQ ID NO:26, and the expression reporter protein is luciferase.

In another embodiment, a method of treating a neoplastic or proliferative disorder, where cells of a subject exhibit de-regulation of self-renewal, is disclosed including administering to the subject a pharmaceutical composition containing an agent which inhibits the expression of SALL4.

In another embodiment, a method of identifying a substance which binds to a polypeptide including an amino acid sequence as set forth in SEQ ID NO: 2, SEQ ID NO: 4, or SEQ ID NO: 6 is provided, where the method comprises contacting the polypeptide with a candidate substance and detecting the binding of the substance to the polypeptide.

In one embodiment, a method of identifying a substance which modulates the function of a polypeptide including an amino acid sequence as set forth in SEQ ID NO: 2, SEQ ID NO: 4, or SEQ ID NO: 6 is disclosed, where the method includes contacting the polypeptide with a candidate substance and determining the activity of the polypeptide, and where a change in the activity in the presence of the candidate substance is indicative of the substance modulating the function of the polypeptide.

In another embodiment, a method of diagnosing myelodysplastic syndrome (MDS) in a subject is described including, but not limited to, providing a biological sample from the subject, contacting the biological sample with a probe having a fragment of at least 15 consecutive nucleotides of a polynucleotide sequence set forth in SEQ ID NO: 1, SEQ ID NO: 3, SEQ ID NO: 5, a complement of SEQ ID NO: 1, a complement of SEQ ID NO: 3, or a complement of SEQ ID NO: 5 under hybridization conditions, and detecting the hybridization between the probe and the biological sample, where detecting of hybridization correlates with MDS. In one aspect, the MDS is acute myeloid leukemia (AML).

In another embodiment, a method of diagnosing a myelodysplastic syndrome (MDS) in a subject is described, including, but not limited to, providing a biological sample from the subject, contacting the biological sample with an antibody which binds to a polypeptide comprising an amino acid as set forth in SEQ ID NO: 2, SEQ ID NO: 4, or SEQ ID NO: 6, and detecting the binding of the antibody to the sample, where detecting binding correlates with MDS. In one aspect, the MDS is acute myeloid leukemia (AML).

In one embodiment, a method of diagnosing a neoplastic or proliferative disorder is disclosed including contacting a cell of a subject with an agent that detects the expression of a SALL family member protein and determining whether a SALL family member protein is expressed in the cell, where determining the expression of the SALL family member protein positively correlates with induction of self-renewal in the cell, whereby such expression is indicative of neoplasia or proliferation.

In one aspect, the agent is labeled and the determining step includes detection of the agent by exposing the subject to a device which images the location of the agent. In a related aspect, the images are generated by magnetic resonance, X-rays, or radionuclide emission.

In one embodiment, a method of modulating the cellular expression of a polynucleotide encoding a zinc finger transcriptional factor which is constitutively expressed in primary acute myeloid leukemia cells, including introducing a double stranded RNA (dsRNA) which hybridizes to the polynucleotide, or an antisense RNA which hybridizes to the polynucleotide, or a fragment thereof, into a cell. In a related aspect, the modulating is down-regulating.

In one embodiment, a transgenic animal is disclosed. In a general aspect, a transgenic animal is produced by the introduction of a foreign gene in a manner that permits the expression of the transgene. Methods for producing transgenic animals are generally described by Wagner and Hoppe (U.S. Pat. No. 4,873,191; which is incorporated herein by reference), Brinster et al. (1985); which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press (1994); which is incorporated herein by reference in its entirety).

Typically, a gene is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer.

The present invention also provides pharmaceutical compositions comprising at least one compound capable of treating a disorder in an amount effective therefor, and a pharmaceutically acceptable vehicle or diluent. The compositions of the present invention may contain other therapeutic agents as described, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Pharmaceutical compositions employed as a component of invention articles of manufacture can be used in the form of a solid, a solution, an emulsion, a dispersion, a micelle, a liposome, and the like, where the resulting composition contains one or more of the compounds described above as an active ingredient, in admixture with an organic or inorganic carrier or excipient suitable for enteral or parenteral applications. Compounds employed for use as a component of invention articles of manufacture may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

Invention pharmaceutical compositions may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above methods, in which cells targeted for modulation is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject compound that will elicit the biological or medical response of a tissue, system, animal or human that is being sought by the researcher, veterinarian, medical doctor or other clinician.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules where the active ingredient is mixed with an inert solid diluent, for example, calcium carbonate, calcium phosphate or kaolin, or as soft gelatin capsules where the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

Nucleic acid according to the present disclosure, encoding a polypeptide or peptide able to interfere with SALL4 may be used in methods of gene therapy, for instance in treatment of individuals with the aim of preventing or curing (wholly or partially) a tumor e.g., in cancer, or other disorder involving loss of proper regulation of the cell-cycle and/or cell growth, or other disorder in which specific cell death is desirable.

Vectors such as viral vectors have been used in the art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the art have used disabled murine retroviruses.

As an alternative to the use of viral vectors other known methods of introducing nucleic acid into cells includes electroporation, calcium phosphate co-precipitation, mechanical techniques such as microinjection, ballistic methods, transfer mediated by liposomes, and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

In the treatment of a subject where cells are targeted for modulation, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The following examples are intended to illustrate but not limit the invention.

EXAMPLE 1

Methods

Molecular Cloning.

Plasmid construction and DNA sequencing were performed in accordance with standard procedures. For cloning of SALL4 isoforms, PCR primers were designed, based on the genomic clone RP5-1112F19 (SEQ ID NO: 25) (GenBank accession no. AL034420). SALL4 isoforms were cloned with the use of the Marathon-Ready cDNA library derived from human fetal kidney (BD Biosciences Clontech, Palo Alto, Calif.), according to the supplier's protocol. The amplified PCR products were cloned into a TA Cloning vector (Invitrogen Corp., Carlsbad, Calif.), and the nucleotide sequences were determined by DNA sequencing. The GAL4-SALL4B construct was generated by PCR with the use of a 5' primer and a 3' primer with a restriction enzyme site, BamHI, at each end:

```
5' primer:
                                        (SEQ ID NO: 7)
5'-TTATCAGGATCCTGGTCGAGGCGCAAGCAGGCGAAACCC-3';
and 3' primer:
                                        (SEQ ID NO: 8)
5'-CCAGGATCCTTAGCTGACCGCCAATCTTGTTTC-3'.
```

The GAL4-SALL4B construct was expected to encode 93 amino acids of minimal GAL4 DNA-binding domain and the full length of SALL4B, except for the first amino acid, methionine.

Determination of Alternative Splicing Patterns in Different Tissues.

Reverse transcription (RT)-PCR was used to evaluate mRNA expression patterns of SALL4 in adult tissues. A panel of eight normalized first-strand cDNA preparations, derived from different adult tissues, was purchased from BD Biosciences Clontech. PCR amplification was performed in a 50-μl reaction volume containing 5 μl of cDNA, 10 mM Tris HCl (pH 8.3), 50 mM KCl, 2 mM $MgCl_2$, 9.2 mM dNTPs, and 1.25 U of Taq DNA polymerase (PerkinElmer Life Sciences, Boston, Mass.). After an initial denaturation at 94° C. for 10 min, amplification was performed for 30 cycles under the following conditions: 30-sec denaturation at 94° C., 30-sec annealing at 55° C., and 30-sec extension at 72° C. The last cycle was followed by a final 7-min extension at 72° C.

Amplification of glyceraldehyde phosphate dehydrogenase (GAPDH) mRNA was used to control for template concentration loading. The primer pairs selected specifically for SALL4 isoforms were the following:

```
1) SALL4A primers (sense primer:
5'-ATTGGCACCGGCAGTTACCACC (SEQ ID NO: 9);
antisense primer: 5'-AGTACTCGTGGGCATATTGTC-3'
(SEQ ID NO: 10))
and 2) SALL4B primers (sense primer:
5'-ATGTCGAGGCGCAAGCAGGCGAAAC-3' (SEQ ID NO: 11);
antisense primer: 5'-TTAGCTGACCGCAATCTTGTTTTCT-3'
(SEQ ID NO: 12)).
```

PCR products were electrophoretically separated on 1% agarose gel. DNA sequencing was also used to confirm amplification products.

Antibody Generation.

The peptide MSRRKQAKPQHIN (SEQ ID NO: 13) of human SALL4 was chosen for its potential antigenicity (amino acids 1-13) and used to prepare an antipeptide antibody. This region is also identical to that of mouse SALL4 so that the generated antibody could be expected to cross-react with mouse SALL4. SALL4 antipeptide antibody was produced in rabbits in collaboration with Lampire Biological Laboratories Inc. (Pipersville, Pa.).

Gel Electrophoresis and Western Blot Analysis.

Sodium dodecyl sulfate-polyacrylamide gel electrophoresis (SDS-PAGE) was carried out in SDS 10% w/v polyacrylamide slab gels according to Laemmli, and the proteins were then transferred to nitrocellulose membranes. Immunoblotting of rabbit immune serum with the SALL4 antipeptide antibody (1:100) was performed with an electrochemiluminescence detection system as described by the manufacturer (Amersham Biosciences, Piscataway, N.J.).

Leukemia and Normal Tissues.

Leukemia and normal samples, either in paraffin blocks or frozen in dimethylsulfoxide (DMSO), were collected from the files of The University of Texas M.D. Anderson Cancer Center, Houston, Tex., and the Dana-Farber Cancer Institute, Boston, Mass., between 1998 and 2004 under approved Institutional Review Board protocols. The diagnosis of all tumors was based on morphologic and immunophenotypic criteria according to the FAB Classification for Hematopoietic Neoplasms. CD34+ fresh cells were purchased from Cambrex.

Real-Time Quantitative RT-PCR.

TaqMan 5' nuclease assay was used (Applied Biosystems, Foster City, Calif.) in these studies. Total RNA from purified CD34+ HSCs/HPCs from normal bone marrow and peripheral blood, 15 AML samples, and three leukemia cell lines was isolated with the RNeasy Mini Kit and digested with DNase I (Qiagen). RNA (1 µg) was reverse-transcribed in 20 µL with the use of Superscript II reverse transcriptase and a poly(dT) 12-18 primer (Invitrogen). After the addition of 80 µL of water and mixing, 5-µL aliquots were used for each TaqMan reaction. TaqMan primers and probes were designed with the use of Primer Express software version 1.5 (Applied Biosystems). Real-time PCR for SALL4 and GAPDH was performed with the TaqMan PCR core reagent kit (Applied Biosystems) and an ABI Prism 7700 Sequence Detection System (PE Applied Biosystems). The PCR reaction mixture contained 3.5 mM $MgCl_2$; 0.2 mM each of deoxyadenosine triphosphate (dATP), deoxycytidine triphosphate (dCTP), and deoxyguanosine triphosphate (dGTP); 0.4 mM deoxyuridine triphosphate (dUTP); 0.5 µM forward primer; 0.5 µM reverse primer; 0.1 µM TaqMan probe; 0.25 U uracil DNA glycosylase; and 0.625 U AmpliTaq Gold polymerase in 1× TaqMan PCR buffer. cDNA (5 µL) was added to the PCR mix, and the final volume of the PCR reaction was 25 µL. All samples were run in duplicate. GAPDH was used as an endogenous control. Thermal cycler conditions were 50° C. for 2 min, 95° C. for 10 min, and 45 cycles of 95° C. for 0.30 min and 60° C. for 1 min. Data were analyzed with the use of Sequence Detection System software version 1.6.3 (Applied Biosystems). Results were obtained as threshold cycle (Ct) values. The software determines a threshold line on the basis of the baseline fluorescent signal, and the data point that meets the threshold is given as the Ct value. The Ct value is inversely proportional to the starting number of template copies. All measurements were performed in duplicate. TaqMan sequences include the following:

```
GAPDH forward primer:
(5'-GAAGGTGAAGGTCGGAGTC-3' (SEQ ID NO: 14))
and reverse primer:
(5'-GAAGATGGTGATGGGATTTC-3' (SEQ ID NO: 15)), TaqMan probe:
(5'-CAAGCTTCCCGTTCTCAGCC-3' (SEQ ID NO: 16)),
and SALL4 forward primer:
(5'-CCTCCTAATGAGAGTATCTGGGTGAT-3' (SEQ ID NO: 17))
and reverse primer:
(5'-TTAAAACATACAGCGCATGATTGG-3' (SEQ ID NO: 18)).
```

Design and Construction of Tissue Arrays.

Tissue arrays that included triplicate tumor cores from leukemia specimens were sectioned (5 µm thick). A manual tissue arrayer (Beecher Instruments, Silver Spring, Md.) was used to construct the tissue arrays.

Immunohistochemistry.

Immunohistochemical staining was performed according to standard techniques. Briefly, formalin-fixed, paraffin-embedded, 4-µm-thick tissue sections were deparafinized and hydrated. Heat-induced epitopes were retrieved with a Tris buffer (pH 9.9; Dako Corp., Carpinteria, Calif.) and a rapid microwave histoprocessor. After incubation at 100° C. for 10 min, slides were washed in running tap water for 5 min and then with phosphate buffered saline (PBS; pH 7.2) for 5 min. Tissue sections were then incubated with anti-SALL4 antibody (1:200) for 5 h in a humidified chamber at room temperature. After three washes with PBS, tissue sections were incubated with antimouse immunoglobulin G and peroxidase for 30 min at room temperature.

After three washes with PBS, tissue sections were incubated with 3,3'-diaminobenzidine/$H_2O_2$ (Dako) for color development; hematoxylin was used to counterstain the sections. Neoplastic cells were considered to be positive for SALL4 when they showed definitive nuclear staining.

Generation of Transgenic Mice.

SALL4B cDNA, corresponding to the entire coding region, was subcloned into a pCEP4 vector (IntroGene; now Crucell, Leiden, The Netherlands) to create the CMV/SALL4B construct for the transgenic experiments. Subsequent digestion with SalI, which does not cut within the SALL4B cDNA, released a linear fragment containing only the CMV promoter, the SALL4 cDNA coding region, the SV40 intron, and polyadenylation signal without additional vector sequences.

Transgenic mice were generated via pronuclear injection performed in the transgenic mouse facility at Yale University. Identification of SALL4B founder mice and transmission of the transgene was determined by PCR analyses. The PCR primers used for the genotyping span the junction of the 5' SALL4B cDNA to the CMV promoter (sense primer: 5'-CAGAGATGC TGAAGAACTCCGCAC-3' (SEQ ID NO: 19); antisense primer: 5'-AGCAGAGCTCGTTTAGTGAACCG-3' (SEQ ID NO: 20)).

Hematologic Analysis.

Complete blood cell counts with automated differentials were determined with a Mascot Hemavet cell counter (CDC Technologies, Oxford, Conn.). For progenitor assays, 1.5×$10^4$ bone marrow cells were plated in duplicate 1.25-ml methylcellulose cultures supplemented with recombinant mouse interleukin-3 (IL-3) (10 ng/ml), IL-6 (10 ng/ml), stem cell factor (SCF) (50 ng/ml), and erythropoietin (3 U/ml) (M3434, StemCell Technologies, Vancouver, British Columbia, Canada). Colonies were recorded between days 7 and 14 (CFU-G, CFU-GM, CFU-M, CFU-GEMM, and BFU-E). Peripheral blood, bone marrow smears, and cytospin from pooled CFU cells were stained with Wright-Giemsa stain.

Flow Cytometric Analysis.

Cells were stained with directly conjugated antibodies to Gr-1, Mac-1, B220, Ter119, c-kit, CD34, CD45, CD41, CD19, CD5, CD3, CD4, CD8, propidium iodide (PI) or Annexin V (BD Biosciences Pharmingen, San Diego, Calif.). Ten thousand scatter-gated red cells were acquired on a FACScan and analyzed with CellQuest software (BD Biosciences Clontech).

Statistical Analysis.

Student's t-Test was used for all the statistical analysis, assuming normal two-tailed distribution and unequal variance.

Cell Culture.

HEK-293 cells (derived from human embryonic kidney) and cell lines KG.1, Kasumi-1, and THP-1 were purchased from the American Type Culture Collection (Manassas, Va.). Cells were maintained at 37° C. in a humidified environment with 5% carbon dioxide and 10% fetal serum.

Transfection.

Transfection was performed with FuGENE 6 transfection reagent (Roche Applied Science, Indianapolis, Ind.) according to the manufacturer's instructions. Cells were plated in 24-well plates at a density of ~1×10$^5$ cells/well. Cells were harvested 24 h after transfection. Plasmid DNA for transient transfection was prepared with the Qiagen Plasmid Midi Kit (Valencia, Calif.).

β-Galactosidase and Luciferase Assays.

The cells were extracted with 100 μl of luciferase cell culture lysis reagent (Promega Corp., Madison Wis.) 24 h after transfection. The β-galactosidase assay, performed with 10 μl of cell extract, used the β-Galactosidase Enzyme Assay System (Promega) and the standard assay protocol provided by the manufacturer (except that 1 M Tris base was used as stopping buffer, instead of sodium carbonate). For the luciferase assay (Promega), 5 μl of extract were used in accordance with the manufacturer's instructions. After subtraction of the background, luciferase activity (arbitrary units) was normalized to β-galactosidase activity (arbitrary units) for each sample.

Promoter Reporter Assays

In general, 0.25-0.3 μg of an OCT4-Luc construct (PMOct4) comprising an OCT4 promoter (SEQ ID NO:26) or SALL-Luc construct containing a SALL family protein (i.e., SALL1, SALL3, SALL4A, or SALL4B) promoter (i.e., SEQ ID NO:27, SEQ ID NO:28, and SEQ ID NO:29, respectively, where SALL4A and SALL4B share the same promoter) was cotransfected with between 0.1 μg and 0.12 μg of renilla plasmid and/or various amounts (0-1.0 μg) of plasmid expressing SALL family proteins or OCT4 protein in HEK-293 or COS-7 cells. Typically, pcDNA3 vector was used as the control. Transfected cells were then monitored for luciferase activity 24 hour s post-transfection.

Results

Molecular Cloning of Two Alternatively Splicing Isoforms of Human SALL4.

Two full-length transcripts of SALL4 were isolated by 5' and 3' RACE-PCR (rapid amplification of the 5' and 3' cDNA ends-polymerase chain reaction) with the use of fetal human kidney Marathon-Ready cDNAs (BD Biosciences Clontech) as templates.

Sequence analysis of the larger cDNA fragment isolated revealed a single, large open reading frame, designated as SALL4A, that started from a strong consensus initiation sequence and was expected to encode 1,053 amino acids. The other splicing variant of SALL4, designated SALL4B, lacked the region corresponding to amino acids 385-820 of the full-length SALL4A (FIG. 1a). The putative protein encoded by SALL4B cDNA was expected to consist of 617 amino acids.

To rule out the possibility that these two apparent splicing variants might result from artifacts, both variant mRNA sequences with corresponding sequences of the human genome were compared. SALL4A contained all exons (1-4) (FIG. 1a), whereas SALL4B lacked the 3' large portion of exon 2. Both exon-intron splice sites satisfied the G-T-A-G rule. Both splicing variants had the same translational reading frame, but SALL4B mRNA encoded a protein with internal deletions. SALL4A contained eight zinc finger domains, while SALL4B had three zinc finger domains.

Expression Pattern of the SALL4 Isoforms in Human Tissues.

Figure 1B:
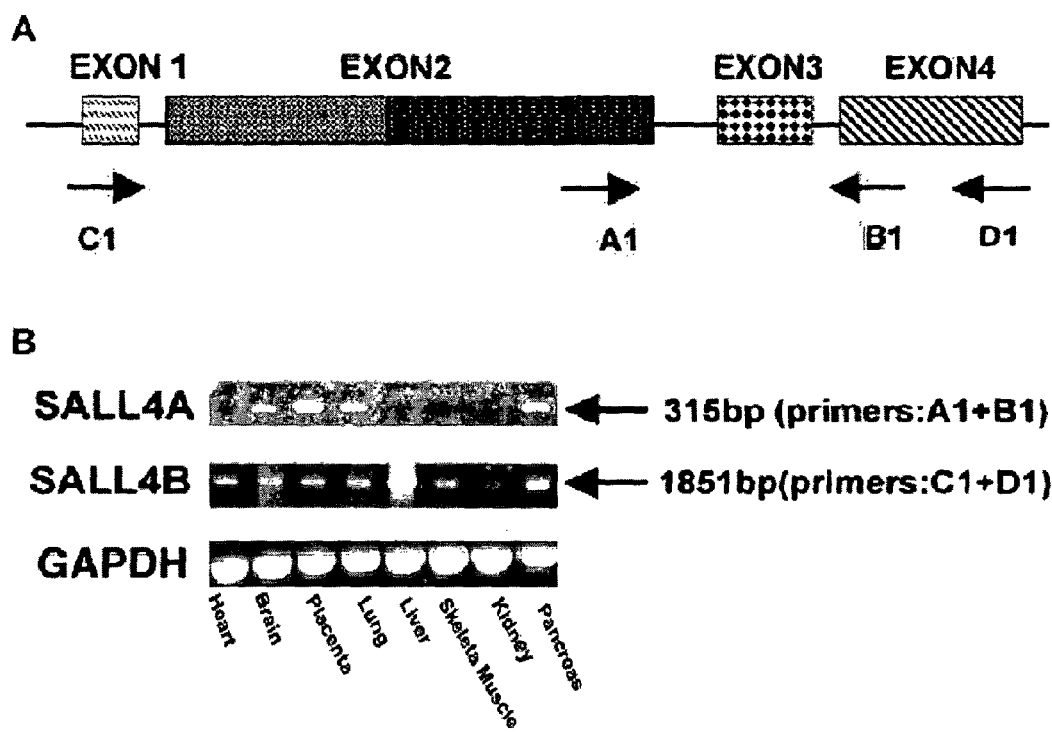
FIG. 1(b) shows the RT-PCR analysis of SALL4 variants in different tissues. Four exons of SALL4 and their potential coding structures are illustrated, with arrows indicating the primers used for PCR amplification of the SALL4 transcripts (A). Tissue-dependent expression of SALL4 transcripts by RT-PCR (B). A 315-bp expected product that was specific for SALL4A with primers A1 (exon 2) and B1 (exon 4) was amplified with cDNAs of various tissues. Primers D1 (exon 4) and C1 (exon 1) were used to amplify the 1,851-bp expected product of SALL4B. Comparable amounts of cDNA were determined by GAPDH.

The alternative splicing patterns of SALL4 were delineated by reverse transcription (RT)-PCR in a variety of human tissues. A fragment of the ubiquitous GAPDH gene cDNA was amplified as a control (FIG. 1b). A 315-bp fragment representing the longer splice variant, SALL4A, was amplified in some tissues, achieving various expression levels. The SALL4B variant was present in every tissue at varying levels of expression. Detailed studies on SALL4 expression in hematopoietic tissues are described in the following results.

Generation of SALL4 Antibody and Identification of SALL4 Protein Products.

Figure 1C:
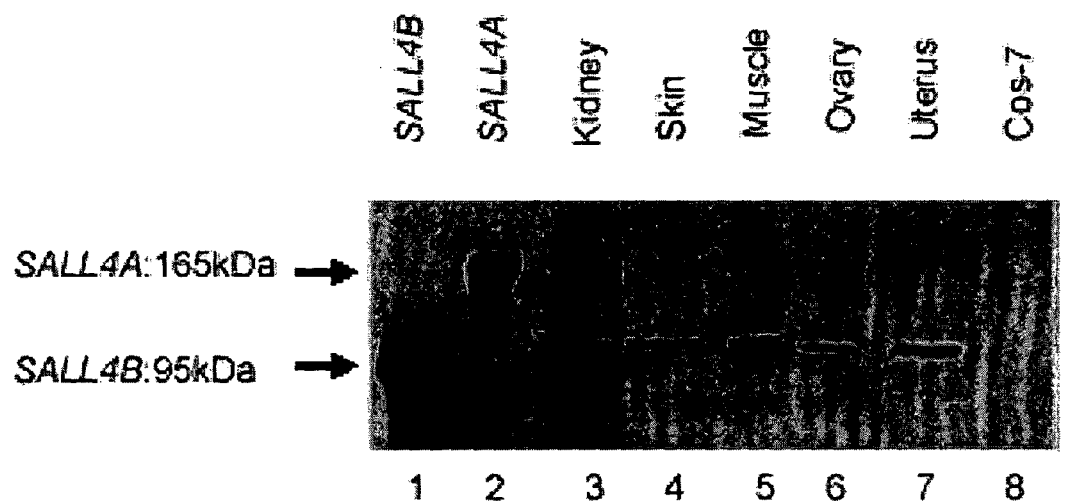
FIG. 1(c) shows SALL4 protein products, SALL4A, and SALL4B identified by a SALL4 peptide antibody. Lysates from Cos-7 cells transiently expressing His-SALL4B (lane 1), His-SALL4A (lane 2), or control vector (lane 8), or lysates from different human tissues were resolved by 10% SDS-PAGE gel, transferred onto a nitrocellulose membrane, and probed with the N-terminal SALL4 peptide antibody.

To identify SALL4 gene products and confirm the presence of SALL4 variants, a polyclonal antibody against a synthetic peptide (amino acids 1-13) of SALL4 was developed. This region was chosen because it is common to both SALL4 variants. The affinity-purified SALL4 peptide antibody recognized specifically two endogenous proteins in a human kidney total lysate. The two proteins were approximately 165 kDa and 95 kDa, which were identical to the molecular weights of overexpressed SALL4A and SALL4B in Cos-7 cells, respectively (FIG. 1c). Western blotting with this antibody confirmed that the SALL4 isoforms had different tissue distributions that were similar to those observed at the mRNA level (FIG. 1b-B).

Failure of SALL4 to Turn Off in Human Primary AML and Myeloid Leukemia Cell Lines.

Figure 2A:
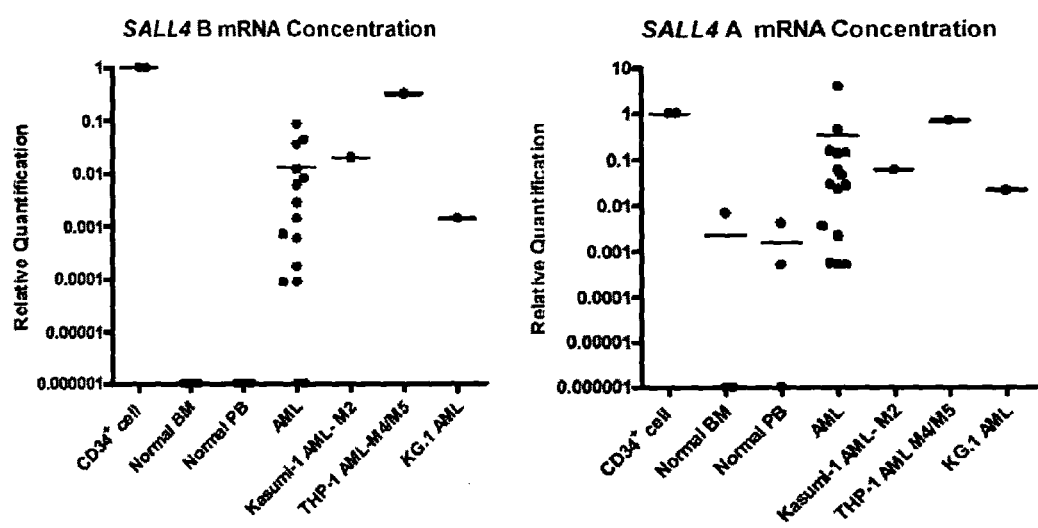
FIG. 2(a) demonstrates the failure of SALL4 to turn off in AML. Real-time PCR quantification of SALL4A and SALL4B normalized to GAPDH showed that both SALL4A and SALL4B were expressed in purified CD34+ cells, but SALL4A was rapidly downregulated and SALL4B turned off in normal bone marrow (N=3) and normal peripheral blood (N=3) cells. In contrast, in 15 primary AML samples and three myeloid leukemia cell lines (Kasumi-1, THP-1, and KG.1), the expression of SALL4A or SALL4B, or both, failed to be down-regulated. The results were calibrated against the expression of SALL4A or SALL4B in purified CD34+ cells.
Figure 2B:
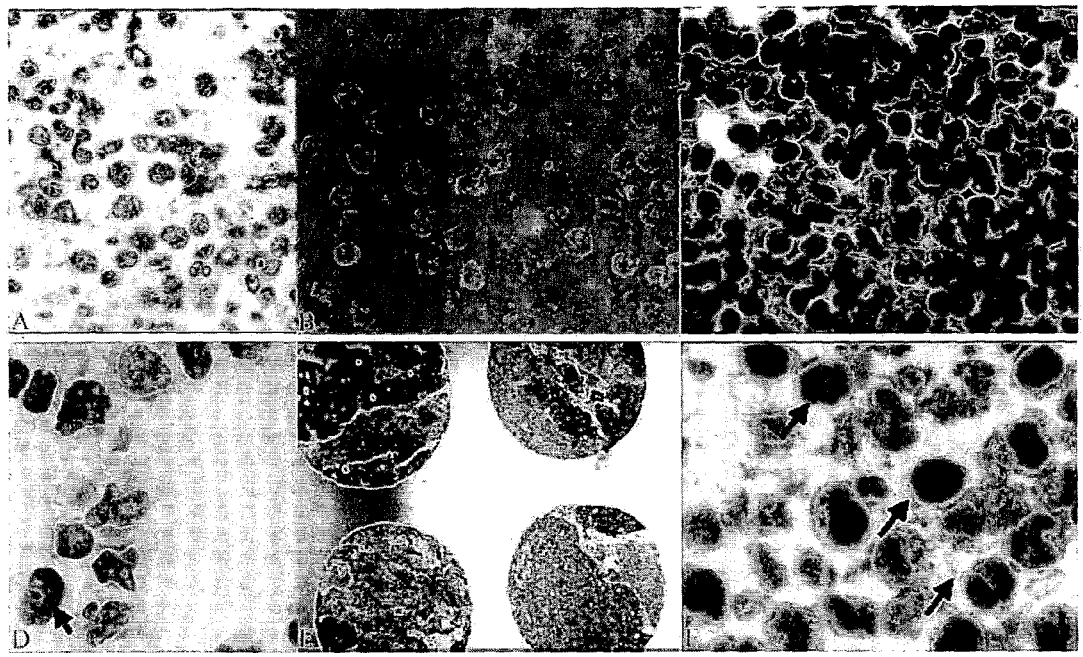
FIG. 2(b) shows constitutive expression of SALL4 protein in human AML (FAB M1-M5, N=81) as demonstrated by immunohistochemical staining. No SALL4 expression was detected in normal bone marrow (A), normal spleen (B), or normal thymus (C). All cell nuclei are stained blue. Nuclei of CD34+ HSC/HPCs showed brown staining indicating SALL4 expression (D); acute myeloid leukemia blasts showed similar staining (E, low power [×4]) in microarray leukemia tissue samples. Each circle represents one leukemia sample. (F) High power (×100) view of one leukemia sample shown in part F. The red arrows indicate positive nuclear staining.

Because the chromosome region 20q13, where SALL4 is located, is frequently involved in tumors, SALL4 mRNA expression in AML was examined. Expression of SALL4 was quantitatively investigated by real-time RT-PCR in bone marrow cells derived from AML samples (N=15), myeloid leukemia cell lines (N=3) and compared with that of non-neoplastic hematopoietic cells from a purified CD34+ stem/progenitor pool (HSCs/HPCs purchased from Cambrex), normal bone marrow (N=3), and normal peripheral blood (N=3). With the use of isoform-specific primers (see FIG. 2a), either or both SALL4B and/or SALL4A, failed to be turned off (SALL4B) or down-regulated (SALL4A) in all AML samples and myeloid leukemia cell lines. The data were normalized to the endogenous expression of GAPDH and calibrated against the level of SALL4A or SALL4B expression in purified CD34+ cells. In contrast to the total absence of SALL4B in normal bone marrow, its expression in primary AML failed to be turned off in 13 of 15 AML samples and in all three myeloid leukemia cell lines. The median normalized level of SALL4A in primary AML samples was 40-fold higher than that in normal bone marrow. SALL4A expression levels in the myeloid leukemia cell lines KG.1, Kasumi-1, and THP-1 were, respectively, 8-, 25-, and 240-fold higher than those in normal bone marrow. Interestingly, both SALL4A and SALL4B expression levels were increased in 60% of AML samples and in all three cell lines, compared with those in normal bone marrow. In the remaining 40% of AML samples, either SALL4A or SALL4B failed to be down-regulated.

Constitutive Expression of SALL4 Protein in Human Primary AML.

To investigate whether the observed aberrant SALL4 expression was also present at the protein level, 81 AML samples were examined, ranging from AML classes M1 to M5 (FAB classification): M1 (N=20), M2 (N=27), M3 (N=8), M4 (N=16), M5 (N=3), and AML nonspecified (N=7); several samples of normal bone marrow, thymus and spleen, as well as normal CD34+ HSCs/HPCs.

Normal bone marrow, spleen and thymus showed no detectable SALL4 protein expression, and normal CD34+ HSCs/HPCs exhibited positive but weaker SALL4 protein staining; however, much stronger SALL4 expression was detected in the nuclei of leukemic cells (FIG. 2b-F). All 81 AML samples showed aberrant SALL4 expression, with the strongest staining seen in AML-M1 and -M2. These findings were consistent with SALL4 mRNA expression levels demonstrated by real-time RT-PCR (FIG. 2a). The data suggested that SALL4 was present in CD34+ HSCs/HPCs and down-regulated in mature granulocytes and lymphocytes. As a result, the constitutive expression of SALL4 in leukemia may have prevented the leukemic blasts from differentiating and/or gaining properties that were normally seen in HSCs.

Generation of Transgenic Mice Constitutively Expressing Full-Length Human SALL4B.

To directly test whether constitutive expression of SALL4 is sufficient to induce AML, a SALL4 transgenic mouse model was generated. The CMV promoter was fused to cDNA that encoded the 617 amino acids of human SALL4B (FIG. 3a-A), which was chosen because it was expressed in every tissue previously examined (FIG. 1b-B). The CMV promoter was previously used to ectopically express human genes in most murine organs. RT-PCR amplification was performed to examine the overexpression of wildtype (WT), full-length SALL4B in the transgenic mice.

Figure 3A:
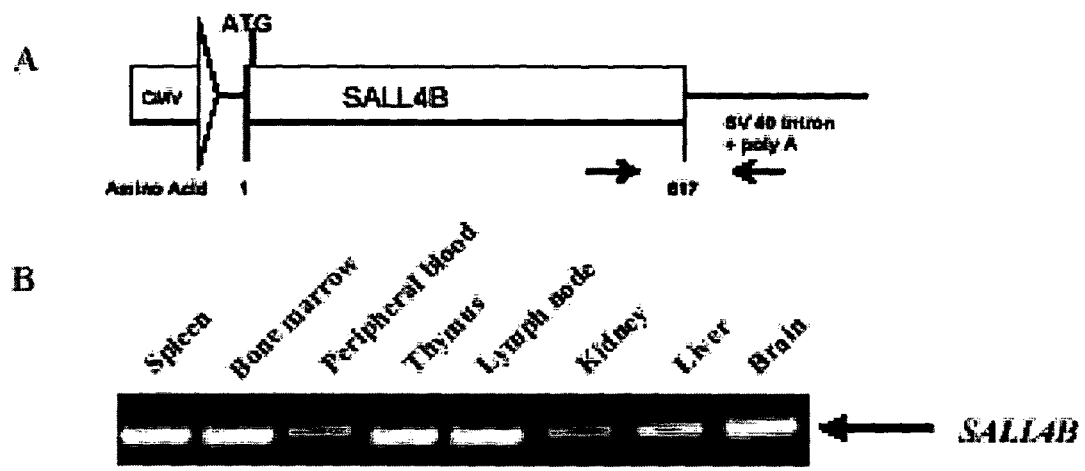
FIG. 3(a) illustrates the generation of SALL4B transgenic mice: CMV/SALL4B transgenic construct and PCR analysis of transgenic line 507. (A) Schematic diagram of transgenic construct. The approximately 1.8-kb cDNA of SALL4B was subcloned into a pCEP4 vector, and the CMV/SALL4 construct was excited by digestion with SalI. (B) Tissue distribution of SALL4B in transgenic mice. The location of primers used for RT-PCR amplification is indicated by arrows in part A. A primer specific for human SALL4B at the C-terminus was used as a 5' primer, in combination with SV40-noncoding sequence-specific primers for RT-PCR of various tissues.
Figure 3B:
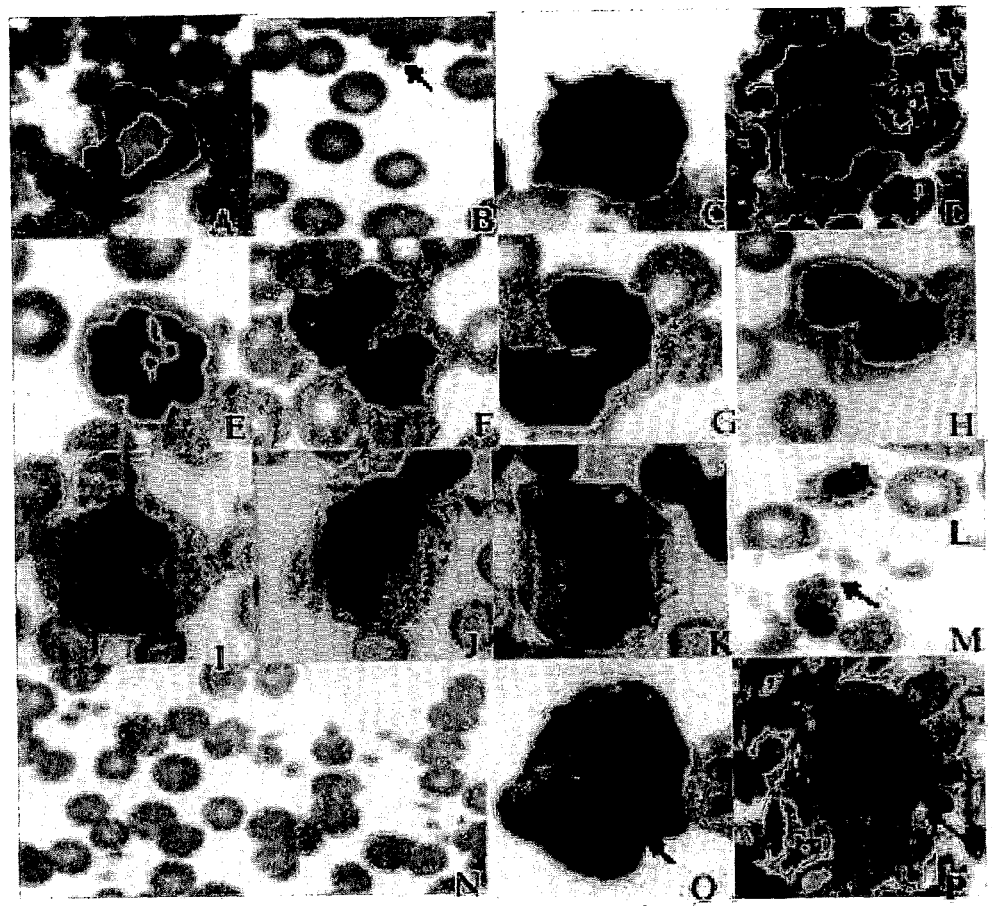
FIG. 3(b) demonstrates the MDS-like changes in SALL4B transgenic mice. Giemsa staining of peripheral blood from normal, age-matched WT litter mates showed normal neutrophils (A), and normal red blood cells and platelets (B, black arrow). In transgenic mice, neutrophils were hypersegmented (E), and pseudo-Pelger-Huet-like atypical white cells were present (F-H), together with increased numbers of immature cells (I-K). Nucleate red cells (L, red arrow), giant platelets (M, red arrow), and polychromasia (N) were also observed in the transgenic mice. A binucleate dysplastic erythrocyte (O, red arrow) and a dysplastic megakaryocyte with a hypolobulated nucleus (P, red arrow) were found in the cytospin from transgenic mouse bone marrow. An erythroid precursor. (C) and a megakaryocyte (D) from WT control animals are shown for comparison.

A SALL4B transcript was detected in a variety of tissues from the transgenic mice, including brain, kidney, liver, spleen, peripheral blood, lymph nodes, and bone marrow (FIG. 3a-B). Abnormal gaits and associated hydrocephalus 3 weeks after birth were observed in 20% of the transgenic mice from multiple lines; 60% had polycystic kidneys. These findings suggest that SALL4B plays an important role in neural and renal development.

MDS-Like Symptoms and AML in SALL4B Transgenic Mice.

Monitoring of hematological abnormalities in a cohort of 14 transgenic mice from all six lines revealed that all mice had apparent MDS-like features at ages 6-8 months. Increased number of immature blasts and many atypical and dysplastic white cells, including hypersegmented neutrophils and pseudo-Pelger-Huet-like cells, were seen on peripheral blood smears (FIG. 3b). Nucleate red blood cells and giant platelets were also present, as well as erythroid and megakaryocyte dysplastic features, such as binucleate erythroid precursors and hypolobulated megakaryocytes.

Six (43%) of these 14 mice eventually progressed to acute leukemia (Table 1).

TABLE 1

Summary of MDS-Like/AML in SALL4B Transgenic Mice

| Mouse ID | Sex | Founder | Age | Phenotype | Outcome and Organs Involved by AML |
|---|---|---|---|---|---|
| 25 | M | 507 | 8 M | AML | Sacrificed, AML in BM, PB, Liver, Spleen, LNs |
| 509 | F | 509 | 18 M | AML | Sacrificed, AML in BM, PB, Liver, Spleen, LNs, Lungs |
| 87 | F | 504 | 8 M | AML | Sacrificed, AML in BM, PB, Liver, Spleen, LNs |
| 504 | M | 504 | 19 M | MDS-like | Sacrificed due to MDS |
| 506 | M | 506 | 19 M | MDS-like | Sacrificed due to MDS |
| 507 | F | 507 | 24 M | AML | Died, AML in BM, PB, Liver, Spleen, LNs |
| 510 | F | 510 | 24 M | MDS-like | Sacrificed due to MDS |
| 464 | M | 464 | 19 M | MDS-like | Died of MDS |
| 23 | M | 507 | 22 M | MDS-like | Sacrificed due to MDS |
| 27 | M | 507 | 22 M | MDS-like | Alive |
| 86 | F | 504 | 18 M | AML | Sacrificed, AML in BM, PB, Liver, Spleen, LNs |
| 4 | M | 464 | 15 M | MDS-like | Alive |
| 3058 | F | 25 | 12 M | AML | Died, AML in BM, PB, Liver, Spleen, LNs |
| 26 | M | 507 | 14 M | MDS | Sacrificed due to MDS |

Figure 3C:
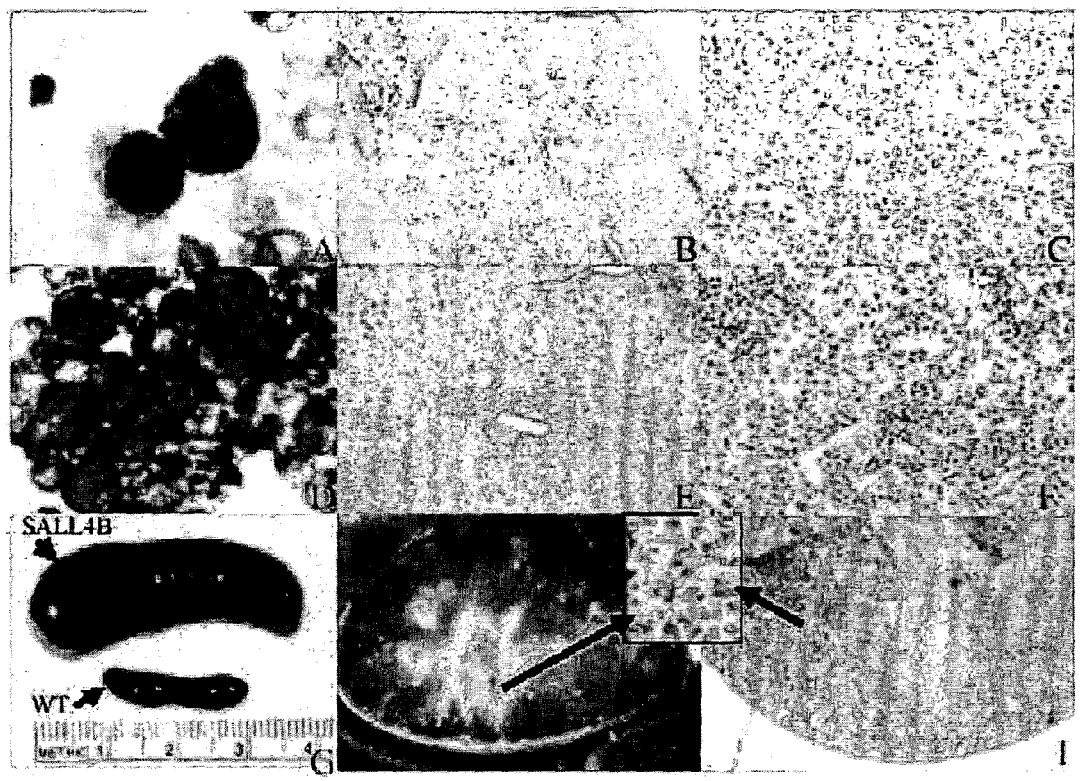
FIG. 3(c) shows that AML is observable in SALL4B transgenic mice. Blasts were present in the peripheral blood (A, ×600), bone marrow biopsy specimen (B, ×100; C, ×400), bone marrow smear (D, ×600), liver (E, ×100), lymph node (F, ×400), and spleen (G and H, gross view; I, ×100; and the inset ×400).
Figure 3D:
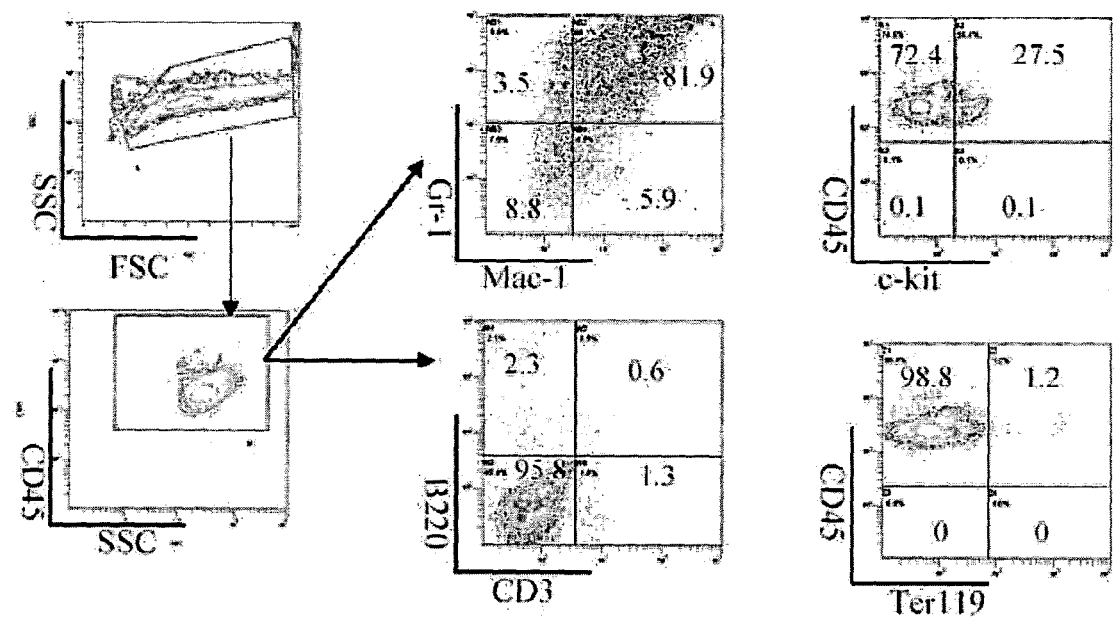
FIG. 3(d) shows the flow cytometric analysis of AML in SALL4B transgenic mice. AML cells were positive for CD45, c-kit, Gr-1, and Mac-1; negative for B220, CD3, and Ter119.

Leukemic infiltration of many organs, including lung, kidney, liver, spleen, and lymph nodes, emphasized the aggressiveness of the disease (FIG. 3c). Leukemia blast cells were considered to be myeloid in origin because they were positive for CD34, c-kit, Gr-1, Mac-1, MPO, and nonspecific esterase; they were negative for B-cell (B220 and CD19), T-cell (CD4, CD8, CD3, and CD5), megakaryocytic (CD41), and erythroid (Ter119) markers (FIG. 3d).

SALL4B-Induced AML was Transplantable.

Figure 3E:
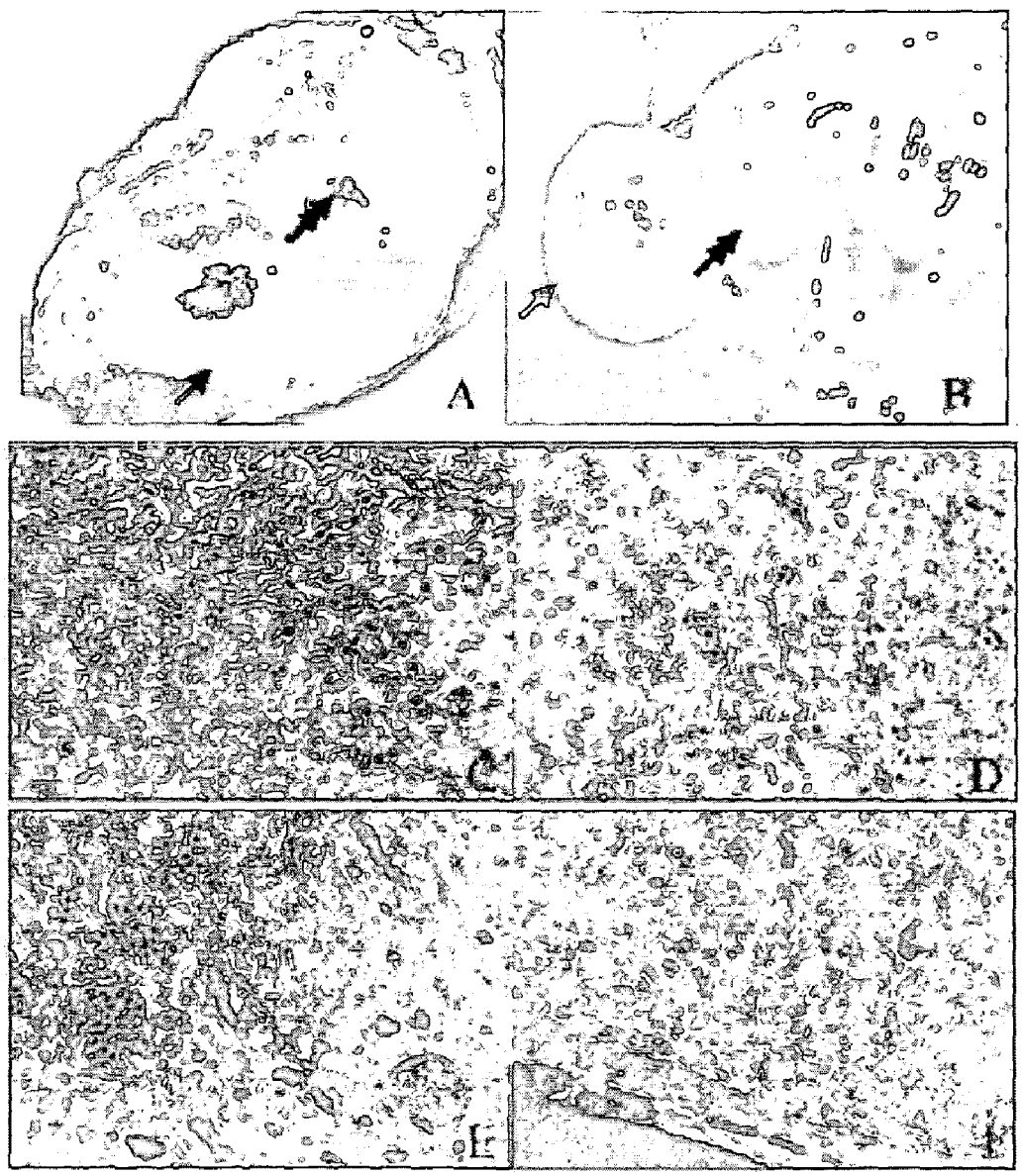
FIG. 3(e) demonstrates the serial transplantation of SALL4B-Induced AML to NOD/SCID mice. Gross picture (A&B) and histology (B, C, D, E, ×200) on splenomegaly (3e-A black arrow, 3e-C), hepatomegaly (3e-A double black arrows, 3e-D), lymph node enlargement (3e-B black arrow, 3e-E) and pale kidney (3e-B double black arrows, 3e-F) caused by leukemia infiltration in a NOD/SCID mouse 6 weeks after leukemia transplantation.

Aggressive fatal AML with onset at approximately 6 weeks developed in immunodeficient NOD/SCID mice after serial transplantation of SALL4B-induced AML cells by subcutaneous injection. The transplanted disease was characterized by dissemination to multiple organs, with marked splenomegaly and hepatomegaly (FIG. 3e).

Ineffective Hematopoiesis and Excessive Apoptosis in SALL4B Transgenic Mice.

Investigation of hematological abnormalities in younger SALL4B transgenic mice (2-6 months old) revealed that their peripheral blood showed minimal myelodysplastic features but statistically significant leukopenia and neutropenia, as well as mild anemia (Table 2).

TABLE 2

CBC from SALL4B Transgenic Mice and Wild Type Control

| | WBC ($\times 10^3/\mu L$) | Neutrophil ($\times 10^3/\mu L$) | Lymphocyte ($\times 10^3/\mu L$) | RBC ($\times 10^6/\mu L$) | Hb (g/dL) | HCT (%) | MCV (fL) | PLT ($\times 10^3/\mu L$) |
|---|---|---|---|---|---|---|---|---|
| Transgenic (n = 20) | 8.38 ± 3.52 | 0.93 ± 1.06 | 6.34 ± 4.62 | 8.85 ± 2.08 | 14.26 ± 3.04 | 50.52 ± 11.82 | 57.15 ± 6.42 | 1616 ± 662 |
| Control (n = 18) | 11.59 ± 5.14 | 1.51 ± 0.86 | 9.04 ± 4.06 | 10.02 ± 1.84 | 15.66 ± 2.44 | 55.75 ± 9.62 | 55.78 ± 7.54 | 1384 ± 806 |
| P value | 0.27 | 0.048 | 0.029 | 0.015 | 0.030 | 0.038 | 0.398 | 0.196 |

To determine whether the cause of cytopenia in these transgenic mice was related to production problems, their bone marrow was studied. Bone marrow samples showed increased cellularity and an increased myeloid population (FIG. 3f), compared with those of WT controls (Gr-1/Mac-1 double-positive population in SALL4B transgenic mice: 67±16%, N=10 vs. WT: 55.3±4%, N=11; P=0.048).

Figure 3F:
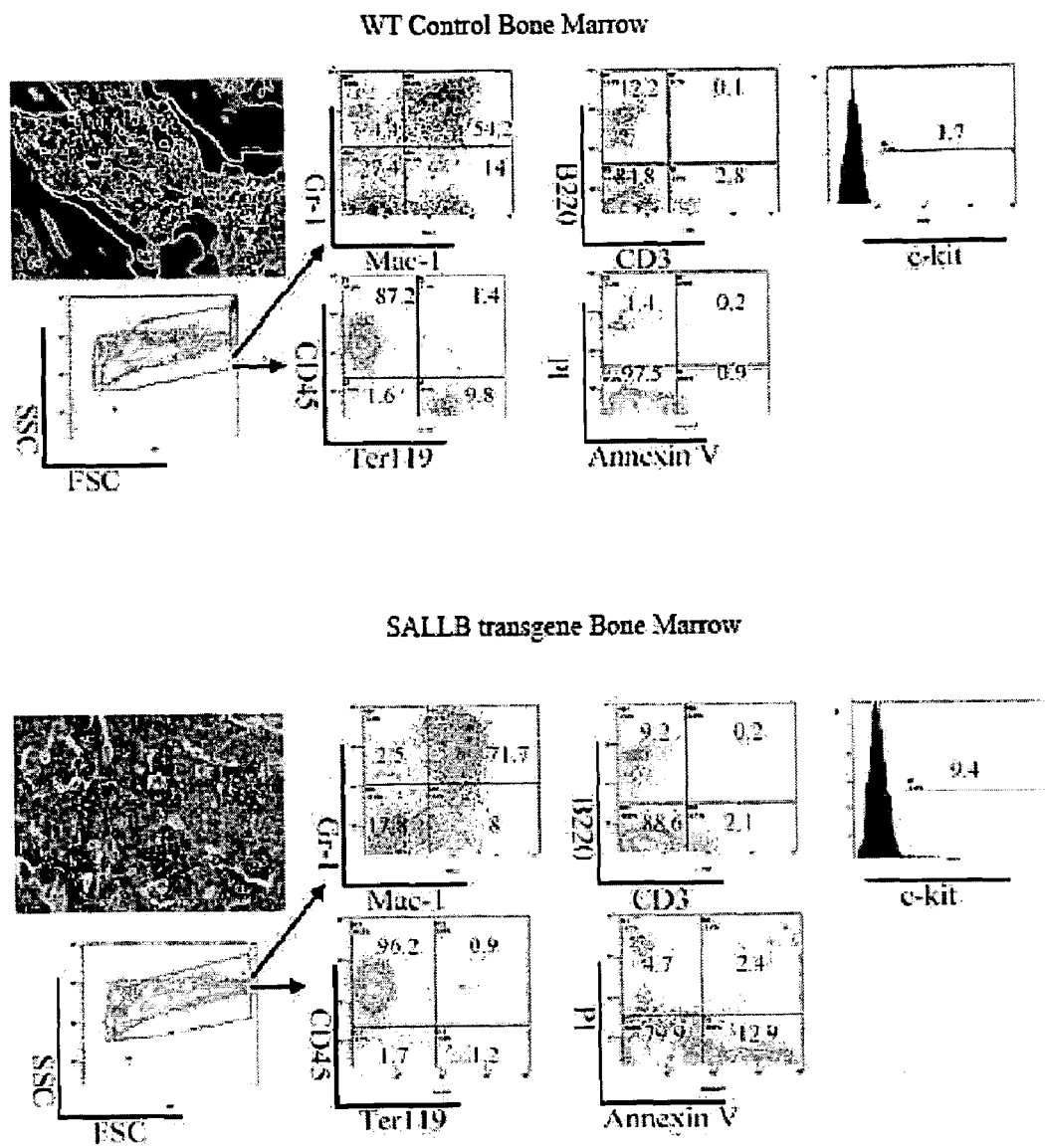
FIG. 3(f) illustrates the comparison between bone marrow of SALL4B transgenic and control mice. SALL4B transgenic mouse bone marrow showed increased cellularity, myeloid population (Gr-1/Mac-1 double positive), immature population (c-kit positive), and apoptosis (Annexin V positive, PI negative), compared with control WT mice.
Figure 3G:
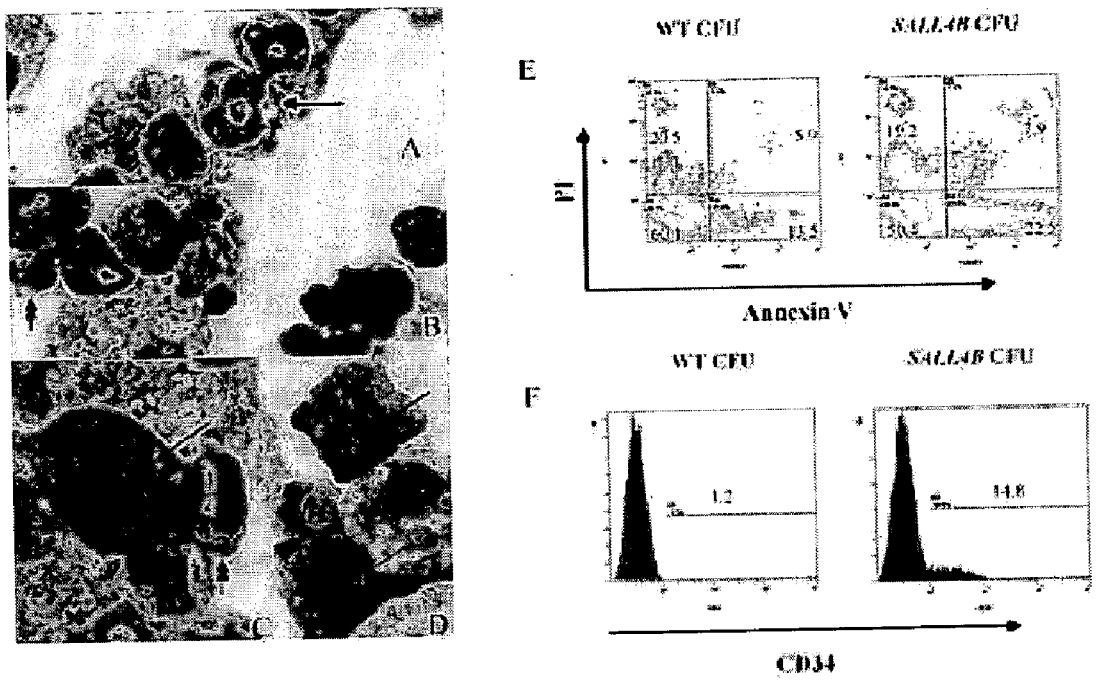
FIG. 3(g) shows that there are an increased number of immature cells and apoptosis in CFUs from SALL4B transgenic mice. On day 7 of culture, a greater number of immature cells (B, C, and D, red arrows) and apoptotic cells (B, C, and D, double red arrows) were observed in transgenic mouse CFUs than in control CFUs (A). Consistent with this morphologic observation, there was increased apoptosis (Annexin V positive, PI negative, E) and more CD34+ immature cells (F).
Figure 3H:
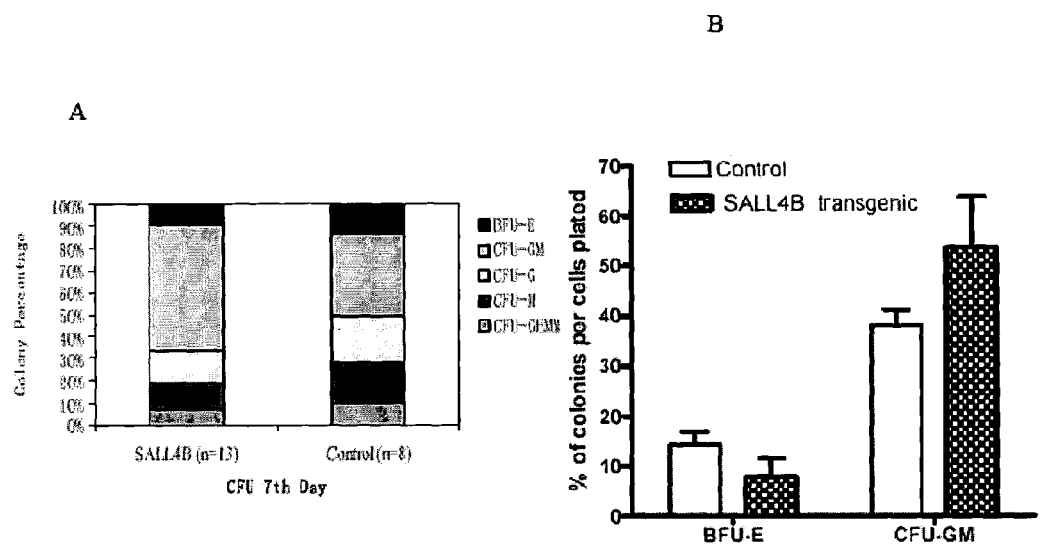
FIG. 3(h) illustrates the comparison between bone marrow CFUs of SALL4B transgenic and control mice. Percentage of different types of colonies found in CFU assays of SALL4B transgenic and control mice (A). CFUs from SALL4B transgenic mice compared with control mice showed a statistically significant increase in CFU-GM (B) (transgenic: 53.6±10.3, N=13 vs. WT: 38.1±3.1, N=8; P=0.002) and decrease in BFU-E (transgenic: 7.8±3.8, N=13 vs. WT: 14.1±2.7, N=8; P=0.001).

As excessive apoptosis plays a central role in ineffective hematopoiesis in human MDS, apoptosis in SALL4 transgenic mice in vivo and in vitro was examined next. Increased apoptosis was observed in SALL4B transgenic mice on both primary bone marrow (Annexin V-positive, PI-negative population in transgenic mice: 4.4±2.4%, N=10 vs. WT: 1.86±1.55%, N=7; P=0.03) and day-7 CFUs (Annexin V-positive, PI-negative population in transgenic mice: 20.1±6%, N=10 vs. WT: 10.9±4%, N=7; P=0.002) (FIGS. 3f and g). These findings may account for the fact that despite an increased myeloid population in bone marrow, these transgenic mice had statistically significant low neutrophil counts in the peripheral blood, secondary to an ongoing ineffective myelopoiesis in their bone marrow. An increased population of immature cells was also noted in SALL4B transgenic mice on both primary bone marrow (c-kit-positive population in SALL4B transgenic mice: 10.2±1.3%, N=14 vs. WT: 6.5±2.5%, N=10; P=0.008) (FIG. 3f) and day-7 CFUs (CD34-positive population in SALL4B transgenic mice: 11±2.2%, N=8 vs. WT: 6.3±2.4%, N=7; P=0.002) (FIG. 3g). Similar numbers of total colonies were observed in SALL4B transgenic mice (mean=51, N=10) and WT controls (mean=40, N=6). Increased myeloid and decreased erythroid colony populations (FIG. 3h), however, were found in SALL4B transgenic mouse CFUs compared with those of WT controls, as has been reported in human MDS patients and other MDS mouse models. These observations suggest that the defect in SALL4B transgenic mice lies at the stem cell/progenitor level affecting hematopoietic differentiation.

Binding of SALL4A and SALL4B to β-Catenin in Vitro.

The potential signaling pathway that SALL4 may affect in leukemogenesis was explored next. In *Drosophila*, spalt (sal) is a downstream target of Wnt signaling. ALL1, another member of the SALL gene family, can interact with β-catenin. The high affinity site for this interaction is located at the C-terminal double zinc finger domain. This region of SALL1 was found to be almost exactly identical to that of SALL4. This finding prompted the investigation of whether SALL4 was also able to bind β-12 catenin. Expression constructs of SALL4A and SALL4B tagged with hemagglutinin (HA) were generated. As shown in FIG. 4a, endogenous β-catenin was pulled down by HA-SALL4A and HA-SALL4B, but not by HA alone.

Activation of the Wnt/β-Catenin Signaling Pathway by Both SALL4A and SALL4B.

To investigate the functional effect of the interaction of the SALL4 isoforms with β-catenin, a luciferase reporter (TOPflash; Upstate USA) containing multiple copies of Wnt-responsive elements to determine the potential of SALL4A and SALL4B to activate the canonical Wnt signaling pathway was used. This reporter construct has been shown to be efficiently stimulated by Wnt1 in a variety of cell lines. TOPflash reporter plasmid was transiently transfected in the HEK-293 cell line, in which both Wnt and its Wnt/β-catenin signal pathways were present. TOPflash reporter plasmid was also cotransfected with SALL4A or SALL4B. Significant activation of the Wnt/β-catenin signaling pathway by both SALL4A and SALL4B was indicated by increased luciferase activity (FIG. 4b).

Similar Expression Patterns of β-Catenin and SALL4 at Different Phases of CML.

Dysregulated Wnt/β-catenin signaling is known to be involved in the development of LSCs. The best evidence for β-catenin's involvement in LSC self-renewal comes from the study of CML blast transformation. It has been demonstrated that Wnt signaling was activated in the blast phase of CML but not the chronic phase, where it was concluded that dysregulated Wnt signaling, such as activation of β-catenin, could confer the property of self-renewal on the GMPs of CML and lead to their blastic transformation.

Given the potential interaction between SALL4 and β-catenin and spalt's position as a downstream target of Wnt signaling in *Drosophila*, SALL4 protein expression in CMLs in different phases was examined. SALL4 expression was present in blast-phase CML (N=12, 75%) but not the chronic phase (N=11, 100%) (FIG. 4c). In the accelerated phase (N=6, 10%), in which blast counts are increased, immature blasts expressing SALL4 were observed upon a background of nonstaining mature myeloid cells, such as neutrophils.

Effect of SALL4 on OCT4 Promoter.

Figure 5:
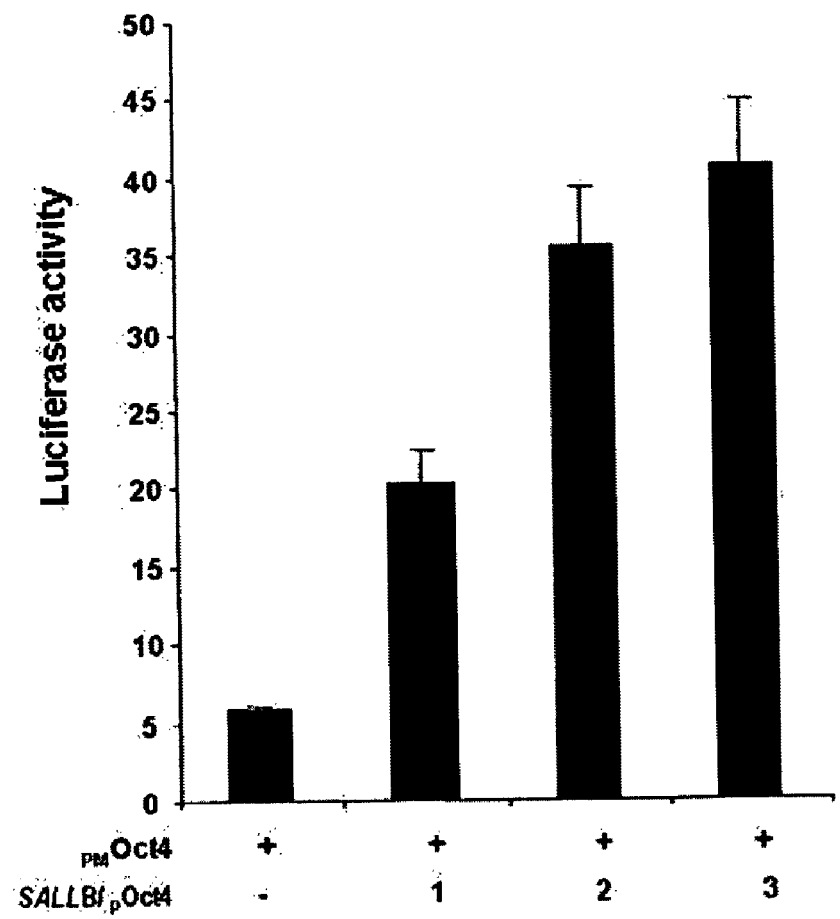
FIG. 5 illustrates dose-dependent effect of SALL4B on the OCT4 promoter. 0.3 μg of OCT4-Luc construct (PMOct4) was cotransfected with 0.1 μg of renilla plasmid and increasing amounts (0-1.0 μg) of SALL4B or pcDNA3 vector control.

To identify the effect of SALL4 on OCT 4, cells, OCT4-Luc constructs were co-transfected with *renilla* plasmids and increasing concentrations of SALL4B (FIG. 5). As the figure shows increasing SALL4B increased OCT4 promoter activity by more than 8 fold.

Figure 6:
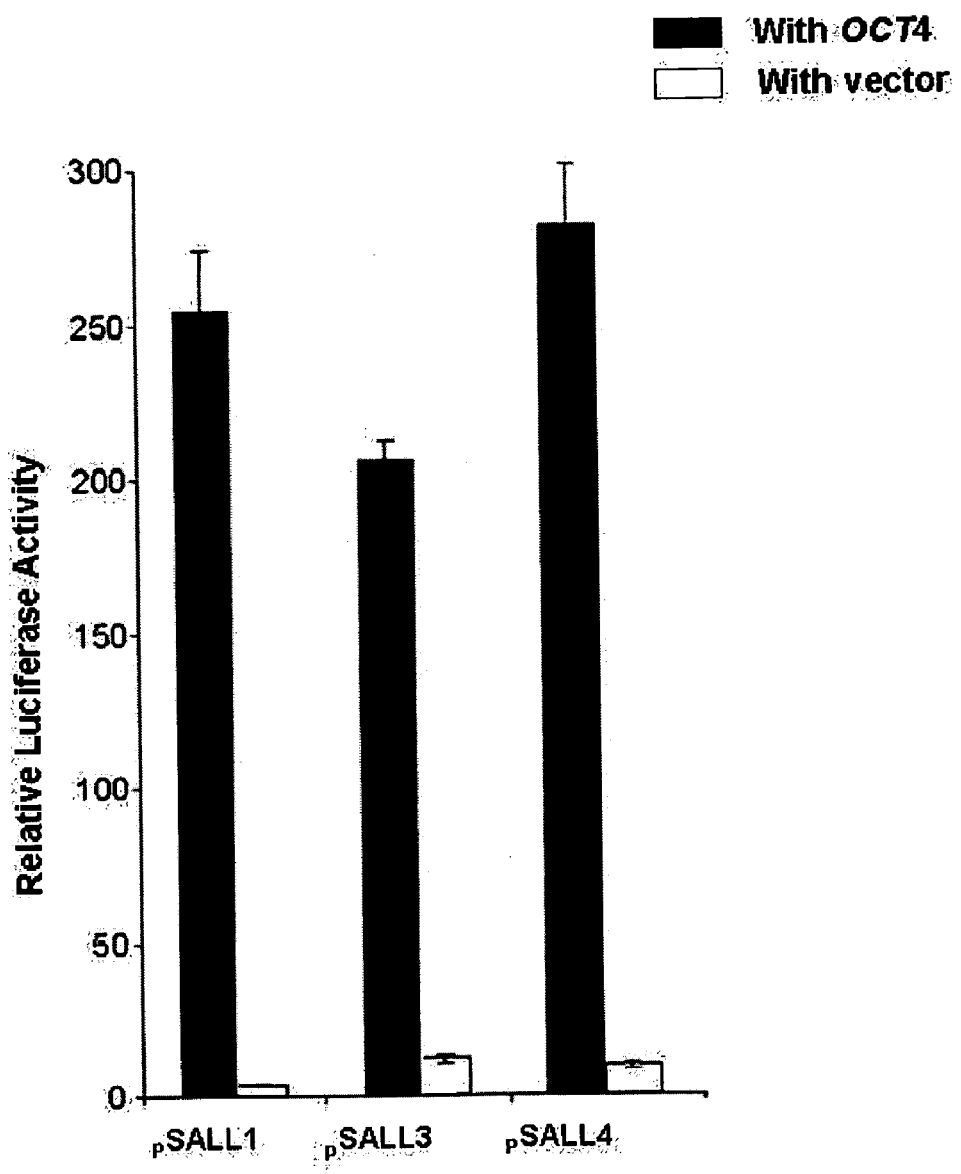
FIG. 6 demonstrates the effect of OCT4 on SALL gene family member promoters. Each (0.3 μg) SALL-Luc promoter construct (i.e., pSALL1, pSALL3, and pSALL4) was co-transfected with 0.9 μg of OCT4 or pcDNA3 vector control in HEK-293 cells. After 24 hr post-transfection, luciferase activity was evaluated for each group.
Figure 10:
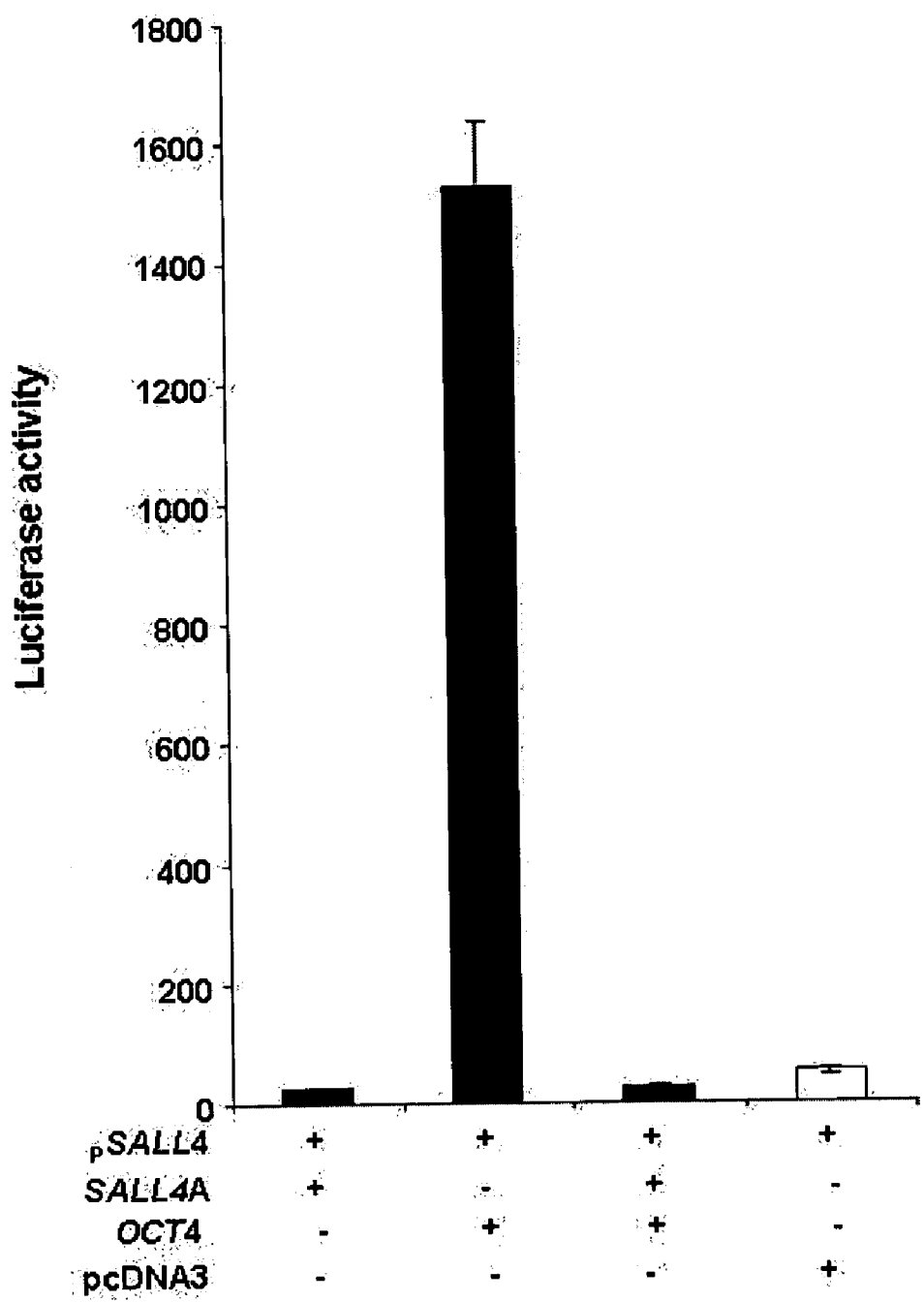
FIG. 10 shows the effect of OCT4 on the SALL4 promoter in the presence of excess SALL4A. 0.25 μg of SALL4-Luc construct (pSALL4) was transiently co-transfected with equal amounts (0.5 μg) of SALL4A and OCT4 plasmid in the HEK-293 cells. pcDNA3 was used as a control.

To determine if OCT4 stimulates the activity of SALL gene member promoters, promoter constructs (pSALL1, pSALL3, and pSALL4) were co-transfected with OCT4 in HEK-293 cells. As can be seen from the data (FIG. 6), after 24 hr post-transfection, the overexpression of OCT4 strikingly stimulated the promoter activities of SALL gene members SALL1, SALL3, and SALL4 when compared with that of the pcDNA3 vector control. Also, this activation was totally blocked by the presence of a small amount of excess SALL4 (FIG. 10).

Figure 7:
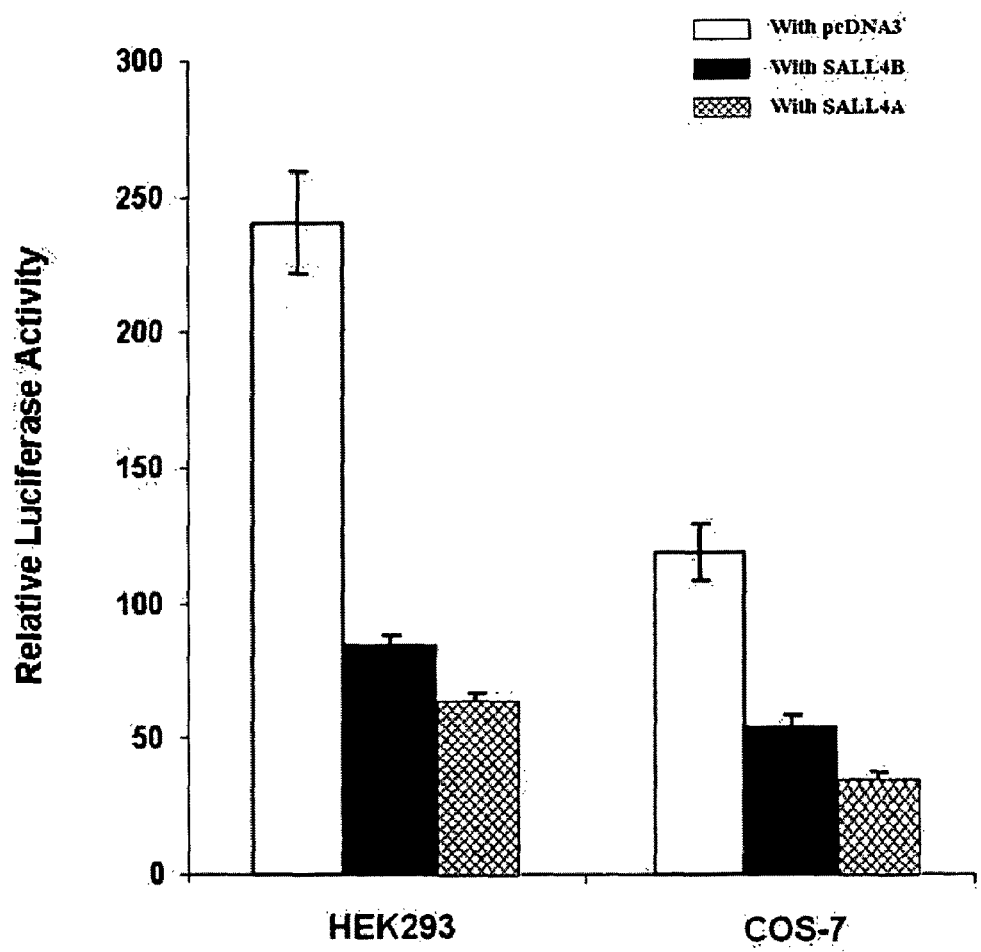
FIG. 7 shows the effect of SALL4 isoforms A and B on SALL4 promoter activity. 0.3 μg of SALL4-Luc was cotransfected with 0.1 μg of either SALL4A or SALL4B expressing plasmid in different cell lines (HEK-293 or COS-7); pcDNA3 vector was used as the control. Luciferase activity was normalized for renilla reporter activity. The values represent the mean±s.e. of three experiments.
Figure 8:
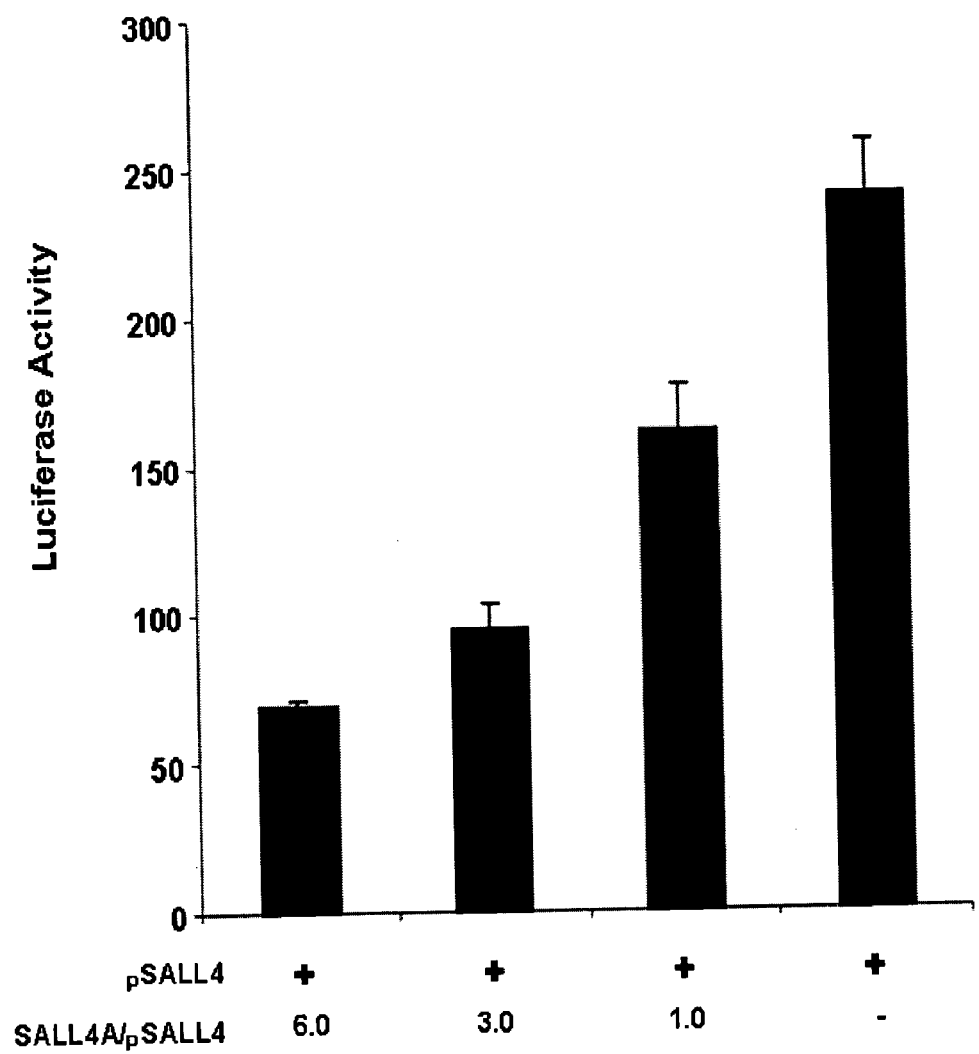
FIG. 8 demonstrates the dose dependent effect of SALL4A on SALL4 promoter activity. In HEK-293 cells, 0.3 μg of the SALL4-Luc was co-transfected with 0.1 μg of renilla plasmid and increasing ratios of the SALL4A construct and the control pcDNA3 vector. The Luciferase activity is normalized for the Renilla reporter activity.
Figure 12:
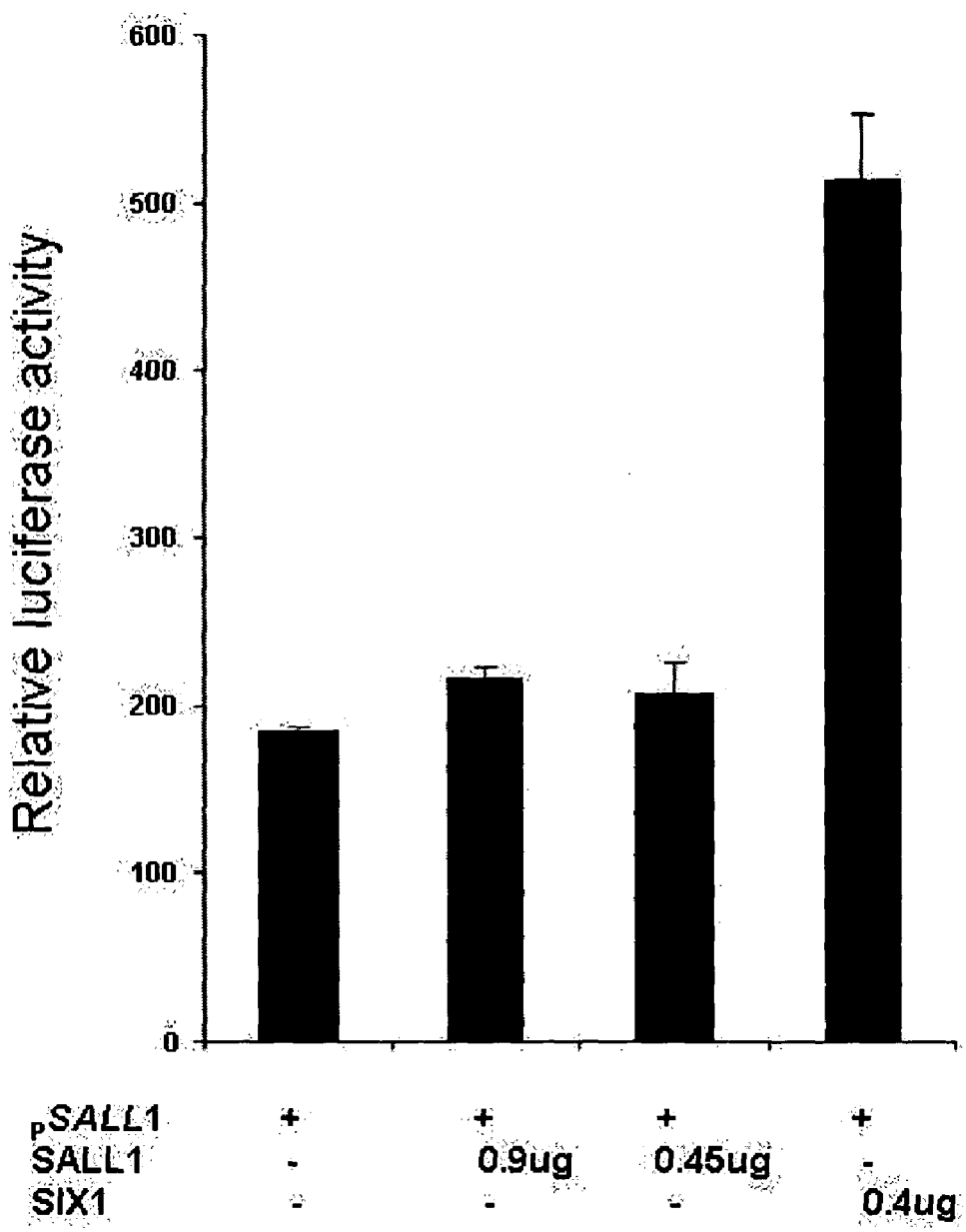
FIG. 12 shows the effect of self promoter interaction on promoter activity for other SALL protein family members. HEK-293 cells were seeded on a 24 well plate and transiently transfected or co-transfected with 0.3 μg SALL1-Luc reporter construct with various amounts of SALL1 plasmid (0.45 and 0.9 μg) SIX1, previously found to activate SALL1 promoter, was used as a positive control. Luciferase activity was normalized for renilla reporter activity.

To determine whether there was any self regulation of SALL promoters by SALL family member proteins, SALL4-Luc was co-transfected with *renilla* reporter and either SALL4A or SALL4B expression plasmids is HEK-293 and COS-7 cells (FIG. 7). As shown in the figure, SALL4 (both A and β isoforms) suppresses its own promoter activity in different cell lines. Further, this self-suppression is dose dependent (see, FIG. 8). When the ratio of SALL4A with SALL4 promoter reached 6:1, the promoter activity dropped approximately 3.5 fold compared with the basal level. This data indicates that SALL4 bears a self-suppression function. This is not true for all SALL members, for example, SALL1 fails to demonstrate self-suppression of its promoter (FIG. 12).

Figure 9:
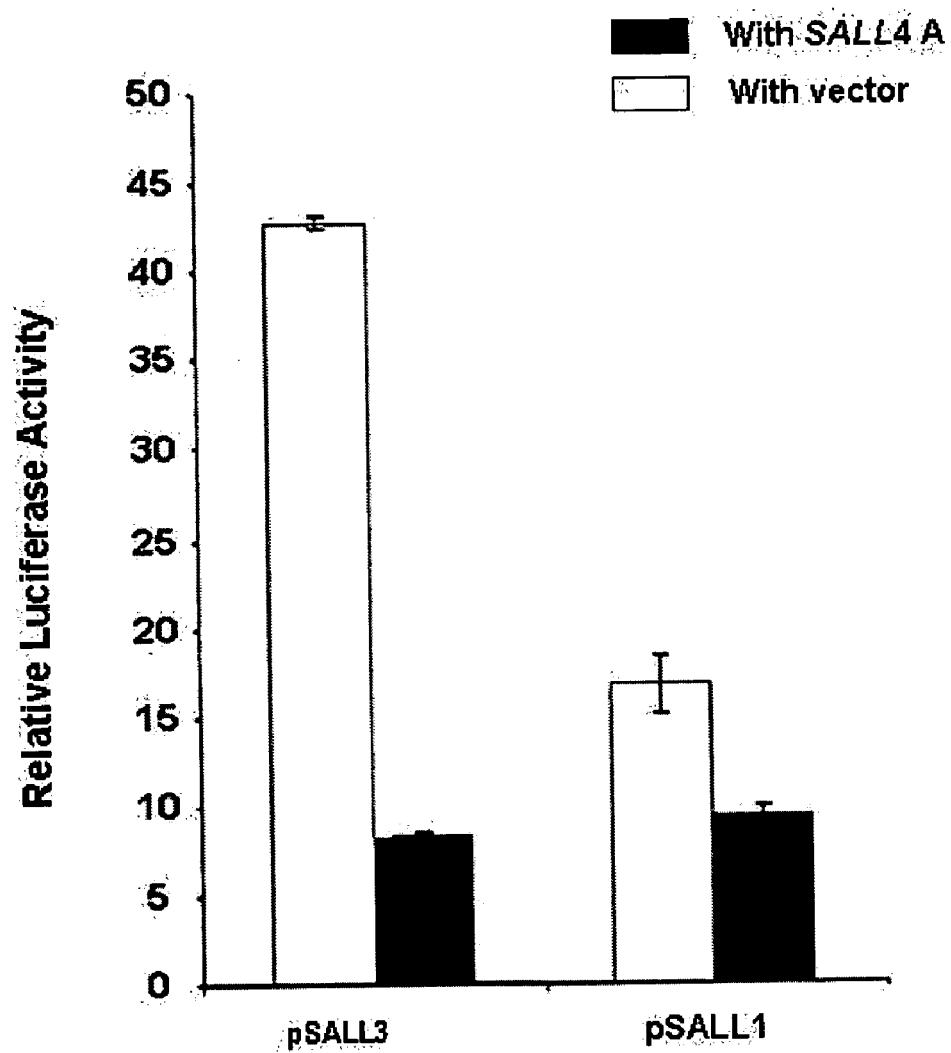
FIG. 9 shows the effect of SALL4 on SALL1 and SALL3 promoter activity. Each (0.3 μg) SALL-Luc promoter construct was transiently co-transfected with 0.9 μg of SALL4A plasmid or pcDNA3 vector (control) in HEK-293 cells.

Data also indicates that SALL1 and SALL3 promoters were strikingly activated by exogenously added SALL4 (See, FIG. 9), indicating that SALL4 is able to regulate other members of the SALL gene family involving embryonic stem cell function.

Figure 11:
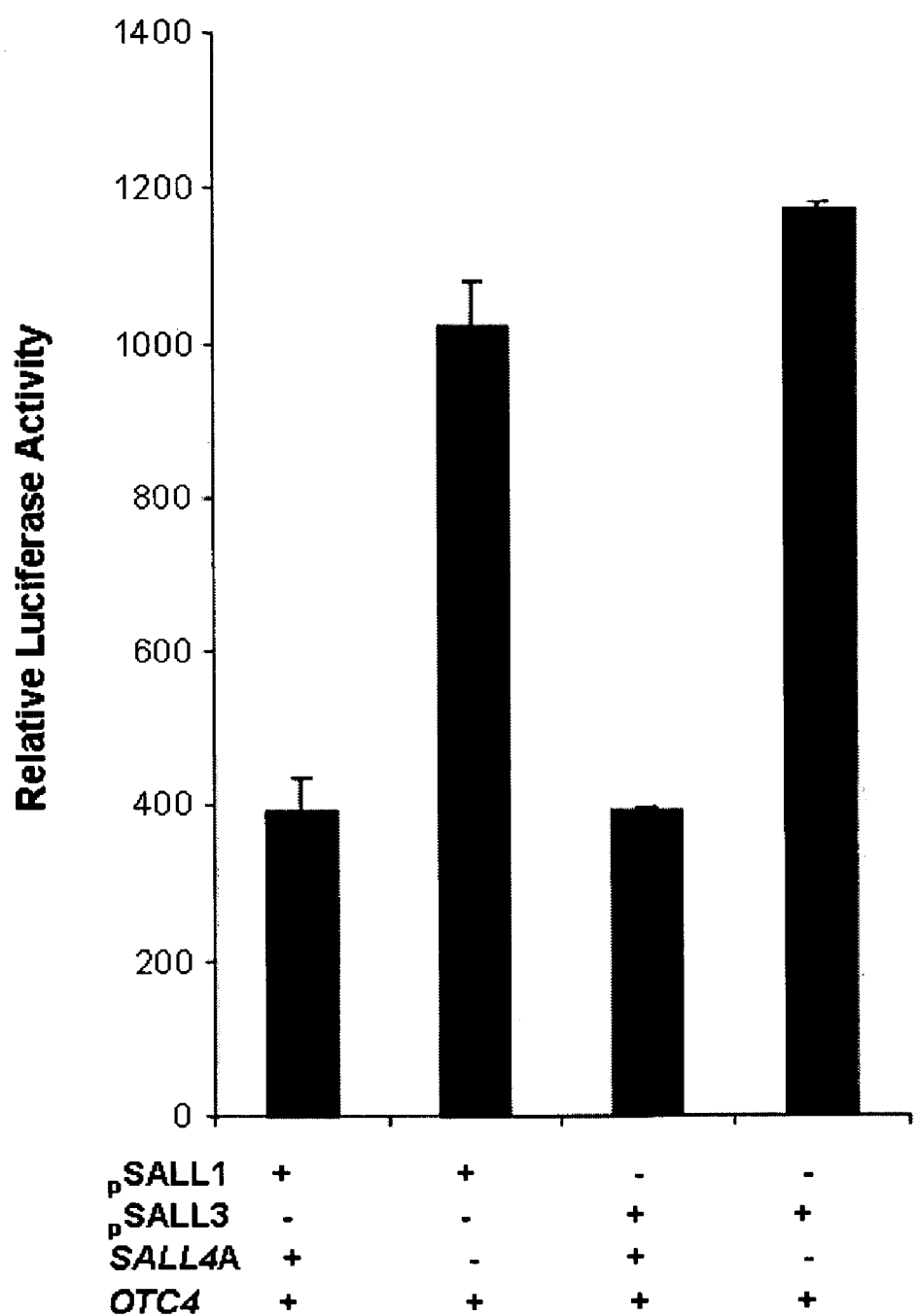
FIG. 11 shows the effect of OCT4 on other SALL member promoters in the presence of SALL4. HEK-293 cells seeded in a 24 well plate were transiently co-transfected with a different SALL member promoter reporter (pSALL1 or pSALL3) and OCT4 plasmid and/or SALL4A construct. pcDNA3 was used as a control.

Since the stimulation of OCT4 on SALL4 promoter can be totally blocked by SALL4 (FIG. 10), SALL4 was examined to determine if it represses the activation of OCT4 on other SALL member promoters. As can be seen in FIG. 11, SALL4 also blocked OCT4 activation of other SALL member promoters.

SALL4 in Adult Stem Cells and Embryonic Carcinoma.

The characterization of tissue stem cell populations remains difficult because of the lack of markers that can distinguish between stem cells and their differentiating progeny. For many tissues, panels of molecular markers have been developed to define the stem cell compartment.

The present data shows that SALL4 is a key regulator of embryonic stem cells in pluripotency and self-renewal. For example, embryonic carcinomas display the phenotype of early embryonic stem cells and possess pluripotent potential. Therefore, the expression of SALL4 protein in this type of tumors by immunohistochemistry was examined. Immunohistochemical data conclusively indicated that all tumor cells of embryonic carcinomas showed a nuclear staining, whereas all non-tumor cells were negative. These observations suggest that SALL4 can be used as a specific marker for normal and malignant embryonic germ cells and embryonic stem cells.

Given that SALL4 was expressed in very early embryonic stem cells, and embryonic carcinoma is reported to arise from transformation of these cells, immunohistochemistry also shows that a) SALL4 positive cells in normal breast lobules, accounted for less than 2% of the epithelium and b) in breast carcinoma samples, SALL4 protein expression in clusters of cells or scattered cells was observed. Further, SALL4 protein was expressed in the nucleus of normal breast epithelial cells and breast carcinoma cells. Moreover, this pluripotent gene expression was observed in other normal adult tissues such as prostate and lung, and carcinoma arising from these tissues with SALL4 antibody. The presence of a small number of SALL4-expressing cells in the broncho-epithelium and prostatic acini, and their stromal cells was observed, as well as the finding that SALL4 was expressed at a similar frequency in normal prostate and lung to that in lobular epithelial cells of breast. In addition, scattered tumor cells in the prostate carcinoma expressed SALL4 protein by immunohistochemistry studies with a SALL4 antibody.

In conclusion, the present examples reveals that (1) immunostaining with anti-SALL4 antibodies are useful diagnostic tools in the identification of embryonic carcinomas, (2) expression of SALL4 is found in several human stem cells and cancer cells; (3) identification of SALL4-expressing cells in human tissues can be used to identify the stem cells, their pre-malignant clones, and malignant cells, and (4) SALL4 represents an ideal marker for embryonic stem cells, adult stem cells and cancer stem cells.

REFERENCES

1. Mufti, G., List, A. F., Gore, S. D. & Ho, A. Y. Myelodysplastic syndrome. Hematology (Am Soc Hematol Educ Program), 176-99 (2003).
2. Gilliland, D. G., Jordan, C. T. & Felix, C. A. The molecular basis of leukemia. Hematology (Am Soc Hematol Educ Program), 80-97 (2004).
3. Tenen, D. G. Disruption of differentiation in human cancer: AML shows the way. Nat Rev Cancer 3, 89-101 (2003).
4. Rosmarin, A. G., Yang, Z. & Resendes, K. K. Transcriptional regulation in myelopoiesis: Hematopoietic fate choice, myeloid differentiation, and leukemogenesis. Exp Hematol 33, 131-43 (2005).
5. Friedman, A. D. Transcriptional regulation of myelopoiesis. Int J Hematol 75, 466-72 (2002).
6. Gilliland, D. G. Molecular genetics of human leukemias: new insights into therapy. Semin Hematol 39, 6-11 (2002).
7. Bonnet, D. & Dick, J. E. Human acute myeloid leukemia is organized as a hierarchy that originates from a primitive hematopoietic cell. Nat Med 3, 730-7 (1997).
8. Huntly, B. J. & Gilliland, D. G. Blasts from the past: new lessons in stem cell biology from chronic myelogenous leukemia. Cancer Cell 6, 199-201 (2004).
9. Huntly, B. J. & Gilliland, D. G. Leukaemia stem cells and the evolution of cancer stem cell research. Nat Rev Cancer 5, 311-21 (2005).
10. Simon, M., Grandage, V. L., Linch, D. C. & Khwaja, A. Constitutive activation of the Wnt/beta-catenin signalling pathway in acute myeloid leukaemia. Oncogene 24, 2410-20 (2005).
11. Jamieson, C. H. et al. Granulocyte-macrophage progenitors as candidate leukemic stem cells in blast-crisis CML. N Engl J Med 351, 657-67 (2004).
12. Reya, T. et al. A role for Wnt signalling in self-renewal of haematopoietic stem cells. Nature 423, 409-14 (2003).
13. Reya, T. & Clevers, H. Wnt signalling in stem cells and cancer. Nature 434, 843-50 (2005).
14. Reya, T. Regulation of hematopoietic stem cell self-renewal. Recent Prog Horm Res 58, 283-95 (2003).
15. Staal, F. J. & Clevers, H. C. WNT signalling and haematopoiesis: a WNT-WNT situation. Nat Rev Immunol 5, 21-30 (2005).
16. Kohlhase, J. et al. Isolation, characterization, and organ-specific expression of two novel human zinc finger genes related to the *Drosophila* gene spalt. Genomics 38, 291-8 (1996).
17. Kohlhase, J. et al. SALL3, a new member of the human spalt-like gene family, maps to 18q23. Genomics 62, 216-22 (1999).
18. Kohlhase, J., Altmann, M., Archangelo, L., Dixkens, C. & Engel, W. Genomic cloning, chromosomal mapping, and expression analysis of msal-2. Mamm Genome 11, 64-8 (2000).
19. Al-Baradie, R. et al. Duane radial ray syndrome (Okihiro syndrome) maps to 20q13 and results from mutations in SALL4, a new member of the SAL family. Am J Hum Genet 71, 1195-9 (2002).
20. Boube, M., Llimargas, M. & Casanova, J. Cross-regulatory interactions among tracheal genes support a co-operative model for the induction of tracheal fates in the *Drosophila* embryo. Mech Dev 91, 271-8 (2000).
21. Mollereau, B. et al. Two-step process for photoreceptor formation in *Drosophila*. Nature 412, 911-3 (2001).
22. Ma, Y. et al. Cloning and characterization of two promoters for the human HSAL2 gene and their transcriptional repression by the Wilms tumor suppressor gene product. J Biol Chem 276, 48223-30 (2001).
23. Ma, Y. et al. SALL1 expression in the human pituitary-adrenal/gonadal axis. J Endocrinol 173, 437-48 (2002).
24. Ma, Y. et al. Hsal 1 is related to kidney and gonad development and is expressed in Wilms tumor. Pediatr Nephrol 16, 701-9 (2001).
25. Marlin, S. et al. Townes-Brocks syndrome: detection of a SALL1 mutation hot spot and evidence for a position effect in one patient. Hum Mutat 14, 377-86 (1999).
26. Nishinakamura, R. et al. Murine homolog of SALL1 is essential for ureteric bud invasion in kidney development. Development 128, 3105-15 (2001).
27. Kohlhase, J. et al. Mutations at the SALL4 locus on chromosome 20 result in a range of clinically overlapping phenotypes, including Okihiro syndrome, Holt-Oram syndrome, acro-renal-ocular syndrome, and patients previously reported to represent thalidomide embryopathy. J Med Genet 40, 473-8 (2003).
28. Kuhnlein, R. P. et al. spalt encodes an evolutionarily conserved zinc finger protein of novel structure which provides homeotic gene function in the head and tail region of the *Drosophila* embryo. Embo J 13, 168-79 (1994).

29. Llimargas, M. Wingless and its signalling pathway have common and separable functions during tracheal development. Development 127, 4407-17 (2000).
30. Sato, A. et al. Sall1, a causative gene for Townes-Brocks syndrome, enhances the canonical Wnt signaling by localizing to heterochromatin. Biochem Biophys Res Commun 319, 103-13 (2004).
31. Arroyo, J. L. et al. Impact of immunophenotype on prognosis of patients with myelodysplastic syndromes. Its value in patients without karyotypic abnormalities. Hematol J 5, 227-33 (2004).
32. Buonamici, S. et al. EVI1 induces myelodysplastic syndrome in mice. J Clin Invest 114, 713-9 (2004).
33. Cuenco, G. M., Nucifora, G. & Ren, R. Human AML1/MDS1/EVI1 fusion protein induces an acute myelogenous leukemia (AML) in mice: a model for human AML. Proc Natl Acad Sci USA 97, 1760-5 (2000).
34. Lin, Y. W., Slape, C., Zhang, Z. & Aplan, P. D. NUP98-HOXD13 transgenic mice develop a highly penetrant, severe myelodysplastic syndrome that progresses to acute leukemia. Blood 106, 287-95 (2005).
35. Marisavljevic, D. et al. Biological and clinical significance of clonogenic assays in patients with myelodysplastic syndromes. Med Oncol 19, 249-59 (2002).
36. Cullen, D. A., Killick, R., Leigh, P. N. & Gallo, J. M. The effect of polyglutamine expansion in the human androgen receptor on its ability to suppress beta-catenin-Tcf/Lef dependent transcription. Neurosci Lett 354, 54-8 (2004).
37. Dong, Y. et al. Wnt-mediated regulation of chondrocyte maturation: modulation by TGF-beta. J Cell Biochem 95, 1057-68 (2005).
38. Esufali, S. & Bapat, B. Cross-talk between Rac1 GTPase and dysregulated Wnt signaling pathway leads to cellular redistribution of beta-catenin and TCF/LEF mediated transcriptional activation. Oncogene 23, 8260-71 (2004).
39. Holmen, S. L., Salic, A., Zylstra, C. R., Kirschner, M. W. & Williams, B. O. A novel set of Wnt-Frizzled fusion proteins identifies receptor components that activate beta-catenin-dependent signaling. J Biol Chem 277, 34727-35 (2002).
40. Merdek, K. D., Nguyen, N. T. & Toksoz, D. Distinct activities of the alpha-catenin family, alpha-catulin and alpha-catenin, on beta-catenin-mediated signaling. Mol Cell Biol 24, 2410-22 (2004).
41. You, L. et al. Inhibition of Wnt-2-mediated signaling induces programmed cell death in non-small-cell lung cancer cells. Oncogene 23, 6170-4 (2004).
42. Warner, D. R., Greene, R. M. & Pisano, M. M. Cross-talk between the TGFbeta and Wnt signaling pathways in murine embryonic maxillary mesenchymal cells. FEBS Lett 579, 3539-46 (2005).
43. Ribeiro, C., Neumann, M. & Affolter, M. Genetic control of cell intercalation during tracheal morphogenesis in *Drosophila*. Curr Biol 14, 2197-207 (2004).

Although the invention has been described with reference to the above examples, it will be understood that modifications and variations are encompassed within the spirit and scope of the invention. Accordingly, the invention is limited only by the following claims.

What is claimed is:

1. A method of diagnosing a myelodysplastic syndrome (MDS) in a subject comprising:
   (a) providing a biological sample from the subject;
   (b) contacting the biological sample with an antibody which binds to a polypeptide comprising an amino acid sequence as set forth in SEQ ID NO: 2, SEQ ID NO: 4, or SEQ ID NO: 6; and
   (c) detecting the binding of the antibody to the sample, wherein detecting binding correlates with MDS.

2. A method of diagnosing acute myeloid leukemia (AML) in a subject comprising:
   (a) providing a biological sample from the subject;
   (b) contacting the biological sample with an antibody which binds to a polypeptide comprising an amino acid sequence as set forth in SEQ ID NO: 2, SEQ ID NO: 4, or SEQ ID NO: 6; and
   (c) detecting the binding of the antibody to the sample, wherein detecting binding correlates with AML.

3. The method of claim 2, wherein the polypeptide comprising an amino acid sequence as set forth in SEQ ID NO: 2.

4. The method of claim 2, wherein the polypeptide comprising an amino acid sequence as set forth in SEQ ID NO: 4.

5. The method of claim 2, wherein the polypeptide comprising an amino acid sequence as set forth in SEQ ID NO: 6.

* * * * *

UNITED STATES PATENT AND TRADEMARK OFFICE
CERTIFICATE OF CORRECTION

| | | |
|---|---|---|
| PATENT NO. | : 7,790,407 B2 | Page 1 of 1 |
| APPLICATION NO. | : 11/606619 | |
| DATED | : September 7, 2010 | |
| INVENTOR(S) | : Yupo Ma | |

It is certified that error appears in the above-identified patent and that said Letters Patent is hereby corrected as shown below:

In the Specification

- In paragraph 2 at column 1, line 16, delete the words "in part"

- In paragraph 2 at column 1, line 19, replace "this" with "the"

Signed and Sealed this
Thirteenth Day of May, 2014

Michelle K. Lee
*Deputy Director of the United States Patent and Trademark Office*

SEQUENCE LISTING

```
<160> NUMBER OF SEQ ID NOS: 29

<210> SEQ ID NO 1
<211> LENGTH: 3162
<212> TYPE: DNA
<213> ORGANISM: Homo sapiens

<400> SEQUENCE: 1
atgtcgaggc gcaagcaggc gaaacccag cacatcaact cggaggagga ccagggcgag      60
cagcagccgc agcagcagac cccggagttt gcagatgcgg ccccagcggc gcccgcggcg     120
ggggagctgg gtgctccagt gaaccaccca gggaatgacg aggtggcgag tgaggatgaa     180
gccacagtaa agcggcttcg tcgggaggag acgcacgtct gtgagaaatg ctgtgcgag     240 ttcttcagca tctctgagtt cctggaacat aagaaaaatt gcactaaaaa tccacctgtc     300
ctcatcatga atgacagcga ggggcctgtg ccttcagaag acttctccgg agctgtactg     360
agccaccagc ccaccagtcc cggcagtaag gactgtcaca gggagaatgg cggcagctca     420
gaggacatga aggagaagcc ggatgcggag tctgtggtgt acctaaagac agagacagcc     480
ctgccaccca ccccccagga cataagctat ttagccaaag gcaaagtggc caacactaat     540
gtgaccttgc aggcactacg gggcaccaag gtggcggtga atcagcggag cgcggatgca     600
ctccctgccc ccgtgcctgg tgccaacagc atcccgtggg tcctcgagca gatcttgtgt     660
ctgcagcagc agcagctaca gcagatccag ctcaccgagc agatccgcat ccaggtgaac     720
atgtgggcct cccacgccct ccactcaagc ggggcagggg ccgacactct gaagaccttg     780
ggcagccaca tgtctcagca ggtttctgca gctgtggctt tgctcagcca gaaagctgga     840
```

```
agccaaggtc tgtctctgga tgccttgaaa caagccaagc tacctcacgc caacatccct    900
tctgccacca gctccctgtc cccagggctg gcaccttca ctctgaagcc ggatgggacc    960
cgggtgctcc cgaacgtcat gtcccgcctc ccgagcgctt tgcttcctca ggccccgggc   1020
tcggtgctct tccagagccc tttctccact gtggcgctag acacatccaa gaaagggaag   1080
gggaagccac cgaacatctc cgcggtggat gtcaaaccca agacgaggc ggccctctac    1140
aagcacaagt gtaagtactg tagcaaggtt tttgggactg atagctcctt gcagatccac   1200
ctccgctccc acactggaga gagcccttc gtgtgctctg tctgtggtca tcgcttcacc    1260
accaagggca acctcaaggt gcactttcac cgacatcccc aggtgaaggc aaaccccag    1320
ctgtttgccg agttccagga caagtggcg gccggcaatg gcatccccta tgcactctct    1380
gtacctgacc ccatagatga accgagtctt tctttagaca gcaaacctgt ccttgtaacc   1440
acctctgtag ggctacctca gaatctttct tcggggacta atcccaagga cctcacgggt   1500
ggctccttgc ccggtgacct gcagcctggg ccttctccag aaagtgaggg tggacccaca   1560
ctccctgggg tgggaccaaa ctataattcc ccaagggctg gtggcttcca agggagtggg   1620
acccctgagc cagggtcaga gaccctgaaa ttgcagcagt tggtggagaa cattgacaag   1680
gccaccactg atcccaacga atgtctcatt tgccaccgag tcttaagctg tcagagctcc   1740
ctcaagatgc attatcgcac ccacaccggg gagagaccgt tccagtgtaa gatctgtggc   1800
cgagccttt ctaccaaagg taacctgaag acacaccttg gggttcaccg aaccaacaca    1860
tccattaaga cgcagcattc gtgccccatc tgccagaaga agttcactaa tgccgtgatg   1920
ctgcagcaac atattcggat gcacatgggc ggtcagattc ccaacacgcc cctgccagag   1980
aatccctgtg actttacggg ttctgagcca atgaccgtgg gtgagaacgg cagcaccggc   2040
gctatctgcc atgatgatgt catcgaaagc atcgatgtag aggaagtcag ctcccaggag   2100
gctcccagca gctcctccaa ggtccccacg cctcttccca gcatccactc ggcatcaccc   2160
acgctagggt ttgccatgat ggcttcctta gatgccccag ggaaagtggg tcctgcccct   2220
tttaacctgc agcgccaggg cagcagagaa acggttccg tggagagcga tggcttgacc    2280
aacgactcat cctcgctgat gggagaccag gagtatcaga gccgaagccc agatatcctg   2340
gaaaccacat ccttccaggc actctccccg gccaatagtc aagccgaaag catcaagtca   2400
aagtctcccg atgctgggag caaagcagag agctccgaga acagccgcac tgagatggaa   2460
ggtcggagca gtcccccttc cacgtttatc cgagccccgc cgacctatgt caaggttgaa   2520
gttcctggca catttgtggg accctcgaca ttgtccccag ggatgacccc tttgttagca   2580
gcccagccac gccgacaggc caagcaacat ggctgcacac ggtgtgggaa gaacttctcg   2640
tctgctagcg ctcttcagat ccacgagcgg actcacactg gagagaagcc ttttgtgtgc   2700
aacatttgtg ggcgagcttt taccaccaaa ggcaacttaa aggttcacta catgacacac   2760
ggggcgaaca ataactcagc ccgccgtgga aggaagttgg ccatcgagaa caccatggct   2820
ctgttaggta cggacggaaa aagagtctca gaaatctttc caaggaaat cctggccct     2880
tcagtgaatg tggaccctgt tgtgtggaac cagtacacca gcatgctcaa tggcggtctg   2940
gccgtgaaga ccaatgagat ctctgtgatc cagagtgggg gggttcctac cctcccggtt   3000
tccttggggg ccacctccgt tgtgaataac gccactgtct ccaagatgga tggctcccag   3060
tcgggtatca gtgcagatgt ggaaaaacca agtgctactg acggcgttcc caaacaccag   3120
tttcctcact tcctggaaga aaacaagatt gcggtcagct aa                      3162
```

<210> SEQ ID NO 2
<211> LENGTH: 1053
<212> TYPE: PRT
<213> ORGANISM: Homo sapiens

<400> SEQUENCE: 2

```
Met Ser Arg Arg Lys Gln Ala Lys Pro Gln His Ile Asn Ser Glu Glu
1               5                   10                  15

Asp Gln Gly Glu Gln Gln Pro Gln Gln Gln Thr Pro Glu Phe Ala Asp
                20                  25                  30

Ala Ala Pro Ala Ala Pro Ala Ala Gly Glu Leu Gly Ala Pro Val Asn
            35                  40                  45

His Pro Gly Asn Asp Glu Val Ala Ser Glu Asp Glu Ala Thr Val Lys
    50                  55                  60

Arg Leu Arg Arg Glu Glu Thr His Val Cys Glu Lys Cys Cys Ala Glu
65                  70                  75                  80

Phe Phe Ser Ile Ser Glu Phe Leu Glu His Lys Lys Asn Cys Thr Lys
                85                  90                  95

Asn Pro Pro Val Leu Ile Met Asn Asp Ser Glu Gly Pro Val Pro Ser
                100                 105                 110

Glu Asp Phe Ser Gly Ala Val Leu Ser His Gln Pro Thr Ser Pro Gly
            115                 120                 125

Ser Lys Asp Cys His Arg Glu Asn Gly Gly Ser Ser Glu Asp Met Lys
    130                 135                 140

Glu Lys Pro Asp Ala Glu Ser Val Val Tyr Leu Lys Thr Glu Thr Ala
145                 150                 155                 160

Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
            180                 185                 190

Val Asn Gln Arg Ser Ala Asp Ala Leu Pro Ala Pro Val Pro Gly Ala
    195                 200                 205

Asn Ser Ile Pro Trp Val Leu Glu Gln Ile Leu Cys Leu Gln Gln Gln
210                 215                 220

Gln Leu Gln Gln Ile Gln Leu Thr Glu Gln Ile Arg Ile Gln Val Asn
225                 230                 235                 240

Met Trp Ala Ser His Ala Leu His Ser Ser Gly Ala Gly Ala Asp Thr
                245                 250                 255

Leu Lys Thr Leu Gly Ser His Met Ser Gln Gln Val Ser Ala Ala Val
            260                 265                 270

Ala Leu Leu Ser Gln Lys Ala Gly Ser Gln Gly Leu Ser Leu Asp Ala
    275                 280                 285

Leu Lys Gln Ala Lys Leu Pro His Ala Asn Ile Pro Ser Ala Thr Ser
290                 295                 300

Ser Leu Ser Pro Gly Leu Ala Pro Phe Thr Leu Lys Pro Asp Gly Thr
305                 310                 315                 320

Arg Val Leu Pro Asn Val Met Ser Arg Leu Pro Ser Ala Leu Leu Pro
                325                 330                 335

Gln Ala Pro Gly Ser Val Leu Phe Gln Ser Pro Phe Ser Thr Val Ala
            340                 345                 350

Leu Asp Thr Ser Lys Lys Gly Lys Gly Lys Pro Pro Asn Ile Ser Ala
    355                 360                 365

Val Asp Val Lys Pro Lys Asp Glu Ala Ala Leu Tyr Lys His Lys Cys
370                 375                 380
```

```
Lys Tyr Cys Ser Lys Val Phe Gly Thr Asp Ser Ser Leu Gln Ile His
385                 390                 395                 400

Leu Arg Ser His Thr Gly Glu Arg Pro Phe Val Cys Ser Val Cys Gly
            405                 410                 415

His Arg Phe Thr Thr Lys Gly Asn Leu Lys Val His Phe His Arg His
        420                 425                 430

Pro Gln Val Lys Ala Asn Pro Gln Leu Phe Ala Glu Phe Gln Asp Lys
            435                 440                 445

Val Ala Ala Gly Asn Gly Ile Pro Tyr Ala Leu Ser Val Pro Asp Pro
    450                 455                 460

Ile Asp Glu Pro Ser Leu Ser Leu Asp Ser Lys Pro Val Leu Val Thr
465                 470                 475                 480

Thr Ser Val Gly Leu Pro Gln Asn Leu Ser Ser Gly Thr Asn Pro Lys
                485                 490                 495

Asp Leu Thr Gly Gly Ser Leu Pro Gly Asp Leu Gln Pro Gly Pro Ser
            500                 505                 510

Pro Glu Ser Glu Gly Gly Pro Thr Leu Pro Gly Val Gly Pro Asn Tyr
            515                 520                 525

Asn Ser Pro Arg Ala Gly Gly Phe Gln Gly Ser Gly Thr Pro Glu Pro
    530                 535                 540

Gly Ser Glu Thr Leu Lys Leu Gln Gln Leu Val Glu Asn Ile Asp Lys
545                 550                 555                 560

Ala Thr Thr Asp Pro Asn Glu Cys Leu Ile Cys His Arg Val Leu Ser
                565                 570                 575

Cys Gln Ser Ser Leu Lys Met His Tyr Arg Thr His Thr Gly Glu Arg
            580                 585                 590

Pro Phe Gln Cys Lys Ile Cys Gly Arg Ala Phe Ser Thr Lys Gly Asn
            595                 600                 605

Leu Lys Thr His Leu Gly Val His Arg Thr Asn Thr Ser Ile Lys Thr
    610                 615                 620

Gln His Ser Cys Pro Ile Cys Gln Lys Lys Phe Thr Asn Ala Val Met
625                 630                 635                 640

Leu Gln Gln His Ile Arg Met His Met Gly Gly Gln Ile Pro Asn Thr
                645                 650                 655

Pro Leu Pro Glu Asn Pro Cys Asp Phe Thr Gly Ser Glu Pro Met Thr
            660                 665                 670

Val Gly Glu Asn Gly Ser Thr Gly Ala Ile Cys His Asp Asp Val Ile
        675                 680                 685

Glu Ser Ile Asp Val Glu Glu Val Ser Ser Gln Glu Ala Pro Ser Ser
    690                 695                 700

Ser Ser Lys Val Pro Thr Pro Leu Pro Ser Ile His Ser Ala Ser Pro
705                 710                 715                 720

Thr Leu Gly Phe Ala Met Met Ala Ser Leu Asp Ala Pro Gly Lys Val
                725                 730                 735

Gly Pro Ala Pro Phe Asn Leu Gln Arg Gln Gly Ser Arg Glu Asn Gly
            740                 745                 750

Ser Val Glu Ser Asp Gly Leu Thr Asn Asp Ser Ser Ser Leu Met Gly
        755                 760                 765

Asp Gln Glu Tyr Gln Ser Arg Ser Pro Asp Ile Leu Glu Thr Thr Ser
    770                 775                 780

Phe Gln Ala Leu Ser Pro Ala Asn Ser Gln Ala Glu Ser Ile Lys Ser
785                 790                 795                 800
```

```
Lys Ser Pro Asp Ala Gly Ser Lys Ala Glu Ser Ser Glu Asn Ser Arg
                805                 810                 815

Thr Glu Met Glu Gly Arg Ser Ser Leu Pro Ser Thr Phe Ile Arg Ala
            820                 825                 830

Pro Pro Thr Tyr Val Lys Val Glu Val Pro Gly Thr Phe Val Gly Pro
                835                 840                 845

Ser Thr Leu Ser Pro Gly Met Thr Pro Leu Leu Ala Ala Gln Pro Arg
    850                 855                 860

Arg Gln Ala Lys Gln His Gly Cys Thr Arg Cys Gly Lys Asn Phe Ser
865                 870                 875                 880

Ser Ala Ser Ala Leu Gln Ile His Glu Arg Thr His Thr Gly Glu Lys
                885                 890                 895

Pro Phe Val Cys Asn Ile Cys Gly Arg Ala Phe Thr Thr Lys Gly Asn
            900                 905                 910

Leu Lys Val His Tyr Met Thr His Gly Ala Asn Asn Asn Ser Ala Arg
        915                 920                 925

Arg Gly Arg Lys Leu Ala Ile Glu Asn Thr Met Ala Leu Leu Gly Thr
    930                 935                 940

Asp Gly Lys Arg Val Ser Glu Ile Phe Pro Lys Glu Ile Leu Ala Pro
945                 950                 955                 960

Ser Val Asn Val Asp Pro Val Val Trp Asn Gln Tyr Thr Ser Met Leu
                965                 970                 975

Asn Gly Gly Leu Ala Val Lys Thr Asn Glu Ile Ser Val Ile Gln Ser
            980                 985                 990

Gly Gly Val Pro Thr Leu Pro Val  Ser Leu Gly Ala Thr  Ser Val Val
        995                 1000                1005

Asn Asn  Ala Thr Val Ser Lys  Met Asp Gly Ser Gln  Ser Gly Ile
    1010                1015                1020

Ser Ala Asp Val Glu Lys Pro  Ser Ala Thr Asp Gly  Val Pro Lys
    1025                1030                1035

His Gln  Phe Pro His Phe Leu  Glu Glu Asn Lys Ile  Ala Val Ser
    1040                1045                1050

<210> SEQ ID NO 3
<211> LENGTH: 1851
<212> TYPE: DNA
<213> ORGANISM: Homo sapiens
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
<220> FEATURE:
<221> NAME/KEY: misc_feature
<222> LOCATION: (1331)..(1331)
<223> OTHER INFORMATION: n is a, c, g, or t
<220> FEATURE:
<221> NAME/KEY: misc_feature
<222> LOCATION: (1334)..(1334)
<223> OTHER INFORMATION: n is a, c, g, or t
<220> FEATURE:
<221> NAME/KEY: misc_feature
```

<222> LOCATION: (1367)..(1367)
<223> OTHER INFORMATION: n is a, c, g, or t
<220> FEATURE:
<221> NAME/KEY: misc_feature
<222> LOCATION: (1805)..(1805)
<223> OTHER INFORMATION: n is a, c, g, or t
<220> FEATURE:
<221> NAME/KEY: misc_feature
<222> LOCATION: (1838)..(1838)
<223> OTHER INFORMATION: n is a, c, g, or t

<400> SEQUENCE: 3

| | | | | | |
|---|---|---|---|---|---|
| atgtcgaggc | gcaagcaggc | gaaacccag | cacatcaact | cggaggagga | ccagggcgag | 60 |
| cagcagccgc | agcagcagac | cccggagttt | gcagatgcgg | ccccagcggc | gcccgcggcg | 120 |
| ggggagctgg | gtgctccagt | gaaccaccca | gggaatgacg | aggtggcgag | tgaggatgaa | 180 |
| gccacagtaa | agcggcttcg | tcgggaggag | acgcacgtct | gtgagaaatg | ctgtgcggag | 240 |
| ttcttcagca | tctctgagtt | cctggaacat | aagaaaaatt | gcactaaaaa | tccacctgtc | 300 |
| ctcatcatga | atgacagcga | ggggcctgtg | ccttcanaag | acttctccgg | agctgtactg | 360 |
| agccaccagc | ccaccagtcc | cggcagtgag | gactgtcaca | gggagaatgg | cggcagctca | 420 |
| naggacataa | aggagaagcc | ggatgcggag | tctgtggtgt | acctaaagac | agagacagcc | 480 |
| ctgccaccca | cccccagga | cataagctat | ttagccaaag | gcaaagtggc | caacactaac | 540 |
| gtgaccttgc | aggcactacg | gggcaccaag | gtggcggtga | atcagcggag | cgcggatgca | 600 |
| ctccctgccc | ccgtgcctgg | tgccaacagc | atcccgtggg | tcctcagcha | gatcttgtgt | 660 |
| ctgcagcagc | agcagctaca | gcagatccag | ctcaccgagc | agatccgcat | ccaggtgaac | 720 |
| atgtgggcct | cccacgccct | ccactcaagc | ggggcagggg | ccgacactct | gaagaccttg | 780 |
| ggcagccaca | tgtctcagca | ggtttctgca | gctgtggctt | tgctcagcca | gaaagctgga | 840 |
| agccaaggtc | tgtctctgga | tgccttgaaa | caagccaagc | tacctcacgc | caacatccct | 900 |
| tctgccacca | gctccctgtc | cccagggctg | gcacccttca | ctctgaagcc | ggatgggacc | 960 |
| cgggtgctcc | cgaacgtcat | gtcccgcctc | ccgagcgctt | gcttcctca | ggccccgggc | 1020 |
| tcggtgctct | tccagagccc | tttctccact | gtggcgctag | acacatccaa | gaaagggaag | 1080 |
| gggaagccac | cgaacatctc | cgcggtggat | gtcaaaccca | aagacgaggc | ggccctctac | 1140 |
| aagcacaagt | gtcggagcag | tctcccttcc | acgtttatcc | gagccccgcc | gacctatgtc | 1200 |
| aaggttgaag | ttcctggcac | atttgtggga | ccctcgacat | tgtccccagg | gatgacccct | 1260 |
| tgttagcag | cccagccacg | cggacaggcc | aagcaacatg | gctgcacacg | gtgtggnaag | 1320 |
| aacttntcgt | ntgntagcgc | tcttcagatc | cacgagcgga | ctcacantgg | agagaagcct | 1380 |
| tttgtgtgca | acatttgtgg | gcgagctttt | accaccaaag | gcaacttaaa | ggttcactac | 1440 |
| atgacacacg | gggcgaacaa | taactcagcc | cgccgtggaa | ggaagttggc | catcgagaac | 1500 |
| accatggctc | tgttaggtac | ggacggaaaa | agagtctcag | aaatctttcc | caaggaaatc | 1560 |
| ctggccccctt | cagtgaatgt | ggaccctgtt | gtgtggaacc | agtacaccag | catgctcaat | 1620 |
| ggcggtctgg | ccgtgaagac | caatgagatc | tctgtgatcc | agagtggggg | ggttcctacc | 1680 |
| ctcccggttt | ccttggggc | cacctccgtt | gtgaataacg | ccactgtctc | caagatggat | 1740 |
| ggctcccagt | cgggtatcag | tgcagatgtg | gaaaaaccaa | gtgctactga | cggcgttccc | 1800 |
| aaacnccagt | ttcctcactt | cctggaagaa | aacaagantg | cggtcagcta | a | 1851 |

<210> SEQ ID NO 4
<211> LENGTH: 616
<212> TYPE: PRT

```
<213> ORGANISM: Homo sapiens
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (444)..(445)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (602)..(602)
<223> OTHER INFORMATION: Xaa can be any naturally occurring amino acid
<220> FEATURE:
<221> NAME/KEY: misc_feature
<222> LOCATION: (613)..(613)
<223> OTHER INFORMATION: Xaa can be any naturally occurring amino acid

<400> SEQUENCE: 4

Met Ser Arg Arg Lys Gln Ala Lys Pro Gln His Ile Asn Ser Glu Glu
  1               5                  10                  15

Asp Gln Gly Glu Gln Gln Pro Gln Gln Thr Pro Glu Phe Ala Asp
             20                  25                  30

Ala Ala Pro Ala Ala Pro Ala Gly Glu Leu Gly Ala Pro Val Asn
         35                  40                  45

His Pro Gly Asn Asp Glu Val Ala Ser Glu Asp Glu Ala Thr Val Lys
 50                  55                  60

Arg Leu Arg Arg Glu Glu Thr His Val Cys Glu Lys Cys Cys Ala Glu
 65                  70                  75                  80

Phe Phe Ser Ile Ser Glu Phe Leu Glu His Lys Lys Asn Cys Thr Lys
             85                  90                  95

Asn Pro Pro Val Leu Ile Met Asn Asp Ser Glu Gly Pro Val Pro Ser
        100                 105                 110

Xaa Asp Phe Ser Gly Ala Val Leu Ser His Gln Pro Thr Ser Pro Gly
        115                 120                 125

Ser Glu Asp Cys His Arg Glu Asn Gly Gly Ser Ser Xaa Asp Ile Lys
        130                 135                 140

Glu Lys Pro Asp Ala Glu Ser Val Val Tyr Leu Lys Thr Glu Thr Ala
145                 150                 155                 160

Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
            180                 185                 190

Val Asn Gln Arg Ser Ala Asp Ala Leu Pro Ala Pro Val Pro Gly Ala
        195                 200                 205

Asn Ser Ile Pro Trp Val Leu Glu Gln Ile Leu Cys Leu Gln Gln Gln
        210                 215                 220

Gln Leu Gln Gln Ile Gln Leu Thr Glu Gln Ile Arg Ile Gln Val Asn
225                 230                 235                 240

Met Trp Ala Ser His Ala Leu His Ser Ser Gly Ala Gly Ala Asp Thr
                245                 250                 255
```

Leu Lys Thr Leu Gly Ser His Met Ser Gln Gln Val Ser Ala Ala Val
            260                 265                 270

Ala Leu Leu Ser Gln Lys Ala Gly Ser Gln Gly Leu Ser Leu Asp Ala
        275                 280                 285

Leu Lys Gln Ala Lys Leu Pro His Ala Asn Ile Pro Ser Ala Thr Ser
    290                 295                 300

Ser Leu Ser Pro Gly Leu Ala Pro Phe Thr Leu Lys Pro Asp Gly Thr
305                 310                 315                 320

Arg Val Leu Pro Asn Val Met Ser Arg Leu Pro Ser Ala Leu Leu Pro
                325                 330                 335

Gln Ala Pro Gly Ser Val Leu Phe Gln Ser Pro Phe Ser Thr Val Ala
                340                 345                 350

Leu Asp Thr Ser Lys Lys Gly Lys Gly Lys Pro Pro Asn Ile Ser Ala
            355                 360                 365

Val Asp Val Lys Pro Lys Asp Glu Ala Ala Leu Tyr Lys His Lys Cys
        370                 375                 380

Arg Ser Ser Leu Pro Ser Thr Phe Ile Arg Ala Pro Pro Thr Tyr Val
385                 390                 395                 400

Lys Val Glu Val Pro Gly Thr Phe Val Gly Pro Ser Thr Leu Ser Pro
                405                 410                 415

Gly Met Thr Pro Leu Leu Ala Ala Gln Pro Arg Gly Gly Ala Lys Gln
            420                 425                 430

His Gly Cys Thr Arg Cys Gly Lys Asn Xaa Ser Xaa Xaa Ser Ala Leu
        435                 440                 445

Gln Ile His Glu Arg Thr His Xaa Gly Glu Lys Pro Phe Val Cys Asn
    450                 455                 460

Ile Cys Gly Arg Ala Phe Thr Thr Lys Gly Asn Leu Lys Val His Tyr
465                 470                 475                 480

Met Thr His Gly Ala Asn Asn Asn Ser Ala Arg Arg Gly Arg Lys Leu
                485                 490                 495

Ala Ile Glu Asn Thr Met Ala Leu Leu Gly Thr Asp Gly Lys Arg Val
            500                 505                 510

Ser Glu Ile Phe Pro Lys Glu Ile Leu Ala Pro Ser Val Asn Val Asp
        515                 520                 525

Pro Val Val Trp Asn Gln Tyr Thr Ser Met Leu Asn Gly Gly Leu Ala
    530                 535                 540

Val Lys Thr Asn Glu Ile Ser Val Ile Gln Ser Gly Gly Val Pro Thr
545                 550                 555                 560

Leu Pro Val Ser Leu Gly Ala Thr Ser Val Val Asn Asn Ala Thr Val
                565                 570                 575

Ser Lys Met Asp Gly Ser Gln Ser Gly Ile Ser Ala Asp Val Glu Lys
            580                 585                 590

Pro Ser Ala Thr Asp Gly Val Pro Lys Xaa Gln Phe Pro His Phe Leu
        595                 600                 605

Glu Glu Asn Lys Xaa Ala Val Ser
    610                 615

<210> SEQ ID NO 5
<211> LENGTH: 831
<212> TYPE: DNA
<213> ORGANISM: Homo sapiens

<400> SEQUENCE: 5
atgtcgaggc gcaagcaggc gaaaccccag cacatcaact cggaggagga ccagggcgag     60

-continued

```
cagcagccgc agcagcagac cccggagttt gcagatgcgg ccccagcggc gcccgcggcg    120
ggggagctgg gtcggagcag tctcccttcc acgtttatcc gagccccgcc gacctatgtc    180
aaggttgaag ttcctggcac atttgtggga ccctcgacat tgtccccagg gatgaccccct   240 tgttagcag cccagccacg ccgacaggcc aagcaacatg gctgcacacg tgtgggaag      300 aacttctcgt ctgctagcgc tcttcagatc cacgagcgga ctcacactgg agagaagcct   360
tttgtgtgca acatttgtgg gcgagctttt accaccaaag gcaacttaaa ggttcactac    420
atgacacacg gggcgaacaa taactcagcc cgccgtggaa ggaagttggc catcgagaac    480
accatggctc tgttaggtac ggacggaaaa agagtctcag aaatctttcc caaggaaatc    540 ctggccccctt cagtgaatgt ggaccctgtt gtgtggaacc agtacaccag catgctcaat   600
ggcggtctgg ccgtgaagac caatgagatc tctgtgatcc agagtggggg ggttcctacc   660
ctcccggttt ccttgggggc cacctccgtt gtgaataacg ccactgtctc caagatggat   720
ggctcccagt cgggtatcag tgcagatgtg gaaaaaccaa gtgctactga cggcgttccc   780
aaacaccagt ttcctcactt cctggaagaa aacaagattg cggtcagcta a             831
```

```
<210> SEQ ID NO 6
<211> LENGTH: 276
<212> TYPE: PRT
<213> ORGANISM: Homo sapiens

<400> SEQUENCE: 6
```

```
Met Ser Arg Arg Lys Gln Ala Lys Pro Gln His Ile Asn Ser Glu Glu
1               5                   10                  15

Asp Gln Gly Glu Gln Gln Pro Gln Gln Gln Thr Pro Glu Phe Ala Asp
            20                  25                  30

Ala Ala Pro Ala Ala Pro Ala Ala Gly Glu Leu Gly Arg Ser Ser Leu
        35                  40                  45

Pro Ser Thr Phe Ile Arg Ala Pro Pro Thr Tyr Val Lys Val Glu Val
    50                  55                  60

Pro Gly Thr Phe Val Gly Pro Ser Thr Leu Ser Pro Gly Met Thr Pro
65                  70                  75                  80

Leu Leu Ala Ala Gln Pro Arg Arg Gln Ala Lys Gln His Gly Cys Thr
                85                  90                  95

Arg Cys Gly Lys Asn Phe Ser Ser Ala Ser Ala Leu Gln Ile His Glu
            100                 105                 110

Arg Thr His Thr Gly Glu Lys Pro Phe Val Cys Asn Ile Cys Gly Arg
        115                 120                 125

Ala Phe Thr Thr Lys Gly Asn Leu Lys Val His Tyr Met Thr His Gly
    130                 135                 140

Ala Asn Asn Asn Ser Ala Arg Arg Gly Arg Lys Leu Ala Ile Glu Asn
145                 150                 155                 160

Thr Met Ala Leu Leu Gly Thr Asp Gly Lys Arg Val Ser Glu Ile Phe
                165                 170                 175

Pro Lys Glu Ile Leu Ala Pro Ser Val Asn Val Asp Pro Val Val Trp
            180                 185                 190

Asn Gln Tyr Thr Ser Met Leu Asn Gly Gly Leu Ala Val Lys Thr Asn
        195                 200                 205

Glu Ile Ser Val Ile Gln Ser Gly Gly Val Pro Thr Leu Pro Val Ser
    210                 215                 220

Leu Gly Ala Thr Ser Val Val Asn Asn Ala Thr Val Ser Lys Met Asp
225                 230                 235                 240
```

Gly Ser Gln Ser Gly Ile Ser Ala Asp Val Glu Lys Pro Ser Ala Thr
            245                 250                 255

Asp Gly Val Pro Lys His Gln Phe Pro His Phe Leu Glu Glu Asn Lys
        260                 265                 270

Ile Ala Val Ser
        275

<210> SEQ ID NO 7
<211> LENGTH: 39
<212> TYPE: DNA
<213> ORGANISM: Artificial sequence
<220> FEATURE:
<223> OTHER INFORMATION: Primer

<400> SEQUENCE: 7
ttatcaggat cctggtcgag gcgcaagcag gcgaaaccc                        39

<210> SEQ ID NO 8
<211> LENGTH: 33
<212> TYPE: DNA
<213> ORGANISM: Artificial sequence
<220> FEATURE:
<223> OTHER INFORMATION: Primer

<400> SEQUENCE: 8
ccaggatcct tagctgaccg ccaatcttgt ttc                              33

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
attggcaccg gcagttacca cc                                          22

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
agtactcgtg ggcatattgt c                                           21

<210> SEQ ID NO 11
<211> LENGTH: 25
<212> TYPE: DNA
<213> ORGANISM: Artificial sequence
<220> FEATURE:
<223> OTHER INFORMATION: Primer

<400> SEQUENCE: 11
atgtcgaggc gcaagcaggc gaaac                                       25

<210> SEQ ID NO 12
<211> LENGTH: 25
<212> TYPE: DNA
<213> ORGANISM: Artificial sequence
<220> FEATURE:
<223> OTHER INFORMATION: Primer

<400> SEQUENCE: 12

```
ttagctgacc gcaatcttgt tttct                                            25

<210> SEQ ID NO 13
<211> LENGTH: 13
<212> TYPE: PRT
<213> ORGANISM: Homo sapiens

<400> SEQUENCE: 13

Met Ser Arg Arg Lys Gln Ala Lys Pro Gln His Ile Asn
1               5                   10

<210> SEQ ID NO 14
<211> LENGTH: 19
<212> TYPE: DNA
<213> ORGANISM: Artificial sequence
<220> FEATURE:
<223> OTHER INFORMATION: Primer

<400> SEQUENCE: 14
gaaggtgaag gtcggagtc                                                   19

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
gaagatggtg atgggatttc                                                  20

<210> SEQ ID NO 16
<211> LENGTH: 20
<212> TYPE: DNA
<213> ORGANISM: Artificial sequence
<220> FEATURE:
<223> OTHER INFORMATION: TaqMan probe

<400> SEQUENCE: 16
caagcttccc gttctcagcc                                                  20

<210> SEQ ID NO 17
<211> LENGTH: 26
<212> TYPE: DNA
<213> ORGANISM: Artificial sequence
<220> FEATURE:
<223> OTHER INFORMATION: Primer

<400> SEQUENCE: 17
cctcctaatg agagtatctg ggtgat                                           26

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
ttaaaacata cagcgcatga ttgg                                             24

<210> SEQ ID NO 19
<211> LENGTH: 24
<212> TYPE: DNA
<213> ORGANISM: Artificial sequence
```

```
<220> FEATURE:
<223> OTHER INFORMATION: Primer

<400> SEQUENCE: 19
cagagatgct gaagaactcc gcac                                           24

<210> SEQ ID NO 20
<211> LENGTH: 23
<212> TYPE: DNA
<213> ORGANISM: Artificial sequence
<220> FEATURE:
<223> OTHER INFORMATION: Primer

<400> SEQUENCE: 20
agcagagctc gtttagtgaa ccg                                            23

<210> SEQ ID NO 21
<211> LENGTH: 4668
<212> TYPE: DNA
<213> ORGANISM: Homo sapiens

<400> SEQUENCE: 21
atgtcgcgga ggaagcaagc gaagcctcaa catttccaat ccgaccccga agtggcctcg      60
ctcccccggc gagatggaga cacagaaaag ggtcaaccga gtcgccctac taagagcaag     120 gatgccacg tctgtggccg gtgctgtgcc gagttctttg aattatcaga tcttctgctc      180
cacaagaaga actgtactaa aaatcaatta gttttaatcg taaatgaaaa tccaggctcc     240
ccacccgaaa ccttctcccc cagcccccct cctgataatc ctgatgaaca aatgaatgac     300
acagttaaca aaacagatca agtggactgc agcgaccttt cagaacacaa cggacttgac     360
agggaagagt ccatggaggt ggaggccccg gttgctaaca aaagcggcag cggcacttcc     420
agcggcagcc acagcagtac cgccccaagc agcagcagca gcagcagcag cagcagcggc     480
ggcggcggca gctcctccac aggtacctca gcgatcacaa cctctctacc tcaactcggg     540
gacctgacaa cactgggcaa cttctccgta atcaacagca acgtcatcat cgagaacctc     600
cagagcacca aggtggcggt ggcccagttc tcccaggaag cgaggtgcgg cggggcctct     660
gggggcaagc tggccgtccc agccctcatg aacaactcc tagctctgca gcagcagcag      720
atccaccagc tgcaattgat cgaacagatt cgtcaccaaa tattgctgtt ggcttctcag     780
aatgcagact tgccaacatc ttctagtcct tctcaaggta ctttacgaac atctgccaac     840
cccttgtcca cgctaagttc ccatttatct cagcagctgg cagcagcagc tggattggca     900
cagagcctcg ccagccaatc tgccagcatt agtggtgtga acagctacc cccaatccag     960 ctacctcaga gcagttctgg caacaccatc attccatcca cagcggctc ttctcccaat     1020 atgaacatat ggcagcggc agttaccacc ccgtcctctg aaaaagtggc ttcaagtgct     1080
ggggcctccc atgtcagcaa cccagcggtc tcatcatcgt cctcaccagc ttttgcaata     1140
agcagtttat taagtcctgc gtctaatcca cttctacctc agcaagcctc cgctaactcg     1200
gttttcccca gcccttttgcc caacatcgga acaactgcag aggatttaaa ctccttgtct     1260
gccttggccc agcaaagaaa aagcaagcca ccaaatgtca ctgcctttga agcgaaaagt     1320
acttccgatg aggcattctt caaacacaag tgcaggttct gcgcgaaggt ctttgggagt     1380
gacagtgcct tgcagatcca cttgcgttcc cataccggag agaggccatt caagtgcaac     1440
atctgcggga acaggttctc caccaagggg aatctgaaag tccactttca gcgccacaaa     1500
gagaaatacc ctcatatcca gatgaacccc tatcctgtgc ctgagcattt ggacaatatc     1560
```

```
cccacgagta ctggcatccc atatggcatg tccatccctc cagagaagcc agtcaccagc    1620
tggctagaca ccaaaccagt cctgcctact ctgaccactt cagtcggcct gccgttgccc    1680
ccaagcctcc caagcctcat acccttcatc aagacggaag agccagcccc catccccatc    1740
agccattctg ccaccagccc cccaggctca gtcaaaagtg actccggggg ccctgagtca    1800
gccacaagaa atctaggtgg gctcccagag gaagccgaag ggtccactct gccaccctct    1860
ggtggcaaaa gcgaagagag tggcatggtc accaactcag tcccgacggc gagcagtagc    1920
gtcctgagct ccccagcggc agactgcggc ccgcgggca gtgccaccac cttcaccaac    1980
cctttgttgc cgctcatgtc cgagcagttc aaggccaagt tccttttgg gggactcctg    2040 gactcagctc aggcatcaga gacgtccaag cttcagcaac tggtagaaaa cattgacaag    2100
aaggccactg accccaatga gtgcatcatc tgtcaccggg ttctcagctg ccagagcgcc    2160
ttgaaaatgc actacaggac acacactggg gagaggccct taagtgtaa gatctgtggc    2220 cgggctttca ccacgaaagg gaatcttaaa acccactaca gtgtccatcg tgctatgccc    2280
ccgctcagag tccagcattc ctgccccatc tgccagaaga agttcacgaa cgctgtggtc    2340
ctgcagcagc acatccgaat gcatatggga ggccagatcc ccaacacccc agtccccgac    2400
agctactctg agtccatgga gtctgacaca ggttcctttg atgagaaaaa ttttgatgac    2460
ctagacaact tctctgatga aaacatggaa gactgtcctg agggcagcat ccctgataca    2520
cctaagtctg cagacgcctc ccaagacagc ttatcctctt cgccttttgcc ccttgagatg    2580 tcgagcatcg ctgctttgga aaatcagatg aagatgatca atgctggcct ggcagagcag    2640
ctacaggcca gcctgaagtc agtggagaat gggtccatcg aggggatgt cctgaccaat    2700 gattcatcct cagtgggtgg tgacatgaaa agccaaagtg ctggcagccc agccatctca    2760
gagtctacct cttccatgca ggctctgtcc ccgtccaaca gcacgcagga gttccacaag    2820
tcacccagca ttgaggagaa accacagaga gcggtcccaa gcgagtttgc caatggtttg    2880
tctcccaccc cagtgaatgg tggggctttg gatttgacat ctagtcacgc agagaaaatc    2940
atcaaagaag attctttggg gatcctcttc cctttagag accggggtaa atttaaaaac    3000
actgcttgtg acatttgtgg caaaacattt gcttgtcaga gtgccttgga cattcactat    3060
agaagtcata ccaaagagag accatttatt tgcacagttt gcaatcgtgg cttttccaca    3120
aagggtaatt tgaagcagca catgttgaca catcagatgc gagatctgcc atcccagctc    3180
tttgagccca gttccaacct tggccccaat cagaactcag cggtgattcc cgccaactcg    3240
ttgtcatctc tcatcaagac agaggtcaac ggcttcgtgc atgtttctcc tcaggacagt    3300
aaggacaccc ccaccagtca cgtcccgtct gggcctctgt cttcctctgc cacatcccca    3360
gttctgctcc ctgctctgcc caggagaact cccaagcagc actactgcaa cacatgtggc    3420
aaaaccttct cctcatcgag tgccctgcag attcacgaga gaactcacac tggagagaaa    3480
ccctttgctt gcactatttg tggaagagct ttcacgacta aagcaatct taaggtacac    3540 atgggcactc acatgtggaa tagcaccccct gcacgacggg gtcggcggct ctctgtggat    3600
ggccccatga catttctagg aggcaatccc gtcaagttcc cagaaatgtt ccagaaggat    3660
ttggcggcaa gatcaggaag tggggatcct tccagcttct ggaatcagta tgcagcagcg    3720
ctctccaacg ggctggcgat gaaggccaac gagatctccg tcattcagaa cggtggcatc    3780
cctccaattc ctggaagcct cggcagtggg aacagctcac ctattagtgg gctgacggga    3840
aacctggaga ggctccagaa ctcagagccc aatgctcccc tggccggcct ggagaaaatg    3900
gcaagcagtg agaacggaac caacttccgc ttcacccgct tcgtggagga cagcaaggag    3960
```

-continued

```
atcgtcacga gttaaagcag ctcgggctgg agacatagca ttcattcctg ttcagaatgc      4020
gacctatggt ggcctcctac tccttgcccc ccaccccgcc ccgccccttc cttctgttcc      4080
ccagatctat gaactacaac attatgaaga cattcttttg taccttgttc aactttagag      4140
ttctaagaaa gcttatttat tagcgatata accttgcttt gcaaacagaa tgcaagcgtt      4200
aactttggtc ttctgtattt tggactaaat actaattgac tagagtgctg taaacttgct      4260
gtaacattta tggcaattgc aagttgccct gctaggcagt tgtaatctgg cattaactta      4320
ttttctatat ccagtttaat atgaatctgg tgttgatgca atgcctcagt gatgcattag      4380
atctctaata aagtctgtat atacatgtac actttgatcc tgctggaaaa ttttatcagc      4440
aaacacattg tctaatcttt caaaacagat ttaaggaaag gactgaaagt acagactgaa      4500
cagtgtggtt ctttgaaagg tttggttttt taattttat tctaaaattc aacctttttt       4560
ttgtcgattt aaccatttcc attttgaact gctatttgta ttgtgctttt tacttgagtc      4620
gtcttcaatg ttaataagtt tctgtacagt aataagcacg cagaattc                   4668
```

<210> SEQ ID NO 22
<211> LENGTH: 1324
<212> TYPE: PRT
<213> ORGANISM: Homo sapiens

<400> SEQUENCE: 22

```
Met Ser Arg Arg Lys Gln Ala Lys Pro Gln His Phe Gln Ser Asp Pro
1               5                   10                  15

Glu Val Ala Ser Leu Pro Arg Arg Asp Gly Asp Thr Glu Lys Gly Gln
                20                  25                  30

Pro Ser Arg Pro Thr Lys Ser Lys Asp Ala His Val Cys Gly Arg Cys
            35                  40                  45

Cys Ala Glu Phe Phe Glu Leu Ser Asp Leu Leu Leu His Lys Lys Asn
        50                  55                  60

Cys Thr Lys Asn Gln Leu Val Leu Ile Val Asn Glu Asn Pro Gly Ser
65                  70                  75                  80

Pro Pro Glu Thr Phe Ser Pro Ser Pro Pro Asp Asn Pro Asp Glu
                85                  90                  95

Gln Met Asn Asp Thr Val Asn Lys Thr Asp Gln Val Asp Cys Ser Asp
            100                 105                 110

Leu Ser Glu His Asn Gly Leu Asp Arg Glu Glu Ser Met Glu Val Glu
        115                 120                 125

Ala Pro Val Ala Asn Lys Ser Gly Ser Gly Thr Ser Ser Gly Ser His
    130                 135                 140

Ser Ser Thr Ala Pro Ser Ser Ser Ser Ser Ser Ser Ser Ser Ser Gly
145                 150                 155                 160

Gly Gly Gly Ser Ser Ser Thr Gly Thr Ser Ala Ile Thr Thr Ser Leu
                165                 170                 175

Pro Gln Leu Gly Asp Leu Thr Thr Leu Gly Asn Phe Ser Val Ile Asn
            180                 185                 190

Ser Asn Val Ile Ile Glu Asn Leu Gln Ser Thr Lys Val Ala Val Ala
        195                 200                 205

Gln Phe Ser Gln Glu Ala Arg Cys Gly Gly Ala Ser Gly Gly Lys Leu
    210                 215                 220

Ala Val Pro Ala Leu Met Glu Gln Leu Leu Ala Leu Gln Gln Gln Gln
225                 230                 235                 240

Ile His Gln Leu Gln Leu Ile Glu Gln Ile Arg His Gln Ile Leu Leu
```

```
                245                 250                 255
Leu Ala Ser Gln Asn Ala Asp Leu Pro Thr Ser Ser Pro Ser Gln
            260                 265                 270
Gly Thr Leu Arg Thr Ser Ala Asn Pro Leu Ser Thr Leu Ser Ser His
            275                 280                 285
Leu Ser Gln Gln Leu Ala Ala Ala Gly Leu Ala Gln Ser Leu Ala
            290                 295                 300
Ser Gln Ser Ala Ser Ile Ser Gly Val Lys Gln Leu Pro Pro Ile Gln
305                 310                 315                 320
Leu Pro Gln Ser Ser Gly Asn Thr Ile Ile Pro Ser Asn Ser Gly
                325                 330                 335
Ser Ser Pro Asn Met Asn Ile Leu Ala Ala Val Thr Thr Pro Ser
                340                 345                 350
Ser Glu Lys Val Ala Ser Ser Ala Gly Ala Ser His Val Ser Asn Pro
            355                 360                 365
Ala Val Ser Ser Ser Ser Pro Ala Phe Ala Ile Ser Ser Leu Leu
            370                 375                 380
Ser Pro Ala Ser Asn Pro Leu Leu Pro Gln Gln Ala Ser Ala Asn Ser
385                 390                 395                 400
Val Phe Pro Ser Pro Leu Pro Asn Ile Gly Thr Thr Ala Glu Asp Leu
            405                 410                 415
Asn Ser Leu Ser Ala Leu Ala Gln Gln Arg Lys Ser Lys Pro Pro Asn
            420                 425                 430
Val Thr Ala Phe Glu Ala Lys Ser Thr Ser Asp Glu Ala Phe Phe Lys
            435                 440                 445
His Lys Cys Arg Phe Cys Ala Lys Val Phe Gly Ser Asp Ser Ala Leu
            450                 455                 460
Gln Ile His Leu Arg Ser His Thr Gly Glu Arg Pro Phe Lys Cys Asn
465                 470                 475                 480
Ile Cys Gly Asn Arg Phe Ser Thr Lys Gly Asn Leu Lys Val His Phe
            485                 490                 495
Gln Arg His Lys Glu Lys Tyr Pro His Ile Gln Met Asn Pro Tyr Pro
            500                 505                 510
Val Pro Glu His Leu Asp Asn Ile Pro Thr Ser Thr Gly Ile Pro Tyr
            515                 520                 525
Gly Met Ser Ile Pro Pro Glu Lys Pro Val Thr Ser Trp Leu Asp Thr
            530                 535                 540
Lys Pro Val Leu Pro Thr Leu Thr Thr Ser Val Gly Leu Pro Leu Pro
545                 550                 555                 560
Pro Ser Leu Pro Ser Leu Ile Pro Phe Ile Lys Thr Glu Glu Pro Ala
                565                 570                 575
Pro Ile Pro Ile Ser His Ser Ala Thr Ser Pro Gly Ser Val Lys
            580                 585                 590
Ser Asp Ser Gly Gly Pro Glu Ser Ala Thr Arg Asn Leu Gly Gly Leu
            595                 600                 605
Pro Glu Glu Ala Glu Gly Ser Thr Leu Pro Pro Ser Gly Gly Lys Ser
            610                 615                 620
Glu Glu Ser Gly Met Val Thr Asn Ser Val Pro Thr Ala Ser Ser Ser
625                 630                 635                 640
Val Leu Ser Ser Pro Ala Ala Asp Cys Gly Pro Ala Gly Ser Ala Thr
                645                 650                 655
Thr Phe Thr Asn Pro Leu Leu Pro Leu Met Ser Glu Gln Phe Lys Ala
                660                 665                 670
```

-continued

```
Lys Phe Pro Phe Gly Gly Leu Leu Asp Ser Ala Gln Ala Ser Glu Thr
            675                 680                 685

Ser Lys Leu Gln Gln Leu Val Glu Asn Ile Asp Lys Lys Ala Thr Asp
        690                 695                 700

Pro Asn Glu Cys Ile Ile Cys His Arg Val Leu Ser Cys Gln Ser Ala
705                 710                 715                 720

Leu Lys Met His Tyr Arg Thr His Thr Gly Glu Arg Pro Phe Lys Cys
                725                 730                 735

Lys Ile Cys Gly Arg Ala Phe Thr Thr Lys Gly Asn Leu Lys Thr His
            740                 745                 750

Tyr Ser Val His Arg Ala Met Pro Pro Leu Arg Val Gln His Ser Cys
        755                 760                 765

Pro Ile Cys Gln Lys Lys Phe Thr Asn Ala Val Val Leu Gln Gln His
770                 775                 780

Ile Arg Met His Met Gly Gly Gln Ile Pro Asn Thr Pro Val Pro Asp
785                 790                 795                 800

Ser Tyr Ser Glu Ser Met Glu Ser Asp Thr Gly Ser Phe Asp Glu Lys
                805                 810                 815

Asn Phe Asp Asp Leu Asp Asn Phe Ser Asp Glu Asn Met Glu Asp Cys
            820                 825                 830

Pro Glu Gly Ser Ile Pro Asp Thr Pro Lys Ser Ala Asp Ala Ser Gln
        835                 840                 845

Asp Ser Leu Ser Ser Ser Pro Leu Pro Leu Glu Met Ser Ser Ile Ala
850                 855                 860

Ala Leu Glu Asn Gln Met Lys Met Ile Asn Ala Gly Leu Ala Glu Gln
865                 870                 875                 880

Leu Gln Ala Ser Leu Lys Ser Val Glu Asn Gly Ser Ile Glu Gly Asp
                885                 890                 895

Val Leu Thr Asn Asp Ser Ser Val Gly Gly Asp Met Glu Ser Gln
            900                 905                 910

Ser Ala Gly Ser Pro Ala Ile Ser Glu Ser Thr Ser Ser Met Gln Ala
        915                 920                 925

Leu Ser Pro Ser Asn Ser Thr Gln Glu Phe His Lys Ser Pro Ser Ile
930                 935                 940

Glu Glu Lys Pro Gln Arg Ala Val Pro Ser Glu Phe Ala Asn Gly Leu
945                 950                 955                 960

Ser Pro Thr Pro Val Asn Gly Gly Ala Leu Asp Leu Thr Ser Ser His
                965                 970                 975

Ala Glu Lys Ile Ile Lys Glu Asp Ser Leu Gly Ile Leu Phe Pro Phe
            980                 985                 990

Arg Asp Arg Gly Lys Phe Lys Asn  Thr Ala Cys Asp Ile  Cys Gly Lys
        995                 1000                1005

Thr Phe Ala Cys Gln Ser Ala  Leu Asp Ile His Tyr  Arg Ser His
        1010                 1015                 1020

Thr Lys Glu Arg Pro Phe Ile  Cys Thr Val Cys Asn  Arg Gly Phe
        1025                 1030                 1035

Ser Thr Lys Gly Asn Leu Lys  Gln His Met Leu Thr  His Gln Met
        1040                 1045                 1050

Arg Asp Leu Pro Ser Gln Leu  Phe Glu Pro Ser Ser  Asn Leu Gly
        1055                 1060                 1065

Pro Asn Gln Asn Ser Ala Val  Ile Pro Ala Asn Ser  Leu Ser Ser
        1070                 1075                 1080
```

| | | | | | | | | | | |
|---|---|---|---|---|---|---|---|---|---|---|
|Leu|Ile|Lys|Thr|Glu|Val|Asn|Gly|Phe|Val|His|Val|Ser|Pro|Gln|
| |1085| | | |1090| | | |1095| | | | | |

Asp Ser Lys Asp Thr Pro Thr Ser His Val Pro Ser Gly Pro Leu
    1100             1105             1110

Ser Ser Ser Ala Thr Ser Pro Val Leu Leu Pro Ala Leu Pro Arg
    1115             1120             1125

Arg Thr Pro Lys Gln His Tyr Cys Asn Thr Cys Gly Lys Thr Phe
    1130             1135             1140

Ser Ser Ser Ser Ala Leu Gln Ile His Glu Arg Thr His Thr Gly
    1145             1150             1155

Glu Lys Pro Phe Ala Cys Thr Ile Cys Gly Arg Ala Phe Thr Thr
    1160             1165             1170

Lys Gly Asn Leu Lys Val His Met Gly Thr His Met Trp Asn Ser
    1175             1180             1185

Thr Pro Ala Arg Arg Gly Arg Leu Ser Val Asp Gly Pro Met
    1190             1195             1200

Thr Phe Leu Gly Gly Asn Pro Val Lys Phe Pro Glu Met Phe Gln
    1205             1210             1215

Lys Asp Leu Ala Ala Arg Ser Gly Ser Gly Asp Pro Ser Ser Phe
    1220             1225             1230

Trp Asn Gln Tyr Ala Ala Ala Leu Ser Asn Gly Leu Ala Met Lys
    1235             1240             1245

Ala Asn Glu Ile Ser Val Ile Gln Asn Gly Gly Ile Pro Pro Ile
    1250             1255             1260

Pro Gly Ser Leu Gly Ser Gly Asn Ser Ser Pro Ile Ser Gly Leu
    1265             1270             1275

Thr Gly Asn Leu Glu Arg Leu Gln Asn Ser Glu Pro Asn Ala Pro
    1280             1285             1290

Leu Ala Gly Leu Glu Lys Met Ala Ser Ser Glu Asn Gly Thr Asn
    1295             1300             1305

Phe Arg Phe Thr Arg Phe Val Glu Asp Ser Lys Glu Ile Val Thr
    1310             1315             1320

Ser

<210> SEQ ID NO 23
<211> LENGTH: 4772
<212> TYPE: DNA
<213> ORGANISM: Homo sapiens

<400> SEQUENCE: 23

```
atgtctcggc gcaagcaggc caagcccag cacctcaagt cggacgagga gctgctgccg      60
cctgacgggg ctcccgagca cgccgccccg ggggaaggtg cggaggacgc agacagcggg    120
cccgagagcc gcagcggggg cgaggagacc agcgtgtgcg agaaatgctg cgccgagttc    180
ttcaagtggg cggacttcct ggagcaccag cggagctgca ccaagctccc gcccgtgctg    240
atcgtgcacg aggacgcgcc cgcgccgccc cacgaggact cccccgagcc ttcgcccgcc    300
agctccccca gcgagcgcgc cgaaagcgag cggccgaggg aggcgggtgc ggagggcgcg    360
gagggcgagg ccaggccggt ggagaaggag gccgagccca tggacgcgga cccgcggggg    420
gacacgcgcg cgccccggcc cccgcctgcg gcccctgcac cccaacgccg gcctacggc    480
gcgcccagca ccaacgtgac cctggaggcg ctgctgagca ccaaggtggc ggtggcgcag    540
ttctcgcagg gcgcgcgcgc ggcaggcggc tcggagcag gtggaggcgt ggcagctgca    600
gccgtgcccc tgatcctgga acagctcatg gccctgcagc agcagcagat ccaccagctg    660
```

-continued

```
cagctcatcg agcagatccg cagccaggtg gccctcatgc agcgcccgcc gccgcggccc      720
tcactcagcc ccgcggccgc cccgagcgca ccgggcccgg cccccagcca gctgcccggg      780
ctggccgcgc tcccgctgtc ggccggggcc cctgccgccg ccatcgcggg ctcgggcccc      840
gccgccccgg ccgccttcga gggcgcgcag ccgctgtccc ggcccgagtc tggcgccagc      900 accccggcg gccctgcgga gccagcgcg ccgccgccc cagcgccgc ccctgccccc       960 gctgccccg cccggcgcc agcgccgcag agcgcagcct cgtcgcagcc gcagagcgca     1020
tccacgccgc ctgccctggc cccggggtcc ctgctgggtg cggcgcccgg cctgccaagt     1080
ccgcttctac ctcagacttc cgccagcggc gtcatcttcc ccaacccgct ggtcagcatc     1140
gcggccacgg ccaacgctct ggacccgctg tccgcgctca tgaagcaccg caagggcaag     1200
ccgcccaatg tgtcggtgtt cgagcccaaa gccagcgccg aggacccgtt cttcaagcac     1260
aaatgccgct tctgcgccaa ggtcttcggc agcgacagcg cgctccagat ccacctgcgc     1320
tcgcacacag gcgagcggcc cttcaagtgc aacatctgcg ggaaccgctt ctccaccaaa     1380
ggcaacctga aggtgcactt ccagaggcac aaggagaagt accccacat ccagatgaac     1440 ccttacccgg tccccgagta cctggacaac gtgcccacct gctcgggcat ccctacggc     1500 atgtcgctgc ccccgagaa gcccgtgacc acctggctgg acagcaagcc cgtgctgccc     1560
accgtgccca cgtccgtggg gctgcaactg ccgcccactg tccctggcgc gcacggctac     1620
gccgactctc ccagcgccac cccagccagc cgctccccgc agaggccctc gcccgcctcc     1680
agcgagtgcg cctccttgtc cccaggcctc aaccacgtgg agtccggcgt gtcggccacc     1740
gccgagtccc cacagtcgct cctcggcggg ccgcccgtca ctaaagccga gcccgtcagc     1800 ctgcccctgca ccaacgccag ggccggggac gctcccgtgg gcgcgcaggc tagcgctgca     1860
cccacatcgg tggacggcgc acccacgagc ctcggcagcc ccgggctgcc cgccgtctcc     1920
gagcagttca aggcccagtt tccgttcggg gggctgctag actcgatgca aacgtcggaa     1980
acctcgaagc tgcagcagct ggtggagaac atcgacaaga agatgacgga cccgaaccag     2040
tgcgtcatct gccaccgggt gctgagctgc agagcgcgc tgaagatgca ctaccggacg     2100
cacacggggg agcggccgtt caagtgcaag atctgcggcc gcgccttcac caccaagggc     2160
aacctcaaga cgcacttcgg cgtgcaccgt gcaaagccgc ccctgcgcgt gcagcactcc     2220
tgccccatct gccagaagaa gttcaccaac gccgtggtcc tgcagcagca catccgcatg     2280
cacatgggcg gccagatccc caacacgccg ctgccggagg gcttccagga tgccatggac     2340
tccgagctgg cctacgacga caagaacgcg gagaccctga gcagctacga tgacgacatg     2400
gacgagaact ccatggagga cgacgctgag ctgaaggacg cggccaccga cccggccaag     2460
ccactcctgt cctatgcggg gtcctgcccg cctcccccgc cctcggtcat ctccagcatt     2520
gccgccctga gaaccagat gaagatgatc gactcggtca tgagctgcca gcagctgacc     2580
ggcctcaagt ccgtggagaa cgggtccggg gagagtgacc gcctgagcaa cgactcctcg     2640
tcggccgtgg gcgacctgga gagccgcagc gcgggcagcc ccgccctgtc cgagtcctcg     2700
tcctcgcagg ccctgtcgcc ggccccagc aatggtgaga gcttccgctc caagtccccg     2760
ggcctgggcg ccccggagga gccccaggaa atcccgctca agaccgagag gcggacagc     2820 ccagccgccg cccccgggcag cggaggcgcc cctggccgcg cgggcatcaa ggaggaggcg     2880
cccttcagcc tgctgttcct gagcagggag cggggtaagt gtcccagcac tgtgtgtggt     2940
gtctgtggca agccttttgc ttgcaagagc gcgttggaaa tccactaccg cagccatact     3000
```

```
aaggagcggc cattcgtctg cgcgctctgc aggcgagggt gctccactat gggtaattta    3060
aaacagcact tactgacaca cagattgaaa gagctgcctt ctcagttatt tgaccccaac    3120
tttgctctag gtcccagcca aagcactcct agcctgatct ccagcgccgc acccaccatg    3180
atcaaaatgg aagtgaacgg tcacggcaag gccatggcgc tgggcgaggg tccccgctg    3240
cccgcgggcg tccaggtccc cgccgggcct cagacagtga tgggcccggg cctggcgccc    3300
atgctggccc cccaccgcg ccggacgccc aagcagcaca actgccagtc gtgcgggaag    3360
accttctcct cggccagcgc cctgcagatc catgagcgca cgcacaccgg cgagaagccg    3420
ttcggctgca ccatctgcgg ccgggccttc accactaagg gcaacctcaa ggtgcacatg    3480
gggacacaca tgtggaataa cgcccccgcg agacgcggcc gccgcctgtc tgtggagaac    3540
cccatggctc tcctaggggg tgatgccctg aagttctctg aaatgttcca gaaggacctg    3600
gcagctcggg caatgaacgt cgaccccagt ttttggaacc agtatgctgc agccatcact    3660
aacgggctcg ccatgaagaa caacgagatc tccgtcatcc agaacggcgg catccccag    3720
ctccccgtga gtcttggggg cagcgccctc cccctctgg gcagcatggc cagtgggatg    3780
gacaaagcac gcactggcag tagcccaccc atcgtcagct tggacaaagc gagctcagaa    3840
acagcagcca gccgcccatt cacgcgggttt atcgaggata caaggagat tggtatcaac    3900
tagccagtga ctcgctcatc tgccctgccc aggcccacgt ttgaagttg agcatcagg    3960
cctccgacct ttcttgcctc ggttctcatt acactttcac ccatagcaga aaacactttg    4020
tgcggctgcc gagaggtggt cttgtaagcg ctgcatggcg ctcccttcaa cagcaagcct    4080
gactgttctc gagaactctg caatctttta aataagcttc cttcaaaaaa aaaagtgctt    4140
ggaaaaccgc cttaggaaca gaaagagctc agaccatgtc cacttccttt ctcctgaaac    4200
ctaataatct ctccgaggga gaaaggggtt ctctgcggta ttccagtgaa actcatttga    4260
tggtttcttt tgaattagtt agacacttga acggtgtttt ttagaactct tcatgttaaa    4320
gacgtggttt agtactccca atgctgtgta tcatgacact atcttcgtct gtagtattta    4380
tgatgttaag ataatgcggg taacagacaa tataatagcc ccgaccttaa acgaagcttt    4440
tgtactgcag aatacatctg ctgtgtgat tttttttta agcaagattt gttttactat    4500
aaataagtgg attatttcaa tgcaggcaaa attgtgaagt tctgttggga agatagcat    4560
gcttttcgtg tgcaagtacc tgtcagtaat aagccttttt ttttttttt taatttaaat    4620
gtttgtagct gctatgtgga cagttgtttt ctagtgtggt ctgtagccca ataactgggg    4680
aacgagttac agacaaacat caccgtaaat gactcacaac attataaaca gttgtgagaa    4740
aatatttcac attatcaaag ctgtacaata aa                                  4772
```

<210> SEQ ID NO 24
<211> LENGTH: 1300
<212> TYPE: PRT
<213> ORGANISM: Homo sapiens

<400> SEQUENCE: 24

Met Ser Arg Arg Lys Gln Ala Lys Pro Gln His Leu Lys Ser Asp Glu
1               5                   10                  15

Glu Leu Leu Pro Pro Asp Gly Ala Pro Glu His Ala Ala Pro Gly Glu
            20                  25                  30

Gly Ala Glu Asp Ala Asp Ser Gly Pro Glu Ser Arg Ser Gly Gly Glu
        35                  40                  45

Glu Thr Ser Val Cys Glu Lys Cys Cys Ala Glu Phe Phe Lys Trp Ala
    50                  55                  60

```
Asp Phe Leu Glu His Gln Arg Ser Cys Thr Lys Leu Pro Pro Val Leu
 65                  70                  75                  80

Ile Val His Glu Asp Ala Pro Ala Pro Pro His Glu Asp Phe Pro Glu
                 85                  90                  95

Pro Ser Pro Ala Ser Ser Pro Ser Glu Arg Ala Glu Ser Glu Ala Ala
            100                 105                 110

Glu Glu Ala Gly Ala Glu Gly Ala Glu Gly Glu Ala Arg Pro Val Glu
        115                 120                 125

Lys Glu Ala Glu Pro Met Asp Ala Glu Pro Ala Gly Asp Thr Arg Ala
130                 135                 140

Pro Arg Pro Pro Ala Ala Pro Ala Pro Thr Pro Ala Tyr Gly
145                 150                 155                 160

Ala Pro Ser Thr Asn Val Thr Leu Glu Ala Leu Leu Ser Thr Lys Val
                165                 170                 175

Ala Val Ala Gln Phe Ser Gln Gly Ala Arg Ala Ala Gly Gly Ser Gly
            180                 185                 190

Ala Gly Gly Gly Val Ala Ala Ala Val Pro Leu Ile Leu Glu Gln
        195                 200                 205

Leu Met Ala Leu Gln Gln Gln Ile His Gln Leu Gln Leu Ile Glu
210                 215                 220

Gln Ile Arg Ser Gln Val Ala Leu Met Gln Arg Pro Pro Arg Pro
225                 230                 235                 240

Ser Leu Ser Pro Ala Ala Ala Pro Ser Ala Pro Gly Pro Ala Pro Ser
                245                 250                 255

Gln Leu Pro Gly Leu Ala Ala Leu Pro Leu Ser Ala Gly Ala Pro Ala
            260                 265                 270

Ala Ala Ile Ala Gly Ser Gly Pro Ala Ala Pro Ala Ala Phe Glu Gly
        275                 280                 285

Ala Gln Pro Leu Ser Arg Pro Glu Ser Gly Ala Ser Thr Pro Gly Gly
290                 295                 300

Pro Ala Glu Pro Ser Ala Pro Ala Ala Pro Ser Ala Ala Pro Ala Pro
305                 310                 315                 320

Ala Ala Pro Ala Pro Ala Pro Ala Pro Gln Ser Ala Ala Ser Ser Gln
                325                 330                 335

Pro Gln Ser Ala Ser Thr Pro Pro Ala Leu Ala Pro Gly Ser Leu Leu
            340                 345                 350

Gly Ala Ala Pro Gly Leu Pro Ser Pro Leu Leu Pro Gln Thr Ser Ala
        355                 360                 365

Ser Gly Val Ile Phe Pro Asn Pro Leu Val Ser Ile Ala Ala Thr Ala
370                 375                 380

Asn Ala Leu Asp Pro Leu Ser Ala Leu Met Lys His Arg Lys Gly Lys
385                 390                 395                 400

Pro Pro Asn Val Ser Val Phe Glu Pro Lys Ala Ser Ala Glu Asp Pro
                405                 410                 415

Phe Phe Lys His Lys Cys Arg Phe Cys Ala Lys Val Phe Gly Ser Asp
            420                 425                 430

Ser Ala Leu Gln Ile His Leu Arg Ser His Thr Gly Glu Arg Pro Phe
        435                 440                 445

Lys Cys Asn Ile Cys Gly Asn Arg Phe Ser Thr Lys Gly Asn Leu Lys
450                 455                 460

Val His Phe Gln Arg His Lys Glu Lys Tyr Pro His Ile Gln Met Asn
465                 470                 475                 480
```

-continued

Pro Tyr Pro Val Pro Glu Tyr Leu Asp Asn Val Pro Thr Cys Ser Gly
            485                 490                 495

Ile Pro Tyr Gly Met Ser Leu Pro Pro Glu Lys Pro Val Thr Thr Trp
            500                 505                 510

Leu Asp Ser Lys Pro Val Leu Pro Thr Val Pro Thr Ser Val Gly Leu
            515                 520                 525

Gln Leu Pro Pro Thr Val Pro Gly Ala His Gly Tyr Ala Asp Ser Pro
            530                 535                 540

Ser Ala Thr Pro Ala Ser Arg Ser Pro Gln Arg Pro Ser Pro Ala Ser
545                 550                 555                 560

Ser Glu Cys Ala Ser Leu Ser Pro Gly Leu Asn His Val Glu Ser Gly
                565                 570                 575

Val Ser Ala Thr Ala Glu Ser Pro Gln Ser Leu Leu Gly Gly Pro Pro
            580                 585                 590

Val Thr Lys Ala Glu Pro Val Ser Leu Pro Cys Thr Asn Ala Arg Ala
            595                 600                 605

Gly Asp Ala Pro Val Gly Ala Gln Ala Ser Ala Ala Pro Thr Ser Val
610                 615                 620

Asp Gly Ala Pro Thr Ser Leu Gly Ser Pro Gly Leu Pro Ala Val Ser
625                 630                 635                 640

Glu Gln Phe Lys Ala Gln Phe Pro Phe Gly Gly Leu Leu Asp Ser Met
                645                 650                 655

Gln Thr Ser Glu Thr Ser Lys Leu Gln Gln Leu Val Glu Asn Ile Asp
                660                 665                 670

Lys Lys Met Thr Asp Pro Asn Gln Cys Val Ile Cys His Arg Val Leu
            675                 680                 685

Ser Cys Gln Ser Ala Leu Lys Met His Tyr Arg Thr His Thr Gly Glu
            690                 695                 700

Arg Pro Phe Lys Cys Lys Ile Cys Gly Arg Ala Phe Thr Thr Lys Gly
705                 710                 715                 720

Asn Leu Lys Thr His Phe Gly Val His Arg Ala Lys Pro Pro Leu Arg
                725                 730                 735

Val Gln His Ser Cys Pro Ile Cys Gln Lys Lys Phe Thr Asn Ala Val
                740                 745                 750

Val Leu Gln Gln His Ile Arg Met His Met Gly Gly Gln Ile Pro Asn
            755                 760                 765

Thr Pro Leu Pro Glu Gly Phe Gln Asp Ala Met Asp Ser Glu Leu Ala
            770                 775                 780

Tyr Asp Asp Lys Asn Ala Glu Thr Leu Ser Ser Tyr Asp Asp Asp Met
785                 790                 795                 800

Asp Glu Asn Ser Met Glu Asp Ala Glu Leu Lys Asp Ala Ala Thr
                805                 810                 815

Asp Pro Ala Lys Pro Leu Leu Ser Tyr Ala Gly Ser Cys Pro Pro Ser
            820                 825                 830

Pro Pro Ser Val Ile Ser Ser Ile Ala Ala Leu Glu Asn Gln Met Lys
            835                 840                 845

Met Ile Asp Ser Val Met Ser Cys Gln Gln Leu Thr Gly Leu Lys Ser
            850                 855                 860

Val Glu Asn Gly Ser Gly Glu Ser Asp Arg Leu Ser Asn Asp Ser Ser
865                 870                 875                 880

Ser Ala Val Gly Asp Leu Glu Ser Arg Ser Ala Gly Ser Pro Ala Leu
                885                 890                 895

Ser Glu Ser Ser Ser Ser Gln Ala Leu Ser Pro Ala Pro Ser Asn Gly

-continued

```
             900                 905                 910
Glu Ser Phe Arg Ser Lys Ser Pro Gly Leu Gly Ala Pro Glu Pro
        915                 920                 925
Gln Glu Ile Pro Leu Lys Thr Glu Arg Pro Asp Ser Pro Ala Ala Ala
                    935                 940
Pro Gly Ser Gly Gly Ala Pro Gly Arg Ala Gly Ile Lys Glu Glu Ala
945                 950                 955                 960
Pro Phe Ser Leu Leu Phe Leu Ser Arg Glu Arg Gly Lys Cys Pro Ser
                965                 970                 975
Thr Val Cys Gly Val Cys Gly Lys Pro Phe Ala Cys Ser Ala Leu
            980                 985                 990
Glu Ile His Tyr Arg Ser His Thr Lys Glu Arg Pro Phe Val Cys Ala
            995                 1000                1005
Leu Cys Arg Arg Gly Cys Ser Thr Met Gly Asn Leu Lys Gln His
        1010                1015                1020
Leu Leu Thr His Arg Leu Lys Glu Leu Pro Ser Gln Leu Phe Asp
        1025                1030                1035
Pro Asn Phe Ala Leu Gly Pro Ser Gln Ser Thr Pro Ser Leu Ile
        1040                1045                1050
Ser Ser Ala Ala Pro Thr Met Ile Lys Met Glu Val Asn Gly His
        1055                1060                1065
Gly Lys Ala Met Ala Leu Gly Glu Gly Pro Pro Leu Pro Ala Gly
        1070                1075                1080
Val Gln Val Pro Ala Gly Pro Gln Thr Val Met Gly Pro Gly Leu
        1085                1090                1095
Ala Pro Met Leu Ala Pro Pro Arg Arg Thr Pro Lys Gln His
        1100                1105                1110
Asn Cys Gln Ser Cys Gly Lys Thr Phe Ser Ser Ala Ser Ala Leu
        1115                1120                1125
Gln Ile His Glu Arg Thr His Thr Gly Glu Lys Pro Phe Gly Cys
        1130                1135                1140
Thr Ile Cys Gly Arg Ala Phe Thr Thr Lys Gly Asn Leu Lys Val
        1145                1150                1155
His Met Gly Thr His Met Trp Asn Asn Ala Pro Ala Arg Arg Gly
        1160                1165                1170
Arg Arg Leu Ser Val Glu Asn Pro Met Ala Leu Leu Gly Gly Asp
        1175                1180                1185
Ala Leu Lys Phe Ser Glu Met Phe Gln Lys Asp Leu Ala Ala Arg
        1190                1195                1200
Ala Met Asn Val Asp Pro Ser Phe Trp Asn Gln Tyr Ala Ala Ala
        1205                1210                1215
Ile Thr Asn Gly Leu Ala Met Lys Asn Asn Glu Ile Ser Val Ile
        1220                1225                1230
Gln Asn Gly Gly Ile Pro Gln Leu Pro Val Ser Leu Gly Gly Ser
        1235                1240                1245
Ala Leu Pro Pro Leu Gly Ser Met Ala Ser Gly Met Asp Lys Ala
        1250                1255                1260
Arg Thr Gly Ser Ser Pro Pro Ile Val Ser Leu Asp Lys Ala Ser
        1265                1270                1275
Ser Glu Thr Ala Ala Ser Arg Pro Phe Thr Arg Phe Ile Glu Asp
        1280                1285                1290
Asn Lys Glu Ile Gly Ile Asn
        1295                1300
```

<210> SEQ ID NO 25
<211> LENGTH: 116368
<212> TYPE: DNA
<213> ORGANISM: Homo sapiens

<400> SEQUENCE: 25

| | | | | | |
|---|---|---|---|---|---|
| gatcttacct | tgatgttgat | ggctgttcac | tgatcagggt | ggtggttgct | gaaggttggg | 60 |
| atggctatgc | caatttcttt | aaaataagac | aacaatgatg | ttggctatat | tgattcttta | 120 |
| tctgagattt | ctttgtaact | tgtgatactg | tctgaaaata | ttttacccac | aacaggccgg | 180 |
| gcgcggtggc | tcatgcctgt | aatcccagca | ctttgggagg | ccgaggcggg | tggatcacaa | 240 |
| ggtcaggaga | tcgagaccat | cctggctaac | acggtgaaat | cccatctcta | ctaaaaatac | 300 |
| aaaaaaatt | acttgggcgt | ggtggcagac | gcctgtagtc | ccagctactt | gggaagctga | 360 |
| ggcagaagaa | ccacttgaac | atgggaggca | gaggttgcag | tgagctgaga | ttgcgccact | 420 |
| gcactccagc | ctgggtgaca | gagcgagact | ctgtctcaat | ctcaaaaaat | actttctttg | 480 |
| ctcatctgta | agaagcagtt | ctttattcat | tcaagttttc | tcctaagatt | gccaccattc | 540 |
| agtcacatct | tcaagcttca | ctgctatttc | cagctctctt | gctatctcca | tcatatctgc | 600 |
| agttacttcc | tccactgaat | tttgttgttt | gtaaagacag | gatttcactg | tgttgactgg | 660 |
| gttggtcttg | aactcctggc | tctcaagcca | tcctcctcgg | cctcccaaag | tgctgggatt | 720 |
| acaggcataa | gccacggtgc | ctggctcttt | cactgaagtc | ttgaacccat | caaagtcatc | 780 |
| catgagggtt | ggaagccact | tcttccaaac | tcctgtttat | gttgatattt | tgaccttctc | 840 |
| ccatgaatta | cgaatgtttt | taacaacatc | tagaatggtg | aatcctttcc | aggttttcac | 900 |
| tttactttgc | ccagacccat | cagagaaata | acaaactatg | gcagcttaca | aaatgtagta | 960 |
| tttctgaaat | aataagacct | ggaagttgaa | actcttagag | gcatttgaac | cagagccact | 1020 |
| ccatctcgaa | caggagctgg | ggaaaataaa | gctgagacct | actgggctgc | attcccagga | 1080 |
| ggttaaggca | ttcttagtca | caggatgaga | taggaggtca | gcacaagata | caggtcataa | 1140 |
| agaccttgct | gataaaacaa | gttgcagtaa | agaagccagc | taaaacccac | caaaaccaag | 1200 |
| atggcgacaa | gagtgacctc | tggttgtcct | cactgctaca | ctcccaccag | cgccatgaca | 1260 |
| gtttacaaat | gccatggcaa | catcaggaag | ttaccctgta | tggtctaaaa | agggaaggca | 1320 |
| tgaacaatcc | accccttgtt | tagcatatca | tcaagaaata | accataaaaa | tgggcaacca | 1380 |
| gcaactctca | gggctgctct | gtctatggac | taaccattct | ttcattcctc | tgctttccta | 1440 |
| ataaacttgc | tttcacttta | tggactcatc | ctgaattctt | tcttacgtga | gatccaagaa | 1500 |
| tcctctctta | gggtctggat | ccagactcct | taccagtaac | aaaaccactc | cttgatccag | 1560 |
| actacaaaat | gaatgttgtg | ttaacaggca | tgaaaacag | tattaatctc | agtattaatc | 1620 |
| tccttgtaca | tttccatcag | agctcttgac | agatgcatta | gatgcattgt | ttttttgttt | 1680 |
| tttgagacgg | gagtcttcct | ctgtcgccca | ggctggagtg | cagtggcgtg | atctcggctc | 1740 |
| actgcaacct | ccgcctccca | ggttcaagca | attctcctgc | ctcagcctct | tgagtagcta | 1800 |
| ggattacagg | cgcccatgac | cacgcccagc | taattttgt | gttttagta | gagacagggt | 1860 |
| ttcaccatgt | tggtcaggct | ggtctcgaac | ccctgacctt | gtgatccacc | cgcctcggcc | 1920 |
| tcccaaagtg | ctgggattac | agatgtgagc | cactgcgccc | ggcctagatg | cattgttaat | 1980 |
| gagcagccat | aatttttgaa | agaaatcttt | ttttttttt | ttctgtgcag | taggtctcaa | 2040 |
| cagtgggctt | aaaatattca | gtaaatcatg | tgataaacag | atatgctaaa | ctgggcgcgg | 2100 |

```
tggctcacac ttgtaatccc aaaactttgg aaggccgagg cgggtggatc acttgaggtc    2160
aggagtttga gaccagcctg accaatatgg tgaaacccca tctctaccaa aaatacaaaa    2220
ggcagcaggt gcctgtaatc ccagctactc aggaggctga ggtaagagaa tcacttgaac    2280
ccaggagaca gaggttgcag tgaactgaga ttgtgccact gcactccagc ctgagtgaca    2340
cagagactcc atctcaaaac aaaaatgaga tatgccatca tccaggcttt gtcattccat    2400
ttccagagca catgcagagt agaaatagca tcattcttaa aggccctaag attttcagaa    2460
tggtaaatga gcattgcttt agcttaatgt caccacctgc attagcccct aacaggagtc    2520
accttgtcct ttgaagcaag gtgttttttt cctttctagc tatgaaagtc ctagatggca    2580
tcttcttcca atagaagact gtcttgtcta ctttgaaaat atgttgttta gtgtagctac    2640
tgtagttatt gtagctagat cttctggata acttgctgta gcttctacat cagcatttac    2700
tgccttacct tgcttttttt tttttgtttt ctttgagaca gagtttcact cttttttgccc    2760 aggctggagt gcgatggcac aatcttggtt caccacaacc tccacctccc atgttcaagt    2820
gattctcctg cctcagcctc ccgagtagct gggattacag gcatgcacct ccaagcccag    2880
ctacttttgt atttttagta gaaatggatt tttctccatg attgtcaggc tggtctcgaa    2940
ttcccaacct caggtgttct gccccctca gcctcccaaa gtgtgaggat acaggtgtg      3000 agccaccacg cccagctgca tttttatatt aggaagatgt cttcttgggc ctggtgcagt    3060
ggctcatgcc tgtaatctca gcactttggg aggctgaggc gggtggatca tctgaggttg    3120
gaagttcgag accatcctga ccaacatggt gaaactccgt ctctactaaa aatacaaaaa    3180
ttaactgggt gtggtggtgc gcacctgtaa tcccagctac tcgggaggct gaggcaggag    3240
aatcacttca atgcgggagg cagacgttaa aaaattaagc agtacttaat ttttttttt     3300 tgagacagag tcttgctctg tcgcctaggc tggagtgcag tggcgtgatc tcggttcact    3360
gcaatctctg cctcccaggt tcaagtgatt ctcctgtctc agtctcctca gtagctggga    3420
ttacaggcgc aatgccacca tggccagcta ctttttttgca ttttagtagg acagggttt    3480 cactgtgttg cccaggctgg tctcgaactc ctgagctcag gtaatttgtc cactttggtc    3540
tcccaaagag ctaggattac aggcgtgagc cactgcgcct ggcctataaa caaatttaaa    3600
cagagaaaag gtacagtaaa aattagtatt acaatcttat gggaccatgg ttgtatatgc    3660
ggtctctaac tgacaaaaca aagttatggc cacactatgc gggcataatc tacttgcata    3720
ggtacaatca caatctaccc tttagaactg acttcaaaga ttaaggctga gaggaatgat    3780
gcacacatat acacactaca cactgtatta tggaaaacag cacacacaca caaagacaat    3840
gataatcttt tccccagcta tcccaagcag gaatttaccc tggaagtgaa ctcaagtata    3900
agaaaagaaa taccacaaag gcaatcaaaa acaaaataaa aaagttcacg gggccaggca    3960
cagtggctca tgcctgtaat cccagcactc taggaggcca aggccagtgg atcattcgag    4020
gccaacctgg gaacatgat gagaccatct ctgcaaaaaa aaaattagct aagaatgatg     4080
gtgtgtgcct gctactccac aggctgaggt ggaaggatca cttgagtcca ggagctcaag    4140
gccagtcagc tgtgatcatg ccactacact gcagcctgag tgatagggac gtttatgggt    4200
aaacaccagc agtgttgtca atagatgact agacatcatt gttacgtaat tgcagttatt    4260 ttaaaggat tagctggaat tgggttttac cttggaaaga tgtctgaaat atgtgagagg     4320
ggagaaaaaa ggctgggcaa ggtggctcac gcctgtaatc ccagcacttt gggaggccga    4380
ggcagatgga tcatttgaag tcaggagttc aagaccagcc tggccaacat gctgaaacct    4440
catctctact caaaatacaa aaattagcca ggtgtggtgg tgggcacctg taatcccaag    4500
```

```
taaggaggct gaggcaggag aatcgcttga acctgggagg cggaggatac agtaagccaa    4560
gatcgagcca ctgcactccc ttgagcctgg gaggtcaagg ctgcagtaag ctgagatcat    4620
accattgcac tccagcctgg atgaaagagt gagaccctgt cttaaaaaaa agaaaaaagg    4680
ccgggtacgg tggctcactc ctgtaatccc agaactttgg gagaccgagg tgggcgggtc    4740
acctgaggtc gggagtttga gaccagcctg accaacatag tgaaacccca tctctgttaa    4800
aaatacaaaa ttagccgagt gtggtggcgc atgcctgtaa tcccagctac tccggaggcc    4860
gaggcaggag aattgcttga acctgggagg cgaaggttat agtgagccga gaccatgcca    4920
ttgctctcca gcctaggaaa caagagggaa actgtcaaaa aaaaaaaaa agtgaggcaa    4980 gtatggacat agccaggtgt gcatcttttt gacgctagga acaagagtgt cacaaggcag    5040
ctgaaagtga ttgtcaagta aagattctca ggtatagagc agaaagtacc agaaaaattt    5100
atatacacct gggtgagaaa aaaaaacatt caaattttat tttccaacag acagacagca    5160
tcagcaggta caactacagg ggtttctccg tagatcatac attcacaagg cattattagc    5220
tcaacagtga gaaagccact ggtgtgtttt ctgtaacaat atccacttca cagtgtaaac    5280
aggtactatt atcgtgttca cttacaattc agaaggaaa ggcacaactt ggcaaaaaaa    5340
aaaaaaaaaa aaaaaaggg gggcggaatc ctaaagtcag gtgcaacgat gaagagacaa    5400
cactttggct aatcgtcttg gatgcatatt tccgtcagga ccttccacat agaggggaaa    5460
gacttttctc ccagaaatta gagttttttt ctttctttct tgttaaacca agagcaatgt    5520
ttcgtttgct caatatcaca tttacaaagg aaactacaaa aaaaaaggc atcacaaaat    5580 catcttgaac gttcacctct tcccaccaat acatcaactc ttaggcttta gacagggcct    5640
gggaatactt cagcggtctt aaaataggaa aatagacact atggctacaa aaaataaaaa    5700
ataaatgagg tagataaatt aaagctttca cacccaggac gtgcctgttc taacttcgta    5760
gccttcatga aatattcagc aaggaaacaa aacaaaacaa aaaatcgtca taattacttg    5820
gcataagtcg caccaaggaa attcaacaaa agcaatcagt atgtgaacct gtgatgggaa    5880
acacgccctt ccacgagttt cttctcgagc atgaaacccc agttcttcaa tagagtaggc    5940
actggcaaac taagtcacct gagattcccc gctcaggtgc ccacctcttc tgggatttgg    6000
gaagaggaag catccaagaa ggtgtgggga aacattggc actctcgggg ctccaactga    6060
actgtattta aataagcagc aacacacaca ttgactccct aaggactaac gtaagtccat    6120
ttgagggcct cctacttaag gttctaaggt tgaagcagtt ttataattct acaaccctag    6180 tttttgttg ttccttttt aagtacattc aaaaaaaaac aataagatgg ggacagggtt    6240
ggggcatata aaacaggtcc ctaaagagat gacagacctt gtccttttac ccgtgtccag    6300
ttaccagtaa gtatacagta cccatctccc ctcaatgagg ctgtgtagtt gtcttttcca    6360
ctgttgttca gtaagttcca acgattctac cttgaaatag gtaacagtct ttggaaaaag    6420
tcactctagg ttgtacaaag gttctatgta tacgtctgtt acaagtaaca aagctacttt    6480
gcaagacccg cttctttcca aaattagaaa aaaaaaaaa aagtgccagg cgtggtagct    6540
catgcctgta atcccagcac tttgggaggc caaggcgggt ggatcacgag gtcagcagtt    6600
cgagaccagc ctgaccaaca tggtgaaacc cagtctctac tcaaaataca aaattagccg    6660
ggcgtggtgg cacctgcctg taatcccagc tactctggag gctaaggcag gagaatcact    6720
tgaacccaga atggggaggt tgcagtgagc cgagatcatg ccactgcact ccagcctggg    6780
tgatagagcg agactccatc tcaaaaaaaa agagtctgta tttgttttgg tatgcatttt    6840
```

| | |
|---|---|
| tttttttattt tttcaactttt ttgcaaagca gcatagcaac aatcgtgatt gtagcacttg | 6900 |
| cctgaggttg tggtcacaac caacgtagta aacatcattt gcatatcagt aagaaaaaga | 6960 |
| aaacaggagg agatgagttc ttacaaaaca aagcagattc tagagatttc actgtgtctg | 7020 |
| cattgctcct tccacgcaag ttctccctta gctgaccgca atcttgtttt cttccaggaa | 7080 |
| gtgaggaaac tggtgtttgg gaacgccgtc agtagcactt ggttttttcca catctgcact | 7140 |
| gatacccgac tgggagccat ccatcttgga gacagtggcg ttattcacaa cggaggtggc | 7200 |
| ccccaaggaa accgggaggg taggaacccc cccactctgg atcacagaga tctcattggt | 7260 |
| cttcacggcc agaccgccat tgagcatgct ggtgtactgg ttccacacaa cagggtccac | 7320 |
| attcactgaa ggggccagga tttccttggg aaagatttct gagactcttt ttccgtccgt | 7380 |
| acctaacaga gccatggtgt tctcgatggc caacttcctt ccacggcggg ctgagttatt | 7440 |
| gttcgccccg tgtgtcatgt agtgaaccta tgggaacagg acagaaaggt ttttaccaaa | 7500 |
| atagagattt gaagctcact ggcaagccaa gaatcaatct gcatatggat ttcattctac | 7560 |
| ccagtgtttt aacatataga tgatccttga cttacagcgg ggttatgccc agataaactg | 7620 |
| attgaaagta gaaaatattc ttagtctaaa atgcatttaa tacccctaac tagccaaaca | 7680 |
| tcatagctca gtttagccta cctcaaacac actcagaaca tttgcattag cttacagtta | 7740 |
| ggcaaaatca tctaacgcaa agcctatttt attttataca tgagcactga aacagctcat | 7800 |
| gtaggccagg cacggtggct cacgcctgta atcccagcac tttgggaagc tgaggtgggc | 7860 |
| agatcacttg aggtcaggag ttcaagacca gcccggccaa catgatgaaa ccctgtctac | 7920 |
| taaaaataca aaaagtagcc aggcatggtg gcacatgcct gtaatcccag ctgctcgcga | 7980 |
| ggctgaggca cgagaatcgc ttgaacctgg gaggcggagg ttgcagtgag ccaagatcat | 8040 |
| gccactgcac tccagcctgg gtgacaaagc aagactccat ctcaaaaaaa aataaaaaat | 8100 |
| aaaaaattag ctcatagctc atgtgattga gcatgtactg aaagtgagaa acagaatggt | 8160 |
| tgtatgggtg ctcaaagtct gatctctact gaatgcctat cacttttgta tcatcgtaaa | 8220 |
| tcaaaccatc ttaagtcagg gactgtctgc actttatatt tagaaaatca gatttcttat | 8280 |
| atcacctaac aaacattcct ccccagagca accaagatgg ggcttatagt ctccaactgt | 8340 |
| ctctgctcca ccaatcatgg gtgtacctat gtgaaaacct actatatcct gggcattgat | 8400 |
| ccaagtgcca gggttaacat tttttttttga gtccttttttt ttttgagacg gagtctcgct | 8460 |
| ctgtcgccca ggctggagtg cagtggcgca atctcggctc gctgcaacct ccgcctcccg | 8520 |
| ggttcaagcg attctcctgc ctcagcctcc tgaatagctg ggactacagg cacgcgccac | 8580 |
| catgcccggc taattttttgt atttttagta gagacgggt ttcaccatgt tggccaggat | 8640 |
| ggtcttgatc tcgtgacctc gtggtccgcc tgcctcggcc tcccaaagtg ctggaattac | 8700 |
| aggcgtgagc caccacgtcc ggcctttttt ttgagtctta atctgtcacc caggctacag | 8760 |
| tgcagtggca cagctcactg cagcctcaac ctccaaggct caagcaaccc acccacctca | 8820 |
| gcttcctgag tacctgggac tacaggtgca caccaccatg cccagctaat tgttttttttt | 8880 |
| ttttttttgag acagagtctc gctctgtcgc ccaggctgga gtacggtgga atgatcttgg | 8940 |
| ctcaatgcaa gctccacctc ccgggttcac accattctcc tgcctcagcc tcccgagtag | 9000 |
| ctgggactac aggcgcccac cgccaccacg cccggctaat ttttttctatt ttgtttttag | 9060 |
| tagagacagg gtttcatcgt gttagccagg atggtcagga tctcctgacc ttgtgatccg | 9120 |
| cccacctcgg cctcccaaag tgctgggatt acaggcgtga gccactgcac ctggccggct | 9180 |
| aatttatttt tatttgtaga gactggatct ccttatgttg ctcaagctgg tctcgaactc | 9240 |

```
ctggcctcaa gcaatcctcc caccttgtcc tcccaaagtg ctgggattac aggcatgagc    9300
cactgcaccc agcctagagt taacattttt aaaatgcaca aacctacgca ggtaataaaa    9360
ctgtagagtg cacaacatgc acacctgagt acaagtaaaa tgggaaaatc tgaatgttga    9420
ttgtaacaat gtcaatatct tgattatgct acaatgttga tactaccgtt ttgcaaagtg    9480
ctaccaatgg ggaaaactgg gcaaagcata caaggatgtc tctgtattac ttttcaaaag    9540
tccagtgaaa atctatactt atttaagtaa aaatttcagt taaaaacaat tgtgggcag     9600 ggcacagtgg ctcacgccta atcccatt actttgggag gctgaggcag gcagatcacc      9660
tgaggtcagg agtttgagac gagcctggcc aacatggtga acccccatct ctactaaaaa    9720
tacaaacagt agccgggtat ggtggcacac gcctgaagtc ccagctactc aggaggctga    9780
ggcaggagaa tcgcttgaac ccaggaggcg gaggttgcag tgagtcaaga tggcaccact    9840
gcactccagc ctgggcaaca agagcaaaac tgtctcagaa acaaacaaac aaacaaaaca    9900
aaccaaaaca aaacaaattt tggggcagga cgcagtggct cacacctaca atccaggact    9960
ttgggaggtc agagcaggtg gatcacctga ggtctgagt tcgagatcag cgtggccaac    10020
atcgtgaaac ctcgactcta ctaaaaatat acaaaaatta gccgggcatg atggcgggcg    10080
cctgtaattc cagccactca agaggctgag gcaggagaat tgcttgaacc cgggaggcag    10140
aggttgcaat gagccgagat tgcaccgttg cactccagcc tgggtgacag agcaaaacga    10200
ccattccctg atgcagctga catctaaata tagagaacat caatgtctct aataattgct    10260
acagagaaaa atgtatctgg ctgggaaagc tacagaaggc catggtggga ataggatgct    10320
atttaatcta aggtggtagg caaggcttct gctgaagaag ggaccttact agcacctggc    10380
tgctttcttt aattattttt cctgtctggc tttcaagttt tgaaatcctt ttcagcttct    10440
ttttttttta tttatatgaa tttaattttt gtagagatgg catcttgcta tgttgcccag    10500
gctggtcttc aactcctggg gtcaagtgat cctcgcacca ccacctccca aagtgctgag    10560
agtacaggca tgagccactg cgtccggccc ttttcagctt cttaagagtt taaaactctt    10620
aagagacagg gtcttactct cttgcccagg ctggagtgca gtggtgtgat cacagctcac    10680
agaagcctcg acctcccagg ttcaagtgat cctcccactt cagcctccca agtagctggg    10740
cctacaggcg catgccacca cgcccatcta attttattt ttatttgta gtgacgggt       10800 ctccttatgt tacccaggct ggtctcaaac tcctgggctc aagcaatcca cctgccttgg    10860
cctctcaaag tactcagatt atgggtgctg agccactgca cccaggtagt atttctaatt    10920
tttaaaatta aaatgtaaac attttaattt ttttaagaga caaggtctca ctttgttttc    10980
taagctggag tgcagtggca tgatcacaga tcactgcagc cttgatctct caggctcaag    11040
tggtcctccc acttcagctt cccaattggc ggggacccaa gcatgcaaca ccatgcccaa    11100
ctaatttgtg tgtgtgtgtg tgtgtgtgtg tgtgtgtgtg taaagacgtt gtctccctat    11160
gttgccaggc tggtctcaaa ctcctggact cagctgggtg cagtggctca tgcctgtaat    11220
cccagcactt tgggaggccg aggcaggcgg atcacgagat caggagatcg agaccatcct    11280
ggctaacgcg gtgaaacccc acctctacta aaaatacaaa aaattagcc ggccatggtg      11340 gcggacgcct gtagtcccag ctactcagga ggctgaggca ggagaatggc atgaacccgg    11400
gaggaggagc ttgcagtgag cttgagcttg agatggcgcc actgcactcc agtctgggcg    11460
acagagtgag actccgtctc aaaaataaat aaataaataa acaaactcct ggactcaagc    11520
aatcctccca cctcggcctc ccaaaggagg aatggaagga tggaagaact catcacggct    11580
```

```
tgtgccaata agaagacacc tggtgcctag cccccatcct gctgaaagcc cacacaaacc    11640
cacctttaag ttgcctttgg tggtaaaagc tcgcccacaa atgttgcaca caaaaggctt    11700
ctctccagtg tgagtccgct cgtggatctg aagagcgcta gcagacgaga agttcttccc    11760
acaccgtgtg cagccatgtt gcttggcctg tcggcgtggc tgggctgcta acaaaggggt    11820
catccctggg gacaatgtcg agggtccac aaatgtgcca ggaacttcaa ccttgacata    11880
ggtcggcggg gctcggataa acgtggaagg gagactgctc cgacctagta cacagagggg    11940
aaaaaagcca gacctttatc atccaacctt cattctttct cttcaaagca aaagagatct    12000
ttaaaaataa ctgcctgcta gtttgagagt ctggagctgg ctttgtaagt aattaacacc    12060
ttcccctttg aattgtttat ctgcacaaag ataaagctt caaatgcttg ggaaaaggta    12120
tcactttggg ttttttttt ttaaaggcat gggcaacata taaacacata tgtaatttaa    12180
gttcaaattt ctgcataaga aactacctt aaagcatatg cccagacacc atctttcttt    12240
gattctttga tacagctttt ccctatttt accattaatg acatcaacaa acctctcaat    12300
agatatgtgc atttaaaatg ggttcatctt tccctgcttc aagagtggct aatttgtgaa    12360
cattacatca ggcagtgggg cctcagagtc agggaaccac ggcttatttc agtggtcaaa    12420
aagcagtggc cacttcctca aacatactct taagacaccc atatacagaa tcatagtgtg    12480
gagaaacaaa aagaaaaaaa ctataacaaa atagaacgac tacccacccc tatgtcccaa    12540
ggggctcaaa gacaaaaata aaaccaaca aaaaggtat gctgtccata cccattttgc    12600
attaaccatc ataaattaaa agcatgttcg ttactaggat agaggcagtt actattgccc    12660
tctacccaga agtaaagaaa agctaattgc cctatagaag gggctgcttc aagtcatact    12720
ctccgtttgt aaagttcaac ccaggctcct ttttgatgac cttgagccca aaatggacat    12780
aagttaaatc caaagctcta tcaccttcca tctcagtgcg gctgttctcg agctctctg    12840 ctttgctccc agcatcggga gactttgact tgatgctttc ggcttgacta ttggccgggg    12900
agagtgcctg gaaggatgtg gtttccagga tatctgggct tcggctctga tactcctggt    12960 ctccatcag cgaggatgag tcgttggtca agccatcgct ctccacggaa ccgttttctc    13020
tgctgccctg gcgctgcagg ttaaaagggg caggacccac tttccctggg gcatctaagg    13080
aagccatcat ggcaaaccct agcgtgggtg atgccgagtg gatgctggga agaggcgtgg    13140
ggaccttgga ggagctgctg ggagcctcct gggagctgac ttcctctaca tcgatgcttt    13200
cgatgacatc atcatggcag atagcgccgg tgctgccgtt ctcacccacg gtcattggct    13260
cagaacccgt aaagtcacag ggattctctg gcagggcgt gttgggaatc tgaccgccca    13320
tgtgcatccg aatatgttgc tgcagcatca cggcattagt gaacttcttc tggcagatgg    13380
ggcacgaatg ctgcgtctta atggatgtgt tggttcggtg aaccccaagg tgtgtcttca    13440
ggttaccttt ggtagaaaag gctcggccac agatcttaca ctggaacggt ctctccccgg    13500
tgtgggtgcg ataatgcatc ttgagggagc tctgacagct taagactcgg tggcaaatga    13560
gacattcgtt gggatcagtg gtggccttgt caatgttctc caccaactgc tgcaatttca    13620
gggtctctga ccctggctca gggtcccac tccttggaa gccaccagcc ttggggaat    13680 tatagtttgg tcccacccca gggagtgtgg gtccaccctc actttctgga gaaggcccag    13740
gctgcaggtc accgggcaag gagccacccg tgaggtcctt gggattagtc cccgaagaaa    13800
gattctgagg tagccctaca gaggtggtta caaggacagg tttgctgtct aaagaaagac    13860
tcggttcatc tatggggtca ggtacagaga gtgcataggg gatgccattg ccggccgcca    13920
ctttgtcctg gaactcggca aacagctggg ggtttgcctt cacctgggga tgtcggtgaa    13980
```

```
agtgcacctt gaggttgccc ttggtggtga agcgatgacc acagacagag cacacgaagg    14040
gtctctctcc agtgtgggag cggaggtgga tctgcaagga gctatcagtc ccaaaaacct    14100
tgctacagta cttacacttg tgcttgtaga gggccgcctc gtctttgggt ttgacatcca    14160
ccgcggagat gttcggtggc ttcccctttcc cttttcttgga tgtgtctagc gccacagtgg    14220
agaaagggct ctggaagagc accgagcccg gggcctgagg aagcaaagcg ctcgggaggc    14280
gggacatgac gttcgggagc acccgggtcc catccggctt cagagtgaag ggtgccagcc    14340
ctggggacag ggagctggtg gcagaaggga tgttggcgtg aggtagcttg gcttgtttca    14400
aggcatccag agacagacct tggcttccag ctttctggct gagcaaagcc acagctgcag    14460
aaacctgctg agacatgtgg ctgcccaagg tcttcagagt gtcggcccct gccccgcttg    14520
agtggagggc gtgggaggcc cacatgttca cctggatgcg gatctgctcg gtgagctgga    14580
tctgctgtag ctgctgctgc tgcagacaca agatctgctc gaggacccac gggatgctgt    14640
tggcaccagg cacgggggca gggagtgcat ccgcgctccg ctgattcacc gccaccttgg    14700
tgccccgtag tgcctgcaag gtcacattag tgttggccac tttgcctttg gctaaatagc    14760
ttatgtcctg gggggtgggt ggcagggctg tctctgtctt taggtacacc acagactccg    14820
catccggctt ctccttcatg tcctctgagc tgccgccatt ctccctgtga cagtccttac    14880
tgccgggact ggtgggctgg tggctcagta cagctccgga gaagtcttct gaaggcacag    14940
gcccctcgct gtcattcatg atgaggacag gtggattttt agtgcaattt ttcttatgtt    15000
ccaggaactc agagatgctg aagaactccg cacagcattt ctcacagacg tgcgtctcct    15060
cccgacgaag ccgctttact gtggcttcat cctcactcgc cacctcgtca ttccctgggt    15120
ggttcactgg agcacctgta acaagacaga aaaagctaag gactctgccc aagtaaaaga    15180
tgtgggggga gccgggcacc gtcgctcaca tctataatcc tagcacttttg ggaggctgag    15240 gtgggcagat cacctgaggt tgggaattca agaccagtct ggccaacatg gtgagaccct    15300
gtcactacta aaaacacaaa aattagctgg gcatggtggt gggctcctgt ggtcccagct    15360
actcggggag ctgaggctca agaattgctt gaacccagga ggcagaggtt gcagtgagct    15420
gagatcccgc cattgcactc cagcctgagc gacagagcga gactccatct caaaaaaaaa    15480
aaaaaaaaaa aaggcaaaaa ggctgatccc tgaatttctt ttgtaactgg ggcttactta    15540
ctttagggtt agtgccagcc tacacattgc aactccgaac ttgggactgt gttttagcca    15600
gatgctgggg tccttcacat gatgcctgga agtctctcga agctacttca ttgttctcac    15660
ctccctgctg tcctctcagg tatacccccat catcaagata tcaatggagc ttggggccac    15720
aggacaaaga caggcatatc tcagacccag cagctaagcc tataaatcta aaccacacaa    15780
gacattcaca cgagcataca atgatctagg ttttcttgtt ttttcagaaa tgttcacagc    15840
agcaaagaag taaattttgg cccacccacc catagtgtga gaaatatgca gaatttctgt    15900
atgccacaga aattaagtga aagaaacggg ttgcgcaaca atatgtacaa catgaccatt    15960
ttgcttaaaa caaacctgt gtttgaaatg tacaaatgtg gctgggtgca gtggctcgca    16020
ccagtcatcc cagcactttg aggccacttt tgagaggccg ggagtttgaa accagcaaca    16080
cagtgacacc ccgtctctat aaaaaaaata agaagataaa aatagctgag catggcagcg    16140
tccatgtata gttcaagcaa ctccagaggc tgaggcagga gaaccgcttg agcctgggaa    16200
gtcaagccac tccagcctgg gtgacagagt gagaccctgt ctggaaaaaa aaagtacaaa    16260
tgcacaagga aaaggccagg aagggctgga gtgcagtggc ccaatcttgg ctcactgtaa    16320
```

```
cctccgcctc ctggattcaa gctattctca tgcctcagtc tcccgagtag ctggctaatt    16380
tttgtatttt tagtagagat ggggtttcac catgttggcc aggctggtct caaactcctg    16440
ggtgcaagtg atccgtctgc ctcagcctcc caaagtgctc ggattacagg catgagccac    16500
cgtgcccagc caaagccacg acttttgac agcacagtcc acccacgggt ttccaggagg    16560
ggctgatctt gaagcatggc cttaacaaac tgatttaatc tttacttatt tcagactggg    16620
tcacaatatg aagtcttgca aggtatgtgt aggctggggg tgggtcaggg gaagagacaa    16680
cagccatggg caggtctggc ctgccagagt taagaaagct aggcagggcc aacctagcct    16740
tgcctatcaa taacaggtag ttattgatag gcaagtcggc acaccctaa gaaagcctac     16800 tgggcacgcg taatcgcgag atgacaacct cgtgattaga tgattaggta gatgcctgga    16860
tttactgatt caaccaggac tgctgagaac aatgccttac aataaaacaa tgtaatgcct    16920
ctcgttccac aatactaacc tcctactgcg tgcaaagcag gggttgggga cccaatggtg    16980
aaaagatgag ccccattatc ttcctataat tcagattttg taccagcaga tgcccatact    17040
gtaatcattc aatcctatta aatatcagct ccattaaagg ctgggcgtga tggctcacac    17100
ctgtgatccc agcactttgg gaggctgaga gttcgaaacc agcctgacca atatggtgaa    17160
actccatctc tactaaaact ataaacttag cccagcgtgg tggcgcatgc ctaatcccag    17220
ctactcagga ggctgaggca ggagaatcac ttgaacccag gaggcggagg ttgcagtgaa    17280
ctgagattgt gccattgtac tccagcctgg gcaacaaaag cgaaactcca tctcaaaaaa    17340
taaataaata aataatgaaa aaataaagat gtgaaaaaca gagactctga gaataatgt     17400 cactcgtgca acataacaaa agttattgac agataacttt tgagcactta ctttgtatgt    17460
gccaggtatg attctaaaca atttgttata ttaacaactc tgaaatagaa actattaccc    17520
tatttgacag aaggggaaac tgaggcacag aggacatgaa cttgcccaag ctaacatgtt    17580
aagtaaactg cagagccagt attaaacccc agacatgcag ttcccacacc ctctattgga    17640
acccttcatt tgtacccctc tgatcatgtt tcttctgtaa agattgcaac tttctttcct    17700
ctcacagaga tgttaagatg ggacaggaaa gcctgggagg ttgccttggt taggaagggg    17760
tgggagtcga ccacccattc ctgtctcatt tctaggactt ccagaagttg ctctgaaagt    17820
gttaagatgc agtgcgatgc tgctacttcc aggtagagtt ctagtagcag gtaccagcac    17880
aaactctcct ttcttaaggc cccaatactg ctgcgaatct gcctcacttc agtgatccag    17940
ataaaaatgt tcggccgggc acggtggctc acaaggtcag gagatcaaga ccatcctggc    18000
taacacggtg aaactccatc tctactaaca atacaaaaaa ttagccgagc acggtggtgg    18060
gcgcctgtag tcccagctac tggggaggct gaggcaggag aatggcgtga acccgggagg    18120
cagaggttgc agtgagccga gacagtgcca ctgcactcca gcctgggcga cagagcgaga    18180
ctccgtgtca aaaaacaaa acaaaaaca gataaaaatg ttcgtcaatt cccagaaccc      18240
tggcaactat ttatctggga accgccaact ctcgataaa tagtatctat ctgtatgatt     18300
ttccaagact ggaaccagc actagtggga gtgctaggtg gcacaatctt tctagaaaag     18360
caattttgac aattatgtgt caagaatgtt aagaagtgaa acttttttaaa acagtttctc    18420 ttgttaggga aggaaataca cgctgctggt acgagtgtat agacagatac agctctttca    18480
gggagtcatc tggcaacatc ttcattttag tacaattttc ctttgaccca gcaattcctg    18540
ctttaggaat ttcctcaatg tacttgcagc atttctcatg ttaacaaaca gcaacaaaat    18600
ggatgcacct tggtccatca gtaagatttt ggttaaataa gttagggtgc agaaaaggcg    18660
aacgctttat agcctccaga aataaagaag accaaggctg ggcacagtgg ctcacacctg    18720
```

```
taatcccagc actttgggag gccgaggtgg gtggatcacc tgggttcagg agtttgagac   18780
cagcctggcc aacatggtga aactctgtct ctactaaaaa tagaaaaatt agccaggtgt   18840
gatggtgtgc gcatcgctgg aatcccagct actcgggagg ctgaggtggg agaattgctt   18900
gaacccggga ggtggaggtt gcagtgagcc gagattgcgc cactgcactc cagcctgggc   18960
aacagaacaa gactgtctca aaaaaaaaaa aaaagaaa gaagaaaga aagaaaaga      19020 aaaaaaaaac cctcaataaa gcccatgcaa aaacattaac cactccatac tacttttag    19080 aggccaaagc taaccaccac caacctctcc aagcaagaac aaaaacatac ttcatactct   19140
tacaccttaa ggcaagcttg tccaaaccag gcccaggcca gctttgaatt cagcccaaca   19200
caaattcata aactttctta aaacgtgaga tagttttaca atttgtttta agctcatcag   19260
ctatcattac tgtccgtgtc ttttatgtgt ggcccaagat aatccttctt ccaatgtgga   19320
ccagggaagc caaagatta gacacccttg ccttaggtcg cttatcttca tagccacata   19380
atcaaacaag ctcctttgtt tccattttgc agatgtggaa acaggctca gaactaaatg    19440 gctcaagatg acatactgct tgctagtcac aatacagagg tgacttaaat actatttaac   19500
agcactaaaa ttagtggccc aattcataat cgtttcttct agagcggagt ttctcccctc   19560
tgtgggagaa acttttttat tttgcccctc tatggaggct tttaagttat ttttccctaa   19620
tagctcccca cttataaagt tctaatatca caaacatatt atatacattt atctcctttg   19680
gaaggccaca aaccactgta ctatcaataa aacgttttca tcccattggt gaaaatatca   19740
cttgattgaa aatgcatgtt ctatttaaca caggcatttt taaacagggg gtctatgaaa   19800
ttagataaga aaaaatact aattttcact aagctgaact aaaattcaac ctttctttca    19860
atgatgaata taagcaacat accacagtgg tattaataga acttgtgact ttgtcatcag   19920
tggagaccac agatattttc atatagtgtt acaagttgtt atgacttgga aattcttgtt   19980
atctgacagg ctactagatc ttgttattta ttgtattaat aaagtagctg atattactaa   20040
gttaaaaatg ttttcatttt tgatgactgt atttcaatgc aatttatttc cttggtcatc   20100
tatgtatttt atacactatg ttgagaaggg atctatggca caaaaaggt taagctccct    20160 cccctagaag gatccagcag ttcccagagt gatttacagc ctgaataccca gcttgccttt   20220 gctgtataca caagcttgcc tcttctgtag cctccaccag caacatccca cttgactctt   20280
aaaacagcag cagctctgtt tgcttgtgca gtaaaaagtg cttctacatc caggccacca   20340
ctggtaaata ccgcaactgt atttgccaag gagtaagaag attctgttat gaacaattgc   20400
tgggcatgct taagttaacc aaaaaggaaa aaaaaaagc aaagttcaga gggattacac     20460
agcaactagt tcttccattt ctccacccca cccccacccc gaattttagg aatgttatct   20520
tgcagcatct agttatccaa taagttggaa gaatgcagta aacccagcag gggtcttaga   20580
ttcaatcact gccaaatgga tagaaaatac tcttactatt gtataggaag aaagttcatc   20640
tactagtggc caatcaaatt ctggagacac tgaaatgctt aaaaagtaaa acctgtatat   20700
cttgataaaa gcattatgac tcaagcttat cttttttca ttcctacatt taaagaacga    20760
caatgagtag attatctaaa gcacacaaca tcttctaccc tcccccaacc ccaggataat   20820
tgcttaccaa aaaacaaaag gaaattatgt gccttcttaa gtatttaacc agttgaaaga   20880
aaactgcctc tttagcagct taattttagc agtcaaaaag ccttcaactc aattcataga   20940
aggcagataa gactttaagt ttccacctaa ttaagatcta aaaaggcaa agtttcaaac    21000 agccttgaac caaaattcgg ggatgctgct ggagaggaaa aaaagagtaa atggctcaaa   21060
```

```
gaaagtttca caggcgctaa ggcgtgtgac ttctgtttgc ttccaaggtt agggaagtgt    21120
cccactcgtc cccaactaga gatcaggcaa gtttgcaaac tccatgaggg cagggttttt    21180
tgtcgcctgt ctccagagcc ccctgaaca aatcctgaca cagacataca atttgttggg    21240 gcggggtgg gggggattg tggtgactgg cgatgcagtt cttatctgga tttagtggct      21300
tttaaaaatg tttagacatt ttaaaaaata gtcaaaagta ctgtaggcta aaggtgatga    21360
ggaagggaca acttctggaa ctcttttcgc catcaattttt tccagggtag tacaacccag   21420
agaagccgac caaactccaa cattgtttta tttctgggac ctcttcatct aaaccgtgtg    21480
aaggcacatc ccaacattta agatggcaga ggagaggcca ccaaacccaa ccagccaagc    21540
accaatcacg gctcccttgt cgaagatgcc aaaagaaca tctcatcaca tcaccaactg     21600
acctaaggtt atttttaaaa aaccaataaa aacaaaacaa aacaaaacaa aacaaaacaa    21660
aaaaaacagt tccttgggct ctggggcgag gcaggacaag acaccatggg ccatcaagca    21720
gggcaaggca ccacgggcaa agccatttca acaggtgct gcaatttaaa atgagtaaaa     21780
acatgactat cacttttggt ctttaatatc ttgaattaaa gatagcgcac tcgagtcccc    21840
agcctggtgt ctggcaggca gcacactgcc atttctgcta gattgcctca actggcagct    21900
caacaccatc ttgacacaat aaacacaaat aaaaacattt tggtatttg aacaaaatta     21960 agactgatca cattcccaat tcatagtagc ccttctatag ttgaaattat ctaaacaggg    22020
cattttatca ctgctatata gaggaggaac ccaaaaactc agaaaaaaca aaaaaacaga   22080
aaacgccacc aagctggctt caaggttaca cagctgaaag tcacacagcc acagtggaac    22140
gcggatccca ttctaaaacc tgacttccca ggcatcaacc taacacttca cattttaaaa    22200
aaggaaatgc taactgcctt ctgcctccca agatggttcc ccaacccaca gcccaggagg    22260
aagctcacta acagcagcac gaatgacaaa gtatcatttg cttctgcact gcacatttt    22320 attcaacaaa aggagctgtt tggcaaattg tagcttctct ccctatggga aacccacatg    22380
aagtctaacg tagaaagttg acctgaaacg ttaactaacg tcaaaatcct tctaagccag    22440
cgtaggtcat tttggtgagt aattggaaat aggaagttat tcgaaacttg ggaatcctaa    22500
tcgttgatgt ttgtaatcca gtttagcaca aagggcattt gaaactcttt tgagaaaatg    22560 ctaattttc ctgtatgtag tgttagccct gcgaccacct gcagattttt tgatctgcta     22620
attgatcgcc agacgtcatt ttcctccctc aaaaactgca ttctcgaatg gctttgcaaa    22680
ataagaccag ctcaatctgc attctaaaaa attatgtgag acatatacat acatctaagt    22740
tagatatgta tgtctacatt atatacctaa cacatataat tttaggcagc tcaaatgcaa    22800
acaacccaaa cgcagccatt aaaaacgcac tgcttgggaa aacaaccttc tctcccaagg    22860
aggcaattgg aggctctgca aacacattct agccgccagg agttattacc aagaattcca    22920
cacttggcaa agaacagcgg gcacagacga cgatcaagca ggcgaccggc acgaatcccc    22980
tagggtaccc atccttggcc cagcccagca ctctccattc accccacaa cccgtcccac    23040 ccaccaggtg tgagccagta cctgcgaagg daccccgcct cccagcaaag ggctaggctt   23100
caagctgggc ctcaggggg cgcccgcgcg caagccgggt gggctgtccg cgacaaccct    23160
ggtgatcaat agccaactcc cctccctccc aaatcgcagt ggcagcgcac ggccaggccc    23220
gaggttttag ctcagctcag gttgactctg attccaaact ccaaccatcg ttaatttcag   23280
aagccctctc gtaacaagct tccctcccga aaggtgccaa acaccaccaa aagccccacg    23340
tgtgtgcgcc cacccaaaat gaaggggaa gggaggtca gcgtaggacc aggggaggg     23400 tcagaaccag gagctcgccc ctcctctccg gaggaagcag gcgggctgag ggttaaccct    23460
```

```
tttgttccag gtgggccagg ccacgaagcc ttcacgctcc cctcaacccc caccccaccc    23520
cgcccccaac caaggcacaa agagagtccc tccaggcgcc tgggacctcg ggtgcgcgct    23580
gcgctgacca cccggcgccc cgaaaacgcc cagccatccc ctccgtcaag ccgatccttt    23640
taatttgccc tggaaaaatg ttaaacgggg aattctattg acgtattata aacttgggaa    23700
atgtattaca ttcagtctcc gacaaaaagg cggggatacg gaagccaaaa agtggcgacc    23760
gtcttctcgg gaaaccccgg gtatcagaga tggtctctga gagtcctccg gggttgccgc    23820
gcacacccgt ctgctgcagg gaaattagaa agcaggcggg gagcggagcg acgaacaagg    23880
ccggagagga ggctacaaat cccccctccc cccacgcgca cgctaaaaac ttatcaggcg    23940
acaatttggc gggccgggat ggagacgaga tagtggaaaa ccgcctcgct cctaaaacct    24000
ccgcggtgaa gtgatgaagt gggaacagag ttggccccgc cgttcctggc gcggctgggg    24060
tcccgaactc ccctcgatct gggaaacgct ggccgcggaa gcgtgggcca ggtcagccgc    24120
gggagttcgc tctggccccc cacctctccc ctttcacacc caagcgcaaa tgtggaaagc    24180
cgagcgctcc agaaaagcca cgcaaaacgg gaggccggtg caccccagtg gggctgccgc    24240
gcgcccgcca ccccggccac tgggggctcg caccctcggg cttgccgcgg ttattttag    24300
gaagtcggaa atcaaagatg gctggaggtc aggcccccgaa aggttagggc gaagatcggc    24360
aggcggcgca gcccgggcag aaaaggcgaa atccagaaaa gaaaaaaatt ttaaagggaa    24420
acattgagcc ctcctccccc acctctctgg gccctccaat ccctgcgca gcgcgggtgg    24480
cccgcacccc agctcctgag ggtggggaga ggtcgcgccc cctccccca cttggcccgg    24540
gagggggcgcg tgcaacagat cgtcctcctc cggggggtct tccagggggtg cgcccctcct    24600
ccagcctcca agaaaagccc caaggggctg gtggagaggg tggggatccc ccggggttct    24660
ttcttttgag agcgacgcga gggaggggga cctaagttac aagggggggg ggtaacacca    24720
gtgaggggag tggaaccaat taagtgaggg gcagaggaca aggagaaggg aacctttcgg    24780
gagcgagaac agaggagcga gtgggggtca attttacaat tagggagaa agctgggggt    24840
gaaacttaca caagagggga gaagaggaaa aaagtgtgaa atgtgcaaaa ggcggggtgg    24900
tggggagagg aggagacctc tcctcccggg cactgagccc ccaaatctcg gctcctgaat    24960
ttgcgctgga cgccgcccgc tccccgaagc ctgcgccctc gaggatcccg cgtacgtccg    25020
ggaagctccc ctccccgggc gggcgccccca gccccactca cccagctccc ccgccgcggg    25080
cgccgctggg gccgcatctg caaactccgg ggtctgctgc tgcggctgct gctcgccctg    25140
gtcctcctcc gagttgatgt gctggggttt cgcctgcttg cgcctcgaca tggtgcgagc    25200
atcgggcgc cggagagcc gcagttattt gccctctccg ccacaaattc ctggagttgg    25260
gaaatttacc ccccttcggc cggaacgcgc atgtcccagt aattattatt atcaataatg    25320
cattgcgatt tatcatgagc cctgacagct gattggcctg ggtccaagac ctcagagatc    25380
atttaaataa gccctcattg atcagggagg ggtgaggcat tctgggcttt gtagtccggg    25440
cctacttgtg acaaaggcgt gttcatcagg ggagcgcagc taattagcat ccgggctcag    25500
attggctggg gcggggacga aatcagaggg ggacccatcc ttgctccagc tatctcagtc    25560
cttggagagg aaaagaaaat ggggagaaat gcgtactcat taaaaagtag gagcttacgt    25620
agaagttttg gaacggcttt atttggtagt tacttgctcc aaagattact tggtaaggtt    25680
gatgtccacc agccgagaag ggagatctct tcacagtgga atattttggc tcagttttca    25740
catctacacg cacacacatt ccccaaaacc tgagatgtga cccgtgtccc ctcccatctt    25800
```

```
tttgattaaa aatgtttaag ttgagtctcg agataactga agaatgatga atggtggtgt   25860
tttcagccct cccacccatc tcaactctta aagtgagctc ggaacttcca aaatttcaga   25920
tacccccacca ccaccatgac ttacctcctt taaaagctga ttaatagcct ccaggattcc   25980
tgttcacaaa gactggtttg tggttacaat gcaaaccttg atttttttt aacttcaaaa   26040
tgactggcta ctaaatatag aaatggcaaa tgataagcaa gcatagtcag agataatatc   26100
aaaacagcaa gcaattgcat ttttttcccc aggagccata aatgcctgat aacatcatat   26160
tttattactg agacaatgct cttgcatctc ccatggaatg gcaatggggc actgtcacag   26220
tatctggttg ttactaatca ctattggaat ttttttgtgc aatacacaca ttattacaga   26280
aaaggtgtat cgttcaaagt gattgtatca ttgacacatg atgcctggaa ttttttaaag   26340
tggggcttgt gtgtgtgtat atgatatatt acatgtatac acatttatac cgtaaattca   26400
tgtatactta atttggctaa ctgctttaca caatgtacat gctcaataaa tgttaaatga   26460
atgatgaaat catcaacctg ctaagtcttt gattggtctt tccataactg ctctgggcat   26520
gcgtctttgt ttggcattta cttcattgta agggactgtg cagatataaa ccctccctcc   26580
acatttgtgc attgcattct cttgattagt tattcatcac gttcccagct tgtaaactca   26640
tcaggaatac aagcaaaatg gaatgctggg ctcatcaatg tgttcacctg ggtatttgga   26700
caacccaagg cagaaaataa atcagcttga tcatcttttt tatattcgtg gccatcagta   26760
aaaacttgtt gaaggaagat taaccttcaa ttttttgagtc tctgaaaaag tcttgcctta   26820
tttatgtat aatatttaaa gcaagtaaga cagaattata gccaacagcc agattgaaaa   26880
ggtaagaatt tggtttaata atacatagaa gcagtttaga attctgatac tgagtaaaaa   26940
ggccaattag cacctgcctt gctgactaat ctactaatat tctcaacacc ttttctgtgt   27000
aagatagtgt ggcaggagat ctaacttaca aatctaaacg aatgtgcagt gggtttatgg   27060
ctcaaaaaat actattgggt taaggaaaat ttcatttata tagttgttta tatttatttt   27120
agtagatgat agttgtaaca tgttagcctt actacgagac aaaattgtgc cgcttgactc   27180
tccaagtgat agtaataata ataattgatt gagccccttg tacatgccac agactgcatt   27240
aaatgaatgc acaccgcctt gttttatctt cccatggagg ttggccctat tgtcctctcc   27300
attttgaaac tgaggctcaa agacatgaag tgacttaatt agaaactggc tgagctggtg   27360
gtcagtttct aagccggtgg tcagtttcta agtctgactc caaaattcta tcacatccta   27420
atacctgtct tccaactata gctgaatata gagaagatag ctaaagaaga aaaatcggag   27480
tacagtaaac taaatttaaa gtgtcctaga aaaatcttgg gtcttcagaa atcactccaa   27540
cagatgaagt caagaagttt ccctcaaatg gaaaccttcc acaaatgtca tatcaagaaa   27600
agcaggacac agtacatgtt ttgaatctac ccccagttta acagctgcag ccaggagcca   27660
gttggtggaa aataaagtaa gtcctagagc aaagcagggg atgaacggag ggcatagcaa   27720
caggcaagtc cgtaatcaaa agttgtttca ggctgagcac agtgtctcac gcctgtaatc   27780
ccagcactct gggaggccaa gactggcggg tcaccagagg tcaggagttc gagactagcc   27840
tggccaacac ggtaaaactc catctctact aaaaatacaa aaattagctg gttgtggtgg   27900
cgcatgcctg taatcccagc tactcaggag cctgacggag gagaatcact tgaatccagg   27960
aggcggtggt tgcagtgagc caagatctag ctactgcact ccaacctggg cgacagagtg   28020
agactctgtc tcatgaaaaa acaacaacaa aaaagttatt tattaaacca aaggacctgg   28080
ttgggaccca agcttgaaaa gaaaatgttc agagtaaagg atgatattaa actttttcat   28140
gttaacgtcc tttgttaggt gactgggttt atataatcca gtcattgtca atgtttatgt   28200
```

```
aatccagtca tgttcaatgt ttgtgccagg caggaatatt caaaaaatac acttcttggt   28260
atatttttca gcagtcttat tgtttataag gagatttggg atgcataatc ccattttatc   28320
ctcactaata tccttttttta attccttttt tttttttttt tttttttttga gacagaccac   28380 tcttgtcacc caggctggaa tgcagtggca cgatctctgc tcattgcaac ctctgcctgg   28440
gttcaagcga ttctcctgcc tcagcctcct gagtacctgg gactataagc acatgccacc   28500
acactcggct aattttttgta ttttttagtag agatggggtt tcaccatgtt caccagttgt   28560
ctccaactcc tgacctcaag tgaggcccac ctcagcctcc caaagtgctg ggattacaga   28620
cgtgagccac cgtgtccggc ttatttctac ttcatttatg gaaaaacaga agctcattgc   28680
tcccatcagc tcctagcgag tactaacgaa tgcatgccaa attatggatt cagtaacttt   28740
gcacaggtct cagtggaagg cagatctttc cctgaaaacc ccacctctgc tcttttctac   28800
aaggaatcgt cttcctttcc actgcttgcc tctcttcacc tggcccactc ctaaaaagcc   28860
tataatctct tcaaatttcc cttccttaaa ccagccttcc ctcttccaaa ctaggtctca   28920
tttattagtt ctctcaggct tcaagaaacc atatctttct ttttatagcg cacttcaaaa   28980
tatataatga cagactttct catgtatctg tttattgctt atttctcaca ctgcaggctc   29040
cgtgagggta gacaccgtca tcacggtgtc cttagcactt agccacagta atggaacaca   29100
gaagtcacaa caaataaata gcgatggact caatccatgc tgagtaactt tagaggcctg   29160
aatatgaaat gaagtgttaa aggcaatata gtaggtggga atgtaaaatg ctgcagccac   29220
tctagatggc agttcctcaa caaatgtaaa aaaggattac catatgatcc agcaattcca   29280
catgtgggta tatatccaaa agaattgaaa gcagggtctc gaagcagtat ttatataccc   29340
atgttcacag cagaattatt cacaatagcc aaaaagtgga aacaactcaa gtgtccatgg   29400
acagatgaat gaataaagta aatgcagtct atccatacaa tggaatatta ctcagcctta   29460
aaaaggaagg aaattctgac acatggtacc acatggatga atctttgttt tcttttgggt   29520
ttttttgttg ttgtttttttg agacagagtc tcgctctgtc acccaggagt gcagtggtgc   29580
gatcttggct cactgcaagc tctgcctccc gggttcacgc cattctcctg cctcagcctc   29640
ccgagtagct gggactacag aagcccacca ccacgcccgg ctaattttttt gttttttttag   29700 tagagatggg gtttcaccat gttagccagg atggtcttca tctcctcacc ttgtgatccg   29760
cccgcctcgg cctcccaaag ttctgggatt acaggcgtga gccaccatgc ccagccaaca   29820
tggatgaaac ttgaagacat tatgccaagt aaaatgagcc agtcacagaa ggacaaaatag   29880 agtagtcaaa ttcatagaga caaaaagtag aatggtggtt gccaggggct ggagggaggg   29940
agagtggggg gtggaggggc cgtttctgct caataggcat gaagttccag ttttgcaaga   30000
tgaaaaggga tctagataaa tgtttagatt ttagctgctt tgccacaaaa acaaacaaaa   30060
tcaggtaaca atgcaagacg gataggttca tttgcttcac tggtaatctt tttactatct   30120
atataaatcc cataacatca tgtagtatgc cttaaatata cacaataatt ttttttttta   30180
aaagatctgg actgggcacg gtggctcacg cctgtaatcc cagcactttg ggaggccaag   30240
gcaggcggat catgagttcg ggagttcgag accaccctga ccaacatggt gaaaccccat   30300
ctctactaaa agtacaaaaa ttaaatgggc gtggtggtgg gcacctgcaa tcccagctac   30360
ttgggaggct gaggcaggag aatcacttga acctgggagg cggaggttgc ccagatggtg   30420
ccactgcact acagcttggg agacaaagcg agactccaac tcgaaagaaa aaaaaaaaa   30480 gaaaaaagaa agagagagat ctggaaattg gttgctcaac aatgtcaatg tactcaacat   30540
```

```
ttcaaaacag cacacttaaa gatgggtcag acagtaaatc ttatgttaag tgtattttaa    30600
cacagttgca gagaaaaaaa ggcaattaca aactagatta tcacgatggc tgcatactgt    30660
atggatttac taaaaataat tcaactgtac actcacagtg agtgagtttc atgatatgta    30720
aagcatatgt acatgaaatg gttttaggaa agacaattac atacttggct atccctgtca    30780
ttgaaaggac cacagttatg tgtgtgtttt tttctgtgtg ggattcccag catcttaagc    30840
tcgaaatgac taaagtagcg aggttgagtc ccataaatca tgatctgcca ctgcaaaagt    30900
attgcccctt tggacctctg tttattcatg ccaggaagca aagtcgactg acttggtaac    30960
cacagctgct tcaatttggg aaatgtaagg gttggatttg ggaagtatct taacatggac    31020
caacgtctta gagtctatgg acttttatgt atcatagtac atttgatatc tgcctacccc    31080
aaatggaagg cttgatgtct ggaaggcact cttcaaattc tagagattta gaagttaagc    31140
taaaattgcc tccaaaatca tgcttgtaat tcaatgggac tgttttatta tggggccaaa    31200
tgtccacttt tctgagtgtc ctggcccaga gcccttctgc tgggacgatt tatgttcgca    31260
aagttggcta attgcaataa tcaccactta actgatgata ttcccccat tttaatatct    31320 ctctgcttgt tgccatttca tcaattccaa attggtattg aacaatttct agctccaatt    31380
agtcttctta gttgcagctg atgtattgaa gcctacaact gtgtattcaa aaaaaaaaa    31440 aaaaggtaaa aatattccag gccagacacc gtggctcata cctgtattct agcactttag    31500
gaggctgaga ccagaggact gcttgagccc agcccaggag tttgagagca gcctggacaa    31560
catagggagt ccccatctct acagaaaata aaccacaaaa aaattagcca ggcatggtgg    31620
cacgcaccta tagtcccagc tactctggag gctgaggtgg gagatcacct gagcctggag    31680
aagtcgaggc tgcggtgagc tgttatcgtg ccactgcatt ccagcctggg tgacggagcg    31740
agaccctgtt tcagaaaaac aaaacaaaac aaacaaataa attaatcagg catggtggtg    31800
tgtacctgta gttccagcta ctcaggagac tgaggtggaa ggattgattg agcccaggag    31860
tttgaggctg cagcgagcct tgttcatgcc actgcactcc agcctgggca acagagtgag    31920
agtcagtctt aaaaaacaaa caaacaaaaa agggcctggc acaatggctc acgcctgtaa    31980
tcccaacact ttgggaggtc gaggccagca gatcacgagg tcagaagttc gagacagcct    32040
ggccaacatg gtaaaaccct gtctctacta aaaatacaaa aattagccag acgtggtggt    32100
ttgcgcctgt aatcccagct actcagaagg ctgaggcagg agaattgctt gaacccagga    32160
ggcagaggtt gcaatgagcc gagatcgcgc aacagcactc cagcctggga cagagtaaga    32220
ctctgtctca agaaacaaa aaaattctgt ctgggcgtgg tggctcacac ctgtaatccc    32280
aatatttggg aggccgaggt gggtgggca tctgaggtca ggagttcgag accagcctgg    32340
ccaacatggt gaaaccctgt ctctacttaa caaaaaaaa attagcaggc atggtagcgg    32400
gcgcctgtaa tcccagctac ttgggaggct gaggcaggag aatcacttga acccgggagg    32460
cggcggttgc agtaagccaa gatcatgcca ttgcactcca gcctggacga caagagcgaa    32520
actccgtctc caaaaaaaaa aaaaaaaa aaaaaattt ccaacaagct tattaaagca    32580
agagtgaatt gtcagaaatg atactttctt ctgtaagttt gctggttaaa gactaaatgg    32640
attaagaata aaagatttgg ccgggcatgg tggctcactc ctgtaatccc agcactttgg    32700
gaggccgagt gggtggatc acgaggtcag gagatcgaga ccatcctggc taacacggtg    32760
aaaccctgtc tctactaaaa atacaaaaat tagccgggct tggtggcggg cccctgtagt    32820
cccagctact cgggaggctg aggcaggaga atcgtttgaa cctgggaggc ggagcttgca    32880
gtgagccgag atcgtgccac tgcactccag cctgggtgac agagcgagac tccgtctcaa    32940
```

-continued

```
aaaaaataaa taaataaaat agtttgtgtg actagctttt tttactcctc agtcgcttga   33000
aactcatgct agtccaagca tgcagtcttt cggtcaatct caggcacaca catacagtcg   33060
agaatgttgg ttctctaagt ccacagcagc agttcttaat gggaacaatg tgccttttcc   33120
cccaccaggg gacatttggc aatgtctaga gacattttcg gttgtcacta ctgtctagta   33180
ggtagaggcc cggggtcatg cttaagatcc tacaatgccc aggataacct ccacaacaaa   33240
ggaatagctg acccaaaagg tcaacggtgc cagagatgag aaacgaggct tacaggtaat   33300
atgatttcaa ggctatatta gcacctaact aataccatta aaaaaaaaaa tagtaaagtc   33360
cttcctaaaa agtattaagt cacaatcaaa tcctcttatc ttctccaggg gaggcttctt   33420
aaccttccca actaaatcaa acttcagcat ttcgacccct tccctcaaag attgcacaat   33480
taccgtctta tattcactca tgtgatgatt tgagtaattt atctacttct ccgcctgcag   33540
attagagaaa gataacattt tggaattctg tttatttcac tgaatgggct atcataagat   33600
tctcctgccg cattgaaaga aatctttgta aatgtgtttt gttattttt  cactctgtgg   33660 atgaaccttt aattcactta accacccct  gttgagtatt tgagatcttt gtctttactt   33720
tagtaacatt tcagggaacg tctttgctca tagacggctc tgtccaaatt ttggatttct   33780
tgccttaagg cctaccatct tgagtctttc tgaagtgaat gttgaaatga atttcacaga   33840
ttcacagccc tttgagagct tttttcaaat actatcttac tccttttgta ggctcttgtg   33900
caagaccagg gcctcagtaa catgagtgat caagctaaat gggtcatctc ataaacatgc   33960
ttatcgggac actcacatat tgcgtaactg gacagcagaa atgtatagat ttcaaaaac   34020 aagtcaaagg ttcaattgat tgaacatttt ttttctgct  agaaatgctt tccttttcat   34080
ttccttttta cataagtctg attcactctt tacttaaata tttctgtact ggcgtccaaa   34140
acccttctta aaagttttct cttgccttaa agaaaatttt tttttgtta  tctaccaggc   34200 acaaatccaa ccccttagtc ccctaaaaag tgcctattgt aaactctatg tttaaaaact   34260
attactgaga aggcgcttct tcaaattcgc tgcaaacttt attataacaa agcttaaaga   34320
gctaaaagcg cggcacaatg gaaagttgac tgttataaat atctatccgg ctttgcaata   34380
taaattataa ttaaaaataa acttgtcaga gaactctagg caacacacaa aaagtgagac   34440
gtttagaacg aggcaattaa gaatgttaat tggaacacag agaaaagcaa aggacagtca   34500
ttgttaagat aactgctcta taaacaccta aatggattct gtgaagggga agaaaggatc   34560
atcttttgac catgaaaggg aatataaaat gttcttttct ttgttttaat gtgtggagag   34620
attttaaact tcttttctcg ctcagacgct caagtaaaca aatgacttgg ccctagtctg   34680
gtgtgggtaa ctaaagagag aaatggaggg aagagagaa  aagccaactg ggtaggcgag   34740
aagagaagag agcaaatgct gaagaagaag aaaacaaag  gaggatgata aatgtagagg   34800
aataaaggga aaaccaaaa  cagaaggcat aaaccctag  gaaacagaac aagagttaaa   34860
cacagagaat aagaaaggag tcatctccct ttcttcactc tccaaatgat ctgcaagtta   34920
atttcttaaa gacagcagag tcgacaagca cagtcagaca gacccagatg tagatcttgc   34980
ttcttggcag tttccatctg ggctggataa tttcctccag gttctcaacc tctctatgcc   35040
ttgatttctt ccctagtcaa tggggagggt aatcgctgct tgtggcttcg ctgcaaaaat   35100
cagaaatgat ttgtgtgaag cccctggcat ataattagtg tttaggaaac atctattacc   35160
acatgaatta tttcagggta cagcaggaat gtttaagctt tctcataata ttaagcagac   35220
gcacaacata catgatagtt ttggagtcgg agttatttaa tttacatggt catttatttg   35280
```

```
atcattcatt cattcaagga gtaataattt tgtctgctat gcacagggcc ttgagctcac    35340
ccagtgctgg gaatttagac atgaaaaacc ttaagtagtt cagcctaaaa tgtctaaaag    35400
tttaatgtca aaattgttgg cttttgcaaa aatgttagcc tgtgggccaa tggtggtcta    35460
tggtacattg actctgccta gaatatggct aggatgggat ggaaacacga aagacatgat    35520
ttagaacata ttcttttcca gaataagcat tccgtgacag aagggccat attcatctca     35580 ttcaccgttg cataaacaaa ttgcattgca taagcaaata tctttaatga acagcatcta    35640
ggagcacgtg ctttgaagac aaagcaaggt aaaggacag aggccatcag tggatgcttt     35700
tcttgtaggg tgatcaggaa aggcttcact gaaaaggaga caagtggccg agacatgaag    35760
gaggtgaggg agaaagtcat atagatctgt gggaattgca ttccagacag aggcaacaga    35820
caatgcaaag gccttgaggc aggaacgtgc ttggcgtgtt tgaggaacca gaaaaaggcc    35880
agtggggctg gggtggagtg agtgaggagt aatagggca gaggacatat gaccttagag      35940
atcatggctc tagatacttt gttttcctat tttttttatt gtggttaaat atccataata    36000
tgaaatttat ttatgtattt attttctga gatgcagttt tgctctgtcg cccaggctgg      36060
agtgcagtgg catgatctca gctcactgca acctccgcct cccaggttca gcgattttc     36120 ctgtctcaga ttccccagta gctgggatta taggcgtgtg ccaccacact cagccaattt    36180
ttatagtttt agtagagacg gggtttcacc atgttggctg gtctggtctt gaactcccga    36240
tctcaggtga tccgcctgcc tcggcctccc aaagtgctgg gattacaggc gtgagccacc    36300
gcatttccac ttatttaaa tgtcatctcg tagtggcagc ttaccaaata gagatccata     36360
taactgctcg aaaattttaa ggcttaagaa atactcaaaa ggagtgatta gtagtagaat    36420
gcttaataaa ttcttaattg tcaggctggg catggtggct cacgcctgta atcccagcac    36480
tttgggaggc cgaggcaggt ggatcacctg aggtcaggag tttgagacca gcctggccaa    36540
catggcgaaa ccctgtctct attaaaaata caaaaattag ccgggcatgg tggcacacac    36600
ctgtaagccc agcttactca ggaggctgag acatgagaat tgcttgagcc tgggagatgg    36660
aggttgcagc gagctgagat aatgccattg cactccagcc tcggtgacag agcgagactc    36720
tgtctcaaaa ataataatga taataaaaaa taaattcttg tttgtttgtt tgttttgttt    36780
tgttttgttt gagacggagt ctcactctgt cacccagact ggagtacaat ggcgtcttct    36840
cagctcactg cagcctccac ctcccaggtt caagcgattc tcccgcctcc acctcccaag    36900
tagccgggac tatacgcgcg tgccaacaca cccggctaat ttttgtattt ttagtagaga    36960 tggagttcg ctatgttggc caggctgatc tcgaactcct gaccttgtga tccgcccacc     37020
tcggcctccc aaagtgctgg gattacaggc atgagccacc gcgcccggcc aataaataaa    37080
ttcttaattg tcctgcagca aaatgtcta agggaaccaa gcatggtggc acatgcctgt     37140
agtaccagct actggggagg gtgaggtagg aggatcactt gagcccagga gttgaaagat    37200
gtatacccca caatcgtgcc tgtgaatagc cacagtgacc cagcctgggc aacatagtga    37260
gacctggatc tctaaaatca aaaacgtaa gagttgaaat atttagatag gtttcatctt     37320
aatatgtctg ccaagtcaat tagcgatagg acagccctcc ccaccccggt ttttttgttt    37380
tgttttgttt ttaagaattt tgctagggct gggcacagtg gctcacacct gtaatcccag    37440
cactttggga ggctgaggca ggtgtatcac gaggtcagga gattgaggcc atcctggcta    37500
acacggtgaa accccttctc tactaaaaac acaaaaaatt aactgggtgt ggtggcacgc    37560
gcctgtagtc ccagctactc aggaggttga ggcaggataa ccgcttgaac ctgggaggca    37620
gaggttgcag tgagccaaga ctgcgccact gtacttcagc ctgggcgaca gagggagact    37680
```

```
ctgtctcaga aaaaaaaaaa aaaagaact  ttgcttttt  ttttttttt  ttttttttgg  37740
tgacatgaaa ggctgtcaga gtgttttgag caggggaatg acaggatttt cctaggtttt  37800
aggagaactc tgagggaggt tatagaccca agtaggtggg ggataggatg gatgtgggga  37860
gagcagtgag gacgctcttg cagtagtcca ggaatgagaa aatggagctt ggaccaaggt  37920
ggaagtggca ggggtgggag agataaaaca gagatgtggg gaattcattg tgatcatgtg  37980
gctgatagaa cttgcaaact gatcggatgc aggtataaga cacaggggtc aaggatgacg  38040
cctagatttt cagcctgagc atccaaaagg ttgcaggtac caggtagaga aatagggaag  38100
gctgtgggag acgtagattt ggcagagggg gtgcttcaga actcgtttgg aacatgttag  38160
gtttgatttg ccaattagac attcaagtgg aaaagttaga tcaacagttg gagacaccag  38220
tctaaagttc agaggcaagg accagcaggc tgttgacatc agtatgagat ggtttttgaa  38280
gccgagaaac tggctgagat catctaggca gtgaatggag ataggaaga  gaaaagagca  38340
aggatgaggc ctggggaact cctgggttta caggagggaa gttgaggaga aaaatacata  38400
ggtgcagaga aagagcagcc agtgaatcag gatgacagag agagcagtcc aggaagccaa  38460
gagaggaacg tgcttcacag ggaggcaggg actcactgtc caaacatgac actgatgtgt  38520
caaggcagac aagcattgga actgagtgtt gggtttggca acacagagac aactagtcat  38580
taagaagatg cctggggata cctagggca  acagctgatt ggagagggtt ggggaaggat  38640
gagaggagat ggcgaactct ttagggtcaa ttcttttaaa actgtctcat ggtgagtggg  38700
gagtggggag catcagggtg aatatgagtg tgagggagat aacatagcaa gtgctggatg  38760
acgttggaag gatccgaggg aagaggaaat gttgatgatg caggagagaa agggaacaat  38820
tacagagtac agatgctcct tgacttctga tgggtttacg tcccgataaa cccactgtaa  38880
gttgaaaata taataaactg aaaatgcatt tagaggccta ggcgggtgga tcacttgagg  38940
ccaggagttt gagaccagcc tggccaacat ggcaaaactc cgtctctact aaaaatacaa  39000
aaattagtca ggcttggcca ggctcaatgg ctcacgcctg taatcccagc actttgggag  39060
gcccaggcag gtggatcacg aggtcaggag ttcaagacca gcctggataa catggtgaaa  39120
ccccgtctct actaaaaata caaaaattag ctggacgtgg tggtggtcac ctgtaatccc  39180
agctacttgg gaggctgagg caggagaatt gtttgaaccc aggaggcaga gcttgcagtg  39240
agccgagatt gtgccactgt actccagcct gggcaacaag aaagagcgag actccgtctc  39300
aaaaaaaaaa aaatagtcag gcttggtagc gcacacctgt gatcccagct actttggagg  39360
ctgagggacg agaattgctt gaacctggga gacagaggtt ggtgtgagct gagatcacgc  39420
cactgcactc cagcctgagt gacagagaga gactgtctta aaaaaatgc  attgaataca  39480
cctaacctac caaacattac agtttagcgt accttcaaca tgctcaaaac acttacatta  39540
gtccacagtt gggcaaagtc atctaacaca aagcctattt tataataaaa tgttaaatag  39600
ctcatgtaat ttattgaata ctgtactaaa ctgaaaagca aaatggttgt gagtacttga  39660
agtacagttt ctactgaatg tactaattgc ccttgtacca ctgtaaaatt gaaaaatctt  39720
aaattgaacc attgtaagtt ggttcatctg tagtgatctc aggaaagtag gaaagagctg  39780
ggcatggtgg ctgctcatgc ctgtagtcac agcaactcgg ggggccgagg cagggagatc  39840
ccttgagccc aggaattcga gaccagcctg ggcaacataa ggtgactgtg tctcaattta  39900
ttttattatt attttttga  gacagagtct cactctgtca cctaggctcg agtgcaatgg  39960
cgcaatctcg gctcactgca acctctgccc cccgggttca gcaattcttc tgcctcagc   40020
```

```
ctcgccagta gccaggatta taggcgtgca ccaccacacc cagctaattt tttatttatt   40080
tattttgttt tttgagacag agtctcactc tgtcacctag gctcgagtgc aatggcgcaa   40140
tctcggctca ctgcaacctc tgcctcccag gttcacgcca ttctcctgcc tcagcctccc   40200
gagtaactgg aactacaggc gcccgccacc atgcccggct aattttttg tattttagt   40260 agagacgggg tttcaccatg ttagccagga tggtcttgat ctcctgacct catgattcac   40320
ccacctcagc ctcccaaatt gctgggatta caggcatgag ccaccgcgcc tggcttttt   40380 tttttttttt tttttttttt tttttgagac ggagtctcac tctgctgctc aggctggagt   40440
acagtggcgg gatctcggct cactgcaacc tccaccttcc cgggttcatg ccattctcct   40500
gcctcagcct cccgagtagc ttggactaca ggcacccgcc accacgcctg gctaatttt   40560 ttgtattttt agtagagacg aggtttcact gtgttagcca ggacggtctt ggtctcctga   40620
cctcatgatc tgcccgcctc agcctcccaa agtgctgaga ttacaagcgt gagccaccac   40680
gcccggccca cacccagcta attttatat tttttgcaga gatgaggttt caccatgttg   40740
gccaggctgg tctcgaactc ctgaccttaa gtgatttgtt caccttggcc ttccaaagtg   40800
ctagaattac aggcacgagt caccgcacct agcctatttt attttacttt attttagttt   40860
tcagacagag tcttactcta ttgcccaggc tggactgcag tggcgcatat cagctcactg   40920
aaacctctgc ctcccgggtg caagtgattc tcctgcctca gcctcctgag tagctgggat   40980
tacaggcacg tgccaccaag cctggctact tttttgtag ttttggtac agacgcggtt   41040 tgtccaggct ggtctttaac tcttggcctc aagtgatccg cccaccttgg cctcccaaag   41100
tgctgggatt ataggcatga gccttttata ttttatttaa aaattttaa aaattcttta   41160 aaaaggaag agatggagtg ctggcctatg acatggtaac atagttcatc cgctgcaata   41220
gcagggaagg cagaatagtt gggtgcagtt caaggcaggt aggttaattt agcttgggaa   41280
tgtgtgggag ttcactactg attgcctcta ttgtgtctat tacattagtg aaattagaaa   41340
caagagtaag gaagggaaga ggatgctgag tgttagaaga gagaaagaaa ggggtaaaag   41400
tcttccagga gagaaagaga aagaatgaag gagggaaatg tagtgggtg gctgggtcca   41460 tgtgggcgct catgcatttc tttctttctt tcttttcttt tcttctttct ttcttccttt   41520 cttcttttc tttcttcttt cttttcttc tttcttcttt cttttctttc ttctttcttt   41580
tcttttcttt ttctcttcct tccttccttc tttccttcct tccttccctc cttcttctct   41640
ctccttccct ccttctttcc tttgttcctt ctttccttcc ttctctccct ccctcttttc   41700
ttttcttttc ttcttttctt ttcttcttt tcttttctt gagatggagt ttcactctca   41760
ttgcccagac tggagtgcaa tggcatgatc tcggctcact gcaacctctg cctgccgggt   41820
tcaagcgatt ctcctgcctc agcctcccga gtagctggga ttacaagcct gtgccaccac   41880
gcccagctaa ttttgttttt ttgttttttt ttttgagac agagtctctc tctctgttgc   41940
ccaggttgca gtgcagtggt gccatctcgg ctcactgcaa gctccgcctc tgggttcac   42000 accattctcc tgcctcagct aattttgtat tttcagtaga cgggggttt caccatgttg   42060 gtcaggctgg tcttgaagtc ctgtccttgg gtaatctgcc caccttgacc tcccaaagtg   42120
ctggaattac aggcgtgagt ggacgcccgg cctatttctt cattttcctt aaaattatat   42180
atatatatat atatatatat atatatatat atatatatat ttaaatagat atttatatat   42240
tttttttttc agagggattt gctctgttgc tcaggttgga gtggtgcgat catggctcac   42300
ggcagcctcc acctcccagg ctcaagcaat cctccatcct tagcctcctg agtagctggg   42360
actacaggtg cacaacacca cacctggcta attttttat ttttttgtaga acagggtct   42420
```

-continued

```
cgctatgttg ctcaggctgg tcttgaactc ctggcctcaa gtggtcctct tgccaaagtc   42480
ctgggatgac aggcatgagg ttcggcacct ggctatggtc atgcatttga agggaaacca   42540
gttagctgtg gtagtgcttt ttttttttccc tcagacattt tcagtggtac ctgtccaagt   42600
gcagaatgga ctaagagttg gattgaaaag gaatggggtt tagccaagca agtacaacag   42660
agaataaaag aacaggggca ctgaggctga atgtggggga ttacaatgat ggaccctaga   42720
ctcaaggcct ggtaagagag gcagagcagg aagaagtgaa gaggagtaaa acaggtttgt   42780
gagcatggag gttgggggaa aatcaagcga ttgttggact tggggtccca aagggacaaa   42840
gccagaaaga ttttagggga tagtcggagg aaaagatgct tgaaattgag atggtggagc   42900
cgatgtcgtg gctggaaagg atgagggtat ggagcacctg ctcaggtggg gtggatgaca   42960
ggagcctcat ggagaggagg acaaggagct gagcagctga ggtatcaaag ggtcatctta   43020
ccaaatactg aaaatgtcaa gaagtattgt aggtgagcaa gacagtcggg tgacagtgtc   43080
tttaggaact gaggagtagg ctctcggggtc tgcagaagag gcaatgagga ggggcatag   43140 acaagaacag gtgagtctga gcttctgagt ctcagctgaa tgctttgggg aggaagaatg   43200
gataattgag gcctcaagag gcaagaaact cacttagccc aactccagtc agtgcaccag   43260
ggtgacagag ggaaacagag cccctggaga gagctgggggg agaagcagtg tccccagggg   43320
agaaccaagg gccaattagg gcaagaacat tccaaaaaaa aagtgaggat aaaggagact   43380
ttgccatgac gaaccagaag acactgagga agtgttgggg gtcggtgaca gggctgagga   43440
ttgggtcaga taagaaacag gtttatgggc cgggcgcggt ggctcacgcc ggtaatccca   43500
gcactttggg aggccgaggt gggtggatca caaggtcagg agttcaagac cagcctggcc   43560
aacatggtga accccgtctc tactaaaaaa tacaaaaatt agctgggcgt ggtggtgcgc   43620
tcctgtaatc ccagctactc gggaggctgt ggcaggagaa tcacttgaac ccgagaggca   43680
gaggtagcag tgagccaaga tcacgccact gtactccagc ctggatccag cccaggctac   43740
agagcgagac tctgtctcca aaaaaaaaaa aaaaaaaaga agggctttat agaattggtc   43800
acgtaggacc agacgctgtc cgaaccactt tgcttgtatc taatcgttta ccccatggga   43860
taattactat tattaacaga tgcatttttcc agatgagaac tttgaggtat agaaagtaat   43920
gaccaagatt cagctataga actaggccac cgcctcagga ccatactggg tgtcagcccc   43980
tgagccaaat ccagcccacc acttgtcttt gtatgacctt cgagctaaca gtgggcttta   44040
gagatgaaca tttcaatcta tttgatgatg aacatttact ttgaatccca gttaaccaac   44100
atgtcatccc ctctaaaaga attccattct tctcattagt agacctatat taggagaaaa   44160
ttaaattgtt attatatttt gaatttcatc aattgcaaat ttgtgaaaat ttgttttctc   44220
acttgtgtac ctacatcata ttcttgattg tgcctcttgg tctgtaaaac ctaaaatctt   44280
ccctttcctt ccttccttcc ttcttttcctt cctctccttc tttccttttc tccttttctct   44340 ctttctctct ttctttcttt ctttcttact ttctttttttg agatagggtg tcactccatc   44400
actcaggctg gagcgcagtg gcacaaacat ggttctgcag tctcaacctc ctgggcttaa   44460
gcggttctcc tacctcagcc taccatgtag tgagactata ggcacactac cgtgcgtggc   44520 taatttttt ttgttgtttt tttagacgga gtctcgctct gttgcccagg atgcagtgta   44580
gtggcacgat cttggctcac tgcaacctct gcctcccagg ttcaaacgat tctcctgcct   44640
cagcttcctg agtagctggg actacaggca cccacctcta cgcctggcta atttttgtat   44700
ttttagtaga gacggggttt cacgatattg gccaggctgg ttgcaaactc ctgacctcag   44760
```

```
gtgatctgcc cgcctctgcc tcccaaagtg ctgggattac aggtgtgagc cactgtgcct   44820
ggcctaattt tttattttta ttttttttgag gcagagtctc actctgttgc ccaggctgga   44880
atgcagtggt gccatcttgg ctcactagaa cctcctcctc ctcccaggtt taagcctgat   44940
tctcctgcct cagccaccca agtagctggg attacaggtg cacaccacca tgccaggcta   45000 attttttgtag ttttaataga dacggggtct caccatgttg accaggctgt tctcaaactc   45060
ctgacctcaa gtgatctgtc caccttggcc tcccaaagtg ctgggattac aggtgtgagt   45120
cactgagcct ggcctaattt ttcttttctc ttttttttt ttttttttt gagacggagt   45180 ctcgctctgt cgcccaggct ggagtgcagt ggcacaatct cggctcactg caagctccgc   45240
ctcccgggtt cacgccattc tcctgtctca gcctcccaag tagctgggac tacaggcacc   45300
cgccaccatg cctggctaat ttttttgtatt tttagtaga dacggggttt caccgtgtta   45360
gcgaggatgt tctcaatctc ctgacctcgt gatctgccca cctcagcctc ccaaagtact   45420
gggattacag gagtgagcca ccgcgcccag cctggcctaa ttttctgta gagacaatgt   45480 cttatcatgt tgccaaagct gaactcctgg gctcaagcca tcctcccgcc ctggcctgcc   45540
aaagtgttgg tattacaggc atgagccacc atgcccggcc cctaaaatat ttctgtctgt   45600
tcctttacag aaagagtgtg ccaacctccg tattatattc acatatctct cggtggagga   45660
aatgctcaat aaatgtccga tattattgtt gatattatta tcatcattga cacctaattc   45720
acaggacttc aaaacaagct agctatgatt ccagccctgc gctgtcacgc aaaagatatt   45780
aaacaaatgt tggctaggca cagtggctca caccctataat cctagcagtc tgggaggctg   45840
aagagggtgg atcacctgag gtcaggagtt cgagaccagc ctggccaaca tgacgaaacc   45900
acgtctctac taaaaataca caaattagcc aggcgtggtg gcgcatgcct gtaatcccag   45960
ctactcggga ggctgaggca ggagaatcgc ttgaacccag gaggcagagg ttgcagtgag   46020
ctgagatcgt gccactgcac tccaccctcg gcgaaagagt gaaactccat ctcaaaataa   46080
ataaataaat aacaaaaaac aaaggttagc tattgaatga atgagtgagt gagtgaatga   46140
atgagtgggt aggtgaagtg gaggaggatg tgaagttggt gggagtgagg gtgctagaaa   46200
tctccacatc tttcaccaag gcagagagct tatcggggga ggaggagcag aagcagtgag   46260
ttcatttcca gaaatgttgc tggaggtgag ttgactagct ccacataaac cctgggaatg   46320
atcactgaag ctgggtaatt tcaccattgt cctcagtatc tgaccccga tggaaaattc   46380 cacagcttca ctaaaagacc tgtataccctc tggaatattt ttataggaa cataaaagaa   46440 atgaatgtgg gatttggggg actggggaga agattctgag gagctggtcc tctgagaaga   46500
gttaatcagg caagtccagt aattatctgg ttccaactac atttgaaaca ctgtgctggg   46560
tcccttatgt aattgtcctt ccaactctga gaagtaaatt tatcattccc ttttcacata   46620
tgcagaaatt gggattgaaa gaagctgtgc tccatcccag ggcattgcct cctccagcac   46680
tgggtctagg ctttgcatca acctgtctac tgccggttgg ccatttgtgt cttcatgcta   46740
cccacagggc cctcgaggct ctacctctga gattcagcaa aggaggtcct gcctcatgga   46800
gctcacagtc cagggagaaa gacagacaat aaacaagcaa acaatacaca aataaaatag   46860
gccaggcatg gtggcccaca cctgtaatcc cagcactttg gaaggctgag acgggtggat   46920
cacttgaggt caggagttcg agaccaacca tggccaacgt ggcaaaccc tatctctact   46980 aataatacaa aaaattagat gggactggta gtgagtgtct gtaatcccag ctactgggag   47040
gcaggagaat agcttgaatc caggaggcag aagttgcagt gagccaaaat tgtgccattg   47100
cagtccagca tggatgacag agcaagacta tgtctctaaa aataaaataa aataataaaa   47160
```

```
aaattggctg ggcacagtgg ctcacacctg tagcactttg ggtggccgaa gcaggcagat    47220
cacctgatgt caggagtttg agaccagcct ggccagcttg gtaaaacccc aactctgcta    47280
aaaatacaaa aattagccgg gcatggtgac acgcacctgt aatctcagct actggggagg    47340
ctgaggcatg agaatcgctt gaacctggga ggcagaagtt gcagtgagcc gcaatcacac    47400
cattgcatga tcaactgtct agcactgagc aacagggcta gactccatct cagaaaaaaa    47460
ataaaataaa ataagaaatg caaaattgtt acaggagttg taagggaata caagataat     47520 agaattaggg agagactgca ggtggaggcc agatgagatg ttcatgggtg ccccttgga     47580 gcagagacct gtagagctac aggaaggatg ttctagaaaa caccaagggc cctgaggtag    47640
gaaggagctt tgaggcatca aaatgaagc tactgtcctt ggtgtacagc caagaaaaaa    47700
aaggtgggag aagttgaggt tagggtggg tgggaccaga tcacagggc cttgtaggcc     47760 ctgcctgtga tttgaatttc attctaagtg atgggggctt taagctgggg agggaggtga   47820
cctgattcac cctggaaaag agtgccctag atgcttgtgg agaagaaaat gaagaggca    47880 agatggaagg caacctcgag acagacctca aggatgccat tccctgcctc accccatcg    47940 ctccccagaa gcttgggtga aaccaccttc catctggtcc ttccagttcc tacctctcta   48000
attgagaggg agcctagcaa gttggggtag ggcctgctat ataattagtt aggcccagtg   48060
caaaatgaaa ataaggactc caagccgggc gtggtggctc gcacctgtaa tcccagcact   48120
tcgggaggcc gaggagggtg gatcacaagg tcaggagatc gagaccatcc tggctaacac   48180
ggtgaaaccc cgtctctact aaaaatacaa aatattagcc aggcgtggtg gcgggcgcct   48240
gtagtcccag ctacttggga ggctgaggca ggaggatggc gggaacctgg gaggcggagc   48300
ttgcagtgag ccaagatcgc gccactgcac tccagcctag gcgaaagagc aagactcagt   48360
ctcaaaaaaa aaaaaaaaa aaaaaagaa atgcaagatg ctaacagcag agtgttcagc     48420
caagcatgat gcccttctga gcacagaccc catgaagttg acagtggggga gaagactttg   48480 gacccaatgg ttagggaggc tgctctgaga aggtgacacc tgacctcctt cagagatcat   48540
ggccttcttg ggcctggtgc ggtggcttac acctgtaagc actttgggag gcccaggcag   48600
gaggatcacc ggaggccagg agttcaagac aagtctgggc aatatagtga aacccttgtc   48660
tctatcaccg tgcccagcct acaaaaaaat ttttaaaaat attaactggg tatggtggcg   48720
catgcttgta gtcccagctt ctcgggaatc tgcggtggga ggatccattg acttcaggag   48780
ttcaaggctg tgatctcact gctgcgctcc agcctgggtg acagagccag cccccttgtct  48840 ttaaaaaaaa aaaaaaaaca ggctggttgc ggtggctcac gcctgtaatc ccagcacttt   48900
gggaggccaa ggtgggtgga tcaactgagg tcaggagttc gagatcagcg tggccaacat   48960
agtgaaaccc catctctact aacaatacaa aaaattatct gagcgtggtg gtgggtgcct   49020
ataatcctag ctacttggga ggctgaggca ggagaaactc tggaacctgg gaggcggagg   49080
ttgcagtgat ccgagatcgc accactgcac tccagcctgg gagacagagt gagactccat   49140
ctcaaacaaa caaaaacaca gagagagaga gagagagaga gattatgact gtcttggtac   49200
cagcagatgt tgctttgtaa tcaccaagtg gggagagggg gtggcagcct gtcttacaca   49260 cctgaccac attgcccaac aacactgctc caccagtcc gtaaaacctc cctcggtggc     49320
tatcttcacc taacatagac acctattcaa agcatctgat gaggtcatgt gcgtgctacc   49380
acttgggaaa acgaaactaa gagcactata ggaacaatga tgaatatcat catcatcatc   49440
atatttacaa aatgcttgca tatcacacct gtaatcccag cactttggga ggctgaggcg   49500
```

```
gcgaatcacc tgaggtcggg agttcgagac cagcctgacc aacatggaga aaccccttgt   49560
ctattaaaaa tacaaaatta gccaggcatg gtggcaggca cctgtaatcc tagctacttg   49620
ggaggctgag gcaggagaat cgcttaaacc caggaggtgg aggttgtggt gagctgagat   49680
cacgccattt tgcactccag cctgggcaac aagagcaaaa ctctgtctca aaaaaaaaaa   49740
aaaaatgctt gtgtaagtat ttattatgtt aatacaaaat atttatcatc aaaaaataaa   49800
caatacattt gattgaacca tcttgtatca tccttcttct tagtgaaaga cattgcatag   49860
acactgtatc tcttatattt ctcctgataa tactacaaga ttgatccttg tccaacagat   49920
atttcctgaa cacctactat gtgctgcaag tactgagatc cacagtgcaa tccggcagcc   49980
agggagcacc cccgatcaca gacactgtgg ccccgcaatg gatgggcgct tccattgctg   50040
gagctcactt ttcctgctct gtaagtactg agatccacag tgcaatccgg cagccaggga   50100 gcaccccga tcacggacac tgtggcccg cagtggacgg gcgcttccgt cgctggagct    50160
cacttttcct gctctattgt tgtcatgaa gaaagttcca tacccaacat cacattctct    50220
acttatttgt ttgtctctct tttcctctag aactgcagga gctgggaatt tgaactgttt   50280
ctctcacttc tggatcccag catttagaac agggctccac tcacagcagc cactattgct   50340
gaagaagcaa atcccgcggg attgcttgag gtcattggac ttcacaagag atgtctgggg   50400
tggagacagg acttgggaag atgctggttc atggatggtg tggggctgc aggaggagat    50460 gcctggggag agagtatcta gtaagaagtg acaatgttgg ttgggcacga tggctcatgc   50520
ttgcaatcct agcactctgg gaggccaagg tgagaggatc acctgaggtt aggagtttga   50580
gaccagcctg gccaacatgg tataaccccg tctctactaa aagtacaaaa attagccagg   50640
cgtggtggtg ggcgcctgta atcccagcta cttgggaggc tgaggcagga gaattgcttg   50700
aacctgggag gcggaggttg cagtgagccg agatcatgcc actgcactcc agcctgggcg   50760
acaaagtgaa actccatcac aaaaaaaaaa aaaaaaaaaa aagaagtgac aatgtccttg   50820
ggtctgcctt ggtgccgcag gggagtgtgg tcataggtcg aagacagaga aagagccatt   50880
aagaaatggg agtaggctgg gcgcagtggc tcatacctgt aatcccagca ctttgggagg   50940
ctgaggtggg tggatcacct gaggtcagga gtttgagatc agcctgacca atatggtgaa   51000
actctgtctc tactaaacat acacaaaatt agctgggcat ggtggcgcat gcctataatc   51060
ccagctactc aggaggctga ggcaggagaa tcacttgaac ccaggaggca gaggttgcag   51120
tgagctgaga tggcgccatt gcactccagc ctggggaca gagcaagact ccgtctcaaa    51180 aaaaaaaga aatgggagta gcccaagggt gtgagtgatg gttacctgag ggctctctct    51240
ggaaagcagg acttatccac actccttagt atcttgatgc tgctgagaga tcaacgtcag   51300
ggctgggaaa agggctgttg gatttgagag aagggatgag agtcatgaag cacactgggg   51360
ggccgcttcc agggacagga gacatcaatg gaggggaaat gagaaataag tggacctgca   51420 cctttttgcta agggaggctg ttaagggagg agagagaccg ggcagttgct agacggatgg   51480
tggccaaggg agggttttgt ttttgtttta agatgggag agattataag tgctgaaggg     51540
aaggatgtaa ttcaaaagga aagcttgcat attcatgggg gatcaggagt aaggaaggtt   51600
ctgaggtggc aggcagggct aggaggcggc gggattggtt tttggaggga catccgttaa   51660
caggaggaga gaagctgggg accaggagca aagcccaagg ccttcccagg ccctggaaac   51720
cctccgtgct gggccggtcc cctgctgctt ctctggtttc acttcctttc tcagccctgt   51780
tcccacttct gctctggccc cctggctccc tggcttttcc ctgagtcctc ccaccaggct   51840
cctgcctttg cctcactttc ctctctccct aggatatttt tgctgcagag atccacgtgg   51900
```

-continued

```
ctcagtccct cgctttatct gggtctctgc tctcctgtcc atttttcaga gctcttccct    51960
gactaccaca taggtaacgg tatcctccta ttaccttcca ttcagaccct ctcctttacc    52020
atagggcctt tgcacctgct attctccctg cctgaaatac tgtgccttgc ctgattatta    52080
ttattattat tattattttg agacagagtc tcactctgtc acccaggctg gagtgcaata    52140
gcacgatctc agctcactgc aacctccacc tgctgggttc aagtgagcaa gcatggctaa    52200
ttttttgtatt tttagtagag atggggtttc accatgttgg ccaggctggt ctcgaactcc    52260
tgacctcaag taatcaacct gcttcagcct cccaaagtgc tgggattaca gacatctgcc    52320
accacacccc cggcccctga ttttttgttt gttttttga dacagactct ccttctgctg    52380
tctaggctgg agtacagtgg agcgatctta gctcactgca acctctgcct cccgggttca    52440
agtgattctc ctgcctcagt tcctaagta gttgagatta caggtgtccg ccaccatgcc    52500
tggctaattt ttgtattttt agtagagaca gggtttcacc atgttggaca tggctggtct    52560
tgaactcctg accacaggtg agctgcctgc cttggcctcc gaaagttctg ggattacagg    52620
cataagccac tgcgcctggc ctgattttt tttttttttt tttttttttt tttttgtaga    52680
gatggggtct tgctttgttg cgtaggctgg tctcgaactc ctgggctgaa gctatcctcc    52740
cgcctcagcc tcccaaaatg ctgggattac gggaatgagt caccaagact ggccccttcc    52800
ctgatcttgt taatgactca atcttcaccc ctagctcagg catctgtctt cagtcttgtc    52860
tcttctttct ccccaactag gtcaggttcc ctcacacagg acccttggag agctgggcac    52920
ttctccaata gcatttgttg aagttactat ttttatctg tgagattggc taagacctct    52980
ttcttgctcc agactacagg taccatccaa gcagaggcca catccatctt acccaaatgt    53040
gtattttcag tgcctgctgg agtgccaggc acccagcggg tacccagaac ttagggtgtt    53100
gggtgtactc atggatcaga acttcatttc agcccgagct gtagacctga agactgaggc    53160
tcaagatatt ccatcatcag atatcgaggg tcggagggta aaaaaaagaa aaagagccag    53220
gcgcagtggc tcccgcctgt agtcccggca ctttgggagg ccgaggcagg cagatcactt    53280
gaggtcagga gttccagacc agcctggaca acactgtgaa accccgtctt tcccgaaaat    53340
acagaaaagt cccagctact caagtggctg aggcaggata attgcttgaa cctgggaggt    53400
ggaggttgca gtgagccgag attgtgccac tgcactccag tctgggtgac agagtgagac    53460
tctgtcacga agaaagaga gaaagaaaaa gagagagaga gagagagcaa gagagagagc    53520
aagagagaga gagcaagaga gcaagagaga gagcaagaga gagagagaga gagatcatcg    53580
atactcattt atcaaatact caaacccgta tctgtctaca catgctattg acctaaacta    53640
tacttttcaa gaatattctt cgctgccaag gctggagtgt agaggcatga tctcatctca    53700
ctgtaacctc tgcctcctga gttcaagcga ttctcctgcc tcacctccct agtagctggg    53760
actacaggcc tgcactgcca cacccagata attttttgtat ttttggtaga gatggagttt    53820
tgtcatgttg gtcaggctgg tctcaaactc ctgaccttag gtgatctgcc cgccttggcc    53880
tcccaaagtg ctgggattac aggcatgagc cactgcgcct ggcttcaaga atattgttca    53940
tttacagagg catagaggtt aagagtaccc tctgaaatta cacagcctgg aattgactgc    54000
tagctctccc ctctgcaatc tttctggcac cagtcatgtt ggttcagctc cctctgggcc    54060
tcacttaccc atctgtagaa tggggataat aacacctgca ttgtacatct attaggagga    54120
tgaatgtgat tatcacatgt aaaaggctag agccatgctt gacacacgat acatattcaa    54180
attccagtca agcttctctc ttttttttg agacggagtt tcgctctgtc gcccaggctg    54240
```

```
gagtgcagtg gcacgatctc ggctcactgc aagctctgcc tcccgggttc aggccattct    54300
cctgcctcag ccttccgagt agctgggact acaggcgcct gcaaccaagc ccggctaatt    54360
tttttttgta tttttagtag agacggggtt tcaccgtgtt agccaggatg gtctcaatct    54420
cctgacctcc tgatccgccc gcctcggcct cccaaagtgc agggattaca ggcgggagct    54480
accgcgcccg gcccagcttc tcttttgaa tgccaggctt tgtgctaaaa ctcttactgg     54540
tttttacact gagcccccaa agattatcaa cccaaatttc aggacgcatg tgtttttatt    54600
aatgtctcag aaaagtcaga ttggaagttg catgcacaat tcctgccgga acaaagtaca    54660
gccatctccc tgcactaatg catttccagc tggtggagtt cagttttta agagcagtaa     54720 atacttgcaa gagacgaacg gcaggaagtg aatgaaggaa tagatacatt tttaagatcc    54780
actgacagct tgtacattct ggaagccatg tgggtcaggg ggatgaattt attggcttta    54840
acgtcagacg ctctgcaggt cgtgagatgt gccttttgtc ctgacgtcag ctgagagcag    54900
atctttggaa ggatttgccc attgagcaca tttgctgaaa catcttggct tcattacatt    54960
tatgagtttt aaaagcatgt aaaatatttt atgtggttct tgcaaaaggg taacaacata    55020 ataacctgc agggatagga tgattttcaa gaaatggggt cagccggcaa gccagtgttc     55080
actctgtgga cattctgagt gtacagaata ttaatacttc atttgcccct ccagatccac    55140
tctccatttt ctcttccctc ctctgtgccc aagaggccgg gcagtgggga ccacatctcc    55200
tggttctgtg acatctggtt tcttgctggg ttcagccaat aaggaggagt gggagatggg    55260
agggccaagg tggggctggg ctattaactc cctggctggc catggtctgg cagtggctgt    55320
gtccctctac tgaaacccac agctcccatg gggtggcctt tttcctatgg atcttgccat    55380
tttctgataa ccactcccctc ctgctgcctt tggaggcctt ggagagggaa gggcttttgg    55440
ttgttggtag ccccggggtg cttcatcaac cctgctgatt tctctatacc ttgcttatat    55500
cttggtaaat acccctttta ttaaacattc ctcagccgga catggtggca tgtgcctgta    55560
gtcccagcac tttgagaggc cgaggcagga ggatctcttg aacctgggag gcggaggttg    55620
cagtgagcca agattgcgcc tctgcactct agactgggcg acagagtgag actgtctcta    55680
aaaaaaaaaa acaaagaacc ccaaaagact ctcctcagtt actctgctca agtgagcctt    55740
ttaattatct tggggacctt gtataggtac agttattatt ttgtttgttt gtctgttttg    55800
agacagagtc tcactctgtt gccgaggctg gagcgcagtg gtacagtctt ggctcactgc    55860
aacctccacc tcctgggttc aagcaattct cctgccttcg cctcccaagt agctgggatt    55920
acaggcatgc acccccaagc ccggctaatt tttgtatttt tggtagagac ggggtttcac    55980
catgttggcc aggctggtct caaactcctg acctcaagtg atcctccgcc ttggcctccc    56040
aaagtgctgg gattgtaggt gtgagccatc acgcccaacg gcacagttg ttaatatcat     56100 gttagattaa aaatcaaaat cttacagaaa cttcagcctt tatatcacga tggcttcctg    56160
tccctatggc aaggtaatcc ttaagagaga ggccaagctc aaagctgtag ccaaataatt    56220
taatatctat gaggtgactt tcacatacct catactaaat atgcaagcta cacatgacct    56280
ctaccatcca gaaatacctg ttttagcagc gaagatagac tatctgatga gaaatcgtac    56340
tatgggagga acatggcttg gcaattaaga gtctctattt gttttctggg gctgctgtaa    56400
cagagagcca cagacggagc ggcttacaca gcacagatgt attgtctgaa ggctctctgg    56460
gtgctgtgag ggaaggatct gtgccaggcc tctctccttg gctcgtagat gaccgtcttc    56520
tccctgtgac tctgccgtca tcttccctct atgtctgtct gtctctgtgt ccacatttct    56580
cccacaggtc accagtccta ttggaatagg gtcttggtaa agaccctatt tccaagtaga    56640
```

```
aacacattct gaggtgctgg gtctcagagc tccaacatct cctttttggg aggatacaat   56700
tcaacgcaga gcagaggccg acatccatga gtttaaatcc aggttgtgtc accttgggca   56760 aattattat  ttatttattt attcattttt gagacggagt ctcactctgt cacccaggct   56820
ggagggcaat ggcgtgatct cagctcactg caacctctgc ctcccgggtt caagtgattc   56880
tcctgcctca gcctcctgag tagctgggat tacaggcacc cgccaccaca cctggctaat   56940
ttttgtattt tttagtggag acggggtttc accatgttga ccagactggt ctcgaactcc   57000
tgacctcagg tgatctgccc gcctcagctt cccaaagtgc tgggattaca ggcgtgaacc   57060
accatgcccg gccaccttgg gcaaattatt taaactgctc agtgtttgtg tttcatcatc   57120
tagaaaatgg ggatagcctg ggcttggtgg ctcgcacatg taatccagca ccttgggagg   57180
cagaggcagg agaatcactt gaacccagga ggcagaagtt gcagtgagct gagattgggc   57240
cactatactc cagcctgggc tacagagcga gactccatct caaaaaaaaa gccaggcatg   57300
gtggtatgtg cctgtagttc cagctactta ggaggctgag gctggaggat tgcttgagcc   57360
tgtgtggtca agctgcagtg agctgtgatg gtgccactac actccagcct gggcaacaga   57420
gcaagaccta tctaaaatat aaagtaaaat aaaataggga taatattttt acaatcactt   57480
tgcaggatac tgtgaaataa ggggtgggag actgcttaaa aagtgcctgg cataggcagg   57540
gcgcggtggc tcatgcctgt ggctcatgcc tgtaatccca gcactttggg aggctgaggc   57600
gggtggatca tgaggtcagg agatagagac catcctggct aacacagtga aaccccgtct   57660
ctactaaaaa tacaaaaaat tagctgggcg tggtggtggg cacctgtagt cccagctact   57720
cgggagactg aagcaggaga atggcatgaa ccctggaggc ggagcttgca gtgagccgag   57780
actgcgccac tgcactccag actgggcgac agagtgtcaa acaaacacaa aaacgtgcct   57840
ggcgtgtggc aaatgttgtc ggtgtgggct ttcgctatta ttaacctaaa gtgttgtact   57900
ttcacataac aactccattg agcgtcttca ggcatctcaa acttcccgt  ccagttggct   57960 cgttttctaa tcctacccat cttggaaaat ggcaccctca ccagcccagt tgctcaagct   58020
gtccatgatc cttctcatca ttgccacttt cactccacca gtgaacctgc tggatacccc   58080
tccaaggaca cgctgtattc tgaattcatt gcttctcttc atctcattag ttagatctga   58140
tgagacggcc ctgccgtcct ctcttggaca ctctcttgaa caaagcagta acctcttagc   58200
ttgttttccc gctttcactg caccccttct agagatcatc ctctgtacag agccaagggg   58260
atctttaaaa acatggatcc cagccgggca tggtggctca cgtctgcaat cccagcactt   58320
tgggaggccg aggagggcag atctcttaag gtcaggagtt cgagaccagc ctggccaata   58380
tggtgaaacc ctgtctctac taaaaatata aaaattagcc aagtgtggtg gcgggcgcct   58440
atagtctcag ctacttggga ggctgaggca ggagaatcgc ttgaacctgg gaggctgagg   58500
ttgcagcaag cagagatcac accattgcac tccagcctgg gcaacagagc gagactccgt   58560
ctcaaaaaca aacaaacaaa caaacaaaaa caaaacacgg atcccatcat gtcttttcct   58620
gcgtaagact ctggatggct ttccattgaa actagaacaa atctacaca  tctttgttct   58680 aaggccctct tccaaggccc taatgatctg gtctctgcct gcctctccaa tgtgacttcc   58740
taccattctc ccctggatca ctagatttta gttacatggg tcttcctgct tttcctccaa   58800
tataacaagc agatccagct tcagtgcctg tgcacttgct gttctccggg cttggaatac   58860
ccttccaaga actttctccc tcacttcatt caggtctttg ctcaaatgtt acctcttcaa   58920
ggaggtcttc cttgcccacc attttttttt gtttgtttgt ttgttttctt ttctttttt    58980
```

```
tttttttttga  gacagagtct  tgctctgtca  cctaggctgg  agtgcagtga  tgcgatctcg   59040
gcccactgca  acctctgcct  cccaggttca  agcaattcct  gtgcctcagc  ctcccgagca   59100
gctggaacga  caggagacac  aagccaccat  gcccagctaa  cttttgtgtt  tttagtagag   59160
acagggtttt  gccatgttgt  ccactctggt  ctcaaactcc  tgaactcaag  caatctgctc   59220
acctcagcct  cctaaattgc  tgggattata  ggcatgagcc  accatgcctg  gccgagattc   59280
cctatttctt  tttttttttt  tttttttttg  agatggactc  ttgctctgtt  gctcaggctg   59340
gagtgcagtg  gtgcgatctt  agctcactcc  aacctccacc  tcccgggttc  aagcgattct   59400
cctgcctcag  cccctgagt   agctgggact  ataagcgcat  gccaccacac  ccggctaatt   59460
tttgtatttt  tagtagagat  ggggtttcac  catgttggcc  aggatggtct  cggtctcctg   59520
accttgtgat  ccacctgcct  tggcctccca  aagtgctggg  atcacaggcg  tgagccactg   59580
cacccggcca  gctcttaatt  gcattatttt  atattaccat  tctcacagca  ttaatcaccc   59640
tcagcagttc  tatttacgca  cttctttgtt  ttgcttacgg  tccacctcta  ccaccagaat   59700
gcaattgatc  tgatagttga  gaggtctccc  atgctcactg  ctgaatcccc  atcacctaga   59760
acagtgcctg  gcacttaata  ggcatccagt  aaatctttgc  gggggtggga  tgggaagcaa   59820
acacaaaatg  atatgtggtt  ctcttctctc  ttttctgccc  cctctccaaa  cgaaaccacc   59880
agcagaggaa  agaaacaaaa  agtctatgag  ttgtcaagat  ttctgctttg  gggcacagtg   59940
gtcatgcctg  tgatcccagc  ttttgggag   gctgagttgg  gatgatcatc  tgagcctagt   60000
tgtttgagac  cagcctgggc  aacatagcaa  gactccatct  ctaaacaaat  ttttttttt    60060
ttttgagaca  aggtcttgct  ctgccacctg  cattggagtg  cagtggcact  atcatagttc   60120
actgcaccct  caacctccaa  ggctcaagtg  atcctctcac  cttagcctcc  caagtagctt   60180
ggactacagg  cgtgcactac  cacacctggc  taatttttt   gtagtgacga  ggtttcgcca   60240
tattaaccag  actggtcttg  aactcctggc  ctcaagtgat  ccttccttct  tggcttccca   60300
aagtgctgag  attataggtg  tgaaccacca  tacctgattc  tacaaaaatt  tttttaaaaa   60360
gttagccagg  catggtggcg  catgcctgta  gttccagcga  ggtgaggtgg  gagcattgct   60420
tgagcccagg  agttggaaac  tgcagtgagc  tttgatcctg  ccactgtctg  ggcaacagca   60480
tgagactctg  tttctagaaa  aacaaaacaa  aacaaaacaa  aaaaagattc  ccgctttgga   60540
acaatggcta  ggggctggga  atctaggatg  gatccagagt  gggcaagtct  tggcttctta   60600
taactgcaga  atcccacgat  ggatgtgtgg  gtgggctggg  gtaacagatc  tactcagggt   60660
gggggctggg  ggtatcgcga  ggtgtttaag  cctgtcaata  aaaaaagtga  ccgctgcttt   60720
gtatctgcag  ctactcaagg  gaaataaagc  cgtttgctta  taagaatttt  ccataaacat   60780
ttctgaggat  gtgtattagg  ggtaatcttg  ggatgtgcat  taaactaaac  agggtagtat   60840
aaacacagga  acaggctgaa  aggggggagaa taaatggccc  aggtttgccc  tggcccaatg   60900
gccttaggca  acttgtgcag  cctgcagaaa  cccagagact  tcagttcatt  atttaaagaa   60960
ggcggagaca  aagagggaaa  accaaacgca  gccctcccat  gggtagatag  attcttgaac   61020
aacctctgga  attaagcttt  ttttttctct  cctcctagtg  ttcaatgctt  tggattcctg   61080
aagttatcta  tgttgaaata  ctcgagagat  ggtaaggaga  acaggaacag  gtagctttgg   61140
gaggcacgtg  ctctgggcta  ggcatagttc  ttttttttgg  gggggcgggg  ggagggagtc   61200
tcgctctgtc  gcccaggctg  gagtgcagtg  gcgcgatctc  ggctcaccgc  aacctccacc   61260
tcccgggttc  aagcgattct  ccctcctcag  cctccagagt  agctgggatt  acaggcacct   61320
gccaccacgc  ccagctaatt  ttttgtattt  ttaatagaga  ctgggtttca  ctgtgttagc   61380
```

```
caggatggtc tcgatctcct gacctcgtga cccacctgcc tcggcctccc aaagtgctgg   61440
gattacaggc gtgagccact gtgcccggct ggctaggcac agttctaaaa gctgcgtgtg   61500
cacgatctca tttcatcctc ccggtaccgc tttggggaag gtaacactat tgcctccact   61560
ttgcagaaga ggaaactgag gcagagagaa gggtgatgac ttgctgaagg atacagagct   61620
cattacagtg gaggttcagg gtctgagctc tagaaaagat gctccaccct atgaaggaaa   61680
aggttcattg gtattatcta tctatctatc tatctatcta tctatctatc tatctatata   61740
tttttttctg ggatggagtc tcactctgtt gcccaggctg gagtgcagtg gtgcgatctc   61800
agctcactgc aaactctgcc tcccgggttt aagctattct cctgcctcag cctcctgagt   61860
agctgggatt acaggtgtgt gccaccacac ctggctaatt tttgtatttt tagtagagac   61920
ggggtttcac catgttggcc aggctggtct caaactcctg acctcaggtg atctgcccgc   61980
cttggcctcc caaagtgctg ggattacagg cgtgagccac cacgcccggc ctaaatcatt   62040
tgaatttgct aactcattca tgtgttgata atataaataa ataattttta aagtgtcccc   62100
ttgtgcaaac caatgatgaa agcaggccat gaatagaggc aggtgatcag ctccactctg   62160
tgccccggag taccctcaaa ataaacccca aggctcagga ccaaatatag atgatgatag   62220
gctaggcggt ggctcacaca caaaaaatca gaggtggata agaatctata tctgcacctg   62280
ccaggagcca ggtcgaggag gattaagagt tgggggagac tttccactgt gcccattctt   62340
tctacatttt gggtcatatg aatgtattat ctttttccaaa gtttgaatta ttattttgt    62400 tttgtttgtt ttgttttttt gaggcggagt ttcactcttg ttgcccaagc tggagtgcta   62460
tggcacgatc tcggctcacc tcaacctccg tctcccaggt tcaagcaatt ctcctgcctc   62520
agcctcccaa agtgctggga ttacaggtgt cagtcaccgc gctcggcctg aattattttt   62580
taaaaacttt gataggatat aaatgaaaag aattttttt tttgagacgg agtcttactc    62640
tgtcacccag cctgaagtgc agtggtgcga tcttggttca ctgcaagctc cgcctctcgg   62700
gttcacgcca ttctcctgtc tcagcctccc aagtagctgg gactacaggc acccaccacc   62760
atgcctggct aattatttgt attttagta gagatgggt ttcaccatgt tagccaggat     62820
gctcttgatc tcctgacctc gtgatccgtc tgcctcggcc tcccaaagtg ctgagattac   62880
aggcgtgagc caccgcgccc ggccaaaatt tttttaata tgatacaaaa taatttttt     62940 ttttttttt tgagacagag tcttgctctg tcgcccaggc tggagtgcag tggcacgatc   63000
tcggctcact gcaagctccg cctcccgggt tcatgccatt ctcctgcctc agcctcctga   63060
gtagctggga ctacaggcgc cctccacccc gcccagctaa ttttttgtat tttttagta    63120 gagacggggt ttcaccatgt tagccaggat ggtctcaatc tcctgacctc gtgatccgcc   63180
cacctcggcc tcccaaagtg ctgggattac aggcgtgagc caccgcgccc ggactaatat   63240
ttttttttaa ataaaaaata tgaaactggc ctgggcacgg tggctcatgc ctgtaatccc   63300
agcactttga ggggccgagg tgggtggatt acctgaggtc aggagttcaa gaccagcctg   63360
accaacatgg tgaaaccctg tctcttctaa aaatacaaaa ttagttgggc gtggtggcgc   63420
atgcctgtaa tcccagctat tgggaggct gaggaaggag aatcacttga cccaggatc     63480 tggaggttgc agtgagccga gatcacgcca ttgcactcca gcctaagcaa tgaagagtga   63540
aactctgtct caaaaaaaaa aaaacaaaa acaaacaaa acaaaacaaa aaactgaaaa     63600
ggtttcagga atgcaaaggc aacatgtccc aaagtattaa aatggtacaa ccttgctttt   63660
gacgtgaagg tcagttacag aacgaaatta gccagcaagc aggtgagagc agagattaaa   63720
```

```
acggtaatga agatggccat tccacagcct tttctaacta catgaaaatt atcttccttg    63780
acagtagcca acctgtgctt acattctctc tctctctctc tctctctctc tttctctctc    63840
tctcctccca cctgcttgcc atgacctatt tcatagtcct ggcacgtgtg aaatgcctgc    63900
caagaactgc agaagacaga gacacagtgc tccaaaaagg ttgaatggca actttatcat    63960
ggacattttg gtgattacaa tatctacatt tcctgggggg tctcagaatc acagaaatta    64020
tttcaagtta gtccgaggct gctcaacgct gaggtcaaaa catctgagag aaaaggttaa    64080
gtaaaaaatc tggttgtttc tataaaactg gactcattca ttcaatggct atgtactgaa    64140
tacctaccat gtaccagacc acgctgagga ccagccagag gcaaggcagg cacctcaggc    64200
acaaaaggca agaaggcctc actctctgtc actgctacac ctgcaaaacc cctagcgtaa    64260
ggttcccttt gcatttcctg cccgtggtgc ctgcctggcc tcatcctagt gcctattcca    64320
taccagacgc tgttctaagc actgacgctg cagcagtgaa caaaacaaaa agaagctgga    64380
caaatgctca agtctccaca tttcagaatt ggatattttg gtgctgaatt gactgcgtta    64440
agaaacagag gtttcccgga tacagtggct catgtgtgta atcccagcac tatgagaggc    64500
tgaggcgaga ggatggcttg agcccaggag ttttgagacc aacctggaca acacggtgaa    64560
atcccagctt tacaaaaaat atgaaaatta gctgggcatg gtggtacacg cctgtagtcc    64620
cagctactcg gaaggctgag gtgggaggat cacctgagtc tgaggaggtt gaggctgcag    64680
tgagttgaga ttgtgccact gcactccgcc tgggcaacag agtgagactc tgtctcaaaa    64740
aaaagaaaca ggtcaggcgc ggtggctcac gcctgtaatc ccagcacttt gggaggctga    64800
ggcgggtgga tcacctgagg tcaggagttc gagaccagcc tgaccaacat attgaaaccc    64860
cgtctctact aaaaatacaa aaattagcca ggcgtggtgg cacacgcctg taatcccagc    64920
tacttgggag gctgaggaag gagaatcact tgaacctggg aagcggaggt tgcagtgagc    64980
tgggatcatg ccactacact ccagcctggg caacaagagc gaaactccat ctcggaaaaa    65040
aaaaaaaaaa aaaagaaac agaggtcttt gcccactctt cagcttggag ttactaagtg    65100
atctcagtct tgcttcagtt gacttcttac tctgcatccc caggtagccc tttgttgttc    65160
aggactagct tggacaatgg aaagccccat cttctgagtg ctccccaatg tctgggacta    65220
tagatagatt gaccaatgca atctatgtca tgccccatga ggtgggacca gtgattctca    65280
ccactttcca aactgaggtc acagttggtc tgaaagctgg gagggttcac ccatagagaa    65340
aactggccaa gacaagattc agatctggcg tgggtccgag agactcctgc aagggtgtac    65400
tctagcactc cacacattac ttaaggttgg ttgagctcag aggtacagat atatgttggc    65460
gacttactga aggctgcaaa gctcattaag atcagggtc cagggtctga gctcttcaaa    65520
agatgttcca ccctaggaag gaaaacgctc gttgttatca tcattgacgt ttggtcactg    65580
agccttgggg tttattttta ggaaactcct aaaaataatg tgttttagga cacacagtga    65640
aactgatcat gtgtctccat tcatggcctg ctttcatcat tggtttgtgc atgaagcacac    65700 ttctaaaatt atttattcat attatcgata tatagatgta ttagccattg cttctccctg    65760
tcacgtataa gacttgacaa gactatcatc cccgaggtga cccccgaagt gctatcatta    65820
ctcaccgtcc taccctctgg cccagctgca agaatgggt ctagcttagc tttctgatcc    65880
tttctgccat cccaacccaa tctgctctga ttcatcactt cctccctaag catcctcacc    65940
aaagcccttc agcaccagtg tcagcaacaa cagccaatat gccctgggtc ttccttcctg    66000 tgctcttca aataaccaga ttattactgg actgcctatt atatgccagg ccctgtgatt    66060
ggcactggaa tgcaacaata agcaaaaaca gacatggtac ctacccatct tcatttagca    66120
```

```
cacagtctag tggagggagg tggacatcag ttaaataatc accccccaagt acgcagaaag    66180 atcttattgc acagtatgat aatggatatg gagaaaaagt gccaggcacc gccaccagga    66240
gttggaactg gtccaggagg gcttctctga ggaagggacc ttggagctga aacctgtagg    66300
atggggcaac tgggtaaagt gggcagagat agcctctggg cagagggttg agcagtgaca    66360
ctggagagga agccagaggc tcacttggga aagaccttga gatggatcag aggcaggtga    66420
tggcgggcat ccatggggtc ttactctgag cattcatggg attcagtttg ggtgcaatgc    66480
agtcgcggcc ggctacagtt gcagaactca ctggagggag gtgagagtgc atgggaagac    66540
cagtgaggaa gctcctgccc gtctacaggt gatggacgat cgggatagtg gggtggtagc    66600
aaggtgcaaa caaatggact catgatgtac ttggagattt ggtgatggag tgcatgaggg    66660
ataaggagca gagtgagggg tccctgacct cctgctcgag caaatagagc aacagtagat    66720
cctcaggtga tcttcataaa ttcaaaccat ccttccctcc cttgcacagg caagaaacaa    66780
cattgaagta tctacattga agacagaact ttgtgttcct atttgttttt ctctatgcta    66840
attaaaatgc cctttgtaat ggccgggcat ggtggctcac acctgtaatc ccagcacttt    66900
gggaggccga ggcaggcaga tcacctgagg tcaggagttt gagaccagcc tgaccaatat    66960
gatgaaaccc cgtctctact gaaaatacaa aaattggccg ggcacggtgg ctcacgcctg    67020
taatcccagc actttggggg gctgaggcgg gtggatcacc tgaggtcagg agttcaggac    67080
cagcctggcc aacatggtga acccccatct ctactaaaaa tacaaaaaaa ttagccagtc    67140
gtggtggcag gcgcctgaaa tcccagctac tgggtgggtg gggggctgag gcaggagaat    67200
tgcttgaacc cggaaagggg aggttgcagt gagccgagat tgcgccattg cactccagct    67260
tgggggacaa aagcaagaag ctgtctcaaa aaaaaaaaaa gtacaaaaat tacccgggca    67320
tggtggcatg tgcctgtaat cccagctact cgggaggctg agacaggaga attgcttgaa    67380
cccgggaggc agaagttgca gtgagcccag atcgtgccat tgcactccag cctgggcgac    67440
aagaaagaaa ctctgtctca aaatatata cataaaaaca aaacgaaaca cccttttgtaa    67500 atcaatccag aggaaacttt tccttttttt gccaatgaaa ttaattatgt cgagaaacct    67560
gaatctcatc tcttctgtct tcatgtctgt tacattctca aaagacacac tattgctcag    67620 tgtcaggggta ggataatgag ctgatcagaa acaatttttca tgtcatttga agcttaattt    67680
cattagcaaa taaaaactgt ttcaaatacc accattggtc ctctaaagtt gatttagaga    67740
ttcaggttga aaatcgatta aagtgatttt tccttcataa aagtttatag ctctgcaggc    67800
acacacagac tccttagact tgcaaagcca catccatatt attttccaga atgaccgtta    67860
ccgaaaaaaa gtgagttgca gagcaataag tagatatgat ctcgtttatg taaaaacaaa    67920
acaaagcagt gacaaaagct aaaactgaaa atcactccaa attcagcagc attggcatca    67980
cagtggagct tgctaaaaat ggggaatctc gcccgggcgc agtggctcac gcctgtaaat    68040
cccagcactt tgagaggccg aggcgcgtgg atcatgaggt caggagatca agaccgtcct    68100
ggctaacacg gtgaaacccc gtctctacta aaaatacaaa aaattagccg ggcgtggtgg    68160
cgggtgcctg cagtcccagc tactcgggag gctgaggcag gagaatggcg tgaacccggg    68220
aggcggagct tgcggtgagc cgagatcgtg cccctgcact ccagcctggg cgacagcgag    68280
actccatctc aaaaaaaaaa aaaaaaaaaa gaaatgggga atctcagatc ctacccaaga    68340
cccactgaat cattttaaca aaatcaacag ctgattcttc agcacattga agtctgacaa    68400
gcactgctgt taacagttct ttttcttttc ttttcttttt aagacaggtt ctcactctgt    68460
```

```
cacccaggct ggagatcaca gtccaccaca gcctcctggg ctcacgcaat cctcccgtct   68520
cagcctccca agcagctggg actgtaggtg catgctatca tacccagcta attttttct   68580 ttcttttctt cctttttatt tttattttta tttattttt attttttcta gatacaaggt    68640
ctcactatat ggcccaggct ggtctcaaac tcctggactc aagcaatcct tccacctcag   68700
cctcccaaag ggctgggatt ataggcgtga gccaccacac ccagtctata tttatattc    68760 tacacacaca caaacacttg tgtgtgttat atatgtagat aaatatatta tctatgtatc   68820
taatatatct attatcctag acatacatag atatgtgtat atgaatagaa atataaatgc   68880
atagaaaagt ctggactaaa ctgctcacgg tggttaattt tgagaagttt ggatttcaag   68940
gtgaatgtgg tggtgaatag taagtgggaa attcaaaggg ggctttcaca ttttaccaga   69000
tataccagat aacctagatt tactgatcta ggcgcccgcc accacgcctg gctaattttt   69060
tttgtatttt tcagtagaga cggggtttca ccgtgtttgc caggatggtc tccatctcct   69120
aacctcatga tctgcccgcg tctgcctccc aaagtgctgg gattacaggt gtgagccacc   69180
gcgcccggcc agacagaact gcttaatgca ttacttgggt aatttaaatt taaatattaa   69240
gatagtataa agctgaggac ctaaaaaact aatcttacaa ataacacgga catctcaagt   69300
ccctcctctc tttgacctac caattcctcc tgggggagg tgccctcaga attactcaca    69360
catgtgagaa atgatgtgca accgagataa ttcacaggag cactgtttgt aatagcccaa   69420
tattgaagac aacttaaagg cccatcatag cccgggcacg gtggctcacg cctgtaatcc   69480
cagcactttg ggaggccag gcaggcggat cacttgaggt caggagtttg ataccagcct    69540
ggccaacatg gtgaaacccc gtctctacta aagacacaaa aagtagctgg gtgtggtagc   69600
gcgtgcctgt aatcccagct acttgggagg ctgagagg agaatcgctt gaacctggga     69660
ggtggaggtt gcagtgatcc aagatcgcat cacagcactc cagcctgggt gacagagaaa   69720
gactgtctca aaaacaataa aggcccatca tttgggaatt ggttaaatag aataaaggac   69780
atttacagcg taacactata cagtcataga aaagagagat caaagggctg ggcgtggtgg   69840
ctcgtgcctg taatcccagc actttgggac gctgaggtgg gaggatcacc tgaggtcagg   69900
agtttgagac cagcctggcc aacatggtga aaccctgtct ctactaaaaa cacaaaaatt   69960 agccggggt ggtggcacac atctgtaatc ccagctactc aggaggctga ctcaggagaa    70020
tcacttaaac ctgggagatg gaggttgcag tgagccgaga tcgcgccact gcactccagc   70080
ctgggtgaca gagcgatact cttgtttcaa aaaaaaaaa aaaaaaaaa caagatcaag     70140 ctctatatgt gttgagatgg aacaatggcc aagagcaatg gttcatgcaa ggacaaaggg   70200
gctgagccat ctggatgata tgttgacaat tgtgtagaaa gggagcgggg agtggaatac   70260
atatttatat ttggttgtat atgcacaatg tagctctgag tatcatatta tacaacataa   70320
aggagtagtg gttgactatg agaagggaa caaatgggtg gctgtgggac agtggttaag    70380
agacttttca ccatttgtta aacttggtga ttatttgaag cacttggatg cattacctat   70440
tcaaaatctt actaaaacaa gaacaaaaca aacaaacaga agcttctagg attcttttat   70500
ttctctgaga atccttactc ctgggaacta catctggaga actcattgtg agcccaataa   70560
cacaggggct tggtttccca tgaaaagaag gctgcctttc aaggaaggag agggacattc   70620
tccatcctga ggggacaccc cccacacacc ccatgcttcc tttattgcca tttcgtcctt   70680
tgctgctctc atttgatgtg gctcggcttt ttttttttc ttaaagttcc caccagttct    70740
ctttaaagac agcaccaaaa ctaaaactaa aaaccaattt aatttttactt ttaaagcact  70800 cccccttttt ttttaatttt tacaataatg aagatcttat tctaggatga aaataatgaa   70860
```

```
taggaaagag ctgtttattc ttccttcttc ccaccoctga atattgaagt aaaactaaat    70920
aacaatgaaa gtgactagga acagcagaca agggggaaata tgtcagaatg agaacatctc    70980
atgtcatctc cagggctggg ggagaaacat ctttcctggt acaaggtccc ggtaccgaag    71040
aaatacaatt tttcaaaaag ttctgtaagt gatacatgct tgttacaaaa aatctctacc    71100
attttcaaag cttagaaggc agaaactcct tgttagttgg taatttcttt atctctctca    71160
tgctttcctg atatctgaat tacgcttgag aaaaagagga aaataaaaca agacagaaaa    71220
taatgcttcc ttaggtaaat acaatcggct aagaaaggct tccaagaaga agcataattc    71280
actgagtccc agcttattga gagaatcccc aaacaaagga cttttgtgaa gggatcagtc    71340
tcagccacca taacttagca tacaatagga tggcttaata aaagaggttt ccaaaggcca    71400
agatggttat caaagatctc ccaaggagag agggagaaga agagacagag agaaaaagag    71460
agagagaaag agggaaggaa taaccttctg gaatgttccc aactatcttt ccagttagca    71520
ttcatgaata cgtgaaaggt ttcatatcac ttggagtccc acccattttt caaaatagga    71580
agcttccgct atttcttct ggatccgtta ttgggtcaag agaagtctct gcctcttgtc    71640
caggacattt ggatatttct tatttgttat ttatttatga gatagggtct cactgtgtcg    71700
cccaggctgg agtgtagtgg cacaaccatg gctcactgca gcctcgacct cccaggttca    71760
agtgattctc ccgtcccagc ctcctgagta gctaggacga caggcaccat gcacttggc    71820 taatttaaa atattttta gagatagggt cttgctatgt tgcccagcct gctctcaaac    71880
tcctggcctc aagtgatcct cccccaccttt ggcttcccaa agtgctcgga ttgcaggtgt    71940
aagccaccca ctgcacctgg cctagatttg gaagtttata taattacttt tcaatgaatg    72000
ttttaatgaa tgttgcaatg aatgtctcct tgtttacctt agatgactgg gtgaaataaa    72060
caactcctca aattttgtta tgttactctg ccatattata tcacgtatga catatattgt    72120
tatattatat tacatatgta tgtctataca tatgtttctg tgtatgtaga tgtttataca    72180
tccagcatat taaatccatc aagcttttcg acaaggtgaa aaggttgtag acttcacaaa    72240
cttaaataat gtaggttgta gagtcagagc aacttctggt tgtcccagtg aacttggata    72300
agtgacttaa cctggctggg cctccatgtc ctcctggcaa gtaggggtgg taaccgccca    72360
tatggagggg gttccacaag ataaatttgg aaagacatag gcaagtggca caaagcaacg    72420
gtagctgtgg ttgtcccctc cggacagtgg ttattaaaaa gacttatagg ttgggcgcgg    72480
tggctcctgc ctataatccc agcactttgg gaggccaaag caggcagatc acttgaggtc    72540
aggagatcca gatcagccca gccaacatgg tgaaaccccg tctctactag aaatacaaaa    72600
attactgagt atggtggcgc aagcctgtag tcccaaccta ctcaggaggc tgaggcatga    72660
gaatcacttg aacctgggag gcagaggttg cagtgggcca agatggcgcc actgtactcc    72720 acctggcaa cagagtgaga ccttgtttca aaaaaaaaa aaaaaaaaaa aaagaagatg    72780
tatgttcccg gctttaggag actaccttgg gggctgtgca acacaggct actctattca    72840 aattctggat ttcttaaaa aacaaaacca caaacaccaa aatactctga tagtgcttca    72900
aaacctcaaa ctggccagtg tgtggctcat gcctgtaatc tagcactcgt gtgtggctca    72960
tgcctgtaat ctagcactct gggaggctga ggcaggtgga ttgcttgagc ccagaagttt    73020
gagaccagcc tgggccacat ggtgaaaccc catctctaca aaaatgataa aagttagcca    73080
ggcgtggtga ctgtgggcct gtagtcccag ctactcagga ggctgaggtg atcaccaga    73140 gcccaggagg tcaaggctgc agtaagccga gatcatgaga tcatgccact gcacaccagc    73200
```

```
ttgggtgaca gaatgagacc ctgtctcaaa aaaaaaaaaa aaaaaaagcc ctgaaattca    73260
gtggtctcaa aatttagagt atattcagct attcagcaaa aagagaaaa gaataaaatt    73320
cttacttgag gccgggcatg gtggctcacg cctgtaatcc caacactttg ggaggccgag    73380
gtaggtggat cacttgaggt caggaattcg agactagcct gaccaacatt gtaaaacccc    73440
atatctacta aaactacaaa cttagccagg aatggtggca catgcctgta atcccagcta    73500
cttgggaggc tgaggcagga aatcgcttg aacccaggag gcagaggttg cagtgagctg    73560
agatagcgcc actgcactac agcctgggtg acagagtgtg tgaaactcca tctcaaaaaa    73620
aaaaaaaaaa agattatggt gagcattgca atgactgtgc gcacactaaa gaccactgaa    73680
ttggtcactt tcgataggta aattgagtat gaagtatatc tcattaaagc tgttatgaaa    73740
cacatttttaa ggccgggcgt ggtggctcac gcctgtaatc ccagcacttt gggaggctga    73800
gggatcacct gaggtcggga gttccagacc agcctgacca acatggagaa atacaaaatt    73860
accccggggt ggtggcacat gcctgtaatc ccagctactc gggaggctga ggcaggagaa    73920
tcacttgaaa ccgggaggcg aaggttaccg tgagccgaga tcgtgccatt gcactctagc    73980
ctgggcaaca agagcgagac tccgtctcaa aaaaaaaaaa aaaaaaaaaa gtaagaaaca    74040
cattttagtg cactttcata tgccctgggc acgcttgttt aaaatgtagg ctggtacact    74100
ttcttccagg gattttgctt ggagagacca ttcttatgcc accaggggcc tttcaaagct    74160
ttgagaaaca ccgcaggagg cctgacccaa gtcttatcca ccatctagac atccactgtg    74220
cctgatgttc catcctgaac accttgtttt gtccatcctt tctgaaattt tatgtccagg    74280
ttgctatcat tgctttatttt tacaggggag gaaatggaag tggtataaaa caaacagcg    74340
aagctcaggg ctgtggcttc agcgggcctg gaaatgggta gatggggact ataggtcaag    74400
tgtgttctcc tgcagcccac acctgatcac tgcagttctt tttttttttt tttttgagac    74460
acagcctcgc tttgtcaccc atgctggagc gcagtggtgt gatctcggct cactgcaagc    74520
tccgcctccc aggttcacat gccattctcc tgcctcagcc tcccgagtag ctgggactac    74580
gggcacccac caccatgcca ggctaatttt tttgtatttt tagtagagac agggtttcac    74640
cgtgttagcc aggatggtct cgatctcctg acctcgtgat ccgcctgtct caggctccca    74700
aagtgctggg attacaggcg tgagccaccg cggccggcct ggtcactgca gttctagcgg    74760
cacctaggaa tgtggttaac acaggcttttt cttgctgtgg tgggccttac tatatacgac    74820
acctaatata gtaaaatacg accatatttc acattcagtt aaacaaatgt gtgtaattttt    74880
tgaaatgttc tgaagtgtgc aattactaat tttgctcaga tagaatattt tgctcttgtg    74940
atttttttttt tttttgagat ggagtctcgc tctgtcgccc aggctggagt gcagtggcgc    75000
gttctcggct cactgcaacc tccgcctccc agattcaagt gattctcctg cctcagcctc    75060
ccaagtagct gggtttacag gtgtgtgcca tcacacctgg ctaattttttg tatttttagt    75120
agggataggg tttcaccata ttggccaggc tggtctcgaa ctcctgacct caggtgatcc    75180
acccgcctcg gcctcccaaa gtgctgggat tacaggagtg agccaccaca cccagcttgc    75240
tcttgtgatc taaagacctc taaaaaccac cagttgcaga tgccagttag tatgatgtaa    75300
caatttgtag ccatttgtga attctctgtg tatatttat cacttattaa attttatttt    75360
aattttttaga gaggaagggt ctcactctgt cacacagact agagtgcagt ggggtgatca    75420
tagttcattg cagtctcaaa ctcataggct caggcagctt ctcacctctg cctcccaagt    75480
aactaggact acaggcatgc accaccacac caagctaatt tttcaatttt ttgtagagac    75540
agggttttgt catgttgcgc aggctggcct ccaactcctg gcctcaagcc atcctcctgc    75600
```

```
cttggcctcc caacatgttg ggattacagg catgagccac tgcatcagcc tctgtctatt    75660
tttaaatttg ttttggtaag ccaggatttg atattttttct ttggttcttg caaagctctt    75720
gcgtccttgg atctagtact gcagcaccct gtaaaaatat ccctgaaagt gtaggcaaag    75780
tcatgcttgg ttttgtggtg gacgtgatcc cacttgttgt ctggtttcat tcactattta    75840
tctcaaagcg catttctgat ttctctactt cattctgtcc attgtagcct gaggaggtgg    75900
aggtggggct ctgaagatgg ctgagaggtg gggactgtgt ccaggtgtgt ctagtaatct    75960
gaatatttct taatcttcca ctgtatgcaa atactttact gagctacatg ataggaagaa    76020
atataaaaca aaccccttt agaagattgc aaatgaatac tgtagaggaa gctagcaggc    76080
atgtataaga aaagattctt gacctcaggc attataagaa aaatgcaaat ataattagta    76140
tatctttttt ttccttatca gatcaacaga tatccaacct tttgataatg ccgtctttgc    76200
agggtgtggg gaatcaggct ctgacataca ctgccaagag ggtgggagtt aaaaatgctt    76260
tagtctcctt gggagtattt ggaaacataa actaaaatag aaactataca cgttcctttt    76320 ttttttttctt ttgagacagg gtctcgctct atcgcccagg ctggagtgca gtggcacgat    76380
cagctcactg caaccttcac ctcctgggtt caagtgattc tcatgcctca ggctccagag    76440
tagctggggc tacaggcgcg cgccaccatg cccagctaat ttttgtgtg tgtgtgtatt    76500 tttatgagag acggggtttc gccatgttgg ccaggctggt cttgaactct caagggatcc    76560
acctgccttg gcgtctcaaa gtgctgggat tacaagcatg aaccaccatg cctgactgag    76620
atgtacatac tcttttgacct aacaattatt ctactgaaaa tttatcctat agaccccac     76680 tcaggaatat atgataagtg atgtacgtat aaggaaatac attgcaacat tgtatgtaaa    76740
agctaagtaa tagaaacaac ccaaatgtcc attagaggaa gctgtcaaaa taagttatgg    76800
tcatctatga tatggcattg tatttctgca gctggaggca gctgtgtttg aactgacatt    76860
ctgtgagaga tagactgaaa ttaaaaacac aagctgggc caggtgcggt ggctcacgcc    76920
tgtaatccca gcatgggagg ctgaggtggt tggatcacct tgaggtcagg agtttgagac    76980
cagcctgacc aacgtggtga aaccccgtct ctactaaaaa tataaaaata acccgggcgt    77040
ggtggcacat gcctgtaatc ccagctactt gggaggctga ggcaggagaa tagcttgaat    77100
ccggaaggca gaggttgcag tgagccaaga tcatgccatt gcactctagc ctgggagaca    77160
agagtgaaga gtgaaacttt gtctcaaaaa aagaaagaaa aacacaagct gccagactgt    77220
tttggatgct accaactgag taggaaaaaa tattaggttg agccatgtga aagtaccaat    77280
atgagaccat ttttgacata taaacatgac agtttcatgt acttcaatgt catatatagg    77340
tatgtagggt tttttttttt tttttttta ctttttattt tgaagcgaag attcacattt    77400 tttttgttt ttcttcttct tttttttttt ttttttttt gagacggagt ctcgctctat    77460
cgcccaggct ggagtgcagt ggtgtgacct cagctcactg caagctctgc ctcccgggtt    77520
cacgccattc tcctgcctca gcctcccgag tagctgggac tacaggcgcc cgccaccacg    77580
cctggctaat ttttgtgtact tttagtagag acggggtttc accgtgttag ccaggatggt    77640
cttgatctcc tgacctcgtg atccacccgc ctcagcctca caaagtgctg gcttacagg    77700 tgtgagccac ctcgccgtgc ccggcctcat gtgtactttt aagaaataat agatactgtg    77760
taaactttac ccagttctcc taatggaaac ctcttacaaa actttagtac agtatcataa    77820
ccaggatgtt gacattgata tattcaagat acagaacatt tccattatca taaagattcc    77880
tcatgttata cttttatagc cacacccact tccctccagg cctaacccct ccttcattcc    77940
```

```
tggcaaccac taatctgttc tacatttcta tagtttcgtc atttcaagaa tgttacataa    78000
atggagtcat atagtatata atcttttgag atcagctttt tctctgtatt tatttatttt    78060
ttgagatagg gtctcgctct gtcactcaga cggcagtaca gtggcactat ctgggctcac    78120
tacagcctcc gactcctgag ctcaatcaat cctcccacct cagcctcctg agtagctggg    78180
gctataggtg tgtgccacca tgcccggaga tttttttttt ttttttttttt ttgagacagg    78240 gtctcattct gtcacccagg ctggagtgca gcggtgcgat ctcggctcac tgcaacctct    78300
gcctcccggg ttcaagtgat tctcctgcct cagcctcccg agtagttggg attacaggca    78360
cctgccacta tgcctggcta attttttgtat ttttagtaga cggggttt caccatgttg    78420 gccaggctgg tctcaaattc ctgacctcag gtgatccgcc catctcagcc tcccaaagtg    78480
ctgggattac aggcgtgagc cactgctccc agctgaacac agttttattt tctctgtgat    78540
aagtgccccg gagcgcaact gctgggtcat gtggtactgc atgtttagtt ttttttttt    78600 taacaaactg acagttttcc agagtggctg taacacgtga cattacctcc agaaatgcat    78660
gggtgctatg tacagagtgg taaaaaaaaa tctctgtcgc caaaccatct gaactctagt    78720
gaaagtgggg tgggtgtgaa caaatgaaca aaatctacat tgtattagac aaggataagt    78780
gctttggaga gaatgaggca gccagtgggg gtggggtctg caagggtctg gatggatcaa    78840
ctgcagtggt gaaaagggaa ggctttggag ggaaagtgac acctgaagat agaataaatg    78900
tgttattgtg gaatgcaatg ctgctccact gccccccccac acctttttttt ttcaatgcct    78960 tgaaaagact taatccagac gaactctctt ctcgcctgct ttctttttttt tttttttgaga    79020 cagagtttcg ctctgtcacc caagctggag tgcagtggca aatctcagc tcactgcaac    79080 ctctgcctcc tgggttcaag tgattatcct gcctcagcct cctgagtaac tgggattaca    79140
ggtgcatgcc accacgctca gctaattttt tgtatttta gtagagacag ggtttcacca    79200
tgttggtcgg gctgatcttg aactcctgac ctgaagtgat ccaccgcct tggcctccca    79260 aagtgctggg attacagaca tgagccactg tgcctggctt gattttagat tcccatctga    79320
tgttctctat aactttgatg actccccaaa caaaggctcc caaacacact ctgaggctta    79380
tggtaatgaa tttaaataag ccagcgtgtg tactgggtgt agcacatgtc cagaagcagg    79440
aaaccctcac tgtcctctat aagctgctgt tctgtcagga acattgtgac agcactgctg    79500
ctgatattat cgttttcata tcccagaatg ggaatggttt cttgccatcc tcagacagag    79560
ttgcctcatc ttgatgacag tggtaggatg agtaataatt atctaccatt gtctaactta    79620
gatatcaagc actttgcacc aattcttatt gggtgctcaa agaaacctca ggaggaatat    79680
gctatcagta taactccctt tttatagcta aggccacaaa ggctctgagt ggcgaagtgg    79740
tccatgaggg tctcagagca gtaatgggga agaatgagat tttgaatcct aaagcactag    79800
aggaaatgtt cttcaactat gcctcagagg tgtcctagaa aatcagaccg gaagagtatt    79860
caccaaattt agtatttgtg ctgcaacgat tggaaatcca taagtaaaag aatgaaagtg    79920
gacttttccc tcacaccata tgcaaaaatt aatttgaaat gaatcaataa cctaaacaga    79980
agagctaaag ccataacact cttaggagaa aacacaggag gaaatttcca tgaacttgga    80040
attggcaatg ggttcttaga tatgaacaca caaaacatga gcaacaaaat aaaaaataaa    80100
gcacaaggaa caaaggaaa taaattggac ttcattaatt tctttttcttt tttttttttg    80160 aggcagagtc ttactgctgt ctcggctcac tacaacctct gttccccagg ttcaagcaat    80220
tctcctgcct cagcctccca gtagctgag aatacagctg tgcaccacca cacccggttt    80280
caccatgttg gccagggtgg tctcaaactc ctgacctcaa gtgattgtcc cacccttggcc    80340
```

-continued

```
tcccaaagtg ctgggattac agaagtgagc caccacaccc ggccgggact tcattaaatt    80400
taaaaacttt tgtacatcaa aggacattat caaggaagga aaaagacaac tcacagaatg    80460
ggagaaaata ttcgcaaatc aatcataaat ctgataaggg tctgggatct aaattttttt    80520
tgtagccacc acgcctggct aattttgtg tttttagtag atggtgtt tcactatgtt    80580 ggccaggctg gtcttgaact cctgatctca ggtgatccaa ccacttcggc ctcccaaagt    80640
gctgggatta caggtgtgag ccaccactcc cagcctggga tctaaaattt gtaaggcatt    80700
cttgcaaagc aacaacaaga caaacaactc agtcaaaata tgggcaaagg acttgaatag    80760
atattttctt ccaaagaaga tgtacaaaag gccagaaagc acatgacaag atgctcagca    80820
tcattagtca ctagagaatg cacttcaaaa tcacaaggca tcatttcaca tccactagga    80880
tggttattat caacaaaacc aaacagaaca caaaaaccca ggttgggtat ggtggctcat    80940
gcctgtaatc ccagcacttt gggaggccaa ggtggttgga ttacctgagg tcaggagttc    81000
gagaccagtc tggccaacat ggcaaaaccc catctctact aaaactacaa aaattagcca    81060
ggcatgatgg cacacgcctg taatcccagc tactcaggag gctgaggcag gagaatagat    81120
tgaacccggg aggcggaggt tgcagtgagc caagattgct ccactgcact cttgcctgtg    81180
cgacagtgag actccatctc aaaaacaaac aaacaggcca ggcgcggtgg ctcatgccta    81240
taatcccagc actttgggag gtcaaggcag gtggatcacg aggtcagaag attgagatca    81300
tcctggcgaa cacggtgaaa ccccgtctgt actaaaaata caaaaattag cctggcttgg    81360
tggtacgcac ctctagtccc agctactcag gaggctgagg caggagaatc acttgaaccc    81420
aggaggcagt ggttatagtg agccgagatc gagatcatgc tactgcactc cagcctgggt    81480
gatacagcaa gactccatct caaaaaaaca aacaaaaca aaacaaaaca aacaaaaaa    81540 acaaaaaata agaaaacagg cattcaaata cacgtacata cgtgttcaga gtagcactat    81600
acacaatagc caaaaggtgt aaatatccca aatgtccatc aactggtgag tgcagaaatg    81660
agatgaagta ctgtataagt tctgttgtac cacagacaat tattcagcca taaaatggaa    81720
tgagatactg atacgtgcta caatgtggat gagccttgaa acattacag taagtaaaag    81780 aagccagaca caaaaagcca catttgattt tgttgataag aaataggaat ctgaatctgt    81840
tcactttaac cagaataggt aaggccatgg cgagatgccg attggcggtt gccaggtcct    81900
gggggctagg gtagaactgg ggagcgactg cctactggct acacggtttc cacttggggt    81960
gatgaaaatg tttcggtgct ggacagaggt ggtgataacg caatactgtg aatataccaa    82020
ctgctcctga attggtcact ttaaaatggt taattttatg ttatgtgaat tcatgtcaa    82080 tttttttct tttttctttt ttttgagaca gagtttcaca cttgttgccc aggctggagt    82140
gcagtggtgc aatctcggct caccacaacc tccgcctccc gggttcaagc gattttcctg    82200
cctcagcctc ccgagtagct gggattacag gcgtgcgcca ccacgcccag ctaattttgt    82260 attttagta gagacagggt ttctccatgt tggtcaggct ggtctcgaac tcccgacctt    82320
aggtgatctg cccgcctcgg cctcccaaag tgctgggatt acaggcgtga gccaccgcgc    82380
ccagcttcat gtcaatttt aaatttcacg tttgattcca ggggttggga gtttgctgcc    82440
cttcatcatg gagtttgctg cagccagtgc aggggtgaaa agggaagagc aaaacaggca    82500
gatctcgttt aggagagata ctgcaattta tctgatgctg atcttttaag tcacttctgg    82560
tgccaaagag cactgggactt ggagcctgaa gaactgagac ttcctgacat ttggccttaa    82620
gcaagcctga gcttagactt cctgagcttt tcccgatgtt ttgtgttggg cagccccatt    82680
```

```
tccctggaca gctgcaggga tggagggaag tgatgcgtgt atgcatgtgg gcttgttcct    82740
tccttctcta ttccacaggc tgtcagtgta caggtatgtt tgcacacaag aaagatgttg    82800 gtcctgggt ctcagaggca ccaaagaact ggccagcttt gtccaattca tccaaaatcc     82860
agtcagtggc gtaaagagga agccatcaca ccaggccttt gccaacaaag cagacaggct    82920
gcccagccca ggagctgcct actcttactc gcctgttggt ttgagcagat gcagccatga    82980
cagcagggtt acaaaggcca ccccagccag gccaccaccc tccaccaggg ctctgccagg    83040
atggattgaa ccctggccct catgtgttac ttgatgacag caagatacct gataagaaac    83100
tgtttggatg tcacagagaa cacattttaa cagcccagag aggtgggatt atcacagagt    83160
ggtgtaaaag aagcaaaatt atttcggata accatgaag gaatttttatt acccagtgca    83220 gttataaatc aagttctctg taaatgcaat aaaacaattg tttagtctgc atgattcata    83280
ccacaaacct caggattctt ggttttgatc ttattgccgc aataaactgt ctagacagca    83340
attaacaaac tgttttttcct tcagatgttt ggagtgctgg tacagcggga atcggcactt    83400
agaaattcag gggcttcttc ctggctccta ttaattatca ggttgggtga gtgggaaaag    83460
cccagaatct tctcagaatt agccttctgg aagtgtcctt ccctgtgaa tgtgccactt     83520 caccacataa tattcactta taactggcag aaaatccaaa tatacagatt ttcttaaacc    83580
ttggcctgtc actttagaga gaagtgagca gaattaactt tttttttttt ttttttttgga   83640 gacagtcttg ctctgttgcc caggctggag tacaatggca tgatcttggc tcactgcaac    83700
ctccacctcc cgagttcaag tgattctcct gtcttagcct cccaagtagc tgggattaca    83760
ggaatgcacc accacgccct gctaattttg tatttttagt agaaacaggg tttcatcatg    83820
ttggtcaggc tggtctcgaa ctcctgactt catgtgatcc acctgccttg gcctcccaaa    83880
gtgctgggat tacaggcatg agccaccatg ccatgcctgg cctagctttt gtatatcctt    83940
ggagcaaaat ttatatacag ataagtcatt tcttcatgta ttcattcatt tattcagcat    84000
tagggtataa tagtttagaa cactcactca ggagtctaat cgactttcgt gccatttcag    84060
gtacgtgatt tcaccttcct gaagtttatt ttgcatatgt tgaaagtcat ggaggaaaat    84120
taaatgaaat tatctgtgta aattgcctgg aacataataa gagctcaaaa ctattcacta    84180
ttattgtcta tcatccatgc attcatctgt ccatccacgt attcaccatc cctctatcta    84240
tccatccatc cacccaccta tccatccatt ccttcaccct tccttctctc cttccttcta    84300
tcatttattc acctatctgt ccattcttcc ttcttttctt tccttccttc caacatttat    84360
ccatccatcc atccatccat ctatgcatcc acccacccac ccacccatcc ttccatccat    84420
ccctccatct atccctccat ctgtccattt atctacacac tcactcattc attccttctt    84480
tgcctggtac tctatgccag attgttgaga ttataaaaac aaataagata tacccgact    84540 tcatggagat cccagtttag ctggaaagac agcattaggt ctctggctgt aggcagcatc    84600
tgatcctgaa ggaaatagtg agagaaaacc tggggaagtg tttagtttct ggtctagccc    84660
tggtgattta agatgatatg tgagacgcac tcacctccca gggctcctga tggctcagag    84720
ctcagtggat gaacatggct tcatccacac agtcagttac acggtgagac tacacatttg    84780
gcaaatgccc caaacaaaca aacaaacaaa caaataatt tgggttcaag gtaacagtaa     84840
atcacactct tcaaacctaa atattcttct ctaggcttct tcccaccttt tcttcccttc    84900
tttctgccaa ctccttctcc tccatttgc gtcagacacc atgtgcattg gaggatgtt     84960 gctaggtcac agtggggaca cttgctctat ttacagagaa aacagggctc tcagattca    85020 caggggtttgc aaaggaaagc cctcccagaa aggaattcca gccttccctt ctgaggctgg   85080
```

```
tgcagcaggg ctgggggctg caggaacaga ccagagaaag tgactcagaa ttcccttcgg   85140
ctacagtacg attgcgagaa ccattttaag tatgagctgt ggctcccctc tccctttttc   85200
ctcagcctcc agggagctgc catttaaaaa atcttggcct ggccaggggc ggtggctcat   85260
gcctgtaatc ccagcacttt gggaggctga ggtgggcgga tcacctgagg tcgggagttt   85320
gagaccagcc tgaccoctga ccaacatgga gaaaccccgt ctctactaaa aatacaaaat   85380
tagctggagg ctgaggtagg agaatcgatt gaactcggga ggcagaggtt gtggtgagct   85440
gagatcacgc cattgcactc cagcctgggc aacaagagca aaactccatc tcaaaaaaaa   85500 aaaaaaaaa aagaaaagaa agaaagtaat ccatgtcttt ctcacgtacc aacatccaga   85560
tagaagcagt ccaggatggg tagagcagct cctttggtag aacccacctc tattgcgctg   85620
ccatgcctgg cacgttgctc ccatccccat ggtccaaggg tcctctcctc cacatcccca   85680
tccagccagc agaaagggga gacaatgaag ggaaggcacg ccccagaagg atgtgcctcc   85740
gaggcctctc acatcactgg aatgctctcc ccatagccta ggatttagtc acgagaccgc   85800
acaggggagc tgagctcttt gttctggttg gccatgtgtc cacatctatt actacacaaa   85860
agtggggatg gccatggagg gagaaccagc aaattctttc atacgctcct atggccttga   85920
tccatccagt gggtacattt ctgagcccct cgctttctca ctgcctcttc tgctgggagc   85980
atgactcccg ggctgcagaa ggacaggctg gtgcattgag agtctttagg cttttgcttga   86040 attgcaaatg ctctggtttt ctggcaagac ggaagtaggt ccctgggcag aagtgtcaga   86100
agacctgggg ttgcctctga acgtcactgt ttctgggtct gagaccttgg actcagaaat   86160
gaaaaaaacc tctgaacctc agtgaaatgg gggaaaaaat aaatgacttc catagagtta   86220 tgggaggac caaactgcat taccaaatac attctgaaaa ggtgaaagtt ctccaaatga   86280
ttgtgtgttt tatcatctcc accaccacca ttttttcttt tcttttttt ttgagacaga   86340 gtcttgctct gttgcccagg ctggagtgca gtagcgcgat ctcggctcac tgcaagctcc   86400
acctcccggg ttcaccccat tctcctgcct cagcctcccg agtagctggg actacaggca   86460
cccgcctcca cgcccggcta attttttgtat tttagtaga cggggttt caccgtgtta   86520 gccaggatgg tctcgatctc ctgacctcgt gatccacctg cctcggcctc ccaaagtgct   86580
gggattacag gagtgagcca ccgcgcacgg cccatttttc ttttttctta atgcatgtat   86640
gtagctgaat ttgtgtaagt acaatggatc catgatgaga gtctatttat tgaattttt   86700 ttttttttc agatggagtc tcactctgtc acccagggta gagtgtagtg gtgtgatctt   86760
ggctcactgc aacttccgcc tcctgggctc aagtggttct cctgactccc aagtagctgg   86820
gattacaggc acccaccgcc acgccaagct aattcttgtg tttttagtag atggggtt   86880 tcgccatgtt ggccaggccg gtctcgaact catgacctta agtgatccgc ccgcctccca   86940
aagtgctggg attacaggca tgagccactg cgccttgcct aattatagaa attgtatttg   87000
gagagaaaag tatactcttt ctctaagcat ttctgacatt acattctttc aaagcaatgc   87060
gaacaacttc tgaaggtact ggtctgggct ccaagctcag atctgggtgg cggaagattc   87120
tatgaacagg tcctggccag gtttggggga ggtccatgag caggtcttct caccaggagc   87180
aatatcccta ggaaaccaac ccacagaata gaaattgaaa gagcaaaaag cttccttt   87240 ctaagaaagg ccatgatgtc tccaggaata gcataaatat cccctgcagg gcttatccca   87300
gaaaagaaca ttcagagggg cctctgagtt gctctgcacc cccagcagat gccctgctcc   87360
aaatggtctc ttgtgtctcc agctctccac ccaggctcta cctggaaggc tcttctctga   87420
```

```
cttgtcctca cgcagcccct tcaactgagc cacagtgacg tcccccatag gcatcctggt   87480
gagtcctggt ggggtatcgt agaggctcaa tgacctttaa aatgagttca ggccaggcac   87540
ggtggctccc acctataatc ccagcacttt gggaggcgag gcaggcggat cacctgaggt   87600
caggagttca agaccagctt gaccaacatg gcatctctac tgaaaataca gaagttagcc   87660
gggtgtggtg gtacatacct gtaatcccag ctactcggga ggctgaggca ggagaatcac   87720
ttgaacctgg gaggcggaga ttgcagtgag ccaagactgg ccactacact ccagcctggg   87780
ttacagagcg agactccgtc tcaaagaaaa aagtcagtt caaactttgc gattcaacaa   87840
ctgggtgact ctccggagtc aatgaattcg ccaatccatg gatactgatg agcttgacct   87900
gagctgcttg ggaagctgag ctgcagtgaa tacgatgcag cagatggagc caacgctgca   87960
aagcagagcc gcgggcaaca cggagttccc gggactccct caaaatcctc cccttatct   88020 acactggctc ccgcagaccc gcgggcaaca cagagagtgc ttgggactcc ctcaaacttc   88080
tctcctttat ctacactggc tcccacaaca ggatctcaac cctggttgta cttgagaatc   88140
agcagggaaa cttctaacag ttctgatgcc tgagccatgc ccacagatca attatatcag   88200
aaaccccgta gctgggacct gggcataagt attttaaagc tccccaggtg attccaaagt   88260
ccagccaagg tagacatcca ctgctctggg gaccttgtcc atcccacagg tagaaggccc   88320
catctgtgac ctttttctg aggtccagac ttgccaattt attttctcaa catcaccatt   88380
tcagtgccta agagacaact catcttgcca gagtaaagtg gattgtcccc tccacacctg   88440
cttctcttct caccagggtc ccccagctgt ttcagggcaa aaactgaaca ccttctgatt   88500
ctttttcttt tctcacagcc catagccaat ttttttggaa ttctcaacag ctataatgtc   88560
aaaatatatc cccattctaa tctctgctcc ccacctcccc tgctagcctg gagatcccct   88620
attcttcttt tgaatccttc tagtttggtc tctgccaaca gctcatgtaa aatctatgaa   88680
aaaatgaagc tccgggttgg gtgtggtggc tcatgtctgt aatctcagaa cttgttgttg   88740
tcgttgctgt tgttttgaga ctgagtcttg ttctgtcgcc caggctggag tgcagtggtg   88800
aaatctcggc tcactacaac ctccacctcc caggttcaag caattttcct gcctcagcct   88860
cgtgagtagc tgagactaca ggcgcgtgcc accacgccca gctaattttt tctttttttt   88920
gtatgtttag tagaagcgag gttttaccat gttggccagg ctggtcttga actactgacc   88980
tcaagtgatc tgcctgcctc ggcctcccaa agtgctggga ttacaggcgt gagccaccac   89040
acccggccaa tcccagtact ttggaaggct gaggtgggag gattgcttga gcccaggaga   89100
tggaggctgc agtgagccat gattgtgcca ctgcactcca gcctgggcaa cagagcaaaa   89160
ccctgtttcc agaaaacaaa caagcccaaa aactcagcat gaaaagatgc tcagctcatt   89220
agccattggg gaaattcaat taaaaccaaa agaagggccg agcacggtgg ctcatacctg   89280
taatcccagc actttgggag gctgatgtgg gtgagtcacc tgaggccagg agttcaagac   89340
tagcctggca aacttgatga aaccccatct ctactaaaaa taaaaaaatt agccgagtgt   89400
ggtgatgcac gcctgtaatc ccagctgctc gggaggctga ggcaggagaa ttgcttgaac   89460
ctggaagaca gagattgcag tgagccgaaa ttccaccact gcactccagc tgggtgaaa   89520 gagcgagact ccatctcaaa aaaaaaataa agatatgttg agatacacaa ataccattgt   89580
gttacaattg tccacatcat tcaaggcaat aacatgtacg tgtttgtagc ctaggagcaa   89640
taggccatac catatagcct aggtgtgtag actcactcca taacgtaccc ataataacga   89700
aatgccataa tgtaccaaca ggagaacaga tgaacaaatt atagtatgtt tatacaatga   89760
aatactactc agcagccggg cacggtggct cacgcctgta atcccagcac tttgggggc   89820
```

```
cgaggtgggc ggatcacgag gtcaggagat cgagaccatc ctggctaaca cagtgaaacc   89880
ctgtctctac taaaaataca aaaattagcc gggcatggtg gcggggcgct tgtagtccca   89940
gctactcggg aggctgaggc aggagaatgg cgtgaaccca ggaggcggag cttgcagtga   90000
gccgagatca cgccactgca ctccagcctg ggcgacagag caagactctg tctcaaaaag   90060
aaaaaaaaac caaaaaacta ctattcagca tacaagaaat gaattactga cgcaagcagc   90120
aacgtcaata aatcttatag acattcctct gagcaaaaga agctgggtaa actttatgaa   90180
tgcatttata agaggttcta gaaaaaaatg attcaagggt gatatgttaa aatatggctt   90240
ctagccagtg ggatggtcag gggtttgact ggattgattg aaaaggagca tgagggagcc   90300
ttctggagtg atggaaatga ttttatctt gttttgggtg gtgattacag gtgtccaaag   90360
ttactgaact cacttaagag ctgtaagtct tggctgggca gtaatcccag cactttgaga   90420
ggccgaggta ggtggatcac ctgaggtcag gagttcaaga gcagcctggc caacatgatg   90480
aaaccctgtc tttactaaaa aaaaaaaaaa actacaaaaa ttagctgggc atggtggtac   90540
gtgcctgtag tcccagctac ttgggaggct gaggcaggag aattgcttga acctgggagg   90600
cggaggttgc acgctgcagc ctgggccaca gagcaagact ccatctcaaa aaaaaagaaa   90660 aaaaaagga actgtaagtc ttactgcatg taaatcatac cttaaaaagt aatttggggg   90720
ccaggcgcgg tggtgcatga ctataattcc agaacttttg gaggccaagg caggcagata   90780
acttgagacc aggaatttga gactgagact aggctgggca acatggcaaa actctgtctc   90840 tataaaaat acaaaaatta gctgggtttg gtggtacaca ccagtagtcc cagctacttg   90900
ggaggctgag gtgggaggat tgcttgagcc caggaagttg aggctgcagt gagccatgag   90960
tgcaccactg cactccagcc tggatgacaa acaagacct tgtctcaaaa aaaaaaaag   91020 aaaaaaaaac acagagtccc acaaacctct gctcaaactc cccctaccct caccccaac   91080 ctttaggaca aaatctggag cacccactct ggtcttcaga gccttgcatg aactgccgtc   91140
ttttccctcc ttggcagtgt ctacaaccac ccttcccttt gctctttttt ttcagacaga   91200
gtctcactct aacacccagg ctggagtgca gtggtgccat ctcagctcac tacaacctct   91260
gcctcccagg ttcaagcgat tctcctgcct tagcctccat gtagctggga ttacaggcat   91320
gtaccatcgc tcctggctaa ttttttgtat ttttagtaga cggggttt caccatgttg   91380 gtcatgctgg ccttgagctc ctgacttcaa atgatctgcc cgcctcagcc tcccaaagtg   91440
ctgggattat aggcgtgagc caccgtgccc ggctggcttt tctttataga atgcctgccg   91500
gtgtatacat cactaagcaa tcattctttt agttctcaca cactttttg gaaacaccat   91560 gcattctttt gtacttaggg gctttgcttt aatattatgt tcctgagatt catccaggac   91620
cactattaat tttcatagtt gtgttctaat ctatgatgat cacataattt agtcacccat   91680
tttcttggga agggcattt aggttgtatc cagattttg ctgttactca caatgctgcc   91740
aagagcattg ttgtacatgg ctcctgggac atgtatgcca gaaatgttta ggatatttat   91800
ctatgaatga aattgcttgg tcagagggta tgtgcgtttt cagctgtatc tgatatttca   91860
aagctatttt ttaaggtggt tgtaccaact acacttttca ccaactgtgt aaaagagttt   91920 ccttttttgtc ctatatcctt atcaatactg ggtgccctta aatttattaa ttttttgccaa   91980 tcttgcggtt ttaatttgca ttgtctcaat cattaataag gttaatcatc actttatata   92040
ttgggcattt atcaaaaaat aaagctgtgt attttttagat gggaacaaat gcacagaaaa   92100
agatctaaaa ccgtgattct aagaagggga gtggaaaagg aggggtggga tgtgaatact   92160
```

-continued

```
ttgttctgtg tgatcttcac attttttacaa caaaaattat ttaatatgct tataaaattc    92220
atataaaaat ggccaggcat ggtggctaat gcctgtaatc tcagaacttt aggaggccct    92280
gggtgggcga aatcacttga ggccaggagt tcgagaccag cctggccaac atggcaaaac    92340
cccatctcta ctaaaaacac gcacacaaaa aaatcagctg ggggtggtgg tgcacacctg    92400
cagtcccggc tacttgggag gctgaggcag gagaattgct ggaacctggg aagtcaaggt    92460
tgcagtgagg caagatcatg ccactgcact ccagcttgga tgacagaatg agactctgtc    92520
tcaagaaaca gaaaaaactg gctgggcgcg gtgtctcatg cctgcaatcc cagcactttg    92580
ggaggctgag gtgggcagat cacaaggtca ggagatcgag accatcctgg tgaacacggt    92640
gaaaccccat ctctactaaa aatacaaaaa attagccagg actggtgggc gcctgtaatc    92700
ccagctactt gggaggctga ggcaggagaa tcacctgaac ccgggaggcg gaatttgcag    92760
tgagctgaga tcatgctact gcactccagc ctgggagacg gagtgagact ccatcccccc    92820
cgcaaaaaaa agaaaaaatt gatctaaaaa ttaagcaaga tatagatcag tacgcatcat    92880 taatttttttt attttaaaaa attatatgta aacacacaca tacatgcatt gctttatatg    92940
tgtgtgtgta tgtgtgtgta tagaagaagg cctgaaataa ttttctcaga gtttttaagg    93000
gtggttttct gtgtggaggt ggggatgcaa ctgtgcagtg gtggagttaa ggagggtagg    93060
ggtagtaggg ggcggtatat aattgttcct tttaaattt atgcacctttt taaattggat    93120 attttcttca gtctttaata caaaattcac tagttctgcg atttaacatt tttatgttat    93180
tttacaaaaa tcttctgat atttccttca ttctcaatat ccaaattttc tttttttttt    93240
ttgagacaga atcttgctct gttgcccagg ctggactgca gtggcacgat ctcgactcac    93300
tgcaagctgt gcgtcccgga ttcatgcctt tctcctgcct cagcctcctg agtagctggg    93360
actataggcg cccgccacca cacctggcta atttttttttg tatttttagt agagacgggg    93420
tttcactgtg ttagccagga tggtctcgat ctcctgacct cgtgatccgc ctgcctcggc    93480
ctcccaaagt gctgggatta caggcgtgag ccactgtgcc cagcctaaat atccaaattt    93540
tctgtggact gtcacaggta taaagtaaag tgccccaccc ccacacccac catgtccaaa    93600
aagaaaagag taaacaaggt tccagtgacc tggaccatac ctaactccgc ctcagttggt    93660
aactctgatg tgaacagcac acatcagaag aacatagggc caccactgtg atataggtgg    93720
taaaattccc tttatcataa acatgtacaa tgattacata tccataataa ttagaaataa    93780
aaacattttt aaaggtaaag ctaagcgaaa aaataaaaaa taaaggttcc tttatgttct    93840
tgagatctga aaaggaaatt atacgtacag cctttacaat acctttttatt ataaatctgt    93900 ttatgagttt aaaactatgc tgtccaatat gtagccacta gccatatgtg gctatttaaa    93960
tttaaattga ctgaaattaa ataacattaa aaattcagtt ccttagtcac atgggcccac    94020
tatttcaagg gtccaacagt tactttgggc tagttgctat tgtattatat aatgcagatt    94080
aaaaatattt ataccaatgt ggaaagttct gatggacagt actggattaa aaccttatat    94140
agatattatt cttgttcacc accatgtgag aaggttttta ccatgggaag gaattcttgt    94200
ttgttttttt tgttttttttg tttttttgtt tttaaattg aggtagggtc ttgctctgtt    94260
gcccaggttg gagtacagtg gcacaatcac agctcacttc agcctcgacc tccaggtctc    94320
aagtgatcct cccacctcag tctcccaagt agctggaact acaggtacct gccaccacac    94380
tcagctaatt ttttttattt tttgtagaaa tgggatctta ctatgttgcc caggctggta    94440
tggaactcct gggctcaagt gatcctcctg cctccagcct cccaaagtgc tgggattaca    94500
ggtgtgagcc accattcctt gggccattct tgtatttta gtactcagag acatccagga    94560
```

```
aaggtaaccg agtgggtaac ttcagcactt cagagagtgc ctagtgtgtg attctaagct    94620
catcactcca gggacccagc acccaattcc agctgtgtct ttcctccatt taaatcaccc    94680
tctgtggatc ctattaagta ttctcccatt ctggtcaaac tggtttatga aactactatt    94740
tgagaagtcc agtcttgcag gccgatggga ccctgccttt gtgtggccgt aataaggtta    94800
tttatgaggg ctggagccga ttctcttgat tcttcgggaa gatgaaaggt ttggtggtaa    94860
aggaaagcag aagcttgggg agcaggtttc tccttatagc aatgactctc cagataggat    94920
aaatcaccca ggaccattaa accttcaaga gagtgctcg taaacctccg ctggaaactc     94980
acaaagcatc ttctctcttg gagcagccta tgtggagagg gactcgcctc ttttccaaa    95040 ccaccagcca gtcacagatt aaccctgctg ccatctctgc ccaggacact gaagcagaaa    95100
atcactttct ttttttttt gagacagagt ctcactccgt cacccaggct ggagtgcagt     95160
ggcgcgatct tggctcactg caacctccac ctccctggtt caagcgattc tcctgcctca    95220
gcctcccgag tagctgggat tacaggcatc cgccaccatg cccagctaat ttttgtatt    95280 tttagtagag atggggtttc accatattgg ccaggatggt ctcaatctct tgacctcacg    95340
atccgcccac attggcctct caaagtgctg ggattacagg cgtgagccac tgcacccagc    95400
cgaaaatcac tttcaaagtc atcctttcag gtggccaact gtccctgttt gtctgagatg    95460
aaagggtttc ctgggacaag agatcaggaa agtcccaagc aagtctggat gaactggtca    95520
ctctatttcc tccgtacctt gggggcaagc aatgcctgcg actcaacagg acaaaaacat    95580
ttgttcatat ttagctccca tttatgaggc tctgcaatgt gtcaggtgct gggcaaagac    95640
agtgctttac ctgacgtgtc tcgtttcatc ttaacaacca aatgagcttg gtgttattat    95700
tatccccatt tgacaggtga agaaaccgag gctcagaaag ctaaagtgac ttgtccaagg    95760
tcacacctta aatggtgtct gtgtctccat agctcatgct ctgaactgct cctctaattc    95820
ttccttatct ttcttttttt ttttttttt tttgagatgg agtctcgctc tgttgcccag    95880
gctggagggc agtggtgcga tcttggctca ctgcaacttc cacttacggg gtgcaagcga    95940
ttcttgtgcc ttagcctcca gagtagctgg gattacaggt gtgcaccacc acattcggct    96000 aattttgga tttttatttg taatttttt tgagttggag tctcactcta ttggccagga    96060
gtacagtggc acaatcttgg ttcacggcaa cctccatctc ctgggttcaa gcgatcctcc    96120
tgccttagcc tcctgagctt accaggcgcc cgccaccaca cccggctaat ttttgtattt    96180
ttagtagaga tagggtttca ccatgttggc caggctggtc tcaaactcct gacctcaagt    96240
gatctgcccg cctcagcctc ccaaagtgct gggattacag gcgtgagcta ccgtgcccag    96300
cctgtatttt tagtagagac ggaatttcgc cgtattgccc aggctggtct caaactcctg    96360
aactcaagcg atccacccgc cttggcctcc caaagtgctg ggattacagt gtgagccact    96420
gcacctggcc ttcatctttc ttaatctgcc ttggatttt ggggttccag aagcttccca     96480
caaaaagagt cattggagat acttatattg ttaaccaacg gggtaggaga atgactttca    96540
gctgaacttt atttgcacgt taaaaagtca agtctaattt tctaaaacta tctggactct    96600
ttcactggca aatgccgagt tggaaggaaa gtccataaat cactcacaga cctacattgg    96660
ccgtggctat atgcaaaccc agtactgctg gtctggccac ctgggagcac caggcatagg    96720
atggggtgag atttccccac caaattcagg gcatatcaga gctcagagta cctgcaccca    96780
aagggaaata ccccaaacac tggcttcagg aaagttctca ttagatagac acaagaaagt    96840
tttgccctaa tcctcagtat tggctaacag atcacttta ttgaggaatt actatgtgcc      96900
```

```
aggcaatgcc tgttttcatc cacttctcat gtccaattat ctgcgaaata gataagatta    96960
ttatcccagc ccagagatga ggaaactgag gtgtggagag ctggcgagat tgatctagac    97020
cagtggttct caagcagggg agggtttgcc ctccatgcac atttgccact atctggacac    97080 attttttgatc atcacaacct gggatggggt tgctgctggc atctagtgaa tagaggccag    97140
ggatgctgct ccacattcta cactgcacag aacggcctcc ctctacccca gtaaagaaa    97200 ttacatggcc ccaaatgcca atagctctga ggttgagaaa ctcttgtcta aatcaagaaa    97260
agggtggcaa ctcctgggga acccttcact ccagagtttg aggggctcac atgcctagca    97320
aggggtagag cagtgattag atcccacttg cttttacctt cctatgccct ggagaaggat    97380
tactgaaagg tcagttcaag agggtatgaa cttgttgtgt gatgctagaa cagtgctggg    97440
cacaaatagg tgcccagtaa atatttgttg aatgaatgaa tgaatactaa gtattaatac    97500
catttattga gggctttctg tcaatgaaca caccaagtat attgccagca tcatctcatt    97560
tgattcttgg agtagacccc agaggcaggt accactcccc acagtcttat tttacagagt    97620
aagagacaga gagggctggg ggcggtggct cacgcctgta atcccagcac ttcgggaggc    97680
caagacgggt ggatcacgag gtcaggagac caagaccatc ctggttaaca tggtgaaatc    97740
ccttctctac taaaaataca aaaagttag ctgggcatgg tggtgggcac ctgtagtccc    97800
agctactccg gaggctgagg caggagaatg gtgtgaatcc gggaggcgga gcttgcggtg    97860
agccgagatc gtgccactgc actccagcct gggtgataga gtaagactcc gtctcaaaaa    97920
aaaaaaaaaa aaaagagac agagagaaga ggtctcatgc cagagtcata cagcttggcc    97980
agtgactgag gttttccatt cagggtggtc caagtttaac ttagaattac attgcctcat    98040
accagaatct ctggaaacaa gaataaattc cagggcttac atcatgtagc aactttttt    98100 ttttttttt agacagagtc tcaactctgt ctcccaggct ggagtgcaat ctcagctcac    98160
tgcaacctct tcctcccagg ttcatgccat tctcctacct ccgcctccca gtagctggg    98220 actacaggtg cccaccacca tgtccagcta atttttttgt attttttag tagagacagg    98280 gtttcaccgt gttagccagg atggtctcag tctcctgacc tcatgatctg cccgccttgg    98340
cctcctaaag tgctgggatt acaggcatga gccaccgtgc ccggcccaca tgtagtaact    98400
tttttcactg ttccaggttt tataaatata tccccttttt cagcacttgc tctcgcttac    98460 ctttttttctt ttgtaggcag ggtctccctt tgtcactcag gctggagtgc agtggtgcga    98520
tcatggctca acctcctggg ttcaagtgat cctcccgcct caggctccca gtagctggg    98580 actatatacg tgtgacacca cacccagcta attttttaat tttttgtaca gacagggtct    98640
cactatgttg ccctggctgg gttcaaattc ctgggcttaa gctatctctg ccacctcagc    98700
ctcacaaagt gctgagatta caggcatgag ccactgcacc caggcagccc ctttctaaaa    98760
aaataaaatg gccgggcgt ggtggctcac acctgtaatc ccagcacttt gggaggccga    98820
ggagggtgga tcatgaggtc aagagaccga gaccatccag ccaacatgg tgaaacccca    98880 tctctactaa aaatacaaaa attagctggg cgtggtggcg ggcgcctgta gtccagctac    98940
ttcggaggct gaggcaggag aatcgcttga acctgggagg cggaggctgc agtgagctaa    99000
gctcatgcca ctgcactcca gcctggcgac agagtgagac tctgtctcaa acaaacaaaa    99060
acgagtttta cactattcta taaataaaag ggtttcaggg ttagccatga aaggcccag    99120 tgacaaagtt gtaatgtgat cagaaatgaa aagctcaaaa aaagatttca gttggtgatg    99180
aaacaaggca aggattatga atctcacagg cgtttccttt ctccagaaac tgaaggcacc    99240
tttgccagga gaaaaaggca gtttccatgg cagggaccca gccttgactt ccccaggatc    99300
```

-continued

```
tgtccacatg aacgttgtaa tgagtccacc cgagatgggg actctccatt gtatttacat    99360
tttatgacat cttttatat ttcacaggag aggattctga ataaaaatga gcccggcttt    99420
tagggctgtt ttttattatc agcatttggt aaaaaacatc cttaatgagg tgttaagagt    99480
catcctgcat cctattgtgg aggaggcctg ggagctcata aacccctgaa aagccacagg    99540
gtaatttata atccttgatg ccaccccttc ctgacacaag cgcttcagag ggagcatctt    99600
tagttctcgg gcacttcctg caatttacac gcccaagctg cttcgaccac aatctgaatt    99660
caaccttatt aagtaaagtt cagcccagga ttcttcttgc caagctgttc acctctgaga    99720
aactctggcc agcctgcctg aaattaatta gagtttccgt tgagtttgga ctgaaggtgt    99780
ggctctagaa agtgttcaca tttctctcct tactggtgag gaatttaaca gttatggttc    99840
tggggaaaaa caataacata acaacaacaa caacaaaaaa aaccactttt gcttctctgc    99900
aagaagagga gtttcttgat actgtgatgt tttactcata agttcatatc ctttctgaaa    99960
tagacttcaa ttaagactga gggtgtccta agccccagaa tgatatacta cttcattgag   100020
aaaaaaatac tgccacttat ataagggatc taaaagagcc agattcatag aatcaaagtg   100080
tggaatggtg gttgccaggg ggttgtggga gagggcaata gggaattacc aatcagccaa   100140
taatcaatgg gcataaggtt tcagttaagc aacaggaata agttctagag atctgctgta   100200
tgacatttaa cctagagtca acgacagtgg attatacact gaaaaatttg ttaagagggc   100260
cagccttgta tggctgggag cagtggctca tggctgtaat cccagcactt tgggaggcca   100320
aggcgggcgc atcacctgag gtcaggagtt cgagaccagc ctaaccaaca tggagaaacc   100380
ccgtctctac taaaaataca aaaaattag ccaggcgtgg tggcgcatgc ctgtaatccc   100440
agctactcgg gaagctgagg caggagaatc gcttgaaccc aggaggtgga ggttgtagtg   100500
agccgagatc gcgccactac actccagcct gggcaacaag agcgaaactc cgtctcaaaa   100560
aaaaaaaaaa aaaaaaaaaa aagaagggcc agccttggtg ggtcacacct gtaatccgag   100620
cactttaaga gcccaaggcg gaaggattcc ttgagcccag gagttcgagg tcagcctcgg   100680
caatatagtg agaccctgcc tctatttttc atttaaaaaa aacccaaaat tgttaaaag   100740 tgtatatctc atgataagtg ttcctctcaa tcaagtaaaa taaaacgacc gccacaaacc   100800
agactttgtg atggcgacaa atatctcagg tttaatcttg aaatctgtaa attgaagaat   100860
aaagaaaata atttaatcct ttcctttata tccttttttg tttgtttgtt tgttttgtt   100920 tgagatggag ttttgatctt gttgcccagg ctggagtgcc atggtgcgat ctcagctcac   100980
tgcgacctcc acctcccagg ttcaagcaat tctcctgcct cagcctcccc agtagctggg   101040
attacaggca tgtatcacca cacccggcta attttgtatt tttagtagag acggggtttc   101100
accatgctgg tcaggctggt ctcgaactcc tgacctgaag tgatccactc accttggcct   101160
cccaaagtgc agggattata gacattagcc acggtgactg gcccttttcct ttatacttta   101220 tatccttctt atttggggat ctctttttta ttttttattt ttttaagaaa agtacatatg   101280
acatggtata tattgaccct tcctgacttt attcaattaa atattataat tgactattag   101340
atggttattt ctttattgct gttaattttt ttttttttt gagacagtct ctctctattg   101400
cccaggctgg agtgcagtgg cgcaatctcg gctcactgca agctccgcct ccctggttca   101460
caccattctc ctgccttagc ttcccgagta gttgggacta caggtgcctg ccaccacgcc   101520
cggctaattt tggtattttt agtagagacg gggtttcacc ttgttagcca ggatggtctc   101580
gatctcctga ccttgtgatc tgcctgcttc agcctcccaa agtgctggga ttacaggcgt   101640
```

```
gagccactgc acctggccta ttgctattaa attttaacat cagcatttca catagtccct  101700
atttggcttt catagttcct gttgactgaa tatcatttat atttaacttg aaaaatagat  101760
atttatattt cacttgtgtg gacatagttg aaaaagtgta ggaattatag attttatcat  101820
gcaacatttt atgttgtttc cagcctctga acgaataaat aatttatatg tgcaatgtat  101880
atgttttgtt cctaggtcct ctggggaggc attgtagggg aaaaacccac aaaacctggt  101940
gttggagggt cagggttcaa gttctgttct tagcaataat gtgatcttga gcccatcaat  102000
cattgtttct gaccccacat gtccttatta gtaaagtgaa actgataata catatgccac  102060
tgcattgtta aattactatt ataataataa ttattattat ttgagacgga gtctcactct  102120
gccacctagg ctggagtaca gtggcgcaat cttgcctcac tgcaatctcc acctcccggg  102180
ttcaagcaat tctcctgcct tgagtagctg ggattatagg tgcatgcaac cacgcccagg  102240 taattttttgt attttttagta gagacagggt ttcagggttt cagggtttca ccatgttggt  102300
caggctggtc tcgaacttct gaccttgtga tccgcccgcc tcggcctccc aaagtgctgg  102360
gattacaggc atgagccatc cgcccggac tgttaaatta gtatttattt tcttttttcct  102420 tttttttgaga cggagtctca ctctgtcgcc caggctggag tgcaatggcg cgatctcggt  102480
tcactgcaac ctccgcctcc tgggttcaag caattctcct gcctcagcct cccgagtagc  102540
tgggactaca ggtgcacact gccacacctg gctaattttt ttctatttta gtagagacag  102600
ggttcaccat gttgcccagg atggtctgga attcctgagc tgaggcaatc cacccttctc  102660
agcctcccaa agtgctggga ttacaggtgt gagccaccgt gcctggccct tcttttttttt  102720 tttctgagac gaattcttgc tctgtcaccc aagctagagt gcagtggcgg atcttggttt  102780
actgaaaccc ccgcctccca ggttcaagca attctccagc ctcagcctcc tgagtaactg  102840
ggattacagg catgtgccat catgcctagc taattttttgt attttttagta gagacggggt  102900 tttaccatgt tggccaggct ggtcttgaac tcctgacatt gtgatttgcc cacctcggcc  102960
tcccaaagtg ctgggattac aggcatgagc caccatgcct ggcctattta ttttcattat  103020
aattgacagt tatttaatta agtataaact tttagctacg tgttgtgaat gtgtgttatg  103080
tcacttgact aacctataaa gtgtgaacag ttattagcat cacaggtgag gttcttgagc  103140
ctcagagagg ttaagtgact tgcccatggt cacacagcct gaaagtggca aacctggat   103200 atgaacctag gaacatatga ctgcaaaaac agtaccccaa gtcattcgac gtgaagctgc  103260
cttttgatga tgtaagtgag attgactgcg acttgtaaag ctgtctgtaa atgcctagtt  103320
aagagagata tggccaagac atcagaaatt ttgagcagaa gaaggttcta ggaatcaact  103380
aattaaataa cgtgattta gaatgatgag gccgagagtc taccttgggt cagaaactaa  103440
gatagagatg tcagatgaga agacagatgc ctagctgcac cctgggctcc ctgtagtgct  103500
gtgtttaggt tctcagaccc gggagtcaga gcctgggctc aatattgagc tccggttcat  103560
actagctgtg taccttggac aagatatgta aattctctat accttagttt ctgcatctct  103620
aaaatgggat agctaagagt aattacaggc tgggtgcagt ggctcatgcc tgtaattcca  103680
gcactttgag aggccaagat ggatggatca cgcgaggcca ggagtttgag actagcatgg  103740
ccaacatgga gaaaccccat ctctactaaa aatacaaaaa ttagccgggc tggtggtgca  103800
tgtctgtgat tccagctact tgggagcctg aggcagaaga attgcttgaa cctaggaggc  103860
agaggttgca gtgagctgag attgcactgc tgtacgcaat cctgggtgac agagcaagac  103920
tctgtcttcg ggaaaaaaaa aaaaagtgta attatagaaa gattaaacaa gtttaaaatg  103980
tgtgacatgc ttaaaatagt ggtaatttat aaatgtatca ttattctggc caccactgat  104040
```

```
cgtctttaaa actgcaccat tcctatttga tgagctgaac atacaaaaac atccatggat   104100
accattatca tctttatctc ttgcgaaaca gcaaatgatg aataaacccg tacaattcat   104160
ttttcttttt ttcttttttt tttgagatgg agtctcactc cgtcacccag gctgcagtgc   104220
agtggcgcga tctcagctca ctgcaacctc cgcctcccgg gttcaagcaa ttctcctgcc   104280
tcagcctcct gagtagctgg taccacaggt gtgcaccacc atgctcggct aattttttgta  104340
tttttagtag cgatggggtt tcaccatgtt ggccaggatg gtcttgatct cctgaccttc   104400
tggtccgccc gccttggcct cccaaagtgc agggattcca agtgtgagcc accatgcccg   104460
gcctgtacaa ttcatttttc taagccacta atctgatcaa ttatttcact gccttgatta   104520
acacttttcc atgaagtatt tacaagtcac atatctgata agtatccaaa atatgaaaac   104580
aactctcacc acttgacaat tgtattcatt gttttttaaga caaaaatcc aattaaaaca   104640
cgggggaaaa aatggaatag acatttcccc aaagtacata tacaaatggc caaaatgtac   104700
atgaaaagat gctgaggatc attagtcatt agcgaaatgc aaatcataac tgcaatgtga   104760
tgccacctga gaccctgtag ggtggctata ataaaaaata tggagagtaa caagtgttgg   104820
caaagatgga gagaaattgg aactctcata cattgttggt gggagtataa gtggtacagc   104880
tgcttttgaa aaatctggta gtttcttaaa atattaaaca taattttcat ttgatccaga   104940
agttctactc ccaggtatat atttgagaga attaaaaaca tatgtctaca aagaaactgt   105000
ttttttttgt ttgtttgttt gttttgtttt tttttttaga cagggtcttg ctctgttgct   105060
caggctgaaa acagtggtg tgatcttggt tcactgcagc ctcttcctcc agggttcaca   105120
caattctcgt gccccagcct cccaaatagc tgggattaca ggcatgtgcc accatacacg   105180
gctaattttt tttttttttt tttttttttt ttgcattttt agtggacatg gggtttcacc   105240
atgttggcct ggctggtctg agactcctgg cctcaagagg tctacccacc ttggcctccc   105300
aaagtgctgg gagccactgt gcctggccct ctacacagaa atgtgtatac aaatgtttat   105360
agcagcatta ttcctaaaact ccaaaaagta gaaataacgt aaatgtccat tgactgatga   105420
actgataaac aaaatatgct ctacctatac aacggaatat tattcagctg taaaaaggga   105480
agaagtagat cactggcaca gaatagagag cccagaaata aaccttcagg tatatgggcc   105540
aatgatcttt gacaagggtg ccaaaactac acaaggggaa aaggattgtc tcttcaacaa   105600
atggtgttgg gaaaattgga tatctacaca aaaagaacta aagacatacc cttttcttct   105660
tgtgccatat acagaaatta attcaaaatg gattaggaac cagggctttg tgtggtgtct   105720
cacgcctgta atcccctcac tgtgggagac ccaggcagga ggattgcttg aggccaggag   105780
tttgaggcca gtctgagcaa cacagcaaga ccacatgtct acaaaaataa taattgtaaa   105840
aaagattaaa aacctaaaca taagacctga gattataaaa cttctagaag gaaatatact   105900
ggggcggggc ggagtggctc atggctataa tcccagcact ttgggaggcc aaggaaggcg   105960
gatcactgga ggtcaggagt tcaagaccag cctggccaac atggtgaaac cccgtctcca   106020
ctaaaaatac aaaaattagc tgggcatggt ggtgggtgcc tgtaatccca ggtactcagg   106080
aggctgaagc aggtagaatt gcttgagcct gggaggcaga ggttgcagtg agccgagatc   106140
ctgccactgc actccggcct gggcaacaag agcgaaactc tgtctcaaaa aacaaaacaa   106200
aacaacaaaa caacacaaaa acagaaaaca aatattggca agaaattggt acccttagat   106260
actgttggtg ggagtgaaaa atggtgtagc caccatggaa acagtatag tggttcctca   106320
aaaaatttaa aataaatggc tgggcgcagt ggctcacacc tgtaatctca acactttggg   106380
```

```
acactgagac gggcagatca cctgaggtca ggagtttgag cctggacaac atggtgaaac 106440
cccgtatcta ctaaaaatac aaaaattagc cagaaatggt ggtgcgcgcc tgtaatccca 106500
gctactctgg agactgaggc aggagaattg tttgaacccg ggagtttaca gtgagctgag 106560
atcgcaccac tgcaacccca gcttgggcga cagagcaaaa cttcatctca aataattaa 106620
ttattaaatt aattaatgac cataaaaaac tatcacctga ttcggcaatc ccacttctgg 106680
gtatatatcc aaaagaattg aaaacaagat ctcagagaga gatttgcaac atgttcattg 106740
cggcactatt gacaatagtc aagatgtaga agcaaccaaa atgcccactg gattaatgga 106800
taaagaaaat gtgggccagg tgcggggggct cgcacctgta atcccagcac tttgggaggc 106860
tgaggcaggc agatcacttg aggtcaggag tttgagacca gcctggccaa catggtgaaa 106920
tgccgcctcc attaaaaata caaaaattag cccggcatgg tggcgtgcgc ctgtggtccc 106980
agctactcag gaagctaagg caggagaata cgatgaaccc aggaggcgga agttgcagtg 107040
agctgagatc gcgccactgc actccagcct gggtgacaca gcaagacttc gtctcaaaaa 107100
ataaataaaa ataaaataat aaataaatac acccagaaaa ggcacttgtt tatagaatga 107160
gagctgcaat tagaaggtag cgtgttttct tgtccatgtt gggcactgct ctgtgcacat 107220
ctgcaaacga ccttaagagc accaggagca ctaatttggg ggttacaaat aaatttcagt 107280
gagtaggtga atttgaaaat atgcaggcct caattaatga ggatcactgt cttttgaaga 107340
ccattattgc ataagtgcat ttggaaaagc cagcctcatt ctgatgaaaa accgtgcgag 107400
tattgctgga gaaatgttag agtcgaaatt tttcctgatt tgcagctgag agtctcctaa 107460
ctgatccaga atcccagatt tcaccaagaa tcatgaatga aagggagtgt tttccatagc 107520
atttgggaga cagagatttc acccccccaa gatgagtcac aactgattat tgagggattc 107580
tctgtggcta ggatatttca gccaagagtt gaagaatgca gaagtccttc ttcctccgta 107640
caggagagcc catcttatta tttccctctc tcttgttcct aagacatggc tgtttactct 107700
tttattttg agacacagtt tcactctgtc gcacaggctg gagtgcagtg gcatgatctt 107760
ggctcactgc aatctccgct tcccgggttc aagtcattct gccattctca tgcctcagcc 107820
tcctgagtga ctaggaatta caggtgtacg ccaccacgcc tggctaagtt ttgtattttt 107880
agtagatacg gagtttcacc atgttggcca ggctggtttt gaactcctga cctcaagtaa 107940
tctgcctgct ttggcctccc aaagtgctag gattacaggc gtgagccatc acacctggct 108000
ggtttcgctg tttaaaaacc cattctgggc caggcgcggt ggctcacgcc tgtaatccaa 108060
gcactttggg aggccgaggc gggcggatca tctgaggtca ggagttcgag accagcctga 108120
ccaacatgga gaaaccctgt ctctactaaa aatacaaaat tagccgggcg tggtgaggca 108180
tgcctgtaat cccagctact caggaaggct gaggcaggag aattgcttga acccaggagg 108240
cggaggccag gaggcagagg ttgcggtgag tcgagatcac gccaccgcac tccagtctgg 108300
gcaacaagag tgaaactcgg tctcaaggga aaaaaaaaa aaagaatctg ctggatgcgg 108360
tggctcacac ctgtaatccc agcactttgg gaggctgagt tgggtggatc atgaggtcag 108420
gagtttgaga ccagcctggc cagcatggtg aaaccccgtc tctactaaaa atacaaaaaa 108480
ttagctgggc atagtggcac acgcctgtag tcccagctac tcgggaggct gaggcaggac 108540
aattgctgga acccagcagg tggaagttgc agtgagccga gatcgcgcca ctgcactcca 108600
gcctgggtga cagactgagc atctgtctca aaaaaaaaa aaaaaaaaa aaacccaac 108660
aaaaaccaat tctaacatgc ttttggttcc agagcgctct ggaaaactca aataagtcac 108720
tatagttaat ataatagtag atccagtttc catttggctg cctgggttct aatctgagct 108780
```

```
ctattctagc tgtgcaatgt tgaaccagct tatgtgcctc agtttccctt gtctgtaaca 108840
atgtaaaatt tttgcagtag atgtaaaaat cattgtgaag attggtgggc tttttgagga 108900
agatgcagtt acaggtactg cgaagcggtg gtctgcctgc tcctgatcct gcctcaccgc 108960
tgtgggctct caaggaacaa gtgggtcagg aagccacacg ctgcagccat ggcttttatc 109020
tgtttattga ttttttagagc tgggggtctc actgtgttgc ccaagatggt ctgaaactct 109080
tgggctcaag cgatcctcct gccttggccg cctgaattgc tgggactaca ggggtgagac 109140
actgtgctca gctcaaaatg tattaagagc aggcattgtg gacctcgtga ggcaattcac 109200
attgccattt taagctacat atttaaatct aagctgtcca ctaggctttg gagaggcatt 109260
tcctgaatgt ctgttctaaa ggaggaactc ttccaaccct cttgttctgt ggcagataac 109320
cctgatcatg acttgcaatt actttatttc aatttatatt ttggtttgtt ctcatcacta 109380
gaaatgaaag cctcataaaa acagggactt tattgctcct gttcatctat atatccccag 109440
gacagtgcca ggcacatagt agatgctcaa taagtatgtg ttgactgaat aaacgaatga 109500
ataacagaat ttggtgtctg actcccaagc ccttgtactt aacacaaggc tgtgcttctt 109560
ctcacaccct tctttgtgtg gtagtgggtt tggtcatgac ttagagcagc attgtccaat 109620
atggtagcca ctagccacat gtggcaattt aaatttaact ttaaagtagt gaaagttaaa 109680
taaagttaaa aacccagctc cccaggcatg ctagtatatt tccagtgctc agtacctaca 109740
tgtgacaaat ggctagtgga gagttcccat ataagaacatt tcaattgtca cagaaagttc 109800
cattaacgga gctgattgag atcagtggtt ctcaactgga gaagattttg cctcccaagg 109860
ggcatttggc aatgtctgga aacctttcta gttatcacag cttggaagat ggacctgaca 109920
tctagtgggt agaggccagg gatgctgcta tacatgctac aatacacagg acagcttcac 109980
gctagagaag tatttggccc aaaatgtcag cagtactaag gctgagaaac atggtttaca 110040
ggaaggcact ggggtgacag ttttctctgt atgaccagaa tgctaaattc ctcaggatct 110100
ggatgggtta atttgcaatt aaaagcctga taaggactct tcagtgtatg tggcatggtg 110160
tctagtttcc tggcttgaat tcctggaatt cctcctaata ttttgaatag gatattaaaa 110220
tccagaaatc attgcccagc tgggtttttca agtgcccaca cttccctgtg agactcattc 110280
aacgggattc acaacactca gaccaaaagg catttctaag gctagattgt tctagatcaa 110340
ggctctgtaa gacacagtcc cggccaagcc tgcccgtgaa cagaatggct tttatatatt 110400
tctttaattg gatgagaaac aatcaaaaga aggccagatg aggtggctca tgcctgtaat 110460
cccagaactt tgggaggcca aggcaggcgg atcacctgag gtcagggtt cgagcgagac 110520
cagcctggcc aacatggcga aaacccatct ctactaaaaa taacaaaaat tagccgggca 110580
tggtggtgca cactgtagtc ccaactactc aggaggctga ggcaggagaa ttgtttgaac 110640
ccgggaggcg gaggttgcag tgagctaaga tcgcaccact gcactccagc cagggtgatg 110700
gggtgagact cggtctcaaa aaaaaaaaa agaaacaatt aaaagaagaa tattttatga 110760
cacatgaaaa ttatataaaa ttcaaatttc agtgtccaca aagaaaactt ctttggaaca 110820
gtcaccacca taatttatat aaaagtattg cccagggctg ctttcgtgtt gttgagtggt 110880
ccagccacag aagccacagg gtccgcaaag ctgaaaatat tcaccacctg cccttttaca 110940
gaaagacttt gctaattcct gctctagata ctaaagacct tactggatt ttcttttcct 111000
tccctccccc tacccatttg ttctttttatt ttcttaagat caaaattatc ctgataattt 111060
gcaggtgtag acacagagca aatgaccaaa tggactttct tcgggaagcc gagggcggag 111120
```

```
gggattagct tccatgcagg ggcgttcatg tgaaagattc ctcttagatg aatttaggga  111180
acaaagaccc cgtggtcaat gatttctgtg ggtctgaaag taaaagactg gctgagttct  111240
tttgtcagtt ttgcagcaca gatcatacag ttactgaata ctcccctcca cggtagtatt  111300
cttttaacgc ttcactccat gacctcacaa aaataattgc tgggaagcaa atttacttcg  111360
ccctctgcct ttatttgctg accaaggggc tcagccgata gccgtattgt tgatggaaat  111420 gcaaagggg gtggagggaa ggagaaagaa tacaatttgg ccagggaaga tggatatatt  111480
gaaaggattc gaggatttgt ccttgcttta taattggagt caggattttc cttcaagtta  111540
ccctgcacag actggaagga aacctctcca gcctcctcca cccccatggc ctgttaaact  111600
ctttctcaac aaattgaaat ctggctttta aatccttgtc atttttatga ttatatgatt  111660
atagcgaaca ttacaacttg tccagtgaat ggactttaaa aaaaatttt ttttttttt  111720 tttgtagtga gcatcaggct atgttgacca ggctggtctt gaactcctgg tctcaagcaa  111780
tcctcttgcc ttggtctcac ttttcaaat tctgagaatg tctttattca gaaagaaagt  111840
aaaaactgat taaaatgat ttgtatgcat tgggaccagt tgggatttga ttttttttc  111900 tctctaagtc tacaggagtt ttcaccgatg gctttcaatt ctttggaatt tctggaaatg  111960
gaagcttgca tcttggaagc aaacctacaa acaaccttat attgtcccat accctcattt  112020
tagaaaacag accactctga ttactgtggg gattacctgg agtgatctgg gattcccttg  112080
gcaggaacaa agtggaaaga ttttccggcc ctttaatttg taaaacgaaa acctgtgttg  112140
gctgctactg gtagaaaaat aaaaaattaa tacacccaaa gtaaagtta gcaaggataa  112200 ctgccaggcc agacacagtt tgttataagc cccgcaatgt gcaatattga aagtggtttc  112260
cttcccctag tacttaggca tccaatcagt caaaccatct gataactgct tatctcctct  112320
aatgcgactg agatgtgttt gatgactctt tgcatttcaa tcgtaaagct caccttaggt  112380
aagcaccttg aggagaaaaa agaaattcac aagtctcagc ttttgcattc atggaatttt  112440
cttttcacaa tggaaggaaa gttaagctgg tgcccgttag ggggaggggt gcagaggtgg  112500
ttgaagatct ttgaaaggga ggggcgcagt gttcagtttg tgtgtagtgc acacacacat  112560
acacacacat acacaaaggt aaaacacttc atttgggtta aatggttgag aaacaatcaa  112620
aagaagaata ttttatgatg cataaaaaga tatgaaattc ccatttcagt gtccattaag  112680
aaagctttat tggaatgtag cttcttgtct caggagccaa aatagtaaag caaagcaaag  112740
caatcccgag agaggggaa gatgaaagat gaacgggcca ctctatgctt cattttagc  112800 tacctgagga cacaggaaaa atagaaaatg tgtataagga aagatttcca ggattttggt  112860
aatcataact tggcatgtct gactccctgc acccacagtg cttttataa tcctctaccc  112920 agcaatcttc tgtgaaatgg ggaagaagcg gggcacctct ctcataggag taaaaggttg  112980
atagataggc acgtgtttat tctagcctgg cacacagtac atgctcagaa aatcttagct  113040
gttattctta tcggggtggt tattgttttg ttttgttttg agatggcgtc tcgctctgtt  113100
gcccaggctg gagtgcaagg catgatctca gctcactgca acctccgcct cccgggttca  113160
agcgattctc ccgcctcaac cacccgagta gctgggacta caggcgcccg ccaccacgcc  113220
cggctaattt ttatactttt aatagagaca gggtttcacc atgttggcca ggatggtctc  113280
ggtctcgtga cctgtgatc caccagcctc ggcctcccaa agtgctggga ttacagggt  113340 aagccaccgt gcccggccag gggggtggtt attgttaaca gcagttgctc ttgtacttt  113400 ccatctccta ttgttggaga agtattagat tggtgcaaaa gtaattgtag tttctgcctt  113460
actttatttt tattttttatt tttttatttt ttattttga gatggagtct tgctctgtca  113520
```

```
cccaggctgg agtgcggtgg tgtgatttcg gctcactaca acctccgcat cctgggttca 113580
agagatcctc ctgcctcagt ctccccagta gctgggatta caggcgctgc aacttctgcc 113640
tcctgggttc aagagatcct cctgcctcag tctcccagt agctgggatt acaggcgctg 113700
caacttctgc ctcctgggtt caagagatcc tcctgcctca gtctcccag tagctgggat 113760
tacaggcact acaaccaagg ctggctaatt tttgtatttt tagtagagac aggatttcac 113820
cacgttggcc aggctggtct cgaattcctg acctcaggtg atccaccgc ctcggcctca 113880
tggagtgctg ggattacagg tgtgagccac tgtccccgac cactttttg ccttacttt 113940
aatggcaatt tatagttggt tggtgcaaaa gtaatttctg caattactta gtataacttc 114000
aacttggtta taacttggta taacttcatt tgggagcagt ttggcaatat cgccaaact 114060
ttaaacatac actttcaccc agcaactcag tttataggag ttcttcctat ggatcaattc 114120
cctcttcata tgccaatcag aattcatatt tttgttttga attccaaacc acgtgcatgt 114180
attattgttt tagttttgtg ttatcaggat atacatattt aggattatgt cacttggtga 114240
attgactcca ttatcatttt gaaatgtccc attttttccc tggaaatatt tctcaaattg 114300
aaatctattt tatctgaaat taatgcagcc aatccacttt attaggcttt gtgtttgcat 114360
ggagtatctt tttcaatccc ttacttctaa tctacctggt ctttatattt aaagtggggt 114420
ttcaggctgg gtgcgatggc tcatgcctat aattccacaa ctttgggaag ctgaagcagg 114480
cagatcacgt gaggtcagga gttcgagacc agcctggcca acacggtgaa acccttctc 114540
tgctaaaaac acaaaaatta gctgggcatg ctggcgcacg cctgtaatcc cagctacttg 114600
gaaggctgag gcaggacaat cacttgaacc caagaggcag aggttgcagt gaactgagac 114660
tgtgccactg cactccagcc taagtaacac acacctaagg tggtgtgaga ctccacctca 114720
aaaaaataat aaataagaaa taaagcagag tttcttagag acagcatatg gttgggtctt 114780
gctctcttac aaaaccaaca acttctgact tcaattggaa tatttagatc atttacccct 114840
ataggaattt tttatatggt tgaacttaaa tttaccatct tgctctttat ttttttattgt 114900
cctatttgta gtctattctt tttccttctt tttgcctggc tcccttttgga atgagttatt 114960
ttttaggatt ccattttatt tccatgactg gtttattagc tatatcttgt ttttttttt 115020
ttggttgctc taaggtataa agtatgcatc ttcagcttat cacaatgtac catcaaatga 115080
taacagttca catataatat aaaaatcttg tagcaatata cttccctctc cccatgtctt 115140
ttgcactgta tttgtcatag attttattac tacttatgtt ataaactctg aaatatttgt 115200
ttttttttc ttgctttaga gtcaattgtc ttttttttt tttttttga gatggagtct 115260
cgctctgtct cccaggctgg agagcagtgg cgtgatctcg gctcactgca tcctcagcct 115320
cctggttcaa gcgattcttc tgcctcagcc tcctgagtag ctgggactac aggcatgtgc 115380
caccacgccc agctaatttt tgtattttta gtagagacgg gtttcacca tgttggcctg 115440
gctggtcttg aactcctgac ctcgtgatcc acctgcctca gcctcacaaa gtgctgggat 115500
tacaggcatg agccattgcg cccagccaat tctcttcttc ataaataaaa ttttaatttt 115560
agaacagttt taggtttaca gaaaaattga aaagattgta ctaagagtta ccatataccc 115620
taaacacagt tttccctgtt attaacatct tacattagca tggcacattt gttttaatca 115680
gttaaactat tagccaaaca ttattatttt attattatta ttatttttga gacggagtct 115740
tgctctgtca cccaggctgg agtgcagtgg tgcaattctg gctcactgca acctccacct 115800
ccaaggttca attgattctc ctgcttcagc ctcctcatta gctgggacta caggcgccca 115860
```

```
ccaccacacc cggctaattt tgtgtatttt tagtagagac aaggtttcac catgttggcc    115920
aggctggtct caaacttctg acctcaagtg attcactcgc cttggccttg caaagtactg    115980
ggattacagg tgtgagccac tgcgcccagc caattttttgt attttttagta gagatggggt    116040 tttaccatgt tggccaggct ggtcttgaac tcctgacctc aagtgattca cccagcttgg    116100 cccccccaaag tgctgggatt acaggcatga gccacctcac ccggccaatt tttgtatttt    116160
tagtagagat ggggttttac catgttggcc atgagtcagt ctcaaactcc tgacttcagg    116220
tgatccaccc accttggcct ctcaaagtgc tgggattaca ggtgtgagcc actgcgcccg    116280
gccagccata cattattgtt aattcaattg catactgtat tcaggtttcc ttggttttta    116340
cctaatgtcc ttttactgcg ttaggatc                                       116368

<210> SEQ ID NO 26
<211> LENGTH: 220
<212> TYPE: DNA
<213> ORGANISM: Homo sapiens

<400> SEQUENCE: 26
ctgagatcaa gttttgggag cagacagaca aacatcatcc ctcacagaca ggcattccgt     60
tggctattct cttgcaaaca gaatcaagca ctagaccagc agcatgagcc tcaggatact    120
gtgggactgg ggagggagag aggggttgag tagtcccttc gcaagccctc atttcaccag    180
gcccccggct tggggcgcct tccttcccca tggcgggaca                          220

<210> SEQ ID NO 27
<211> LENGTH: 269
<212> TYPE: DNA
<213> ORGANISM: Homo sapiens

<400> SEQUENCE: 27
cagaaacatt catcggcaca cacacacatt tacaccttaa aagaaaagat ttaagaagct     60
aagagaaagg gaagggtcct ctaccggagc gcagtacagg tccggagtac acgaagtcgg    120
ctcgggagac cggtgcccac ttcgcgcgaa ccgaccgtgg caccggccag actcaagggc    180
tttccgtaat tttgagaaga ttttttttttg taattttta ttctgcccca gctgatgttt    240
gagccagcat gtcgcggagg aagcaagcg                                      269

<210> SEQ ID NO 28
<211> LENGTH: 320
<212> TYPE: DNA
<213> ORGANISM: Homo sapiens

<400> SEQUENCE: 28
taaacgggat aactagagat ttcaaacacc ttttatttgc ctgtcttgaa aaaaaaatct     60
aaatgaatac gcccgctacc aaaaggcaaa ataaaaccaa ccttaagggt ttttgttgtt    120
tttttttttt ttcaaaagtg gcgataggga ctgtttggac attcaccagc ctaattgctc    180
agccccatgc gcggcccgcg cagccgccgc cgccccgcgc cccgcgccgc gcgcccgcca    240
ggccgccccg cgccgtcccc gccggccgcc ccgctgatgc cgctgccccg cgcggggccc    300
gagcgccgct agcagcatgt                                                320

<210> SEQ ID NO 29
<211> LENGTH: 300
<212> TYPE: DNA
<213> ORGANISM: Homo sapiens

<400> SEQUENCE: 29
```

-continued

```
tgcagtctgt ggcatgtaca aggggctcaa tcaattatta ttattactat cacttggaga        60
gtcaagcggc acaatttttgt ctcgtagtaa ggctaacatg ttacaactat catctactaa      120
aataaatata aacaactata ctgtcagggc tcatgataaa tcgcaatgca ttattgataa       180
taataattac tgggacatgc gcgttccggc cgaaggggg taaatttccc aactccagga        240
atttgtggcg gagagggcaa ataactgcgg ctctcccggc gccccgatgc tcgcaccatg       300
```